US008987553B2

(12) United States Patent
Bate et al.

(10) Patent No.: US 8,987,553 B2

(45) Date of Patent: Mar. 24, 2015

(54) MODULATION OF ACC SYNTHASE IMPROVES PLANT YIELD UNDER LOW NITROGEN CONDITIONS

(75) Inventors: Nicholas J. Bate, Urbandale, IA (US); Sarah T. Collinson, Woodland, CA (US); Jeffrey E. Habben, Urbandale, IA (US); Honor Renee Lafitte, Davis, CA (US); Kellie Reimann, Ankeny, IA (US)

(73) Assignee: Pioneer Hi Bred International Inc, Johnston, IA (US)

( * ) Notice: Subject to any disclaimer, the term of this patent is extended or adjusted under 35 U.S.C. 154(b) by 555 days.

(21) Appl. No.: 12/760,019

(22) Filed: Apr. 14, 2010

(65) Prior Publication Data

US 2010/0287669 A1 Nov. 11, 2010

Related U.S. Application Data

(60) Provisional application No. 61/290,902, filed on Dec. 30, 2009, provisional application No. 61/248,060, filed on Oct. 2, 2009, provisional application No. 61/169,082, filed on Apr. 14, 2009.

(51) Int. Cl.

| | |
|---|---|
| ***C12N 15/82*** | (2006.01) |
| ***C12N 15/113*** | (2010.01) |
| ***A01H 5/00*** | (2006.01) |

(52) U.S. Cl.

CPC ........ *C12N 15/8218* (2013.01); *C12N 15/8271* (2013.01)

USPC ........... 800/283; 800/285; 800/286; 800/287; 800/320.1

(58) Field of Classification Search

USPC .......................................................... 800/285

See application file for complete search history.

(56) References Cited

U.S. PATENT DOCUMENTS 7,230,161 B2 * 6/2007 Gallie et al. .................. 800/283

FOREIGN PATENT DOCUMENTS

| | | | |
|---|---|---|---|
| WO | WO 2007/076115 | A2 | 7/2007 |
| WO | WO 2007/092704 | A2 | 8/2007 |
| WO | WO 2008/157375 | A1 | 12/2008 |

OTHER PUBLICATIONS

Foyer et al. (1998) Plant Physiol. 117: 283-292.*

Richards et al. (2002) Crop Sci. 42: 111-121.*

Crafts-Brandner et al. (1998) Physiologia Plantarum 102: 192-200.*

Young et al. (2004) Plant J. 40: 813-825.*

WI, S.J., and K.Y. Park, "Antisense Expression of Carnation cDNA Encoding ACC Synthase or ACC Oxidase Enhances Polyamine Content and Abiotic Stress Tolerance in Transgenic in Transgenic Tobacco Plants," *Molecules and Cells*, 2002, pp. 209-220, vol. 13(2).

* cited by examiner

*Primary Examiner* — David T Fox

*Assistant Examiner* — Steven Bernacki

(74) *Attorney, Agent, or Firm* — Pioneer Hi-Bred Int'l Inc.

(57) ABSTRACT

The invention provides methods for improving plant yield, particularly under nitrogen limiting conditions. According to the invention, applicants have discovered that modulating ACC synthase activity in plants improves yield of plants, even when grown under low nitrogen conditions. The same plants, while demonstrating improved yield over non-modified plants, exhibited no deleterious effects under normal nitrogen conditions. The invention further provides methods using recombinant expression cassettes, host cells and transgenic plants.

11 Claims, 9 Drawing Sheets

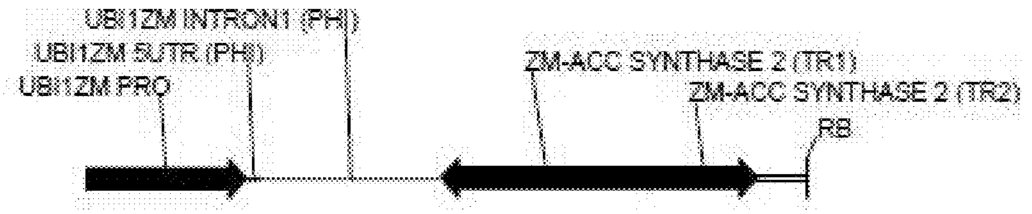

FIG. 2A

GGCCGCCCTTTTTTTTTTTTTTTTTTTTTTTTTTTTTTTGATATGTAAACTGGTCTTTTATTCACCCTTGAG
CTACGCCTTCTGTGTCCTGAAGTTACGTGACAGGTTTTCAACAACAATTGATCGGGAGGTCTAAAT
TACCATACCCGATCGTTATTCTACCGTGTACTAACGTTAAACCAAACCATACATGCGATTTGGCAA
AACAGAAAAAAGAACATATATACACGAAAAAATCGAGGACAAATGCGTCCTGCTTGACTAGCTGC
TTACCGCCGACGCCTGCTGACGCCTGTGCAACGTCTCTGTGTAATGTCAAGCTAGCTACTAATGCC
CTTTATTAGTCTTGTCTAATATTTTTTGTCCACTTGTTTGCAGTTATGTGAGGGCACACCCTACAGC
CAGTCTTACCGAACGCTCGGTGACTAGCTAGCTGGCGTGGACCATCGGGGACTGCGGCGACAGCA
ACGCCAAGGGGCTGGGGATGGCGAGGTGCGAAGCGGTGGTTGCTCCCCGGCGCGGCAAGCTGAG
GCGGAGGGGCCGCGTGGCCGCCCAGCGCTCGGCCTTGGCCTTGCTGTGCTGGTGCTGGCGCACGA
AGCGGCGGATCCGGTCGAGCGCGACCTCCATGGTGTCGTCGTCCATGTTGGCGTAGCAGACGCCG
AACCAGCCGGGCTCGTTGCAGTGGAACGACGTGCCGGGCGACACGTTGAGCTTCACCCTGTGTAC
GATGACCCGCCACAGCTCCAGCTCCGCGTCGTGCGTCCTCTCCCGGAGCATGCCCCGCAGGTCCAT
CCACGAGAAGAGGCCCGCGTTGCCCGGCAGGCACGCGATGCCGACCTCGCGGAGGCCCGCGACGA
AGCGGTCGTGGCGCGCCGCCAGCCGCCGCGCGCTCTCCGCGAGGAAGCGTGCCATGAACTCCGCG
TCGGCGAGCATCATCGCCAGGAAGTGCTGCGTCTGCGACGAGACGAGGCCGAAGCTGGACATCTT
GCGCGCGCAGGCCACCACGTCGTCGTTGTAGGAGTAGACGATGCCGACGCGGAAGCCCGGGAGGC
CGAAGTCCTTGGAGAGGCTGTACGCGATGTGGACGAGGTCCCTGTTGCAGCCCGGGGCGTCGCCG
CGCTCGATGACCTCGGCGATGCTCACGAAGCCCGGCTTGGCGAAGACGGAGCCCGCGTA

FIG. 2B

GATCCGCCGCTTCGTGCGCCAGCACCAGCACAGCAAGGCCAAGGCCGAGCGCTGGGCGGCCACGC
GGCCCCTCCGCCTCAGCTTGCCGCGCCGGGGAGCAACCACCGCTTCGCACCTCGCCATCCCCAGCC
CCTTGGCGTTGCTGTCGCCGCAGTCCCCGATGGTCCACGCCAGCTAGCTAGTCACCGAGCGTTCGG
TAAGACTGGCTGTAGGGTGTGCCCTCACATAACTGCAAACAAGTGGACAAAAAATATTAGACAAG
ACTAATAAAGGGCATTAGTAGCTAGCTTGACATTACACAGAGACGTTGCACAGGCGTCAGCAGGC
GTCGGCGGTAAGCAGCTAGTCAAGCAGGACGCATTTGTCCTCGATTTTTTCGTGTATATATGTTCTT
TTTTCTGTTTTGCCAAATCGCATGTATGGTTTGGTTTAACGTTAGTACACGGTAGAATAACGATCGG
GTATGGTAATTTAGACCTCCCGATCAATTGTTGTTGAAAACCTGTCACGTAACTTCAGGACACAGA
AGGCGTAGCTCAAGGGTGAATAAAAGACCAGTTTACATATCAAAAAAAAAAAAAAAAAAAAAAA
AAAAAGGGC

FIG. 2C

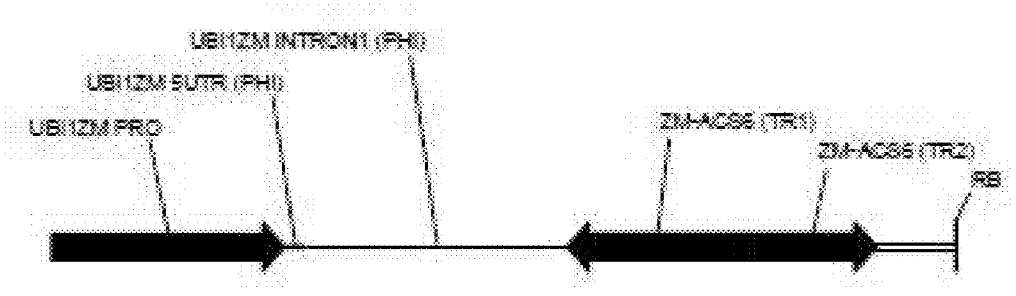

FIG. 3A

TAGCAGACGCGGAACCAGCCGGGCTCCCGGCAGTGGCAGGAGGAGCCCGGGGAGATGTTGAGCC
CCACCTCGAAGACCACCTTCTTCCACAGCTCCATCTCGCCCTCGAACGACCGGCTCCGCATCAGGC
GCCGCATGTTGACCCAGCAGAAGAGCCCCGCGTTGCTCTCCAGGCACTCGATGCCCACGGCCGCC
AGGCCCTCCGCCAGCTGCTCGCGCCGCTCCCTGATCCGCCGCGTGTTCTCCGCGATGTACCTCCGC
GTGAAGTCCCTGTCGCCCAGGAGCGACGCCAGGAGGTGCTGCGTCTGGGACGACACCAGGCCGAA
GCTCGACATCTTGGTGGCCGCGGAGACCACGCCGGCGTTGGACGAGTAGATGGCGCCCACGCGGA
ACCCCGGGAGGCCCAGGTCCTTGGACAGGCTGTACACCACGTGCACGCGGTCCGACAGCGGCCCA
ACGCCGACGACGCCGTCGTCCGTGGCGGCGCGCGCGGCCACCACCTCGAGGACGCTCACGAAGCC
CGGGTCCGCGAAGACCGTGCCCGAGTATATCTCGTCGCTCACCAGGTGGATGCCCTTGGCGGCCAC
GAAGTCCACCAGCATCTCCAGGTCGGCGCGCGGCGACGTGGTGCCCAGCGGGTTGGAAGGGTTGG
TGATGAGCACGCCCTTGACGGGCAGCCGCAGCTTCTGCGCCGCGCCGGTA

FIG. 3B

CGCGCCGCCCACGGACGACGGCGTCGTCGGCGTTGGGCCGCTGTCGGACCGCGTGCACGTGGTGTA
CAGCCTGTCCAAGGACCTGGGCCTCCCGGGGTTCCGCGTGGGCGCCATCTACTCGTCCAACGCCGG
CGTGGTCTCCGCGGCCACCAAGATGTCGAGCTTCGGCCTGGTGTCGTCCCAGACGCAGCACCTCCT
GGCGTCGCTCCTGGGCGACAGGGACTTCACGCGGAGGTACATCGCGGAGAACACGCGGCGGATCA
GGGAGCGGCGCGAGCAGCTGGCGGAGGGCCTGGCGGCCGTGGGCATCGAGTGCCTGGAGAGCAA
CGCGGGGCTCTTCTGCTGGGTCAACATGCGGCGGCCTGATGCGGAGCCGGTCGTTCGAGGGCGAGA
TGGAGCTGTGGAAGAAGGTGGTCTTCGAGGTGGGGCTCAACATCTCCCCGGGCTCCTCCTGCCACT
GCCGGGAGCCCGGCTGGTTCCGCGTCTGCTAA

FIG. 3C

MODULATION OF ACC SYNTHASE IMPROVES PLANT YIELD UNDER LOW NITROGEN CONDITIONS

CROSS-REFERENCE TO RELATED APPLICATIONS

This application claims the benefit of U.S. Provisional Application No. 61/290,902, filed Dec. 30, 2009, U.S. Provisional Application No. 61/248,060, filed Oct. 2, 2009, and U.S. Provisional Application No. 61/169,082, filed Apr. 14, 2009, each of which are herein incorporated by reference in its entirety.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of 387145SEQLIST.TXT, a creation date of Apr. 13, 2010, and a size of 200 KB. The sequence listing filed via EFS-Web is part of the specification and is hereby incorporated in its entirety by reference herein.

FIELD OF THE INVENTION

The invention relates generally to the field of molecular biology, specifically the modulation of ACC synthase activity to improve plant yield and nitrogen stress tolerance.

BACKGROUND OF THE INVENTION

The domestication of many plants has correlated with dramatic increases in yield. Most phenotypic variation occurring in natural populations is continuous and is effected by multiple gene influences. The identification of specific genes responsible for the dramatic differences in yield in domesticated plants has become an important focus of agricultural research.

Nitrogen utilization efficiency (NUE) genes affect yield and have utility for improving the use of nitrogen in crop plants, especially maize. Increased nitrogen use efficiency can result from enhanced uptake and assimilation of nitrogen fertilizer and/or the subsequent remobilization and reutilization of accumulated nitrogen reserves, as well as increased tolerance of plants to stress situations such as low nitrogen environments. The genes can be used to alter the genetic composition of the plants, rendering them more productive with current fertilizer application standards or maintaining their productive rates with significantly reduced fertilizer or reduced nitrogen availability. Improving NUE in corn would increase corn harvestable yield per unit of input nitrogen fertilizer, both in developing nations where access to nitrogen fertilizer is limited and in developed nations where the level of nitrogen use remains high. Nitrogen utilization improvement also allows decreases in on-farm input costs, decreased use and dependence on the non-renewable energy sources required for nitrogen fertilizer production and reduces the environmental impact of nitrogen fertilizer manufacturing and agricultural use.

SUMMARY OF THE INVENTION

Methods and compositions for improving plant yield are provided. In some embodiments, plant yield is improved under stress, particularly abiotic stress, such as nitrogen limiting conditions. Methods of improving plant yield include inhibiting the ethylene synthesis pathway, such as, for example, inhibiting the activity of at least one 1-aminocyclopropane-1-carboxylic acid (ACC) synthase. The activity of an ACC synthase can be inhibited using any method known in the art, including but not limited to the disruption of an ACC synthase gene, or a decrease in the expression of the gene through the use of co-suppression, antisense, or RNA silencing or interference.

Inhibiting the activity of at least one ACC synthase in a plant can improve the nitrogen stress tolerance of the plant and such plants can maintain their productive rates with significantly less nitrogen fertilizer input and/or exhibit enhanced uptake and assimilation of nitrogen fertilizer and/or remobilization and reutilization of accumulated nitrogen reserves. In addition to an overall increase in yield, the improvement of nitrogen stress tolerance through the inhibition of ACC synthase can also result in increased root mass and/or length, increased ear, leaf, seed, and/or endosperm size, and/or improved standability. Accordingly, in some embodiments, the methods further comprise growing said plants under nitrogen limiting conditions and optionally selecting those plants exhibiting greater tolerance to the low nitrogen levels.

Further, methods and compositions are provided for improving yield under abiotic stress, which include evaluating the environmental conditions of an area of cultivation for abiotic stressors (e.g., low nitrogen levels in the soil) and planting seeds or plants having reduced ethylene synthesis, which in some embodiments, is due to reduced activity of at least one ACC synthase, in stressful environments.

Constructs and expression cassettes comprising nucleotide sequences that can efficiently reduce the expression of an ACC synthase are also provided herein.

Ethylene is then produced from the oxidation of ACC through the action of ACC oxidase (also known as the ethylene forming enzyme) with hydrogen cyanide as a secondary product that is detoxified by β-cyanoalanine synthase. Finally, ethylene is metabolized by oxidation to $CO_2$ or to ethylene oxide and ethylene glycol.

FIG. 2, panels A-C, illustrate the ACS2 hairpin construct. Panel A is a schematic diagram of a PHP plasmid containing an ubiquitin promoter (UBI1ZM PRO) driving expression of the ACS2 hairpin (a terminal repeat consisting of TR1 and TR2). RB represents the *Agrobacterium* right border sequence. A 4126 bp fragment of the 49682 bp cassette is illustrated. Panel B presents the sequence of ZM-ACS2 TR1 (SEQ ID NO: 12) and Panel C presents the sequence of ZM-ACS2 TR2 (SEQ ID NO: 13).

FIG. 3, panels A-C, illustrate the ACS6 hairpin construct. Panel A is a schematic diagram of a PHP plasmid containing an ubiquitin promoter (UBI1ZM PRO) driving expression of the ACS6 hairpin (a terminal repeat consisting of TR1 and TR2). RB represents the *Agrobacterium* right border sequence. A 3564 bp fragment of the 49108 bp cassette is illustrated. Panel B presents the sequence of ZM-ACS6 TR1 (SEQ ID NO: 14) and Panel C presents the sequence of ZM-ACS6 TR2 (SEQ ID NO: 15).

Figure 4:
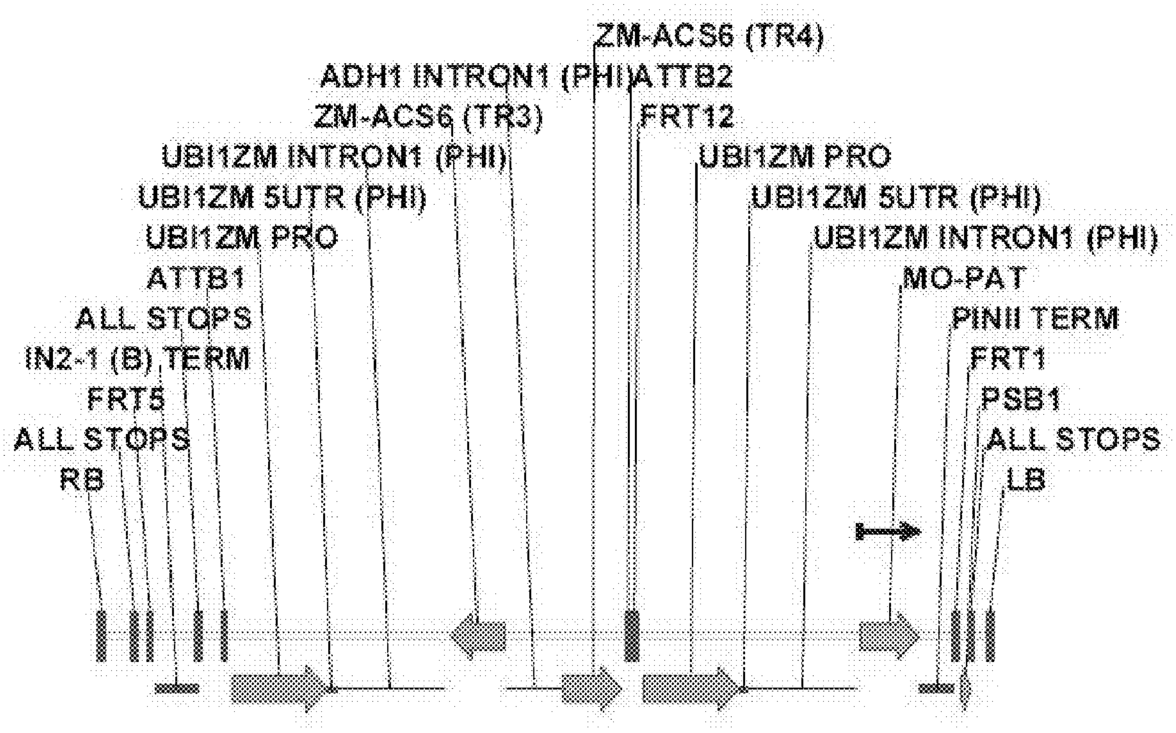

FIG. 4 is a schematic of an improved ACS6 inhibition expression cassette, which is set forth in SEQ ID NO:57.

Figure 5:
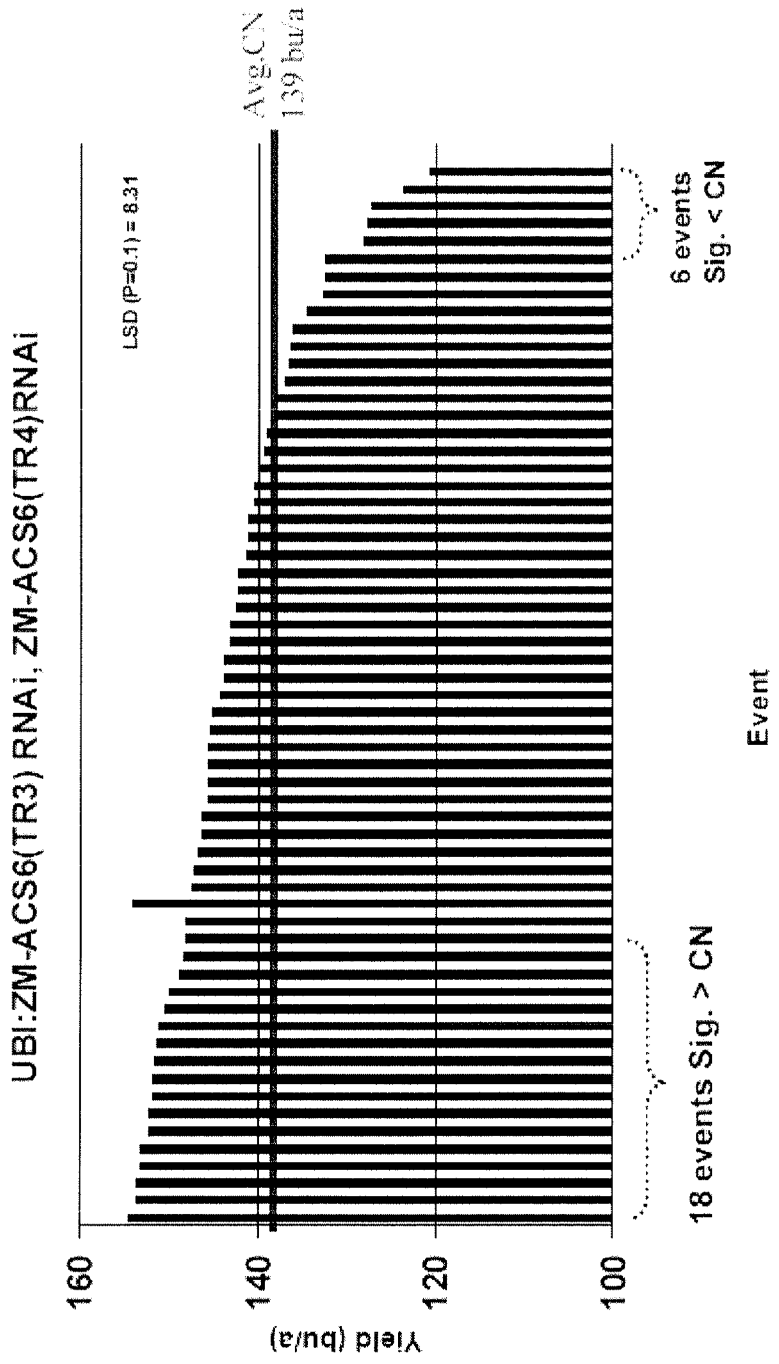

FIG. 5 shows the yield of transformed plants of the invention under flowering stress in Environment 1. Each bar represents a separate transformation event. Average yield of transgene-negative segregants is shown (139 bu/a) as control (CN). A total of 74% of the events yielded nominally more than the control plants. Plants representing 18 transgenic events outyielded the control at P<0.10.

Figure 6:
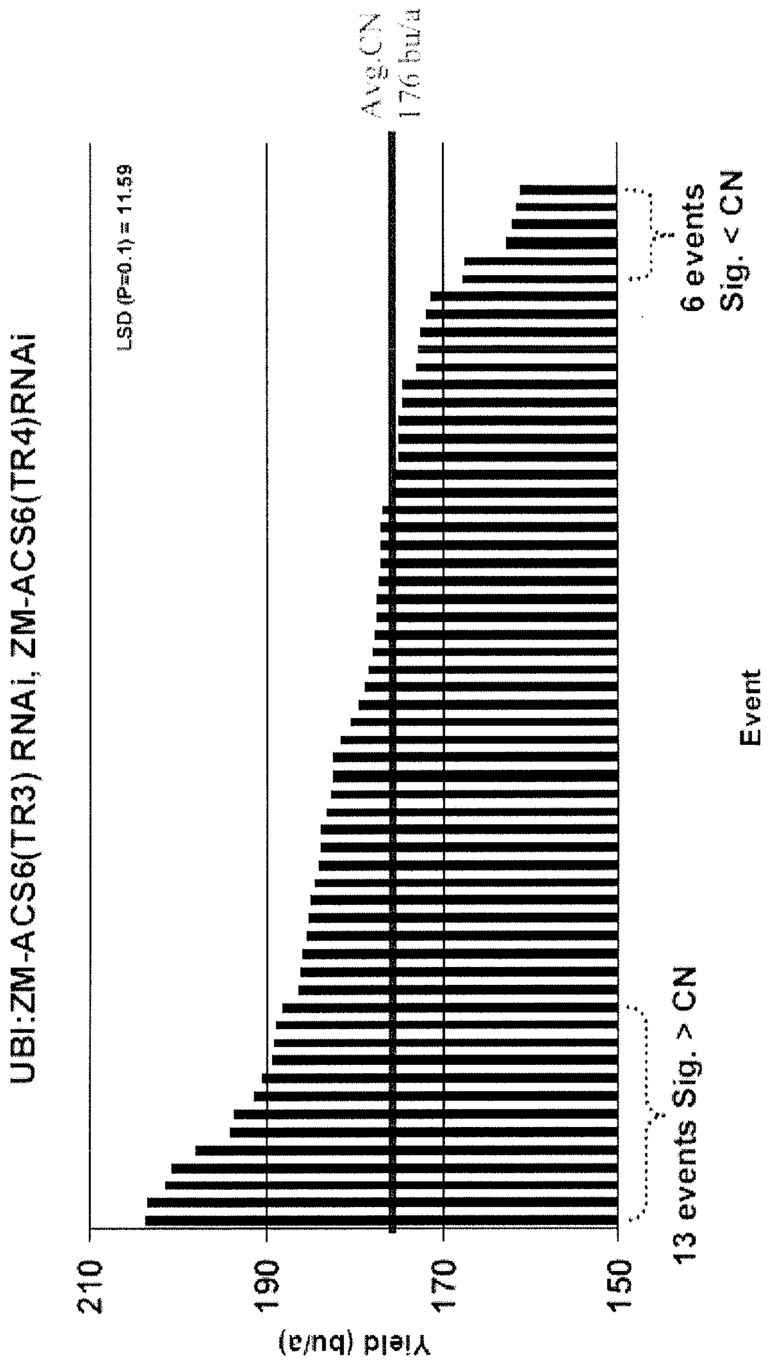

FIG. 6 shows the yield of transformed plants of the invention under grain-fill stress in Environment 2. Each bar represents a separate transformation event. Average yield of transgene-negative segregants is shown (176 bu/a) as control (CN). Thirteen events out-yielded the CN at P<0.10. Of these, eight had also shown significant improvement under flowering stress.

Figure 7:
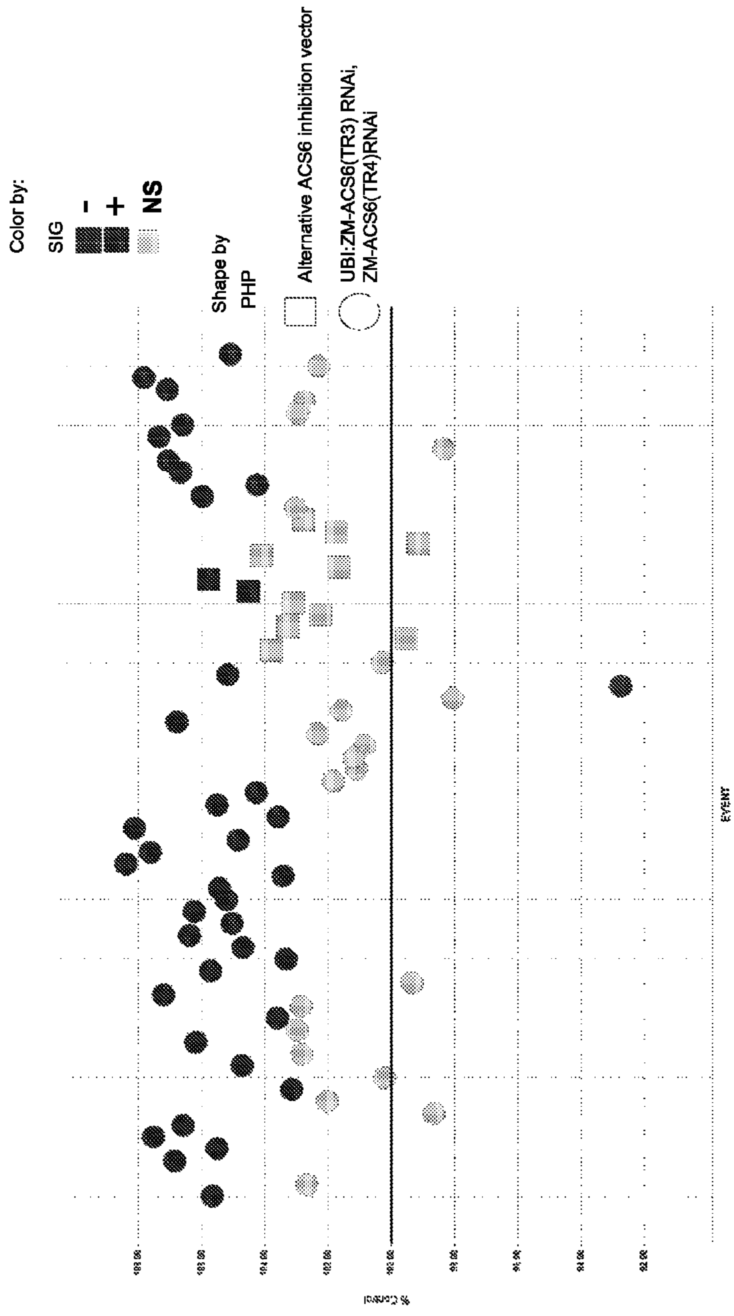

FIG. 7 shows the yield, as a percent of control, of transformed plants of the invention (indicated by a circle), as well as plants transformed using an alternative ACS6 inhibition vector (indicated by a square) under grain fill stress in Environment 3. Each data point represents a separate transformation event. NS=not significant. The control plants are bulked transgene-negative segregants. As can be seen, 64% of the events of the invention had significantly superior yield; only 17% of the alternative ACS6 inhibition events had significantly superior yield, relative to the control.

Figure 8:
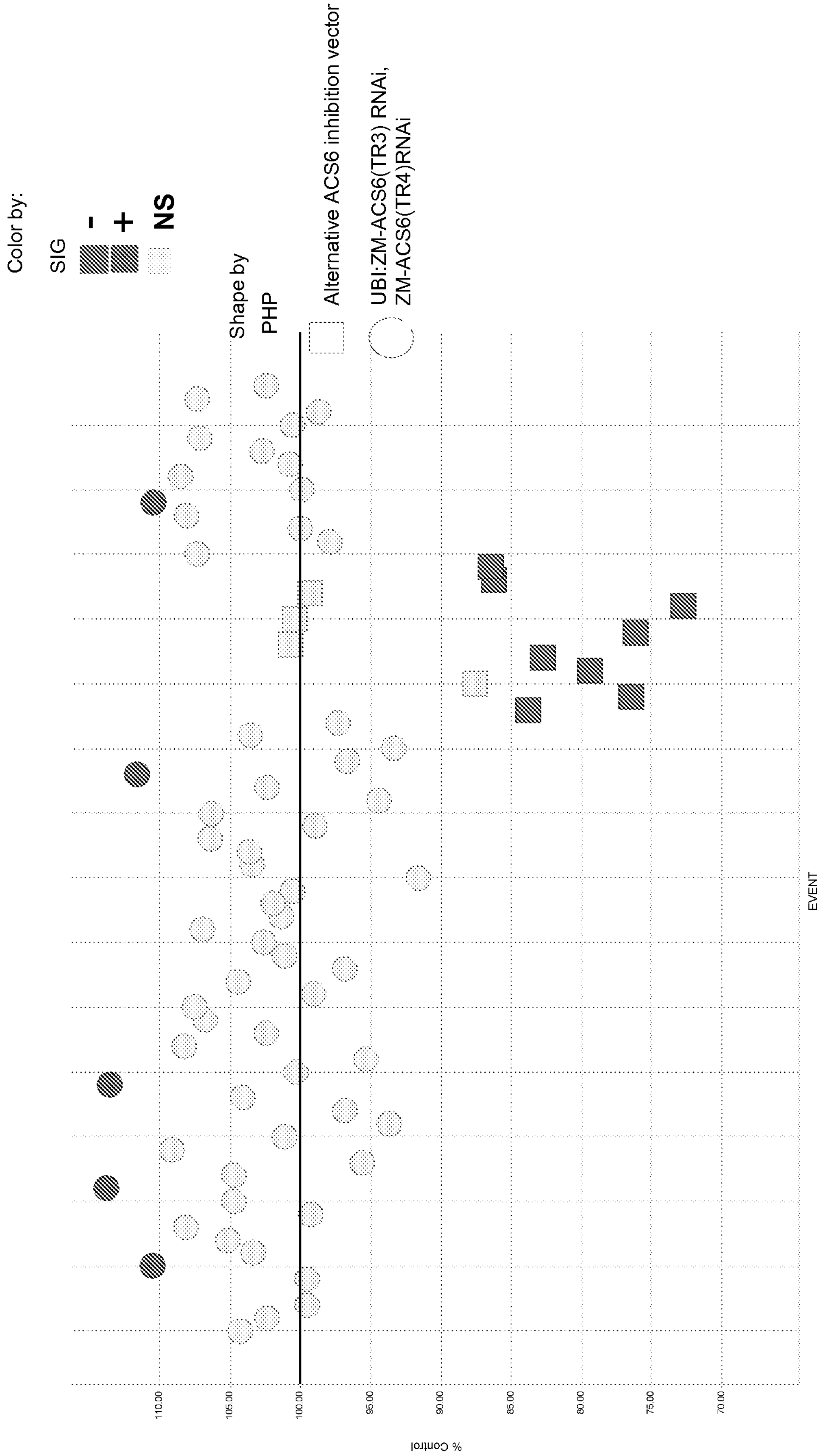

FIG. 8 shows the yield, as a percent of control, of transformed plants of the invention (indicated by a circle), as well as plants transformed using an alternative ACS6 inhibition vector (indicated by a square) under rain-fed conditions in Environment 4. Each data point represents a separate transformation event. NS=not significant. The control plants are bulked transgene-negative segregants. As can be seen, all points exhibiting statistically significant increases in yield represent events of the invention disclosed herein. In addition, all points exhibiting statistically significant decreases in yield are events containing the alternative ACS6 inhibition vector.

DETAILED DESCRIPTION OF THE INVENTION

The present invention is based on the surprising finding that modulation of ACC synthase (ACS) improves plant responses in low nitrogen conditions, with no deleterious effect on plant performance under normal nitrogen conditions. In fact, plants with ACS inhibition constructs actually had superior yield not only in low nitrogen conditions, but also under normal nitrogen conditions. Accordingly, methods for improving plant yield, particularly under abiotic stress, by modulating the ethylene synthesis pathway are provided.

Figure 1:
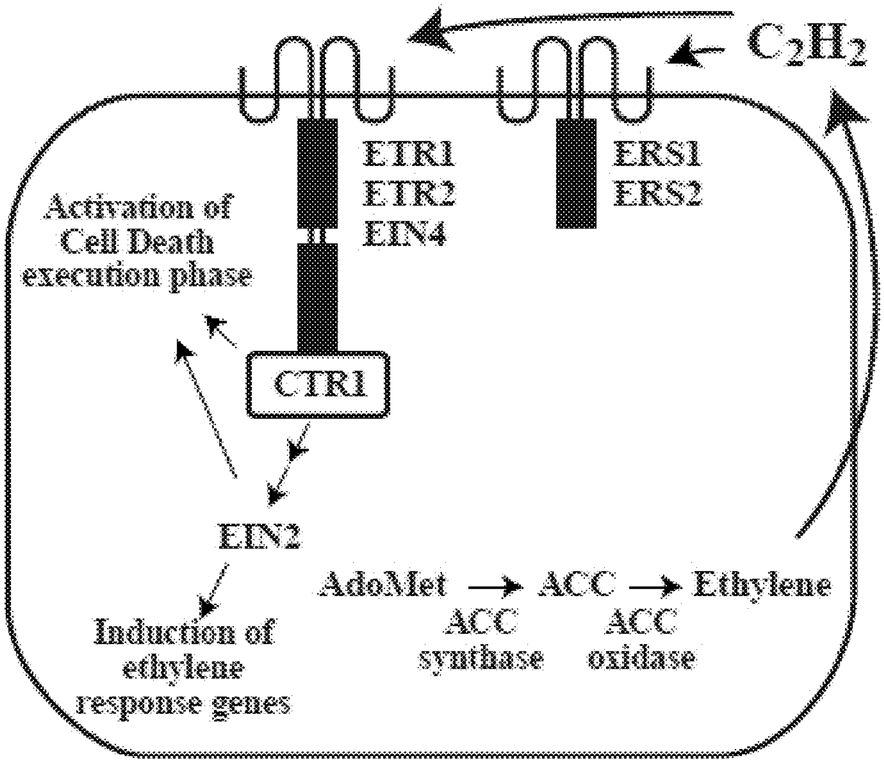
FIG. 1 is a schematic illustration of the ethylene biosynthetic and signaling genes in plants, e.g., *Arabidopsis*. Ethylene is generated from methionine by a well-defined pathway involving the conversion of S-adenosyl-L-methionine (SAM or Ado Met) to the cyclic amino acid 1-aminocyclopropane-1-carboxylic acid (ACC) which is facilitated by ACC synthase. ACC synthase is an aminotransferase which catalyzes the rate limiting step in the formation of ethylene by converting S-adenosylmethionine to ACC.

Ethylene is generated from methionine by a well-defined pathway involving the conversion of S-adenosyl-L-methionine (SAM or Ado Met) to the cyclic amino acid 1-aminocyclopropane-1-carboxylic acid (ACC) which is facilitated by ACC synthase. ACC synthase is an aminotransferase which catalyzes the rate limiting step in the formation of ethylene by converting S-adenosylmethionine to ACC. Ethylene is then produced from the oxidation of ACC through the action of ACC oxidase (also known as the ethylene forming enzyme) with hydrogen cyanide as a secondary product that is detoxified by β-cyanoalanine synthase. ACC oxidase is encoded by multigene families in which individual member's exhibit tissue-specific regulation and/or are induced in response to environmental and chemical stimuli. Activity of ACC oxidase can be inhibited by anoxia and cobalt ions. The ACC oxidase enzyme is stereospecific and uses cofactors, e.g., $Fe^{+2}$, $O_2$, ascorbate, etc. Finally, ethylene is metabolized by oxidation to carbon dioxide ($CO_2$) or to ethylene oxide and ethylene glycol. See, FIG. 1.

In some embodiments of the presently disclosed methods, the activity of at least one ACC synthase is modulated or inhibited to enhance plant yield and improve nitrogen stress tolerance. An "ACC synthase" is an enzyme having amino transferase activity that catalyzes the conversion of S-adenosylmethionine to ACC. Non-limiting examples of ACC synthases include ACS1 through ACS11. In maize, this includes ACS2, ACS6 and/or ACS 7. In dicots, ACC synthase is part of a larger superfamily of amino transferases with nine members being ACS genes. The genes fall into three different classes which are distinguished by their C-terminal structure and their post-translational regulation. In maize and other monocots, there are only 3 members and one member falls into each class. See, Table 4 in Example 16 for a non-limiting list of some publicly available ACS sequences which may be used for the invention.

The term "ACC synthase polypeptide" refers to one or more amino acid sequences and is inclusive of fragments, variants, homologs, alleles or precursors (e.g., preproproteins or proproteins) thereof that retain the function of catalyzing the conversion of S-adenosylmethionine to ACC. An "ACC synthase protein" comprises an ACC synthase polypeptide. Unless otherwise stated, the term "ACC synthase nucleic acid" means a nucleic acid comprising a polynucleotide ("ACC synthase polynucleotide") encoding an ACC synthase polypeptide.

As used herein the term "modulation of ACC synthase activity" shall be interpreted to mean any change in an ACC synthase biological activity, which can include an altered level of ACC synthase present in a plant cell, altered efficacy of the enzyme or any other means which affects one or more of the biological properties of ACC synthase in relation to its role in converting S-adenosylmethionine to ACC in the formation of ethylene. Accordingly, "inhibition of ACC synthase activity" encompasses a reduction in the efficacy of the enzyme, or a reduction in the level of ACC synthase present in a plant cell, for example, due to a reduction in the expression of an ACC synthase gene.

In other embodiments, other steps along the ethylene synthesis pathway could be modulated to improve plant yield or nitrogen stress tolerance of a plant. For example, the rate of conversion of SAM to polyamines could be increased, or the level or activity of ACC oxidase could be decreased, or the level or activity of ACC could be increased, or the level or activity of SAM could be increased, or some combination of these and/or other modifications in the ethylene synthesis pathway could occur as a result of the genetic modulation described herein. While not wishing to be bound by any theory, it is postulated that modification of one or more steps towards ethylene synthesis results in decreased ethylene activity. In any event, the invention is directed to increasing plant yield under abiotic stress conditions, and in some embodiments, improving nitrogen stress tolerance, resulting from modulated expression of an ACC synthase gene, regardless of the precise effect of that modulation on the ethylene synthesis pathway, ethylene production or ethylene activity.

The methods of the invention provide for an improved yield of plants. As used herein, "yield" may include reference to bushels per acre of a grain crop at harvest, as adjusted for grain moisture (15% typically for maize, for example) and/or the volume of biomass generated (for forage crops such as alfalfa and plant root size for multiple crops). Grain moisture is measured in the grain at harvest. The adjusted test weight of grain is determined to be the weight in pounds per bushel, adjusted for grain moisture level at harvest. Biomass is measured as the weight of harvestable plant material generated.

In some embodiments of the presently disclosed methods, the modulation of the ethylene synthesis pathway results in improved nitrogen stress tolerance of a plant. As used herein, a plant having "improved nitrogen stress tolerance" shall include but is not limited to, plants that have improved tolerance to low nitrogen conditions, plants that maintain their productive rates with significantly less nitrogen fertilizer input, enhanced uptake and assimilation of nitrogen fertilizer and/or remobilization and reutilization of accumulated nitrogen reserves, or any combination thereof, compared to a corresponding control plant (e.g., non-modified plant).

The term "low nitrogen conditions" or "nitrogen limiting conditions" as used herein shall be interpreted to mean any environmental condition in which plant-available nitrogen is less than would be optimal for expression of maximum yield potential.

The methods of the invention provide for improved plant performance in nitrogen limiting conditions. This performance may be demonstrated in a number of ways including a modulation of root development, shoot and leaf development, and/or reproductive tissue development.

Accordingly, methods for modulating root development in a plant are provided. By "modulating root development" is intended any alteration in the development of the plant root under nitrogen limiting conditions when compared to a control plant. Such alterations in root development include, but are not limited to, alterations in the growth rate of the primary root, the fresh root weight, the extent of lateral and adventitious root formation, the vasculature system, meristem development or radial expansion.

Methods for modulating root development of a plant in nitrogen limiting conditions are provided. The methods comprise modulating the level and/or activity of an ACC synthase polypeptide in the plant. In one method, an ACC synthase sequence inhibition construct is provided to the plant. In another method, the nucleotide sequence is provided by introducing into the plant a polynucleotide comprising an ACC synthase inhibiting nucleotide sequence, expressing the same and thereby modifying root development under conditions of low nitrogen. In still other methods, the ACC synthase inhibition nucleotide construct introduced into the plant is stably incorporated into the genome of the plant. A change in ACC synthase activity can result in at least one or more of the following alterations to root development, including, but not limited to, alterations in root biomass and length when the plant is grown under nitrogen limiting conditions.

As used herein, "root growth" encompasses all aspects of growth of the different parts that make up the root system at different stages of its development in both monocotyledonous and dicotyledonous plants. It is to be understood that enhanced root growth can result from enhanced growth of one or more of its parts including the primary root, lateral roots, adventitious roots, etc.

Methods of measuring such developmental alterations in the root system are known in the art. See, for example, US Patent Application Publication Number 2003/0074698 and Werner, et al., (2001) *PNAS* 18:10487-10492, both of which are herein incorporated by reference.

As discussed elsewhere herein, one of skill will recognize the appropriate promoter to use to modulate root development in the plant. Exemplary promoters for this embodiment include constitutive promoters and root-preferred promoters. Exemplary root-preferred promoters have been disclosed elsewhere herein.

Stimulating root growth and increasing root mass in the presence of low nitrogen or nitrogen associated stress by decreasing the activity and/or level of an ACC synthase polypeptide also finds use in improving the standability of a plant. The term "resistance to lodging" or "standability" refers to the ability of a plant to fix itself to the soil. For plants with an erect or semi-erect growth habit, this term also refers to the ability to maintain an upright position under adverse (environmental) conditions. This trait relates to the size, depth and morphology of the root system. In addition, stimulating root growth and increasing root mass in nitrogen limiting conditions by altering the level and/or activity of the ACC synthase polypeptide also finds use in promoting in vitro propagation of explants.

Furthermore, higher root biomass production has a direct effect on the yield and an indirect effect of production of compounds produced by root cells or transgenic root cells or cell cultures of said transgenic root cells.

Accordingly, the present invention further provides plants having modulated root development in nitrogen limiting conditions when compared to the root development of a control plant. In normal conditions no such modulation is observed.

Methods are also provided for modulating shoot and leaf development in a plant, particularly under nitrogen limiting conditions. By "modulating shoot and/or leaf development" is intended any alteration in the development of the plant shoot and/or leaf in nitrogen limiting conditions. Such alterations in shoot and/or leaf development include, but are not limited to, alterations in shoot meristem development, in leaf number, leaf size, leaf and stem vasculature, internode length and leaf senescence. As used herein, "leaf development" and "shoot development" encompasses all aspects of growth of the different parts that make up the leaf system and the shoot system, respectively, at different stages of their development, both in monocotyledonous and dicotyledonous plants. Methods for measuring such developmental alterations in the shoot and leaf system are known in the art. See, for example, Werner, et al., (2001) *PNAS* 98:10487-10492 and US Patent Application Publication Number 2003/0074698, each of which is herein incorporated by reference.

The method for modulating shoot and/or leaf development in a plant in low nitrogen conditions comprises modulating the activity and/or level of an ACC synthase polypeptide. In one embodiment, an ACC synthase nucleotide sequence can be provided by introducing into the plant a polynucleotide comprising an ACC synthase nucleotide sequence inhibition construct, expressing the same and thereby modifying shoot and/or leaf development in nitrogen limiting conditions. In other embodiments, the ACC synthase inhibition nucleotide construct introduced into the plant is stably incorporated into the genome of the plant.

A change in ACC synthase activity can result in at least one or more of the following alterations in shoot and/or leaf development under low nitrogen conditions, including, but not limited to, changes in leaf number, altered leaf surface, altered vasculature, internodes and plant growth and alterations in leaf senescence, when compared to a control plant in the same conditions.

As discussed elsewhere herein, one of skill will recognize the appropriate promoter to use to modulate shoot and leaf development of the plant. Exemplary promoters for this embodiment include constitutive promoters, shoot-preferred promoters, shoot meristem-preferred promoters and leaf-preferred promoters. Exemplary promoters have been disclosed elsewhere herein.

Methods for modulating reproductive tissue development, particularly under nitrogen limiting conditions are provided. In one embodiment, methods are provided to modulate floral development in a plant. By "modulating floral development" is intended any alteration in a structure of a plant's reproductive tissue as compared to a control plant in which the activity or level of the ACC synthase polypeptide has not been modulated. "Modulating floral development" further includes any alteration in the timing of the development of a plant's reproductive tissue (i.e., a delayed or an accelerated timing of floral development) when compared to a control plant in which the activity or level of the ACC synthase polypeptide has not been modulated. Macroscopic alterations may include changes in size, shape, number or location of reproductive organs, the developmental time period that these structures form or the ability to maintain or proceed through the flowering process in times of environmental stress. Microscopic alterations may include changes to the types or shapes of cells that make up the reproductive organs.

The method for modulating floral development in a plant comprises modulating ACC synthase activity in a plant. Such methods can comprise introducing an ACC synthase nucleotide sequence into the plant and changing the activity of the ACC synthase polypeptide. In some embodiments, the ACC synthase nucleotide construct introduced into the plant is stably incorporated into the genome of the plant. Altering expression of the ACC synthase sequence of the invention can modulate floral development during periods of stress. Such methods are described elsewhere herein. Accordingly, the present invention further provides plants having modulated floral development when compared to the floral development of a control plant. Compositions include plants having an altered level/activity of ACC synthase polypeptide and having an altered floral development. Compositions also include plants having a modified level/activity of the ACC synthase polypeptide wherein the plant maintains or proceeds through the flowering process in times of stress.

As discussed elsewhere herein, one of skill will recognize the appropriate promoter to use to modulate floral development of the plant or to increase seed size and/or seed weight. Exemplary promoters of this embodiment include constitutive promoters, inducible promoters, seed-preferred promoters, embryo-preferred promoters and endosperm-preferred promoters.

Thus, a plant having reduced ACC synthase activity can have at least one of the following phenotypes in nitrogen limiting conditions, including but not limited to: increased overall plant yield, increased root mass, increased root length, increased leaf size, increased ear size, increased seed size, increased endosperm size, improved standability, alterations in the relative size of embryos and endosperms leading to changes in the relative levels of protein, oil and/or starch in the seeds, altered floral development, changes in leaf number, altered leaf surface, altered vasculature, altered internodes, alterations in leaf senescence, absence of tassels, absence of functional pollen bearing tassels, or increased plant size when compared to a non-modified plant under conditions of low nitrogen.

Any method known in the art to reduce or eliminate the activity of an ACC synthase polypeptide can be used to improve nitrogen stress tolerance of a plant. In some embodiments, a polynucleotide is introduced into a plant that may inhibit the expression of the ACC synthase polypeptide directly, by preventing transcription or translation of the ACC synthase messenger RNA, or indirectly, by encoding a polypeptide that inhibits the transcription or translation of an ACC synthase gene encoding an ACC synthase polypeptide. Methods for inhibiting or eliminating the expression of a gene in a plant are well known in the art, and any such method may be used in the present invention to inhibit the expression of the ACC synthase polypeptide. In other embodiments, a polynucleotide that encodes a polypeptide that inhibits the activity of an ACC synthase polypeptide is introduced into a plant. In yet other embodiments, the activity of an ACC synthase is inhibited through disruption of an ACC synthase gene. Many methods may be used to reduce or eliminate the activity of an ACC synthase polypeptide. In addition, more than one method may be used to reduce the activity of a single ACC synthase polypeptide.

In some embodiments, the ACC synthase activity is reduced through the disruption of at least one ACC synthase gene or a reduction in the expression of at least one ACC synthase gene. As used herein, an "ACC synthase gene" refers to a gene that encodes an ACC synthase polypeptide. An ACC synthase gene can encode one or more ACC synthases and in some embodiments can comprise, e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 99.5% or more sequence identity to SEQ ID NO: 1 (gACS2), SEQ ID NO: 2 (gACS6) or SEQ ID NO: 3 (gACS7). Many ACS genes are known to those of skill in the art and are readily available through sources such as GENBANK and the like and Table 4 in Example 16 lists several. The expression of any ACS gene may be reduced according to the invention.

In accordance with the present invention, the expression of an ACC synthase is inhibited if the transcript or protein level of the ACC synthase is statistically lower than the transcript or protein level of the same ACC synthase in a plant that has not been genetically modified or mutagenized to inhibit the expression of that ACC synthase. In particular embodiments of the invention, the transcript or protein level of the ACC synthase in a modified plant according to the invention is less than 95%, less than 90%, less than 85%, less than 80%, less than 75%, less than 70%, less than 60%, less than 50%, less than 40%, less than 30%, less than 20%, less than 10%, or less than 5% of the protein level of the same ACC synthase in a plant that is not a mutant or that has not been genetically modified to inhibit the expression of that ACC synthase. The expression level of the ACC synthase may be measured directly, for example, by assaying for the level of ACC synthase expressed in the cell or plant, or indirectly, for example, by measuring the ACC synthase activity in the cell or plant. The activity of an ACC synthase protein is "eliminated" according to the invention when it is not detectable by at least one assay method. Methods for assessing ACC synthase activity are known in the art and include measuring levels of ACC or ethylene, which can be recovered and assayed from cell extracts. For example, internal concentrations of ACC can be assayed by gas chromatography-mass spectroscopy, in acidic plant extracts as ethylene after decomposition in alkaline hypochlorite solution, etc. The concentration of ethylene can be determined by, e.g., gas chromatography-mass spectroscopy, etc. See, e.g., Nagahama, et al., (1991) *J. Gen. Microbiol.* 137:2281 2286. For example, ethylene can be measured with a gas chromatograph equipped with, e.g., an alumina based column (such as an HP-PLOT A1203 capillary column) and a flame ionization detector. methods.

In other embodiments of the invention, the activity of one or more ACC synthases is reduced or eliminated by transforming a plant cell with an expression cassette comprising a polynucleotide encoding a polypeptide that inhibits the activity of one or more ACC synthases. The activity of an ACC synthase is inhibited according to the present invention if the activity of that ACC synthase in the transformed plant or cell is statistically lower than the activity of that ACC synthase in a plant that has not been genetically modified to inhibit the activity of at least one ACC synthase. In particular embodiments of the invention, an ACC synthase activity of a modified plant according to the invention is less than 95%, less than 90%, less than 85%, less than 80%, less than 75%, less than 70%, less than 60%, less than 50%, less than 40%, less than 30%, less than 20%, less than 10%, or less than 5% of that ACC synthase activity in an appropriate control plant that has not been genetically modified to inhibit the expression or activity of that ACC synthase.

In other embodiments, the activity of an ACC synthase may be reduced or eliminated by disrupting at least one gene encoding the ACC synthase. The disruption inhibits expression or activity of at least one ACC synthase protein compared to a corresponding control plant cell lacking the disruption. In one embodiment, the at least one endogenous ACC synthase gene comprises two or more endogenous ACC synthase genes or subsequences thereof (e.g., any two or more of ACS2, ACS6 and ACS7, e.g., ACS2 and ACS6). Similarly, in another embodiment, the at least one endogenous ACC synthase gene comprises three or more endogenous ACC synthase genes. In certain embodiments, the disruption results in reduced or decreased ethylene production by the knockout plant cell as compared to the control plant cell. The disruption results in the plant's improved performance in low nitrogen conditions as compared to a control plant in similar conditions.

In another embodiment, the disruption step comprises insertion of one or more transposons, where the one or more transposons are inserted into the at least one endogenous ACC synthase gene. In yet another embodiment, the disruption comprises one or more point mutations in the at least one endogenous ACC synthase gene. The disruption can be a homozygous disruption in the at least one ACC synthase gene. Alternatively, the disruption is a heterozygous disruption in the at least one ACC synthase gene. In certain embodiments, when more than one ACC synthase gene is involved, there is more than one disruption, which can include homozygous disruptions, heterozygous disruptions or a combination of homozygous disruptions and heterozygous disruptions.

Detection of expression products is performed either qualitatively (by detecting presence or absence of one or more product of interest) or quantitatively (by monitoring the level of expression of one or more product of interest). In one embodiment, the expression product is an RNA expression product. Aspects of the invention optionally include monitoring an expression level of a nucleic acid, polypeptide or chemical (e.g., ACC, ethylene, etc.) as noted herein for detection of ACC synthase, ethylene production, nitrogen utilization or tolerance to low nitrogen conditions, etc. in a plant or in a population of plants.

Thus, many methods may be used to reduce or eliminate the activity of an ACC synthase. More than one method may be used to reduce the activity of a single plant ACC synthase. In addition, combinations of methods may be employed to reduce or eliminate the activity of two or more different ACC synthases. Non-limiting examples of methods of reducing or eliminating the expression of a plant ACC synthase are given below.

In some embodiments of the present invention, a polynucleotide is introduced into a plant that upon introduction or expression, inhibits the expression of an ACC synthase polypeptide of the invention. The term "expression" as used herein refers to the biosynthesis of a gene product, including the transcription and/or translation of said gene product. For example, for the purposes of the present invention, an expression cassette capable of expressing a polynucleotide that inhibits the expression of at least one ACC synthase polypeptide is an expression cassette capable of producing an RNA molecule that inhibits the transcription and/or translation of at least one ACC synthase polypeptide of the invention. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide. Further, "expression" of a gene can refer to the transcription of the gene into a non-protein coding transcript.

As used herein, "polynucleotide" includes reference to a deoxyribopolynucleotide, ribopolynucleotide or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "encoding" or "encoded," with respect to a specified nucleic acid, is meant comprising the information for transcription into a RNA and in some embodiments, translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolumn* (Yamao, et al., (1985) *Proc. Natl. Acad. Sci. USA* 82:2306-9) or the ciliate Macronucleus, may be used when the nucleic acid is expressed using these organisms.

Examples of polynucleotides that inhibit the expression of an ACC synthase polypeptide are given below.

In some embodiments of the invention, inhibition of the expression of an ACC synthase polypeptide may be obtained by sense suppression or cosuppression. For cosuppression, an expression cassette is designed to express an RNA molecule corresponding to all or part of a messenger RNA encoding an ACC synthase polypeptide in the "sense" orientation. Over expression of the RNA molecule can result in reduced expression of the native gene. Accordingly, multiple plant lines transformed with the cosuppression expression cassette are screened to identify those that show the greatest inhibition of ACC synthase polypeptide expression.

The polynucleotide used for cosuppression may correspond to all or part of the sequence encoding the ACC synthase polypeptide, all or part of the 5' and/or 3' untranslated region of an ACC synthase polypeptide transcript or all or part of both the coding sequence and the untranslated regions of a transcript encoding an ACC synthase polypeptide. A polynucleotide used for cosuppression or other gene silencing methods may share 99%, 98%, 97%, 96%, 95%, 94%, 93%, 92%, 91%, 90%, 89%, 88%, 87%, 85%, 80%, or less sequence identity with the target sequence, which in some embodiments is SEQ ID NO:4, 5, or 6. When portions of the polynucleotides (e.g., SEQ ID NO:4, 5, or 6) are used to disrupt the expression of the target gene, generally, sequences of at least 15, 19, 20, 21, 22, 23, 24, 25, 26, 27, 28, 29, 30, 35, 40, 45, 50, 60, 70, 80, 90, 100, 200, 300, 400, 450, 500, 550, 600, 650, 700, 750, 800, 900, or 1000 contiguous nucleotides or greater may be used. In some embodiments where the polynucleotide comprises all or part of the coding region for the ACC synthase polypeptide, the expression cassette is designed to eliminate the start codon of the polynucleotide so that no protein product will be translated.

Cosuppression may be used to inhibit the expression of plant genes to produce plants having undetectable protein levels for the proteins encoded by these genes. See, for example, Broin, et al., (2002) *Plant Cell* 14:1417-1432. Cosuppression may also be used to inhibit the expression of multiple proteins in the same plant. See, for example, U.S. Pat. No. 5,942,657. Methods for using cosuppression to inhibit the expression of endogenous genes in plants are described in Flavell, et al., (1994) *Proc. Natl. Acad. Sci. USA* 91:3490-3496; Jorgensen, et al., (1996) *Plant Mol. Biol.* 31:957-973; Johansen and Carrington, (2001) *Plant Physiol.* 126:930-938; Broin, et al., (2002) *Plant Cell* 14:1417-1432; Stoutjesdijk, et al., (2002) *Plant Physiol.* 129:1723-1731; Yu, et al., (2003) *Phytochemistry* 63:753-763 and U.S. Pat. Nos. 5,034,323, 5,283,184 and 5,942,657, each of which is herein incorporated by reference. The efficiency of cosuppression may be increased by including a poly-dT region in the expression cassette at a position 3' to the sense sequence and 5' of the polyadenylation signal. See, US Patent Publication Number 2002/0048814, herein incorporated by reference. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See, U.S. Pat. Nos. 5,283,184 and 5,034,323, herein incorporated by reference.

In some embodiments of the invention, inhibition of the expression of the ACC synthase polypeptide may be obtained by antisense suppression. For antisense suppression, the expression cassette is designed to express an RNA molecule complementary to all or part of a messenger RNA encoding the ACC synthase polypeptide. Over expression of the antisense RNA molecule can result in reduced expression of the native gene. Accordingly, multiple plant lines transformed with the antisense suppression expression cassette are screened to identify those that show the greatest inhibition ACC synthase polypeptide expression.

The polynucleotide for use in antisense suppression may correspond to all or part of the complement of the sequence encoding the ACC synthase polypeptide, all or part of the complement of the 5' and/or 3' untranslated region of the ACC synthase transcript or all or part of the complement of both the coding sequence and the untranslated regions of a transcript encoding the ACC synthase polypeptide.

In addition, the antisense polynucleotide may be fully complementary (i.e., 100% identical to the complement of the target sequence) or partially complementary (i.e., less than 100%, including but not limited to, 99%, 98%, 97%, 96%, 95%, 94%, 93%, 92%, 91%, 90%, 89%, 88%, 87%, 85%, 80%, identical to the complement of the target sequence, which in some embodiments is SEQ ID NO:4, 5, or 6) to the target sequence. Antisense suppression may be used to inhibit the expression of multiple proteins in the same plant. See, for example, U.S. Pat. No. 5,942,657. Furthermore, portions of the antisense nucleotides may be used to disrupt the expression of the target gene. Generally, sequences of at least 50 nucleotides, 100 nucleotides, 200 nucleotides, 300, 400, 450, 500, 550 or greater may be used.

Methods for using antisense suppression to inhibit the expression of endogenous genes in plants are described, for example, in Liu, et al., (2002) *Plant Physiol.* 129:1732-1743 and U.S. Pat. Nos. 5,759,829 and 5,942,657, each of which is herein incorporated by reference. Efficiency of antisense suppression may be increased by including a poly-dT region in the expression cassette at a position 3' to the antisense sequence and 5' of the polyadenylation signal. See, US Patent Application Publication Number 2002/0048814, herein incorporated by reference.

In some embodiments of the invention, inhibition of the expression of an ACC synthase polypeptide may be obtained by double-stranded RNA (dsRNA) interference. For dsRNA interference, a sense RNA molecule like that described above for cosuppression and an antisense RNA molecule that is fully or partially complementary to the sense RNA molecule are expressed in the same cell, resulting in inhibition of the expression of the corresponding endogenous messenger RNA.

Expression of the sense and antisense molecules can be accomplished by designing the expression cassette to comprise both a sense sequence and an antisense sequence. Alternatively, separate expression cassettes may be used for the sense and antisense sequences. Multiple plant lines transformed with the dsRNA interference expression cassette or expression cassettes are then screened to identify plant lines that show the greatest inhibition of ACC synthase polypeptide expression. Methods for using dsRNA interference to inhibit the expression of endogenous plant genes are described in Waterhouse, et al., (1998) *Proc. Natl. Acad. Sci. USA* 95:13959-13964, Liu, et al., (2002) *Plant Physiol.* 129:1732-1743 and WO 99/49029, WO 99/53050, WO 99/61631 and WO 00/49035, each of which is herein incorporated by reference.

In some embodiments of the invention, inhibition of the expression of an ACC synthase polypeptide may be obtained by hairpin RNA (hpRNA) interference or intron-containing hairpin RNA (ihpRNA) interference. These methods are highly efficient at inhibiting the expression of endogenous genes. See, Waterhouse and Helliwell, (2003) *Nat. Rev. Genet.* 4:29-38 and the references cited therein.

For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene whose expression is to be inhibited, and an antisense sequence that is fully or partially complementary to the sense sequence. The antisense sequence may be located "upstream" of the sense sequence (i.e., the antisense sequence may be closer to the promoter driving expression of the hairpin RNA than the sense sequence). The base-paired stem region may correspond to a portion of a promoter sequence controlling expression of the gene to be inhibited. A polynucleotide designed to express an RNA molecule having a hairpin structure comprises a first nucleotide sequence and a second nucleotide sequence that is the complement of the first nucleotide sequence, and wherein the second nucleotide sequence is in an inverted orientation relative to the first nucleotide sequence.

Thus, the base-paired stem region of the molecule generally determines the specificity of the RNA interference. The sense sequence and the antisense sequence are generally of similar lengths but may differ in length. Thus, these sequences may be portions or fragments of at least 10, 19, 20, 21, 22, 23, 24, 25, 26, 27, 28, 29, 30, 50, 70, 90, 100, 120, 140, 160, 180, 200, 220, 240, 260, 280, 300, 320, 340, 360, 380, 400, 500, 600, 700, 800, 900 nucleotides in length, or at least 1, 2, 3, 4, 5, 6, 7, 8, 9, or 10 kb in length. The loop region of the expression cassette may vary in length. Thus, the loop region may be at least 100, 200, 300, 400, 500, 600, 700, 800, 900 nucleotides in length, or at least 1, 2, 3, 4, 5, 6, 7, 8, 9, or 10 kb in length.

hpRNA molecules are highly efficient at inhibiting the expression of endogenous genes and the RNA interference they induce is inherited by subsequent generations of plants. See, for example, Chuang and Meyerowitz, (2000) *Proc. Natl. Acad. Sci. USA* 97:4985-4990; Stoutjesdijk, et al., (2002) *Plant Physiol.* 129:1723-1731 and Waterhouse and Helliwell, (2003) *Nat. Rev. Genet.* 4:29-38. Methods for using hpRNA interference to inhibit or silence the expression of genes are described, for example, in Chuang and Meyerowitz, (2000) *Proc. Natl. Acad. Sci. USA* 97:4985-4990; Stoutjesdijk, et al., (2002) *Plant Physiol.* 129:1723-1731; Waterhouse and Helliwell, (2003) *Nat. Rev. Genet.* 4:29-38; Pandolfini et al., *BMC Biotechnology* 3:7 and US Patent Application Publication Number 2003/0175965, each of which is herein incorporated by reference. A transient assay for the efficiency of hpRNA constructs to silence gene expression in vivo has been described by Panstruga, et al., (2003) *Mol. Biol. Rep.* 30:135-140, herein incorporated by reference.

For ihpRNA, the interfering molecules have the same general structure as for hpRNA, but the RNA molecule additionally comprises an intron in the loop of the hairpin that is capable of being spliced in the cell in which the ihpRNA is expressed. The use of an intron minimizes the size of the loop in the hairpin RNA molecule following splicing, and this increases the efficiency of interference. See, for example, Smith, et al., (2000) *Nature* 407:319-320. In fact, Smith, et al., show 100% suppression of endogenous gene expression using ihpRNA-mediated interference. In some embodiments, the intron is the ADH1 intron 1. Methods for using ihpRNA interference to inhibit the expression of endogenous plant genes are described, for example, in Smith, et al., (2000) *Nature* 407:319-320; Wesley, et al., (2001) *Plant J.* 27:581-590; Wang and Waterhouse, (2001) *Curr. Opin. Plant Biol.* 5:146-150; Waterhouse and Helliwell, (2003) *Nat. Rev. Genet.* 4:29-38; Helliwell and Waterhouse, (2003) *Methods* 30:289-295 and US Patent Application Publication Number 2003/0180945, each of which is herein incorporated by reference.

The expression cassette for hpRNA interference may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene. Thus, it is the loop region that determines the specificity of the RNA interference. See, for example, WO 02/00904; Mette, et al., (2000) *EMBO J* 19:5194-5201; Matzke, et al., (2001) *Curr. Opin. Genet. Devel.* 11:221-227; Scheid, et al., (2002) *Proc. Natl. Acad. Sci.*, USA 99:13659-13662; Aufsaftz, et al., (2002) *Proc. Nat'l. Acad. Sci.* 99(4): 16499-16506; Sijen, et al., *Curr. Biol.* (2001) 11:436-440), herein incorporated by reference.

Amplicon expression cassettes comprise a plant virus-derived sequence that contains all or part of the target gene but generally not all of the genes of the native virus. The viral sequences present in the transcription product of the expression cassette allow the transcription product to direct its own replication. The transcripts produced by the amplicon may be either sense or antisense relative to the target sequence (i.e., the messenger RNA for the ACC synthase polypeptide). Methods of using amplicons to inhibit the expression of endogenous plant genes are described, for example, in Angell and Baulcombe, (1997) *EMBO J.* 16:3675-3684, Angell and Baulcombe, (1999) *Plant J.* 20:357-362 and U.S. Pat. No. 6,635,805, each of which is herein incorporated by reference.

In some embodiments, the polynucleotide expressed by the expression cassette of the invention is catalytic RNA or has ribozyme activity specific for the messenger RNA of the ACC synthase polypeptide. Thus, the polynucleotide causes the degradation of the endogenous messenger RNA, resulting in reduced expression of the ACC synthase polypeptide. This method is described, for example, in U.S. Pat. No. 4,987,071, herein incorporated by reference.

In some embodiments of the invention, inhibition of the expression of an ACC synthase polypeptide may be obtained by RNA interference by expression of a polynucleotide encoding a micro RNA (miRNA). miRNAs are regulatory agents consisting of about 22 ribonucleotides. miRNA are highly efficient at inhibiting the expression of endogenous genes. See, for example Javier, et al., (2003) *Nature* 425:257-263, herein incorporated by reference.

For miRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). For suppression of ACC synthase expression, the 22-nucleotide sequence is selected from an ACC synthase transcript sequence and contains 22 nucleotides of said ACC synthase sequence in sense orientation and 21 nucleotides of a corresponding antisense sequence that is complementary to the sense sequence. miRNA molecules are highly efficient at inhibiting the expression of endogenous genes, and the RNA interference they induce is inherited by subsequent generations of plants.

In some embodiments, polypeptides or polynucleotide encoding polypeptides can be introduced into a plant, wherein the polypeptide is capable of inhibiting the activity of an ACC synthase polypeptide. The terms "polypeptide," "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

The terms "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogs of natural amino acids that can function in a similar manner as naturally occurring amino acids.

In one embodiment, the polynucleotide encodes a zinc finger protein that binds to a gene encoding an ACC synthase polypeptide, resulting in reduced expression of the gene. In particular embodiments, the zinc finger protein binds to a regulatory region of an ACC synthase gene. In other embodiments, the zinc finger protein binds to a messenger RNA encoding an ACC synthase polypeptide and prevents its translation. Methods of selecting sites for targeting by zinc finger proteins have been described, for example, in U.S. Pat. No. 6,453,242, and methods for using zinc finger proteins to inhibit the expression of genes in plants are described, for example, in US Patent Application Publication Number 2003/0037355, each of which is herein incorporated by reference.

In some embodiments of the invention, the polynucleotide encodes an antibody that binds to at least one ACC synthase polypeptide and reduces the activity of the ACC synthase polypeptide. In another embodiment, the binding of the antibody results in increased turnover of the antibody-ACC synthase complex by cellular quality control mechanisms. The expression of antibodies in plant cells and the inhibition of molecular pathways by expression and binding of antibodies to proteins in plant cells are well known in the art. See, for example, Conrad and Sonnewald, (2003) *Nature Biotech.* 21:35-36, incorporated herein by reference.

In some embodiments of the present invention, the activity of an ACC synthase polypeptide is reduced or eliminated by disrupting the gene encoding the ACC synthase polypeptide. The gene encoding the ACC synthase polypeptide may be disrupted by any method known in the art. For example, in one embodiment, the gene is disrupted by transposon tagging. In another embodiment, the gene is disrupted by mutagenizing plants using random or targeted mutagenesis and selecting for plants that have reduced nitrogen utilization activity.

In one embodiment of the invention, transposon tagging is used to reduce or eliminate the ACC synthase activity of one or more ACC synthase polypeptides. Transposon tagging comprises inserting a transposon within an endogenous ACC synthase gene to reduce or eliminate expression of the ACC synthase polypeptide.

In this embodiment, the expression of one or more ACC synthase polypeptides is reduced or eliminated by inserting a transposon within a regulatory region or coding region of the gene encoding the ACC synthase polypeptide. A transposon that is within an exon, intron, 5' or 3' untranslated sequence, a promoter or any other regulatory sequence of an ACC synthase gene may be used to reduce or eliminate the expression and/or activity of the encoded ACC synthase polypeptide.

Methods for the transposon tagging of specific genes in plants are well known in the art. See, for example, Maes, et al., (1999) *Trends Plant Sci.* 4:90-96; Dharmapuri and Sonti, (1999) *FEMS Microbiol. Lett.* 179:53-59; Meissner, et al., (2000) *Plant J.* 22:265-274; Phogat, et al., (2000) *J. Biosci.* 25:57-63; Walbot, (2000) *Curr. Opin. Plant Biol.* 2:103-107; Gai, et al., (2000) *Nucleic Acids Res.* 28:94-96; Fitzmaurice, et al., (1999) *Genetics* 153:1919-1928). In addition, the TUSC process for selecting Mu insertions in selected genes has been described in Bensen, et al., (1995) *Plant Cell* 7:75-84; Mena, et al., (1996) *Science* 274:1537-1540 and U.S. Pat. No. 5,962,764, each of which is herein incorporated by reference.

Additional methods for decreasing or eliminating the expression of endogenous genes in plants are also known in the art and can be similarly applied to the instant invention. These methods include other forms of mutagenesis, such as ethyl methanesulfonate-induced mutagenesis, deletion mutagenesis and fast neutron deletion mutagenesis used in a reverse genetics sense (with PCR) to identify plant lines in which the endogenous gene has been deleted. For examples of these methods see, Ohshima, et al., (1998) *Virology* 243: 472-481; Okubara, et al., (1994) *Genetics* 137:867-874 and Quesada, et al., (2000) *Genetics* 154:421-436, each of which is herein incorporated by reference. In addition, a fast and automatable method for screening for chemically induced mutations, TILLING (Targeting Induced Local Lesions In Genomes), using denaturing HPLC or selective endonuclease digestion of selected PCR products is also applicable to the instant invention. See, McCallum, et al., (2000) *Nat. Biotechnol.* 18:455-457, herein incorporated by reference.

Mutations that impact gene expression or that interfere with the function of the encoded protein are well known in the art. Insertional mutations in gene exons usually result in null-mutants. Mutations in conserved residues are particularly effective in inhibiting the activity of the encoded protein. Conserved residues of plant ACC synthase polypeptides suitable for mutagenesis with the goal to eliminate ACC synthase activity have been described. Such mutants can be isolated according to well-known procedures, and mutations in different ACC synthase loci can be stacked by genetic crossing. See, for example, Gruis, et al., (2002) *Plant Cell* 14:2863-2882.

In another embodiment of this invention, dominant mutants can be used to trigger RNA silencing due to gene inversion and recombination of a duplicated gene locus. See, for example, Kusaba, et al., (2003) *Plant Cell* 15:1455-1467.

The invention encompasses additional methods for reducing or eliminating the activity of one or more ACC synthase polypeptides. Examples of other methods for altering or mutating a genomic nucleotide sequence in a plant are known in the art and include, but are not limited to, the use of RNA:DNA vectors, RNA:DNA mutational vectors, RNA:DNA repair vectors, mixed-duplex oligonucleotides, self-complementary RNA:DNA oligonucleotides and recombinogenic oligonucleobases. Such vectors and methods of use are known in the art. See, for example, U.S. Pat. Nos. 5,565,350; 5,731,181; 5,756,325; 5,760,012; 5,795,972 and 5,871,984, each of which are herein incorporated by reference. See also, WO 98/49350, WO 99/07865, WO 99/25821 and Beetham, et al., (1999) *Proc. Natl. Acad. Sci. USA* 96:8774-8778, each of which is herein incorporated by reference.

Where polynucleotides are used to decrease or inhibit ACC synthase activity, it is recognized that modifications of the exemplary sequences disclosed herein may be made as long as the sequences act to decrease or inhibit expression of the corresponding mRNA. Thus, for example, polynucleotides having at least 70%, 80%, 85%, 86%, 87%, 88%, 89%, 90%, 91%, 92%, 93%, 94%, 95%, 96%, 97%, 98%, 99%, or 100% sequence identity to the exemplary sequences disclosed herein (e.g., SEQ ID NO:4, 5, or 6) may be used. Furthermore, portions or fragments of the exemplary sequences or portions or fragments of polynucleotides sharing a particular percent sequence identity to the exemplary sequences may be used to disrupt the expression of the target gene. Generally, fragments or sequences of at least 10, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 220, 240, 250, 260, 280, 300, 350, 400, 450, 500, 600, 700, 800, 900, 1000, or more contiguous nucleotides, or greater of, for example, SEQ ID NO:4, 5, or 6 may be used. It is recognized that in particular embodiments, the complementary sequence of such sequences may be used. For example, hairpin constructs comprise both a sense sequence fragment and a complementary, or antisense, sequence fragment corresponding to the gene of interest. Antisense constructs may share less than 100% sequence identity with the gene of interest, and may comprise portions or fragments of the gene of interest, so long as the object of the embodiment is achieved, i.e., so long as expression of the gene of interest is decreased.

The ACC synthase nucleic acids that may be used for the present invention comprise at least one ACC synthase polynucleotide selected from the group consisting of:

(a) a polynucleotide encoding an ACC synthase polypeptide and conservatively modified and polymorphic variants thereof;

(b) a polynucleotide having at least 70% sequence identity with polynucleotides of (a);

(c) a fragment of a polynucleotide encoding an ACC synthase polypeptide; and (d) complementary sequences of polynucleotides of (a), (b), or (c).

Thus, in some embodiments, the method comprises introducing at least one polynucleotide sequence comprising an ACC synthase nucleic acid sequence, or subsequence thereof, into a plant cell, such that the at least one polynucleotide sequence is linked to a promoter in a sense or antisense orientation, and where the at least one polynucleotide sequence comprises, e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, about 99.5% or more sequence identity to SEQ ID NO: 1 (gACS2), SEQ ID NO: 2 (gACS6) or SEQ ID NO: 3 (gACS7) or a subsequence thereof or a complement thereof. In another embodiment, the disruption is effected by introducing into the plant cell at least one polynucleotide sequence comprising one or more subsequences of an ACC synthase nucleic acid sequence configured for RNA silencing or interference.

In other embodiments, the methods of the invention are practiced with a polynucleotide comprising a member selected from the group consisting of: (a) a polynucleotide or a complement thereof, comprising, e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, about 99.5% or more sequence identity to SEQ ID NO: 1 (gACS2), SEQ ID NO: 2 (gACS6), SEQ ID NO: 3 (gACS7), SEQ ID NO: 4 (ACS2 cDNA), SEQ ID NO: 5 (ACS6 cDNA), or SEQ ID NO: 6 (ACS7 cDNA) or a subsequence thereof, or a conservative variation thereof; (b) a polynucleotide, or a complement thereof, encoding a polypeptide sequence of SEQ ID NO: 7 (ACS 2), SEQ ID NO: 8 (ACS6) or SEQ ID NO: 9 (ACS7) or a subsequence thereof, or a conservative variation thereof; (c) a polynucleotide, or a complement thereof, that hybridizes under stringent conditions over substantially the entire length of a polynucleotide subsequence comprising at least 100 contiguous nucleotides of SEQ ID NO: 1 (gACS2), SEQ ID NO: 2 (gACS6), SEQ ID NO: 3 (gACS7), SEQ ID NO: 4 (ACS2 cDNA), SEQ ID NO: 5 (ACS6 cDNA), or SEQ ID NO: 6 (ACS7 cDNA) or that hybridizes to a polynucleotide sequence of (a) or (b); and (d) a polynucleotide that is at least about 85% identical to a polynucleotide sequence of (a), (b) or (c). In certain embodiments, the polynucleotide inhibits ethylene production when expressed in a plant.

In particular embodiments, a heterologous polynucleotide is introduced into a plant, wherein the heterologous polynucleotide is selected from the group consisting of: a) a nucleic acid comprising an ACC synthase nucleic acid; b) a nucleic acid comprising at least 15 contiguous nucleotides of the complement of an ACC synthase nucleic acid; and c) a nucleic acid encoding a transcript that is capable of forming a double-stranded RNA (e.g., a hairpin) and mediated RNA interference of an ACC synthase nucleic acid, wherein said nucleic acid comprises a first nucleotide sequence comprising at least 21 contiguous nucleotides of an ACC synthase nucleic acid, and a second nucleotide sequence comprising the complement of said first nucleotide sequence.

In other particular embodiments, the methods comprise introducing into a plant a heterologous polynucleotide selected from the group consisting of: a) the nucleotide sequence set forth in SEQ ID NO:1, 2, 3, 4, 5, or 6, or a complete complement thereof; b) a nucleotide sequence having at least 70%, at least 75%, at least 80%, at least 85%, at least 90%, at least 91%, at least 92%, at least 93%, at least 94%, at least 95%, at least 96%, at least 97%, at least 98%, at least 99% or greater sequence identity to SEQ ID NO: 1, 2, 3, 4, 5, or 6, or a complete complement thereof; c) a nucleotide sequence encoding the polypeptide sequence of SEQ ID NO: 7, 8, or 9; d) a nucleotide sequence encoding a polypeptide sequence having at least 70%, at least 75%, at least 80%, at least 85%, at least 90%, at least 91%, at least 92%, at least 93%, at least 94%, at least 95%, at least 96%, at least 97%, at least 98%, at least 99% or greater sequence identity to SEQ ID NO: 7, 8, or 9; e) a nucleotide sequence comprising at least 15 contiguous nucleotides of SEQ ID NO:1, 2, 3, 4, 5, or 6; f) a nucleotide sequence comprising at least 15 contiguous nucleotides of the complement of SEQ ID NO:1, 2, 3, 4, 5, or 6; and g) a nucleotide sequence encoding a transcript that is capable of forming a double-stranded RNA (e.g., hairpin) and mediating RNA interference of an ACC synthase nucleic acid, wherein said nucleotide sequence comprises at least 21 contiguous nucleotides of SEQ ID NO:1, 2, 3, 4, 5, or 6, and the complement thereof. In other embodiments, the heterologous polynucleotide comprises at least 500 contiguous nucleotides of SEQ ID NO: 1, 2, 3, 4, 5, or 6 and the complement thereof. In some of these embodiments, the heterologous polynucleotide encodes a transcript that is capable of forming a double-stranded RNA (e.g., hairpin) and mediating RNA interference of an ACC synthase nucleic acid. In some of these embodiments, the plant comprises an mRNA encoded by a polynucleotide having the target sequence set forth in SEQ ID NO:1, 2, 3, 4, 5, or 6.

In yet other particular embodiments, the methods comprise introducing into a plant a heterologous polynucleotide comprising a sequence that encodes a transcript having a hairpin structure, wherein the sequence comprises a first nucleotide sequence having the sequence set forth in SEQ ID NO:14 and a second nucleotide sequence having the sequence set forth in SEQ ID NO:15. In other embodiments, the heterologous polynucleotide that comprises a sequence that encodes a transcript having a hairpin structure comprises a first nucleotide sequence having the sequence set forth in SEQ ID NO: 51 and a second nucleotide sequence having the sequence set forth in SEQ ID NO:52. In other embodiments, the methods comprise introducing into a plant a construct comprising SEQ ID NO:53, 54, 55, 56, or 57.

Methods are provided for improving yield under low nitrogen conditions comprising planting seeds or plants having a reduced activity of at least one ACC synthase in an area of cultivation having nitrogen limiting conditions.

Prior to the planting of the seeds or plants in the area of cultivation having nitrogen limiting conditions, the environment can be evaluated to determine if nitrogen limiting conditions are present, including measuring the amount of nitrogen or nitrogen fertilizer in the soil. As used herein, an "area of cultivation" comprises any region in which one desires to grow a plant. Such areas of cultivations include, but are not limited to, a field in which a plant is cultivated (such as a crop field, a sod field, a tree field, a managed forest, a field for culturing fruits and vegetables, etc), a greenhouse, a growth chamber, etc.

The present invention provides methods utilizing, inter alia, isolated nucleic acids of RNA, DNA, homologs, paralogs and orthologs and/or chimeras thereof, comprising an ACC synthase polynucleotide. This includes naturally occurring as well as synthetic variants and homologs of the sequences.

The terms "isolated" or "isolated nucleic acid" or "isolated protein" refer to material, such as a nucleic acid or a protein, which is substantially or essentially free from components which normally accompany or interact with it as found in its naturally occurring environment. The isolated material optionally comprises material not found with the material in its natural environment. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived.

Sequences homologous, i.e., that share significant sequence identity or similarity, to those provided herein derived from maize, *Arabidopsis thaliana* or from other plants of choice, can also be used in the methods of the invention. Homologous sequences can be derived from any plant including monocots and dicots and in particular agriculturally important plant species, including but not limited to, crops such as soybean, wheat, corn (maize), potato, cotton, rice, rape, oilseed rape (including canola), sunflower, alfalfa, clover, sugarcane and turf, or fruits and vegetables, such as banana, blackberry, blueberry, strawberry and raspberry, cantaloupe, carrot, cauliflower, coffee, cucumber, eggplant, grapes, honeydew, lettuce, mango, melon, onion, papaya, peas, peppers, pineapple, pumpkin, spinach, squash, sweet corn, tobacco, tomato, tomatillo, watermelon, rosaceous fruits (such as apple, peach, pear, cherry and plum) and vegetable brassicas (such as broccoli, cabbage, cauliflower, Brussels sprouts and kohlrabi). Other crops, including fruits and vegetables, whose phenotype can be changed and which comprise homologous sequences include barley; rye; millet; sorghum; currant; avocado; citrus fruits such as oranges, lemons, grapefruit and tangerines, artichoke, cherries; nuts such as the walnut and peanut; endive; leek; roots such as arrowroot, beet, cassava, turnip, radish, yam and sweet potato and beans. The homologous sequences may also be derived from woody species, such pine, poplar and eucalyptus or mint or other labiates. In addition, homologous sequences may be derived from plants that are evolutionarily-related to crop plants, but which may not have yet been used as crop plants. Examples include deadly nightshade (*Atropa belladona*), related to tomato; jimson weed (*Datura strommium*), related to peyote, and teosinte (*Zea* species), related to corn (maize).

Homologous sequences as described above can comprise orthologous or paralogous sequences. Several different methods are known by those of skill in the art for identifying and defining these functionally homologous sequences. Three general methods for defining orthologs and paralogs are described; an ortholog, paralog or homolog may be identified by one or more of the methods described below.

Orthologs and paralogs are evolutionarily related genes that have similar sequence and similar functions. Orthologs are structurally related genes in different species that are derived by a speciation event. Paralogs are structurally related genes within a single species that are derived by a duplication event.

Within a single plant species, gene duplication may result in two copies of a particular gene, giving rise to two or more genes with similar sequence and often similar function known as paralogs. A paralog is therefore a similar gene formed by duplication within the same species. Paralogs typically cluster together or in the same clade (a group of similar genes) when a gene family phylogeny is analyzed using programs such as CLUSTAL (Thompson, et al., (1994) *Nucleic Acids Res.* 22:4673-4680; Higgins, et al., (1996) *Methods Enzymol.* 266:383-402). Groups of similar genes can also be identified with pair-wise BLAST analysis (Feng and Doolittle, (1987) *J. Mol. Evol.* 25:351-360).

For example, a clade of very similar MADS domain transcription factors from *Arabidopsis* all share a common function in flowering time (Ratcliffe, et al., (2001) *Plant Physiol.* 126:122-132) and a group of very similar AP2 domain transcription factors from *Arabidopsis* are involved in tolerance of plants to freezing (Gilmour, et al., (1998) *Plant J.* 16:433-442). Analysis of groups of similar genes with similar function that fall within one clade can yield sub-sequences that are particular to the clade. These sub-sequences, known as consensus sequences, can not only be used to define the sequences within each clade, but define the functions of these genes; genes within a clade may contain paralogous sequences, or orthologous sequences that share the same function (see also, for example, Mount, (2001), in *Bioinformatics: Sequence and Genome Analysis* Cold Spring Harbor Laboratory Press, Cold Spring Harbor, N.Y., page 543.)

Speciation, the production of new species from a parental species, can also give rise to two or more genes with similar sequence and similar function. These genes, termed orthologs, often have an identical function within their host plants and are often interchangeable between species without losing function. Because plants have common ancestors, many genes in any plant species will have a corresponding orthologous gene in another plant species. Once a phylogenic tree for a gene family of one species has been constructed using a program such as CLUSTAL (Thompson, et al., (1994) *Nucleic Acids Res.* 22:4673-4680; Higgins, et al., (1996) supra) potential orthologous sequences can be placed into the phylogenetic tree and their relationship to genes from the species of interest can be determined. Orthologous sequences can also be identified by a reciprocal BLAST strategy. Once an orthologous sequence has been identified, the function of the ortholog can be deduced from the identified function of the reference sequence.

Orthologous genes from different organisms have highly conserved functions, and very often essentially identical functions (Lee, et al., (2002) *Genome Res.* 12:493-502;

Remm, et al., (2001) *J. Mol. Biol.* 314:1041-1052). Paralogous genes, which have diverged through gene duplication, may retain similar functions of the encoded proteins. In such cases, paralogs can be used interchangeably with respect to certain embodiments of the instant invention (for example, transgenic expression of a coding sequence).

ACC synthase polynucleotides, such as those disclosed herein, can be used to isolate homologs, paralogs and orthologs. In this manner, methods such as PCR, hybridization, and the like can be used to identify such sequences based on their sequence homology to the ACC synthase polynucleotide.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like. By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS) and strand displacement amplification (SDA). See, e.g., *Diagnostic Molecular Microbiology: Principles and Applications*, Persing, et al., eds., American Society for Microbiology, Washington, D.C. (1993). The product of amplification is termed an amplicon.

In hybridization techniques, all or part of a known polynucleotide is used as a probe that selectively hybridizes to other nucleic acids comprising corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the ACC synthase sequences disclosed herein. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire ACC synthase sequences disclosed herein, or one or more portions thereof, may be used as probes capable of specifically hybridizing to corresponding ACC synthase sequences and messenger RNAs. To achieve specific hybridization under a variety of conditions, such probes include sequences that are unique among ACC synthase sequences and are at least about 10, 12, 15, 16, 17, 18, 19, 20, 21, 22, 23, 24, 25, 30, 35, 40, 50, 60, 70, 80, 90, or more nucleotides in length. Such probes may be used to amplify corresponding ACC synthase sequences from a chosen plant by PCR. This technique may be used to isolate additional coding sequences from a desired plant or as a diagnostic assay to determine the presence of coding sequences in a plant. Hybridization techniques include hybridization screening of plated nucleic acid (e.g., DNA) libraries (either plaques or colonies; see, for example, Sambrook et al. (1989) *Molecular Cloning: A Laboratory Manual* (2d ed., Cold Spring Harbor Laboratory Press, Plainview, N.Y.). By "nucleic acid library" is meant a collection of isolated DNA or RNA molecules, which comprise and substantially represent the entire transcribed fraction of a genome of a specified organism. Construction of exemplary nucleic acid libraries, such as genomic and cDNA libraries, is taught in standard molecular biology references such as Berger and Kimmel, (1987) *Guide To Molecular Cloning Techniques*, from the series *Methods in Enzymology*, vol. 152, Academic Press, Inc., San Diego, Calif.; Sambrook, et al., (1989) *Molecular Cloning: A Laboratory Manual*, $2^{nd}$ ed., vols. 1-3; and *Current Protocols in Molecular Biology*, Ausubel, et al., eds, Current Protocols, a joint venture between Greene Publishing Associates, Inc. and John Wiley & Sons, Inc. (1994 Supplement).

Hybridization of such sequences may be carried out under stringent conditions. The terms "stringent conditions" or "stringent hybridization conditions" include reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which can be up to 100% complementary to the probe (homologous probing). Alternatively, stringency conditions can be adjusted to allow some mismatching in sequences so that lower degrees of similarity are detected (heterologous probing). Optimally, the probe is approximately 500 nucleotides in length, but can vary greatly in length from less than 500 nucleotides to equal to the entire length of the target sequence.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide or Denhardt's. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C. and a wash in 0.5× to 1×SSC at 55 to 60° C. Exemplary high stringency conditions include hybridization in 50% formamide, 1 M NaCl, 1% SDS at 37° C. and a wash in 0.1×SSC at 60 to 65° C. Specificity is typically the function of post-hybridization washes, the critical factors being the ionic strength and temperature of the final wash solution. For DNA-DNA hybrids, the $T_m$ can be approximated from the equation of Meinkoth and Wahl, (1984) *Anal. Biochem.*, 138:267-84: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, part I, chapter 2, "Overview of principles of hybridization and the strategy of nucleic acid probe assays," Elsevier, New York (1993); and *Current Protocols in Molecular Biology*, chapter 2, Ausubel, et al., eds, Greene Publishing and Wiley-Interscience, New York (1995). Unless otherwise stated, in the present application high stringency is defined as hybridization in 4×SSC, 5×Denhardt's (5 g Ficoll, 5 g polyvinylpyrrolidone, 5 g bovine serum albumin in 500 ml of water), 0.1 mg/ml boiled salmon sperm DNA and 25 mM Na phosphate at 65° C. and a wash in 0.1×SSC, 0.1% SDS at 65° C.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 40% sequence identity, preferably 60-90% sequence identity and most preferably 100% sequence identity (i.e., complementary) with each other.

The term "hybridization complex" includes reference to a duplex nucleic acid structure formed by two single-stranded nucleic acid sequences selectively hybridized with each other.

As used herein, "consisting essentially of" means the inclusion of additional sequences to an object polynucleotide where the additional sequences do not selectively hybridize, under stringent hybridization conditions, to the same cDNA as the polynucleotide and where the hybridization conditions include a wash step in 0.1×SSC and 0.1% sodium dodecyl sulfate at 65° C.

The ACC synthase nucleotide sequences can be used to generate variant nucleotide sequences having the nucleotide sequence of the 5'-untranslated region, 3'-untranslated region, or promoter region that is approximately 70%, 75%, 80%, 85%, 90%, 91%, 92%, 93%, 94%, 95%, 96%, 97%, 98%, and 99% identical to the original nucleotide sequence. These variants are then associated with natural variation in the germplasm for component traits related to NUE. The associated variants are used as marker haplotypes to select for the desirable traits.

Variant amino acid sequences of the ACC synthase polypeptides are generated. In this example, one or more amino acid is altered. Specifically, the open reading frames are reviewed to determine the appropriate amino acid alteration. The selection of the amino acid to change is made by consulting the protein alignment (with the other orthologs and other gene family members from various species). An amino acid is selected that is deemed not to be under high selection pressure (not highly conserved) and which is rather easily substituted by an amino acid with similar chemical characteristics (i.e., similar functional side-chain). Using a protein alignment, an appropriate amino acid can be changed. Once the targeted amino acid is identified, the procedure outlined herein is followed. Variants having about 70%, 75%, 80%, 85%, 90%, 91%, 92%, 93%, 94%, 95%, 96%, 97%, 98%, 99%, or higher nucleic acid sequence identity are generated using this method. These variants are then associated with natural variation in the germplasm for component traits related to NUE. The associated variants are used as marker haplotypes to select for the desirable traits.

The present invention also includes polynucleotides optimized for expression in different organisms. For example, for expression of the polynucleotide in a maize plant, the sequence can be altered to account for specific codon preferences and to alter GC content as according to Murray, et al, supra. Maize codon usage for 28 genes from maize plants is listed in Table 4 of Murray, et al., supra.

The term "conservatively modified variants" applies to both amino acid and nucleic acid sequences. With respect to particular nucleic acid sequences, conservatively modified variants refer to those nucleic acids that encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also describes every possible silent variation of the nucleic acid. One of ordinary skill will recognize that each codon in a nucleic acid (except AUG, which is ordinarily the only codon for methionine; one exception is *Micrococcus rubens*, for which GTG is the methionine codon (Ishizuka, et al., (1993) *J. Gen. Microbiol.* 139:425-32) can be modified to yield a functionally identical molecule. Accordingly, each silent variation of a nucleic acid, which encodes a polypeptide of the present invention, is implicit in each described polypeptide sequence and incorporated herein by reference.

As to amino acid sequences, one of skill will recognize that individual substitutions, deletions or additions to a nucleic acid, peptide, polypeptide or protein sequence which alters, adds or deletes a single amino acid or a small percentage of amino acids in the encoded sequence is a "conservatively modified variant" when the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7 or 10 alterations can be made. Conservatively modified variants typically provide similar biological activity as the unmodified polypeptide sequence from which they are derived. For example, substrate specificity, enzyme activity or ligand/receptor binding is generally at least 30%, 40%, 50%, 60%, 70%, 80% or 90%, preferably 60-90% of the native protein for its native substrate. Conservative substitution tables providing functionally similar amino acids are well known in the art.

The following six groups each contain amino acids that are conservative substitutions for one another:

1) Alanine (A), Serine (S), Threonine (T);

2) Aspartic acid (D), Glutamic acid (E);

3) Asparagine (N), Glutamine (Q);

4) Arginine (R), Lysine (K);

5) Isoleucine (I), Leucine (L), Methionine (M), Valine (V); and

6) Phenylalanine (F), Tyrosine (Y), Tryptophan (W).

See also, Creighton, Proteins, W.H. Freeman and Co. (1984).

The following terms are used to describe the sequence relationships between two or more nucleic acids or polynucleotides or polypeptides: (a) "reference sequence," (b) "comparison window," (c) "sequence identity," (d) "percentage of sequence identity" and (e) "substantial identity."

As used herein, "reference sequence" is a defined sequence used as a basis for sequence comparison. A reference sequence may be a subset or the entirety of a specified sequence; for example, as a segment of a full-length cDNA or gene sequence or the complete cDNA or gene sequence.

As used herein, "comparison window" means includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100 or longer. Those of skill in the art understand that to avoid a high similarity to a reference sequence due to inclusion of gaps in the polynucleotide sequence a gap penalty is typically introduced and is subtracted from the number of matches.

Methods of alignment of nucleotide and amino acid sequences for comparison are well known in the art. The local homology algorithm (BESTFIT) of Smith and Waterman, (1981) *Adv. Appl. Math* 2:482, may conduct optimal alignment of sequences for comparison; by the homology alignment algorithm (GAP) of Needleman and Wunsch, (1970) *J. Mol. Biol.* 48:443-53; by the search for similarity method (Tfasta and Fasta) of Pearson and Lipman, (1988) *Proc. Natl. Acad. Sci. USA* 85:2444; by computerized implementations of these algorithms, including, but not limited to: CLUSTAL in the PC/Gene program by Intelligenetics, Mountain View, Calif., GAP, BESTFIT, BLAST, FASTA and TFASTA in the Wisconsin Genetics Software Package®, Version 8 (available from Genetics Computer Group (GCG® programs (Accelrys, Inc., San Diego, Calif.).). The CLUSTAL program is well described by Higgins and Sharp, (1988) *Gene* 73:237-44; Higgins and Sharp, (1989) *CABIOS* 5:151-3; Corpet, et al., (1988) *Nucleic Acids Res.* 16:10881-90; Huang, et al., (1992) *Computer Applications in the Biosciences* 8:155-65, and Pearson, et al., (1994) *Meth. Mol. Biol.* 24:307-31. The preferred program to use for optimal global alignment of multiple sequences is PileUp (Feng and Doolittle, (1987) *J. Mol. Evol.,* 25:351-60 which is similar to the method described by Higgins and Sharp, (1989) *CABIOS* 5:151-53 and hereby incorporated by reference). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences and TBLASTX for nucleotide query sequences against nucleotide database sequences. See, *Current Protocols in Molecular Biology*, Chapter 19, Ausubel et al., eds., Greene Publishing and Wiley-Interscience, New York (1995).

GAP uses the algorithm of Needleman and Wunsch, supra, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package® are 8 and 2, respectively. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, 40, 50 or greater.

GAP presents one member of the family of best alignments. There may be many members of this family, but no other member has a better quality. GAP displays four figures of merit for alignments: Quality, Ratio, Identity and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package® is BLOSUM62 (see, Henikoff and Henikoff, (1989) *Proc. Natl. Acad. Sci. USA* 89:10915).

Unless otherwise stated, sequence identity/similarity values provided herein refer to the value obtained using the BLAST 2.0 suite of programs using default parameters (Altschul, et al., (1997) *Nucleic Acids Res.* 25:3389-402).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) *Comput. Chem.* 17:149-63) and XNU (Claverie and States, (1993) *Comput. Chem.* 17:191-201) low-complexity filters can be employed alone or in combination.

As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) *Computer Applic. Biol. Sci.* 4:11-17, e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55-100%, preferably at least 55%, preferably at least 60%, more preferably at least 70%, 80%, 90% and most preferably at least 95%.

Another indication that nucleotide sequences are substantially identical is if two nucleic acid molecules hybridize to each other under stringent conditions as described elsewhere herein. However, the degeneracy of the genetic code allows for many nucleic acid substitutions that lead to variety in the nucleotide sequence that code for the same amino acid, hence it is possible that the DNA sequence could code for the same polypeptide but not hybridize to each other under stringent conditions. This may occur, e.g., when a copy of a nucleic acid is created using the maximum codon degeneracy permitted by the genetic code. One indication that two nucleic acid sequences are substantially identical is that the polypeptide which the first nucleic acid encodes is immunologically cross-reactive with the polypeptide encoded by the second nucleic acid.

The term "substantial identity" in the context of a peptide indicates that a peptide comprises a sequence with between 55-100% sequence identity to a reference sequence; in some embodiments, at least 55% sequence identity, 60%, 70%, 80%, at least 90%, 91%, 92%, 93%, 94%, 95%, 96%, 97%, 98%, or 99% sequence identity to the reference sequence over a specified comparison window. In some embodiments, optimal alignment is conducted using the homology alignment algorithm of Needleman and Wunsch, supra. An indication that two peptide sequences are substantially identical is that one peptide is immunologically reactive with antibodies raised against the second peptide. Thus, a peptide is substantially identical to a second peptide, for example, where the two peptides differ only by a conservative substitution. In addition, a peptide can be substantially identical to a second peptide when they differ by a non-conservative change if the epitope that the antibody recognizes is substantially identical. Peptides which are "substantially similar" share sequences as noted above, except that residue positions which are not identical may differ by conservative amino acid changes.

The nucleic acids used in the presently disclosed methods can be made using (a) standard recombinant methods, (b) synthetic techniques, or combinations thereof. In some embodiments, the polynucleotides of the present invention will be cloned, amplified or otherwise constructed from a fungus or bacteria.

The nucleic acids may conveniently comprise sequences in addition to a polynucleotide useful in the methods of the present invention. For example, a multi-cloning site comprising one or more endonuclease restriction sites may be inserted into the nucleic acid to aid in isolation of the polynucleotide. Also, translatable sequences may be inserted to aid in the isolation of the translated polynucleotide useful in the methods of the present invention. For example, a hexa-histidine marker sequence provides a convenient means to purify proteins useful in the methods of the present invention. The nucleic acid useful in the methods of the present invention—excluding the polynucleotide sequence—is optionally a vector, adapter or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Typically, the length of a nucleic acid for use in the methods of the present invention less the length of its polynucleotide of the present invention is less than 20 kilobase pairs, often less than 15 kb and frequently less than 10 kb. Use of cloning vectors, expression vectors, adapters and linkers is well known in the art. Exemplary nucleic acids include such vectors as: M13, lambda ZAP Express, lambda ZAP II, lambda gt10, lambda gt11, pBK-CMV, pBK-RSV, pBluescript II, lambda DASH II, lambda EMBL 3, lambda EMBL 4, pWE15, SuperCos 1, SurfZap, Uni-ZAP, pBC, pBS+/−, pSG5, pBK, pCR-Script, pET, pSPUTK, p3'SS, pGEM, pSK+/−, pGEX, pSPORTI and II, pOPRSVI CAT, pOPI3 CAT, pXT1, pSG5, pPbac, pMbac, pMC1neo, pOG44, pOG45, pFRTβGAL, pNEOβGAL, pRS403, pRS404, pRS405, pRS406, pRS413, pRS414, pRS415, pRS416, lambda MOSSlox and lambda MOSElox. Optional vectors for the present invention, include but are not limited to, lambda ZAP II and pGEX. For a description of various nucleic acids see, e.g., Stratagene Cloning Systems, Catalogs 1995, 1996, 1997 (La Jolla, Calif.) and Amersham Life Sciences, Inc, Catalog '97 (Arlington Heights, Ill.).

The nucleic acids used in the methods of the present invention can also be prepared by direct chemical synthesis by methods such as the phosphotriester method of Narang, et al., (1979) *Meth. Enzymol.* 68:90-9; the phosphodiester method of Brown, et al., (1979) *Meth. Enzymol.* 68:109-51; the diethylphosphoramidite method of Beaucage, et al., (1981) *Tetra. Letts.* 22(20):1859-62; the solid phase phosphoramidite triester method described by Beaucage, et al., supra, e.g., using an automated synthesizer, e.g., as described in Needham-VanDevanter, et al., (1984) *Nucleic Acids Res.* 12:6159-68 and the solid support method of U.S. Pat. No. 4,458,066. Chemical synthesis generally produces a single stranded oligonucleotide. This may be converted into double stranded DNA by hybridization with a complementary sequence or by polymerization with a DNA polymerase using the single strand as a template. One of skill will recognize that while chemical synthesis of DNA is limited to sequences of about 100 bases, longer sequences may be obtained by the ligation of shorter sequences.

In general, translational efficiency has been found to be regulated by specific sequence elements in the 5' non-coding or untranslated region (5' UTR) of the RNA. Positive sequence motifs include translational initiation consensus sequences (Kozak, (1987) *Nucleic Acids Res.* 15:8125) and the 5<G> 7 methyl GpppG RNA cap structure (Drummond, et al., (1985) *Nucleic Acids Res.* 13:7375). Negative elements include stable intramolecular 5' UTR stem-loop structures (Muesing, et al., (1987) *Cell* 48:691) and AUG sequences or short open reading frames preceded by an appropriate AUG in the 5' UTR (Kozak, supra, Rao, et al., (1988) *Mol. and Cell. Biol.* 8:284). Accordingly, the present invention provides 5' and/or 3' UTR regions for modulation of translation of heterologous coding sequences.

Further, the polypeptide-encoding segments of the polynucleotides used in the present invention can be modified to alter codon usage. Altered codon usage can be employed to alter translational efficiency and/or to optimize the coding sequence for expression in a desired host or to optimize the codon usage in a heterologous sequence for expression in maize. Codon usage in the coding regions of the polynucleotides useful in the methods of the present invention can be analyzed statistically using commercially available software packages such as “Codon Preference” available from the University of Wisconsin Genetics Computer Group. See, Devereaux, et al., (1984) *Nucleic Acids Res.* 12:387-395); or MacVector 4.1 (Eastman Kodak Co., New Haven, Conn.). Thus, the present invention provides a codon usage frequency characteristic of the coding region of at least one of the polynucleotides useful in the methods of the present invention. The number of polynucleotides (3 nucleotides per amino acid) that can be used to determine a codon usage frequency can be any integer from 3 to the number of polynucleotides of the present invention as provided herein. Optionally, the polynucleotides will be full-length sequences. An exemplary number of sequences for statistical analysis can be at least 1, 5, 10, 20, 50 or 100.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledonous plants or dicotyledonous plants as these preferences have been shown to differ (Murray, et al., (1989) *Nucleic Acids Res.* 17:477-98, herein incorporated by reference). Thus, the maize preferred codon for a particular amino acid might be derived from known gene sequences from maize. Maize codon usage for 28 genes from maize plants is listed in Table 4 of Murray, et al., supra.

Polynucleotides used in the methods of the present invention can be obtained through sequence shuffling using ACC synthase-encoding polynucleotides. Sequence shuffling is described in PCT Publication Number 96/19256. See also, Zhang, et al., (1997) *Proc. Natl. Acad. Sci. USA* 94:4504-9 and Zhao, et al., (1998) *Nature Biotech* 16:258-61. Generally, sequence shuffling provides a means for generating libraries of polynucleotides having a desired characteristic, which can be selected or screened for. Libraries of recombinant polynucleotides are generated from a population of related sequence polynucleotides, which comprise sequence regions, which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property. In some embodiments, the selected characteristic will be an altered $K_m$ and/or $K_{cat}$ over the wild-type protein as provided herein. In other embodiments, a protein or polynucleotide generated from sequence shuffling will have a ligand binding affinity greater than the non-shuffled wild-type polynucleotide. In yet other embodiments, a protein or polynucleotide generated from sequence shuffling will have an altered pH optimum as compared to the non-shuffled wild-type polynucleotide. The increase in such properties can be at least 110%, 120%, 130%, 140% or greater than 150% of the wild-type value.

The components for practicing the methods of the invention may be included in a kit, comprising polynucleotides encoding ACC synthase or their complements or nucleic acids configured for RNA interference of ACC synthase, with instructional materials for improving plant yield under low nitrogen conditions. In some of these embodiments, the kit comprises a nucleic acid comprising the sequence of SEQ ID NO:1, 2, 3, 4, 5, or 6, or a complete complement thereof; a nucleic acid comprising at least 70%, at least 75%, at least 80%, at least 85%, at least 90%, at least 91%, at least 92%, at least 93%, at least 94%, at least 95%, at least 96%, at least 97%, at least 98%, at least 99% or greater sequence identity to SEQ ID NO:1, 2, 3, 4, 5, or 6, or a complete complement thereof; a nucleic acid encoding the polypeptide sequence of SEQ ID NO:8 or a polypeptide sequence having at least 70%, at least 75%, at least 80%, at least 85%, at least 90%, at least 91%, at least 92%, at least 93%, at least 94%, at least 95%, at least 96%, at least 97%, at least 98%, at least 99% or greater sequence identity to SEQ ID NO:8; or a nucleic acid configured for RNA silencing or interference, wherein said nucleic acid comprises a polynucleotide with at least 19, 20, 21, 22, 23, 24, 25, 26, 27, 28, 29, 30, 50, 60, 70, 80, 90, 100, 200, 300, 400, 500, or more contiguous nucleotides of SEQ ID NO:1, 2, 3, 4, 5, or 6, and the complement of said polynucleotide.

The present invention further provides the use of recombinant expression cassettes comprising a nucleic acid useful in the methods of the present invention. As used herein, a “recombinant expression cassette” is a nucleic acid construct, generated recombinantly or synthetically, with a series of specified nucleic acid elements, which permit transcription of a particular nucleic acid in a target cell. The recombinant expression cassette can be incorporated into a plasmid, chromosome, mitochondrial DNA, plastid DNA, virus or nucleic acid fragment. Typically, the recombinant expression cassette portion of an expression vector includes, among other sequences, a nucleic acid to be transcribed and a promoter.

A nucleic acid sequence coding for the desired polynucleotide or polypeptide useful in the methods of the present invention, for example a polynucleotide encoding a nucleic acid that can reduce the expression of an ACC synthase gene, can be used to construct a recombinant expression cassette which can be introduced into the desired host cell. A recombinant expression cassette will typically comprise a polynucleotide useful in the methods of the present invention operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site and/or a polyadenylation signal.

As used herein "operably linked" includes reference to a functional linkage between a first sequence, such as a promoter, and a second sequence, wherein the promoter sequence initiates and mediates transcription of the DNA corresponding to the second sequence. Generally, operably linked means that the nucleic acid sequences being linked are contiguous and, where necessary to join two protein coding regions, contiguous and in the same reading frame.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses, and bacteria which comprise genes expressed in plant cells such *Agrobacterium* or *Rhizobium*. Examples are promoters that preferentially initiate transcription in certain tissues, such as leaves, roots, seeds, fibres, xylem vessels, tracheids or sclerenchyma. Such promoters are referred to as "tissue-preferred." A "cell type" specific promoter primarily drives expression in certain cell types in one or more organs, for example, vascular cells in roots or leaves. An "inducible" or "regulatable" promoter is a promoter which is under environmental control. Examples of environmental conditions that may effect transcription by inducible promoters include anaerobic conditions or the presence of light. Another type of promoter is a developmentally regulated promoter, for example, a promoter that drives expression during pollen development. Tissue preferred, cell type specific, developmentally regulated and inducible promoters constitute the class of "non-constitutive" promoters. A "constitutive" promoter is a promoter, which is active under most environmental conditions. Constitutive promoters are classified as providing for a range of constitutive expression. Thus, some are weak constitutive promoters and others are strong constitutive promoters. Generally, by "weak promoter" is intended a promoter that drives expression of a coding sequence at a low level. By "low level" is intended at levels of about 1/10,000 transcripts to about 1/100,000 transcripts to about 1/500,000 transcripts. Conversely, a "strong promoter" drives expression of a coding sequence at a "high level," or about 1/10 transcripts to about 1/100 transcripts to about 1/1,000 transcripts.

A plant promoter fragment can be employed which will direct expression of a polynucleotide useful in the methods of the present invention in all tissues of a regenerated plant. Such promoters are referred to herein as "constitutive" promoters and are active under most environmental conditions and states of development or cell differentiation. Examples of constitutive promoters include the core promoter of the Rsyn7 promoter and other constitutive promoters disclosed in WO 99/43838 and U.S. Pat. No. 6,072,050; the 1'- or 2'-promoter derived from T-DNA of *Agrobacterium tumefaciens*, the Smas promoter, the cinnamyl alcohol dehydrogenase promoter (U.S. Pat. No. 5,633,439), the Nos promoter, the rubisco promoter, the GRP1-8 promoter, the 35S promoter from cauliflower mosaic virus (CaMV), as described in Odell, et al., (1985) *Nature* 313:810-2; rice actin (McElroy, et al., (1990) *Plant Cell* 163-171); ubiquitin (Christensen, et al., (1992) *Plant Mol. Biol.* 12:619-632 and Christensen, et al., (1992) *Plant Mol. Biol.* 18:675-89); pEMU (Last, et al., (1991) *Theor. Appl. Genet.* 81:581-8); MAS (Velten, et al., (1984) *EMBO J.* 3:2723-30) and maize H3 histone (Lepetit, et al., (1992) *Mol. Gen. Genet.* 231:276-85 and Atanassvoa, et al., (1992) *Plant Journal* 2(3):291-300); ALS promoter, as described in PCT Application Number WO 96/30530 and other transcription initiation regions from various plant genes known to those of skill. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611. In some embodiments, the ubiquitin promoter is used for expression in monocot plants.

Alternatively, the plant promoter can direct expression of a polynucleotide of the present invention in a specific tissue or may be otherwise under more precise environmental or developmental control. Such promoters are referred to here as "inducible" promoters. Environmental conditions that may effect transcription by inducible promoters include pathogen attack, anaerobic conditions or the presence of light. Examples of inducible promoters are the Adh1 promoter, which is inducible by hypoxia or cold stress, the Hsp70 promoter, which is inducible by heat stress and the PPDK promoter, which is inducible by light.

Generally, it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference.

Of interest are promoters that are expressed locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189-200).

Additionally, as pathogens find entry into plants through wounds or insect damage, a wound-inducible promoter may be used in the constructions of the invention. Such wound-inducible promoters include potato proteinase inhibitor (pin II) gene (Ryan (1990) *Ann. Rev. Phytopath.* 28:425-449; Duan et al. (1996) *Nature Biotechnology* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J.* 6(2):141-150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Examples of promoters under developmental control include promoters that initiate transcription only, or preferentially, in certain tissues, such as leaves, roots, fruit, seeds or flowers. The operation of a promoter may also vary depending on its location in the genome. Thus, an inducible promoter may become fully or partially constitutive in certain locations.

Tissue-preferred promoters can be utilized to target expression of a polynucleotide useful in methods of the present invention within a particular plant tissue. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Root-preferred promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2):343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and rolB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Cim1 (cytokinin-induced message); cZ19B1 (maize 19 kDa zein); milps (myo-inositol-1-phosphate synthase) (see WO 00/11177 and U.S. Pat. No. 6,225,529; herein incorporated by reference). Gamma-zein is an endosperm-specific promoter. Globulin 1 (Glb-1) is a representative embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, gamma-zein, waxy, shrunken 1, shrunken 2, Globulin 1, etc. See also WO 00/12733, where seed-preferred promoters from end1 and end2 genes are disclosed; herein incorporated by reference.

The regulatory regions (i.e., promoters, transcriptional regulatory regions, and translational termination regions) and/or the ACC synthase polynucleotide may be native/analogous to the host cell or to each other. Alternatively, the regulatory regions and/or the ACC synthase polynucleotide may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from that from which the polynucleotide was derived, or, if from the same/analogous species, one or both are substantially modified from their original form, or the promoter is not the native promoter for the operably linked polynucleotide. Likewise, a heterologous protein may originate from a foreign species or, if from the same species, is substantially modified from its original form by deliberate human intervention.

If polypeptide expression is desired, it is generally desirable to include a polyadenylation region at the 3'-end of a polynucleotide coding region. The polyadenylation region can be derived from a variety of plant genes, or from T-DNA. The 3' end sequence to be added can be derived from, for example, the nopaline synthase or octopine synthase genes, or alternatively from another plant gene, or less preferably from any other eukaryotic gene. Examples of such regulatory elements include, but are not limited to, 3' termination and/or polyadenylation regions such as those of the *Agrobacterium tumefaciens* nopaline synthase (nos) gene (Bevan, et al., (1983) *Nucleic Acids Res.* 12:369-85); the potato proteinase inhibitor II (PINII) gene (Keil, et al., (1986) *Nucleic Acids Res.* 14:5641-50 and An, et al., (1989) *Plant Cell* 1:115-22) and the CaMV 19S gene (Mogen, et al., (1990) *Plant Cell* 2:1261-72).

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, (1988) *Mol. Cell Biol.* 8:4395-4405; Callis, et al., (1987) *Genes Dev.* 1:1183-200). Such intron enhancement of gene expression is typically greatest when placed near the 5' end of the transcription unit. Use of maize introns Adh1-S intron 1, 2 and 6, the Bronze-1 intron are known in the art. See generally, *The Maize Handbook*, Chapter 116, Freeling and Walbot, eds., Springer, New York (1994).

Plant signal sequences, including, but not limited to, signal-peptide encoding DNA/RNA sequences which target proteins to the extracellular matrix of the plant cell (Dratewka-Kos, et al., (1989) *J. Biol. Chem.* 264:4896-900), such as the *Nicotiana plumbaginifolia* extension gene (DeLoose, et al., (1991) *Gene* 99:95-100); signal peptides which target proteins to the vacuole, such as the sweet potato sporamin gene (Matsuka, et al., (1991) *Proc. Natl. Acad. Sci. USA* 88:834) and the barley lectin gene (Wilkins, et al., (1990) *Plant Cell,* 2:301-13); signal peptides which cause proteins to be secreted, such as that of PRIb (Lind, et al., (1992) *Plant Mol. Biol.* 18:47-53) or the barley alpha amylase (BAA) (Rahmatullah, et al., (1989) *Plant Mol. Biol.* 12:119, and hereby incorporated by reference) or signal peptides which target proteins to the plastids such as that of rapeseed enoyl-Acp reductase (Verwaert, et al., (1994) *Plant Mol. Biol.* 26:189-202) are useful in the invention.

The vector comprising the sequences from a polynucleotide useful in the methods of the present invention will typically comprise a marker gene, which confers a selectable phenotype on plant cells. Usually, the selectable marker gene will encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance, genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicide basta, and the ALS gene encodes resistance to the herbicide chlorsulfuron. Other genes that confer resistance to herbicidal compounds, such as such as glufosinate ammonium, bromoxynil, imidazolinones, and 2,4-dichlorophenoxyacetate (2,4-D) can be used. Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) *Ph.D. Thesis*, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference.

The above list of selectable marker genes is not meant to be limiting. Any selectable marker gene can be used in the present invention.

Typical vectors useful for expression of genes in higher plants are well known in the art and include vectors derived from the tumor-inducing (Ti) plasmid of *Agrobacterium tumefaciens* described by Rogers, et al. (1987), *Meth. Enzymol.* 153:253-77. These vectors are plant integrating vectors in that on transformation, the vectors integrate a portion of vector DNA into the genome of the host plant. Exemplary *A. tumefaciens* vectors useful herein are plasmids pKYLX6 and pKYLX7 of Schardl, et al., (1987) *Gene* 61:1-11 and Berger, et al., (1989) *Proc. Natl. Acad. Sci. USA,* 86:8402-6. Another useful vector herein is plasmid pBI101.2 that is available from CLONTECH Laboratories, Inc. (Palo Alto, Calif.). As used herein, "vector" includes reference to a nucleic acid used in transfection of a host cell and into which can be inserted a polynucleotide. Vectors are often replicons. Expression vectors permit transcription of a nucleic acid inserted therein as described elsewhere herein.

One may express a protein in a recombinantly engineered cell such as bacteria, yeast, insect, mammalian or preferably plant cells. The cells produce the protein in a non-natural condition (e.g., in quantity, composition, location and/or time), because they have been genetically altered through human intervention to do so.

By "host cell" is meant a cell, which comprises a heterologous nucleic acid sequence of the invention, which contains a vector and supports the replication and/or expression of the expression vector. Host cells may be prokaryotic cells such as *E. coli*, or eukaryotic cells such as yeast, insect, plant, amphibian or mammalian cells. Preferably, host cells are monocotyledonous or dicotyledonous plant cells, including but not limited to maize, sorghum, sunflower, soybean, wheat, alfalfa, rice, cotton, sugarcane, canola, lawn grass, barley, millet and tomato. In some embodiments, the monocotyledonous host cell is a maize host cell.

As used herein "recombinant" includes reference to a cell or vector that has been modified by the introduction of a heterologous nucleic acid, or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention or may have reduced or eliminated expression of a native gene. The term "recombinant" as used herein does not encompass the alteration of the cell or vector by naturally occurring events (e.g., spontaneous mutation, natural transformation/transduction/transposition) such as those occurring without deliberate human intervention.

It is expected that those of skill in the art are knowledgeable in the numerous expression systems available for expression of a nucleic acid encoding a protein useful in the methods of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or inducible), followed by incorporation into an expression vector. The vectors can be suitable for replication and integration in either prokaryotes or eukaryotes. As described above, typical expression vectors contain transcription and translation terminators, initiation sequences and promoters useful for regulation of the expression of the DNA encoding a protein useful in the methods of the present invention. To obtain high level expression of a cloned gene, it is desirable to construct expression vectors which contain, at the minimum, a strong promoter, such as ubiquitin, to direct transcription, a ribosome binding site for translational initiation and a transcription/translation terminator.

One of skill would recognize that modifications could be made to a protein useful in the methods of the present invention without diminishing its biological activity. Some modifications may be made to facilitate the cloning, expression or incorporation of the targeting molecule into a fusion protein. Such modifications are well known to those of skill in the art and include, for example, a methionine added at the amino terminus to provide an initiation site or additional amino acids (e.g., poly His) placed on either terminus to create conveniently located restriction sites or termination codons or purification sequences.

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang, et al., (1977) *Nature* 198:1056), the tryptophan (trp) promoter system (Goeddel, et al., (1980) *Nucleic Acids Res.* 8:4057) and the lambda derived P L promoter and N-gene ribosome binding site (Shimatake, et al., (1981) *Nature* 292:128). The inclusion of selection markers in DNA vectors transfected in *E. coli* is also useful. Examples of such markers include genes specifying resistance to ampicillin, tetracycline or chloramphenicol.

The vector is selected to allow introduction of the gene of interest into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein useful in the methods of the present invention are available using *Bacillus* sp. and *Salmonella* (Palva, et al., (1983) *Gene* 22:229-35; Mosbach, et al., (1983) *Nature* 302:543-5). The pGEX-4T-1 plasmid vector from Pharmacia is the preferred *E. coli* expression vector for the present invention.

A variety of eukaryotic expression systems such as yeast, insect cell lines, plant and mammalian cells, are known to those of skill in the art. As explained briefly below, the present invention can be expressed in these eukaryotic systems. In some embodiments, transformed/transfected plant cells, as discussed infra, are employed as expression systems for production of the proteins of the instant invention.

Synthesis of heterologous proteins in yeast is well known. Sherman, et al., (1982) *Methods in Yeast Genetics*, Cold Spring Harbor Laboratory is a well recognized work describing the various methods available to produce the protein in yeast. Two widely utilized yeasts for production of eukaryotic proteins are *Saccharomyces cerevisiae* and *Pichia pastoris*. Vectors, strains and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase and an origin of replication, termination sequences and the like as desired.

A protein useful in the methods of the present invention, once expressed, can be isolated from yeast by lysing the cells and applying standard protein isolation techniques to the lysates or the pellets. The monitoring of the purification process can be accomplished by using Western blot techniques or radioimmunoassay of other standard immunoassay techniques.

The sequences encoding proteins useful in the methods of the present invention can also be ligated to various expression vectors for use in transfecting cell cultures of, for instance, mammalian, insect or plant origin. Mammalian cell systems often will be in the form of monolayers of cells although mammalian cell suspensions may also be used. A number of suitable host cell lines capable of expressing intact proteins have been developed in the art, and include the HEK293, BHK21 and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen, et al., (1986) *Immunol. Rev.* 89:49) and necessary processing information sites, such as ribosome binding sites, RNA splice sites, polyadenylation sites (e.g., an SV40 large T Ag poly A addition site) and transcriptional terminator sequences. Other animal cells useful for production of proteins of the present invention are available, for instance, from the American Type Culture Collection Catalogue of Cell Lines and Hybridomas ($7^{th}$ ed., 1992).

Appropriate vectors for expressing proteins of the present invention in insect cells are usually derived from the SF9 baculovirus. Suitable insect cell lines include mosquito larvae, silkworm, armyworm, moth and *Drosophila* cell lines such as a Schneider cell line (see, e.g., Schneider, (1987) *J. Embryol. Exp. Morphol.* 27:353-65).

As with yeast, when higher animal or plant host cells are employed, polyadenlyation or transcription terminator sequences are typically incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague, et al., (1983) *J. Virol.* 45:773-81). Additionally, gene sequences to control replication in the host cell may be incorporated into the vector such as those found in bovine papilloma virus type-vectors (Saveria-Campo, "Bovine Papilloma Virus DNA a Eukaryotic Cloning Vector," in *DNA Cloning: A Practical Approach*, vol. II, Glover, ed., IRL Press, Arlington, Va., pp. 213-38 (1985)).

In addition, the ACC synthase polynucleotide placed in the appropriate plant expression vector can be used to transform plant cells. The polypeptide can then be isolated from plant callus or the transformed cells can be used to regenerate transgenic plants. Such transgenic plants can be harvested, and the appropriate tissues (seed or leaves, for example) can be subjected to large scale protein extraction and purification techniques.

Numerous methods for introducing foreign polynucleotides into plants are known and can be used to insert an ACC synthase polynucleotide into a plant host, including biological and physical plant transformation protocols. See, e.g., Miki, et al., "Procedure for Introducing Foreign DNA into Plants," in *Methods in Plant Molecular Biology and Biotechnology*, Glick and Thompson, eds., CRC Press, Inc., Boca Raton, pp. 67-88 (1993). The methods chosen vary with the host plant and include chemical transfection methods such as calcium phosphate, microorganism-mediated gene transfer such as *Agrobacterium* (Horsch, et al., *Science* 227:1229-31 (1985)), electroporation, micro-injection and biolistic bombardment.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon or transiently expressed (e.g., transfected mRNA). When a polynucleotide or polypeptide is introduced into a plant, "introducing" is intended to mean presenting to the plant the polynucleotide or polypeptide in such a manner that the sequence gains access to the interior of a cell of the plant. The methods of the invention do not depend on a particular method for introducing a sequence into a plant, only that the polynucleotide or polypeptides gains access to the interior of at least one cell of the plant. Methods for introducing polynucleotide or polypeptides into plants are known in the art, including, but not limited to, stable transformation methods, transient transformation methods, and virus-mediated methods.

Expression cassettes and vectors and in vitro culture methods for plant cell or tissue transformation and regeneration of plants are known and available. See, e.g., Gruber, et al., "Vectors for Plant Transformation," in *Methods in Plant Molecular Biology and Biotechnology*, supra, pp. 89-119.

The polynucleotides or polypeptides may be introduced into the plant by one or more techniques typically used for direct delivery into cells. Such protocols may vary depending on the type of organism, cell, plant or plant cell, i.e. monocot or dicot, targeted for gene modification. Suitable methods of transforming plant cells include microinjection (Crossway, et al., (1986) *Biotechniques* 4:320-334 and U.S. Pat. No. 6,300,543), electroporation (Riggs, et al., (1986) *Proc. Natl. Acad. Sci. USA* 83:5602-5606, direct gene transfer (Paszkowski et al., (1984) *EMBO J.* 3:2717-2722) and ballistic particle acceleration (see, for example, Sanford, et al., U.S. Pat. No. 4,945,050; WO 91/10725 and McCabe, et al., (1988) *Biotechnology* 6:923-926). Also see, Tomes, et al., "Direct DNA Transfer into Intact Plant Cells Via Microprojectile Bombardment". pp. 197-213 in *Plant Cell, Tissue and Organ Culture, Fundamental Methods*. eds. Gamborg and Phillips, Springer-Verlag Berlin Heidelberg New York, 1995; U.S. Pat. No. 5,736,369 (meristem); Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); WO 91/10725 (maize); Klein, et al., (1988) *Plant Physiol.* 91:440-444 (maize); Fromm, et al., (1990) *Biotechnology* 8:833-839 and Gordon-Kamm, et al., (1990) *Plant Cell* 2:603-618 (maize); Hooydaas-Van Slogteren and Hooykaas, (1984) *Nature* (London) 311:763-764; Bytebierm, et al., (1987) *Proc. Natl. Acad. Sci. USA* 84:5345-5349 (Liliaceae); De Wet, et al., (1985) *In The Experimental Manipulation of Ovule Tissues*, ed. Chapman, et al., pp. 197-209, Longman, N.Y. (pollen); Kaeppler, et al., (1990) *Plant Cell Reports* 9:415-418; and Kaeppler, et al., (1992) *Theor. Appl. Genet.* 84:560-566 (whisker-mediated transformation); U.S. Pat. No. 5,693,512 (sonication); D'Halluin, et al., (1992) *Plant Cell* 4:1495-1505 (electroporation); Li, et al., (1993) *Plant Cell Reports* 12:250-255 and Christou and Ford, (1995) *Annals of Botany* 75:407-413 (rice); Osjoda, et al., (1996) *Nature Biotech.* 14:745-750; *Agrobacterium* mediated maize transformation (U.S. Pat. No. 5,981,840); silicon carbide whisker methods (Frame, et al., (1994) *Plant J.* 6:941-948); laser methods (Guo, et al., (1995) *Physiologia Plantarum* 93:19-24); sonication methods (Bao, et al., (1997) *Ultrasound in Medicine & Biology* 23:953-959; Finer and Finer, (2000) *Lett Appl Microbiol.* 30:406-10; Amoah, et al., (2001) *J Exp Bot* 52:1135-42); polyethylene glycol methods (Krens, et al., (1982) *Nature* 296:72-77); protoplasts of monocot and dicot cells can be transformed using electroporation (Fromm, et al., (1985) *Proc. Natl. Acad. Sci. USA* 82:5824-5828) and microinjection (Crossway, et al., (1986) *Mol. Gen. Genet.* 202:179-185), all of which are herein incorporated by reference.

The most widely utilized method for introducing an expression vector into plants is based on the natural transformation system of *Agrobacterium. A. tumefaciens* and *A. rhizogenes* are plant pathogenic soil bacteria, which genetically transform plant cells. The Ti and Ri plasmids of *A. tumefaciens* and *A. rhizogenes*, respectively, carry genes responsible for genetic transformation of plants. See, e.g., Kado, (1991) *Crit. Rev. Plant Sci.* 10:1. Descriptions of the *Agrobacterium* vector systems and methods for *Agrobacterium*-mediated gene transfer are provided in Gruber, et al., supra; Miki, et al., supra and Moloney, et al., (1989) *Plant Cell Reports* 8:238.

Similarly, the gene can be inserted into the T-DNA region of a Ti or Ri plasmid derived from *A. tumefaciens* or *A. rhizogenes*, respectively. Thus, expression cassettes can be constructed as above, using these plasmids. Many control sequences are known which when coupled to a heterologous coding sequence and transformed into a host organism show fidelity in gene expression with respect to tissue/organ specificity of the original coding sequence. See, e.g., Benfey and Chua, (1989) *Science* 244:174-81. Particularly suitable control sequences for use in these plasmids are promoters for constitutive leaf-specific expression of the gene in the various target plants. Other useful control sequences include a promoter and terminator from the nopaline synthase gene (NOS). The NOS promoter and terminator are present in the plasmid pARC2, available from the American Type Culture Collection and designated ATCC Deposit Number 67238. If such a system is used, the virulence (vir) gene from either the Ti or Ri plasmid must also be present, either along with the T-DNA portion or via a binary system where the vir gene is present on a separate vector. Such systems, vectors for use therein and methods of transforming plant cells are described in U.S. Pat. No. 4,658,082; U.S. patent application Ser. No. 913,914, filed Oct. 1, 1986, as referenced in U.S. Pat. No. 5,262,306, issued Nov. 16, 1993 and Simpson, et al., (1986) *Plant Mol. Biol.* 6:403-15 (also referenced in the '306 patent), all incorporated by reference in their entirety.

Once constructed, these plasmids can be placed into *A. rhizogenes* or *A. tumefaciens* and these vectors used to transform cells of plant species, which are ordinarily susceptible to *Fusarium* or *Alternaria* infection. Several other transgenic plants are also contemplated by the present invention including but not limited to soybean, corn, sorghum, alfalfa, rice, clover, cabbage, banana, coffee, celery, tobacco, cowpea, cotton, melon and pepper. The selection of either *A. tumefaciens* or *A. rhizogenes* will depend on the plant being transformed thereby. In general *A. tumefaciens* is the preferred organism for transformation. Most dicotyledonous plants, some gymnosperms, and a few monocotyledonous plants (e.g., certain members of the Liliales and Arales) are susceptible to infection with *A. tumefaciens. A. rhizogenes* also has a wide host range, embracing most dicots and some gymnosperms, which includes members of the Leguminosae, Compositae and Chenopodiaceae. Monocot plants can now be transformed with some success. EP Patent Application Number 604 662 A1 discloses a method for transforming monocots using *Agrobacterium*. EP Patent Application Number 672 752 A1 discloses a method for transforming monocots with *Agrobacterium* using the scutellum of immature embryos. Ishida, et al., discuss a method for transforming maize by exposing immature embryos to *A. tumefaciens* (*Nature Biotechnology* 14:745-50 (1996)).

Once transformed, these cells can be used to regenerate transgenic plants. As used herein, "transgenic plant" includes reference to a plant, which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition or spontaneous mutation.

For example, whole plants can be infected with these vectors by wounding the plant and then introducing the vector into the wound site. Any part of the plant can be wounded, including leaves, stems and roots. Alternatively, plant tissue, in the form of an explant, such as cotyledonary tissue or leaf disks, can be inoculated with these vectors, and cultured under conditions, which promote plant regeneration. Roots or shoots transformed by inoculation of plant tissue with *A. rhizogenes* or *A. tumefaciens*, containing the gene coding for the fumonisin degradation enzyme, can be used as a source of plant tissue to regenerate fumonisin-resistant transgenic plants, either via somatic embryogenesis or organogenesis. Examples of such methods for regenerating plant tissue are disclosed in Shahin, (1985) *Theor. Appl. Genet.* 69:235-40; U.S. Pat. No. 4,658,082; Simpson, et al., supra and U.S. patent application Ser. No 913,913 and 913,914, both filed Oct. 1, 1986, as referenced in U.S. Pat. No. 5,262,306, issued Nov. 16, 1993, the entire disclosures therein incorporated herein by reference.

Despite the fact that the host range for *Agrobacterium*-mediated transformation is broad, some major cereal crop species and gymnosperms have generally been recalcitrant to this mode of gene transfer, even though some success has recently been achieved in rice (Hiei, et al., (1994) *The Plant Journal* 6:271-82). Several methods of plant transformation, collectively referred to as direct gene transfer, have been developed as an alternative to *Agrobacterium*-mediated transformation.

A generally applicable method of plant transformation is microprojectile-mediated transformation, where DNA is carried on the surface of microprojectiles measuring about 1 to 4 μm. The expression vector is introduced into plant tissues with a biolistic device that accelerates the microprojectiles to speeds of 300 to 600 m/s which is sufficient to penetrate the plant cell walls and membranes (Sanford, et al., (1987) *Part. Sci. Technol.* 5:27; Sanford, (1988) *Trends Biotech* 6:299; Sanford, (1990) *Physiol. Plant* 79:206 and Klein, et al., (1992) *Biotechnology* 10:268).

Another method for physical delivery of DNA to plants is sonication of target cells as described in Zang, et al., (1991) *BioTechnology* 9:996. Alternatively, liposome or spheroplast fusions have been used to introduce expression vectors into plants. See, e.g., Deshayes, et al., (1985) *EMBO J.* 4:2731 and Christou, et al., (1987) *Proc. Natl. Acad. Sci. USA* 84:3962. Direct uptake of DNA into protoplasts using $CaCl_2$ precipitation, polyvinyl alcohol, or poly-L-ornithine has also been reported. See, e.g., Hain, et al., (1985) *Mol. Gen. Genet.* 199:161 and Draper, et al., (1982) *Plant Cell Physiol.* 23:451.

Electroporation of protoplasts and whole cells and tissues has also been described. See, e.g., Donn, et al., (1990) *Abstracts of the VIIth Int'l. Congress on Plant Cell and Tissue Culture IAPTC*, A2-38, p. 53; D'Halluin, et al., (1992) *Plant Cell* 4:1495-505 and Spencer, et al., (1994) *Plant Mol. Biol.* 24:51-61.

In addition to modulating ethylene synthesis, the methods of the invention can be used along with sequences or methods that alter additional phenotypes in the plant. Various changes in phenotype are of interest including modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases and those involved in housekeeping, such as heat shock proteins. More specific categories of transgenes, for example, include genes encoding important traits for agronomics, insect resistance, disease resistance, herbicide resistance, sterility, grain characteristics and commercial products. Genes of interest include, generally, those involved in oil, starch, carbohydrate or nutrient metabolism as well as those affecting kernel size, sucrose loading and the like.

In certain embodiments the nucleic acid sequences of the present invention can be used in combination ("stacked") with other polynucleotide sequences of interest in order to create plants with a desired phenotype. The combinations generated can include multiple copies of any one or more of the polynucleotides of interest. The polynucleotides of the present invention may be stacked with any gene or combination of genes to produce plants with a variety of desired trait combinations, including but not limited to traits desirable for animal feed such as high oil genes (e.g., U.S. Pat. No. 6,232,529); balanced amino acids (e.g., hordothionins (U.S. Pat. Nos. 5,990,389; 5,885,801; 5,885,802 and 5,703,049); barley high lysine (Williamson, et al., (1987) *Eur. J. Biochem.* 165:99-106 and WO 98/20122) and high methionine proteins (Pedersen, et al., (1986) *J. Biol. Chem.* 261:6279; Kirihara, et al., (1988) *Gene* 71:359 and Musumura, et al., (1989) *Plant Mol. Biol.* 12:123)); increased digestibility (e.g., modified storage proteins (U.S. patent application Ser. No. 10/053,410, filed Nov. 7, 2001) and thioredoxins (U.S. patent application Ser. No. 10/005,429, filed Dec. 3, 2001)), the disclosures of which are herein incorporated by reference. The polynucleotides of the present invention can also be stacked with traits desirable for insect, disease or herbicide resistance (e.g., *Bacillus thuringiensis* toxic proteins (U.S. Pat. Nos. 5,366,892; 5,747,450; 5,736,514; 5,723,756; 5,593,881; Geiser, et al., (1986) *Gene* 48:109); lectins (Van Damme, et al., (1994) *Plant Mol. Biol.* 24:825); fumonisin detoxification genes (U.S. Pat. No. 5,792,931); avirulence and disease resistance genes (Jones, et al., (1994) *Science* 266:789; Martin, et al., (1993) *Science* 262:1432; Mindrinos, et al., (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)) and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)) and polymers or bioplastics (e.g., U.S. Pat. No. 5,602,321; beta-ketothiolase, polyhydroxybutyrate synthase and acetoacetyl-CoA reductase (Schubert, et al., (1988) *J. Bacteriol.* 170:5837-5847) facilitate expression of polyhydroxyalkanoates (PHAs)), the disclosures of which are herein incorporated by reference. One could also combine the polynucleotides of the present invention with polynucleotides affecting agronomic traits such as male sterility (e.g., see, U.S. Pat. No. 5,583,210), stalk strength, flowering time or transformation technology traits such as cell cycle regulation or gene targeting (e.g., WO 99/61619; WO 00/17364; WO 99/25821), the disclosures of which are herein incorporated by reference.

In one embodiment, sequences of interest improve plant growth and/or crop yields. For example, sequences of interest include agronomically important genes that result in improved primary or lateral root systems. Such genes include, but are not limited to, nutrient/water transporters and growth induces. Examples of such genes, include but are not limited to, maize plasma membrane $H^+$-ATPase (MHA2) (Frias, et al., (1996) *Plant Cell* 8:1533-44); AKT1, a component of the potassium uptake apparatus in *Arabidopsis*, (Spalding, et al., (1999) *J Gen Physiol* 113:909-18); RML genes which activate cell division cycle in the root apical cells (Cheng, et al., (1995) *Plant Physiol* 108:881); maize glutamine synthetase genes (Sukanya, et al., (1994) *Plant Mol Biol* 26:1935-46) and hemoglobin (Duff, et al., (1997) *J. Biol. Chem* 27:16749-16752, Arredondo-Peter, et al., (1997) *Plant Physiol.* 115:1259-1266; Arredondo-Peter, et al., (1997) *Plant Physiol* 114:493-500 and references sited therein). The sequence of interest may also be useful in expressing antisense nucleotide sequences of genes that that negatively affects root development.

Additional, agronomically important traits such as oil, starch and protein content can be genetically altered in addition to using traditional breeding methods. Modifications include increasing content of oleic acid, saturated and unsaturated oils, increasing levels of lysine and sulfur, providing essential amino acids and also modification of starch. Hordothionin protein modifications are described in U.S. Pat. Nos. 5,703,049, 5,885,801, 5,885,802 and 5,990,389, herein incorporated by reference. Another example is lysine and/or sulfur rich seed protein encoded by the soybean 2S albumin described in U.S. Pat. No. 5,850,016, and the chymotrypsin inhibitor from barley, described in Williamson, et al., (1987) *Eur. J. Biochem.* 165:99-106, the disclosures of which are herein incorporated by reference.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. patent application Ser. No. 08/740,682, filed Nov. 1, 1996 and WO 98/20133, the disclosures of which are herein incorporated by reference. Other proteins include methionine-rich plant proteins such as from sunflower seed (Lilley, et al., (1989) *Proceedings of the World Congress on Vegetable Protein Utilization in Human Foods and Animal Feedstuffs*, ed. Applewhite (American Oil Chemists Society, Champaign, Ill.), pp. 497-502, herein incorporated by reference); corn (Pedersen, et al., (1986) *J. Biol. Chem.* 261:6279; Kirihara, et al., (1988) *Gene* 71:359, both of which are herein incorporated by reference) and rice (Musumura, et al., (1989) *Plant Mol. Biol.* 12:123, herein incorporated by reference). Other agronomically important genes encode latex, Floury 2, growth factors, seed storage factors and transcription factors.

Insect resistance genes may encode resistance to pests that have great yield drag such as rootworm, cutworm, European Corn Borer and the like. Such genes include, for example, *Bacillus thuringiensis* toxic protein genes (U.S. Pat. Nos. 5,366,892; 5,747,450; 5,736,514; 5,723,756; 5,593,881 and Geiser, et al., (1986) *Gene* 48:109) and the like.

Genes encoding disease resistance traits include detoxification genes, such as against fumonosin (U.S. Pat. No. 5,792,931); avirulence (avr) and disease resistance (R) genes (Jones, et al., (1994) *Science* 266:789; Martin, et al., (1993) *Science* 262:1432 and Mindrinos, et al., (1994) *Cell* 78:1089) and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene) or other such genes known in the art. The bar gene encodes resistance to the herbicide basta, the nptII gene encodes resistance to the antibiotics kanamycin and geneticin and the ALS-gene mutants encode resistance to the herbicide chlorsulfuron.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

The quality of grain is reflected in traits such as levels and types of oils, saturated and unsaturated, quality and quantity of essential amino acids and levels of cellulose. In corn, modified hordothionin proteins are described in U.S. Pat. Nos. 5,703,049, 5,885,801, 5,885,802 and 5,990,389.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase) and acetoacetyl-CoA reductase (see, Schubert, et al., (1988) *J. Bacteriol.* 170:5837-5847) facilitate expression of polyhyroxyalkanoates (PHAs).

Exogenous products include plant enzymes and products as well as those from other sources including procaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

The cells that have been transformed may be grown into plants in accordance with conventional ways. See, for example, McCormick et al. (1986) *Plant Cell Reports* 5: 81-84. These plants may then be grown and either pollinated with the same transformed strain or different strains; the resulting progeny having the desired phenotypic characteristic can then be identified. Two or more generations may be grown to ensure that the desired phenotypic characteristic is stably maintained and inherited and then seeds harvested to ensure that stable transformants exhibiting the desired phenotypic characteristic have been achieved. In this manner, the present invention provides transformed seed (also referred to as "transgenic seed") having a nucleotide construct of the invention, for example, a cassette of the invention, stably incorporated into their genome.

As used herein, the term "plant" includes reference to whole plants, plant organs (e.g., leaves, stems, roots, etc.), seeds and plant cells and progeny of same. The term plant also includes plant protoplasts, plant calli, and plant clumps. Plant cell, as used herein includes, without limitation, cells in or from seeds, suspension cultures, embryos, meristematic regions, callus tissue, leaves, roots, shoots, gametophytes, sporophytes, pollen and microspores. Plant cells can be part of an intact plant or part of a plant, such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

The present invention may be used for transformation of any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), *sorghum* (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), *macadamia* (*Macadamia integrifolia*), almond (*Prunus amygdalus*), sugar beets (*Beta vulgaris*), sugarcane (*Saccharum* spp.), oats, barley, vegetables, ornamentals, and conifers. In particular embodiments of the presently disclosed methods, the plant is *Zea mays*.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean and sugarcane plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

The practice of the present invention will employ, unless otherwise indicated, conventional techniques of botany, microbiology, tissue culture, molecular biology, chemistry, biochemistry and recombinant DNA technology, which are within the skill of the art. Such techniques are explained fully in the literature. See, e.g., Langenheim and Thimann, (1982) *Botany: Plant Biology and Its Relation to Human Affairs*, John Wiley; *Cell Culture and Somatic Cell Genetics of Plants*, vol. 1, Vasil, ed. (1984); Stanier, et al., (1986) *The Microbial World*, $5^{th}$ ed., Prentice-Hall; Dhringra and Sinclair, (1985) *Basic lant Pathology Methods*, CRC Press; Maniatis, et al., (1982) *Molecular Cloning: A Laboratory Manual; DNA Cloning*, vols. I and II, Glover, ed. (1985); *Oligonucleotide Synthesis*, Gait, ed. (1984); *Nucleic Acid Hybridization*, Hames and Higgins, eds. (1984) and the series *Methods in Enzymology*, Colowick and Kaplan, eds, Academic Press, Inc., San Diego, Calif.

Units, prefixes and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

It is to be noted that the term “a” or “an” entity refers to one or more of that entity; for example, “a polypeptide” is understood to represent one or more polypeptides. As such, the terms “a” (or “an”), “one or more,” and “at least one” can be used interchangeably herein.

Throughout this specification and the claims, the words “comprise,” “comprises,” and “comprising” are used in a non-exclusive sense, except where the context requires otherwise.

As used herein, the term “about,” when referring to a value is meant to encompass variations of, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the presently disclosed subject matter be limited to the specific values recited when defining a range.

This invention can be better understood by reference to the following non-limiting examples. It will be appreciated by those skilled in the art that other embodiments of the invention may be practiced without departing from the spirit and the scope of the invention as herein disclosed and claimed.

EXAMPLES

Example 1

ACC Synthase Knockouts by Hairpin RNA Expression

As noted previously, knockout plant cells and plants can be produced, for example, by introduction of an ACC synthase polynucleotide sequence configured for RNA silencing or interference. This example describes hairpin RNA expression cassettes for improving plant nitrogen utilization phenotype, e.g., in maize. As noted previously, knockout of ACC synthase(s), e.g., by hpRNA expression, can result in plants or plant cells having reduced expression (up to and including no detectable expression) of one or more ACC synthases.

Expression of hairpin RNA (hpRNA) molecules specific for regions of ACC synthase genes (e.g., promoters, other untranslated regions or coding regions) in plants can alter nitrogen utilization potential of the plants, e.g., through RNA interference and/or silencing.

hpRNA constructs of ACS2 and ACS6 were generated by linking a ubiquitin promoter to an inverted repeat of a portion of the coding sequence of either the ACS2 or ACS6 gene (see, FIGS. 2 and 3). Each construct was transformed into maize using *Agrobacterium*-mediated transformation techniques. Nucleic acid molecules and methods for preparing the constructs and transforming maize were as previously described and known in the art and as described herein. Expression of hpRNA specific for either ACS2 or ACS6 coding sequences resulted in maize plants that displayed no abnormalities in vegetative and reproductive growth. A total of 36 and 40 individual maize transgenic events were generated for ACS2- and ACS6-hairpin constructs, respectively.

Approximately 10 low-copy-number events per hpRNA construct were selected for additional backcrossing and transgene evaluation. Nitrogen utilization potential phenotype is evaluated for the backcrossed lines comprising the hpRNA transgene(s), e.g., as described herein (for example, by visual inspection, measurements of photosynthetic activity, determination of chlorophyll or protein content, grain yield, or the like, under normal conditions or under nitrogen-depleted, drought or other stress conditions).

Corn hybrids containing the inhibition constructs and nulls were planted in the field under nitrogen stress and normal nitrogen conditions. The planting density was 36,000 plants per acre and plants were fully irrigated. Under normal nitrogen conditions, 100 lbs nitrogen per acre was applied in the form of urea ammonium nitrate (UAN) pre-plant, then another 150 lbs per acre UAN was applied as a sidedress at the V6 stage of development. Nitrogen stress was achieved through depletion of soil nitrogen reserves by planting corn with no added nitrogen for two years. After each season of depletion, corn grain and stover were removed to deplete organic matter sources of nitrogen through mineralization. Soil nitrate reserves were monitored to assess the level of depletion. To achieve the target level of stress, UAN was applied by fertigation between V2 and VT, for a total of 150 lbs nitrogen.

Transgenic events from the construct were nested together with the null to minimize the spatial effects of field variation.

The grain yield of events containing the transgene was compared to the yield of a transgenic null. Statistical analysis was conducted to assess whether there is a significant improvement in yield compared with the transgenic null, taking into account row and column spatial effects.

Treatments: Low nitrogen (LN) and Normal N (NN)

Nested design, 6 reps in LN, 4 reps in NN

Table 1 below shows yield data (bushels per acre) of 7 events with the RNAi inhibition construct Ubi:ACS6 and wild type controls.

TABLE 1

| EVENT | Low Nitrogen | Normal Nitrogen |
|---|---|---|
| E5678.29.1.20 | 128 | 266* |
| E5678.29.1.22 | 162* | 256* |
| E5678.29.1.26 | 148* | 251* |
| E5678.29.1.3 | 150* | 244 |
| E5678.29.1.30 | 151* | 236 |
| E5678.29.1.32 | 160* | 276* |
| E5678.29.1.33 | 125 | 265* |
| wild type | 117 | 231 |
| Lsd | 14.9 | 20.0 |

*significantly different from wild type ($P < 0.1$)

As can be seen, 5 out of 7 events showed superior yield to wild type in low nitrogen. Also interestingly, 5 out of 7 events also showed superior yield in normal nitrogen.

Example 2

Improved ACC Synthase Inhibition by Hairpin RNA Expression

An improved hpRNA construct, the sequence of which is set forth in SEQ ID NO:53 (the expression cassette is set forth in SEQ ID NO:57 and depicted in FIG. 4), was generated by linking a ubiquitin promoter to a portion of the coding sequence of the ACS6 gene and its inverted repeat (SEQ ID NOs: 51 and 52), separated by an ADH1 intron.

Provided below is a general description of the improved hpRNA plasmid (SEQ ID NO:53):

```
 DNA SEQ ID NO: 53
 UBI:ZM-ACS6 RNAi + UBI:MOPAT:PINII Co-integrate.
 length: 51280 bp
 storage type: Basic
 form: Circular
Functional Map
 CDS (10 signals)
  MO-PAT
   Start: 7109 End: 7660
  SPC
   Start: 9525 End: 10313 (Complementary)
   SPECTINOMYCIN RESISTANCE
  TET
   Start: 14622 End: 15272 (Complementary)
   tetracycline resistance
  TET
   Start: 15378 End: 16028 (Complementary)
   tetracycline resistance
  TRF A
   Start: 17208 End: 19397 (Complementary)
  CTL
   Start: 24763 End: 31033 (Complementary)
  VIR C1
   Start: 34264 End: 34958
  VIR C2
   Start: 34961 End: 35569
  VIR G
   Start: 35680 End: 36483 (Complementary)
   Agrobacterium virG (region approximated)
  VIR B
   Start: 36615 End: 46051 (Complementary)
   Agrobacterium virB (region approximated)
 Intron (3 signals)
  UBI1ZM INTRON1 (PHI)
   Start: 2196 End: 3208
  ADH1 INTRON1 (PHI)
   Start: 3791 End: 4327
   Isolated from B73 at Pioneer (Notebook 4136.51)
  UBI1ZM INTRON1 (PHI)
   Start: 6060 End: 7072
 Misc_feature (11 signals)
  RB
   Start: 1 End: 25
  ALL STOPS
   Start: 306 End: 339
   A synthetic sequence of stop codons designed to stop all 6 open reading
frames.
  FRT5
   Start: 452 End: 499
  ALL STOPS
   Start: 910 End: 943
```

-continued

A synthetic sequence of stop codons designed to stop all 6 open reading frames.
ATTB1
Start: 1155 End: 1175
ATTB2
Start: 4931 End: 4951 (Complementary)
FRT12
Start: 4998 End: 5045
FLP recombination target 12
FRT1
Start: 8004 End: 8051
PSB1
Start: 8052 End: 8146
A synthetic sequence designed to facilitate PCR analysis of recombined FRT sites.
ALL STOPS
Start: 8147 End: 8180
A synthetic sequence of stop codons designed to stop all 6 open reading frames.
LB
Start: 8325 End: 8350
tDNA Left border sequence from Japan Tobacco
Promoter_prokaryotic (2 signals)
UBI1ZM PRO
Start: 1218 End: 2113
Maize ubiquitin promoter
UBI1ZM PRO
Start: 5082 End: 5977
Maize ubiquitin promoter
Rep_origin (2 signals)
COLE1 ORI
Start: 11588 End: 11857 (Complementary)
ORI V
Start: 32041 End: 32751 (Complementary)
Terminator (2 signals)
IN2-1 (B) TERM
Start: 505 End: 902 (Complementary)
98bp deletion from 3'-end of the terminator. IN stands for INducible and 2-1 relates to an internal code used to designate the same
PINII TERM
Start: 7671 End: 7989
Potato PINII terminator
5'UTR (2 signals)
UBI1ZM 5UTR (PHI)
Start: 2114 End: 2195
UBI1ZM 5UTR (PHI)
Start: 5978 End: 6059
Misc_RNA (2 signals)
ZM-ACS6 (TR3)
Start: 3272 End: 3776 (Complementary)
Maize ACC synthase 6 (Aminocyclopropane carboxylate synthase) Truncated fragment for gene silencing. PCR'd from genomic
ZM-ACS6 (TR4)
Start: 4332 End: 4874
Maize ACC synthase 6 (Aminocyclopropane carboxylate synthase) Truncated fragment for gene silencing. PCR'd from genomic
Restriction Map
G|TGCAC
ApaLI: 14 sites
CACGT|G
N1: 287
N2: 2517
N3: 3704
N4: 4391
N5: 6381
N6: 10036
N7: 10810
N8: 11376
N9: 11874
N10: 13564
N11: 45696
N12: 48291
N13: 48789
N14: 50471
C|YCGRG
AvaI: 37 sites
GRGCY|C
N1: 1144
N2: 1909
N3: 3318
N4: 3666

-continued

N5: 4429
N6: 4777
N7: 4922
N8: 5072
N9: 5773
N10: 7116
N11: 10391
N12: 15995
N13: 16761
N14: 17741
N15: 20628
N16: 21650
N17: 22422
N18: 24908
N19: 28599
N20: 30815
N21: 31984
N22: 33215
N23: 33223
N24: 33231
N25: 34047
N26: 34545
N27: 35022
N28: 35445
N29: 35491
N30: 36128
N31: 36869
N32: 37358
N33: 37895
N34: 38948
N35: 41282
N36: 43949
N37: 51174

G|GATCC
BamHI: 11 sites
CCTAG|G

N1: 3230
N2: 4329
N3: 4865
N4: 5066
N5: 7094
N6: 34434
N7: 35775
N8: 37634
N9: 38570
N10: 38770
N11: 43916

AT|CGAT
ClaI: 18 sites
TAGC|TA

N1: 2445
N2: 2710
N3: 2935
N4: 6309
N5: 6574
N6: 6799
N7: 33943
N8: 34189
N9: 34622
N10: 36384
N11: 36728
N12: 36855
N13: 41483
N14: 42530
N15: 44527
N16: 46781
N17: 47943
N18: 48057

G|AATTC
EcoRI: 11 sites
CTTAA|G

N1: 2609
N2: 3261
N3: 4834
N4: 4877
N5: 6473
N6: 13890
N7: 37680
N8: 40564
N9: 40976
N10: 42287

-continued

```
 N11: 43685
                  A|AGCTT
HindIII: 8 sites
                  TTCGA|A
 N1: 649
 N2: 1202
 N3: 3864
 N4: 33254
 N5: 44317
 N6: 45226
 N7: 46347
 N8: 47862
                  C|CATGG
NcoI: 2 sites
                  GGTAC|C
 N1: 17026
 N2: 17554
                  CTGCA|G
PstI: 15 sites
                  G|ACGTC
 N1: 1218
 N2: 3208
 N3: 3777
 N4: 5082
 N5: 7072
 N6: 12698
 N7: 13142
 N8: 33407
 N9: 38321
 N10: 41155
 N11: 42206
 N12: 42791
 N13: 48045
 N14: 49613
 N15: 50049
                  CCC|GGG
SmaI: 10 sites
                  GGG|CCC
 N1: 1146
 N2: 3320
 N3: 3668
 N4: 4431
 N5: 4779
 N6: 4924
 N7: 5074
 N8: 15997
 N9: 16763
 N10: 34049
```

Each construct was transformed into maize using *Agrobacterium*-mediated transformation techniques. Nucleic acid molecules and methods for preparing the constructs and transforming maize are as previously described and known in the art.

Transformed plants of the invention were evaluated for yield under four environments. Eight reps were grown under flowering stress in Environment 1, 6 reps were grown under grain fill stress in Environment 2, 6 reps were grown under grain fill stress in Environment 3, and 4 reps were grown under rain-fed conditions in Environment 4. Yields were compared with a highly repeated construct null (CN). The data are shown in FIGS. 5-8.

FIG. 5 shows the yield of transformed plants of the invention under flowering stress in Environment 1. Each bar represents a separate transformation event. Average yield of transgene-negative segregants is shown (139 bu/a) as control (CN). A total of 74% of the events yielded nominally more than the control plants. Plants representing 18 transgenic events outyielded the control at P<0.10.

FIG. 6 shows the yield of transformed plants of the invention under grain-fill stress in Environment 2. Each bar represents a separate transformation event. Average yield of transgene-negative segregants is shown (176 bu/a) as control (CN). Thirteen events out-yielded the CN at P<0.10. Of these, eight had also shown significant improvement under flowering stress.

FIG. 7 shows the yield, as a percent of control, of transformed plants of the invention (indicated by a circle), as well as plants transformed using an alternative ACS6 inhibition vector (indicated by a square) under grain fill stress in Environment 3. Each data point represents a separate transformation event. NS=not significant. The control plants are bulked transgene-negative segregants. As can be seen, 64% of the events of the invention had significantly superior yield; only 17% of the alternative ACS6 inhibition events had significantly superior yield, relative to the control.

FIG. 8 shows the yield, as a percent of control, of transformed plants of the invention (indicated by a circle), as well as plants transformed using an alternative ACS6 inhibition vector (indicated by a square) under rain-fed conditions in Environment 4. Each data point represents a separate transformation event. NS=not significant. The control plants are bulked transgene-negative segregants. As can be seen, all points exhibiting statistically significant increases in yield represent events of the invention disclosed herein. In addition, all points exhibiting statistically significant decreases in yield are events containing the alternative ACS6 inhibition vector.

Without being limited to any particular theory, it is speculated that the construct of the invention provides the documented improvement in yield by refining the modulation of ACS expression. For example, inclusion of the Adh1 intron within the ACS6 hairpin may result in ACS6 being downregulated to a lesser extent in plants of the invention than in plants transformed with the previous (alternative) ACS6 inhibition vector. Alternatively or additionally, the construct of the invention may impact expression of genes other than ACS6, for example ACS2.

Methods:

Protein Extraction

For total protein isolation, leaves of B73 or mutant plants are collected at the indicated times, quick-frozen in liquid nitrogen and ground to a fine powder. One ml of extraction buffer (20 mM HEPES (pH 7.6), 100 mM KCl, 10% Glycerol) is added to approximately 0.1 g frozen powder and mixed thoroughly. Samples are centrifuged 10 minutes at 10,000 rpm, the supernatant removed to a new tube and the concentration determined spectrophotometrically according to the methods of Bradford, (1976). See, Bradford, (1976) *Anal. Biochem.* 72:248-254.

Chlorophyll Extraction

Leaves are frozen in liquid nitrogen and ground to a fine powder. Samples of approximately 0.1 g are removed to a 1.5 ml tube and weighed. Chlorophyll is extracted 5× with 1 ml (or 0.8 ml) of 80% acetone. Individual extractions are combined and the final volume adjusted to 10 ml (or 15 ml) with additional 80% acetone. Chlorophyll content (a+b) is determined spectrophotometrically according to the methods of Wellburn, (1994). See, Wellburn, (1994) *J. Plant Physiol.* 144:307-313.

Measurement of Photosynthesis

Plants are grown in the field under normal and drought-stress conditions. Under normal conditions, plants are watered for eight hours twice a week. For drought-stressed plants, water is limited to approximately four hours per week for a period starting approximately one week before pollination and continuing through three weeks after pollination. During the period of limited water availability, drought-stressed plants may show visible signs of wilting and leaf rolling. Transpiration, stomatal conductance and $CO_2$ assimilation are determined with a portable TPS-1 Photosynthesis System (PP Systems). Each leaf on a plant is measured at forty days after pollination. Values typically represent a mean of six determinations.

DNA and RNA Purification

For total nucleic acid isolation, leaves of B73 are collected at desired times, quick-frozen in liquid nitrogen and ground to a fine powder. Ten ml of extraction buffer (100 mM Tris (pH 8.0), 50 mM EDTA, 200 mM NaCl, 1% SDS, 10 μ/ml β-mercaptoethanol) is added and mixed thoroughly until thawed. Ten ml of Phenol/Chloroform (1:1, vol:vol) is added and mixed thoroughly. Samples are centrifuged 10 min at 8,000 rpm, the supernatant is removed to a new tube and the nucleic acid is precipitated at −20° C. following addition of 1/10 vol 3M sodium acetate and 1 vol isopropanol. Total nucleic acid is pelleted by centrifugation at 8,000 rpm and resuspended in 1 ml TE. One half of the prep is used for DNA purification and the remaining half is used for RNA purification. (Alternatively, DNA or total nucleic acids can be extracted from 1 $cm^2$ of seedling leaf, quick-frozen in liquid nitrogen, and ground to a fine powder. 600 μl of extraction buffer [100 mM Tris (pH 8.0), 50 mM EDTA, 200 mM NaCl, 1% SDS, 10 μl/ml β-mercaptoethanol] is added and the sample mixed. The sample is extracted with 700 μl phenol/chloroform (1:1) and centrifuged for 10 minutes at 12,000 rpm. DNA is precipitated and resuspended in 600 μl H2O.)

For DNA purification, 500 μg Dnase-free Rnase is added to the tube and incubated at 37° C. for 1 hr. Following Rnase digestion, an equal volume of Phenol/Chloroform (1:1, vol:vol) is added and mixed thoroughly. Samples are centrifuged 10 min at 10,000 rpm, the supernatant is removed to a new tube and the DNA precipitated at −20° C. following addition of 1/10 vol 3M sodium acetate and 1 vol isopropanol. DNA is resuspended in sterile water and the concentration is determined spectrophotometrically. To determine DNA integrity, 20 mg of DNA is separated on a 1.8% agarose gel and visualized following staining with ethidium bromide. RNA is purified by 2 rounds of $LiCl_2$ precipitation according to methods described by Sambrook, et al., supra.

Real-Time RT-PCR Analysis

Fifty μg total RNA is treated with RQ1™ Dnase (Promega) to ensure that no contaminating DNA is present. Two μg total RNA is used directly for cDNA synthesis using the Omniscript™ reverse transcription kit (Qiagen) with oligo-dT(20) as the primer.

Analysis of transcript abundance is accomplished using the QuantiTect™ SYBR Green PCR kit (Qiagen). Reactions contain 1.times. buffer, 0.5 μl of the reverse transcription reaction (equivalent to 50 ng total RNA) and 0.25 μM (final concentration) forward and reverse primers in a total reaction volume of 25 μl.

Reactions are carried out using an ABI PRISM 7700 sequence detection system under the following conditions: 95° C./15 minutes (1 cycle); 95 C/30 sec, 62° C./30 sec, 72° C./2 minute (50 cycles); 72° C./5 minutes (1 cycle). Each gene is analyzed a minimum of four times.

All the primer combinations are initially run and visualized on an agarose gel to confirm the presence of a single product of the correct size. All amplification products are subcloned into the pGEM-T Easy vector system (Promega) to use for generation of standard curves to facilitate conversion of expression data to a copy/μg RNA basis.

Ethylene Determination

Ethylene is measured from the second fully-expanded leaf of seedlings at the 4-leaf stage or from the terminal 15 cm of leaves of plants 20, 30 or 40 days after pollination (DAP). Leaves are harvested at the indicated times and allowed to recover for 2 hr prior to collecting ethylene, between moist paper towels. Leaves are placed into glass vials and capped with a rubber septum. Following a 3- to 4-hour incubation, 0.9 mL of headspace is sampled from each vial and the ethylene content measured using a 6850 series gas chromatography system (Hewlett-Packard, Palo Alto, Calif.) equipped with a HP Plot alumina-based capillary column (Agilent Technologies, Palo Alto, Calif.). Tissue fresh weight is measured for each sample. Three replicates are typically measured and the average and standard deviation reported.

Western Blot Analysis

B73 leaves are collected at the indicated times and ground in liquid nitrogen to a fine powder. One ml of extraction buffer [20 mM HEPES (pH 7.6), 100 mM KCl, 10% glycerol, 1 mM PMSF] is added to approximately 0.1 g frozen powder and mixed thoroughly. Cell debris is pelleted by centrifugation at 10,000 rpm for 10 min and the protein concentration determined as described (Bradford, 1976). Antiserum raised against the large subunit of rice Rubisco is obtained from Dr. Tadahiko Mae (Tohoku University, Sendai, Japan). Protein extracts are resolved using standard SDS-PAGE and the protein transferred to 0.22 μm nitrocellulose membrane by electroblotting. Following transfer, the membranes are blocked in 5% milk, 0.01% thimerosal in TPBS (0.1% TWEEN® 20, 13.7 mM NaCl, 0.27 mM KCl, 1 mM Na2HPO4, 0.14 mM KH2PO4) followed by incubation with primary antibodies diluted typically 1:1000 to 1:2000 in TPBS with 1% milk for 1.5 hrs. The blots are then washed twice with TPBS and incubated with goat anti-rabbit horseradish peroxidase-conjugated antibodies (Southern Biotechnology Associates, Inc.)

diluted to 1:5000 to 1:10,000 for 1 hr. The blots are washed twice with TPBS and the signal detected typically between 1 to 15 min using chemiluminescence (Amersham Corp).

Example 3

Yield of Plants Comprising Improved ACS6 Inhibition Construct Under Reduced Nitrogen Plants comprising the improved ACS6 inhibition construct described in Example 2 were planted in the field under nitrogen-stress and normal-nitrogen conditions.

Nitrogen stress was achieved through targeted depletion of soil nitrogen reserves by previous corn production and/or limited application of nitrogen fertilizer. In addition to cropping history, soil type and other environmental factors were taken into consideration in creating appropriate nitrogen-stress conditions.

The grain yield of plants containing the transgene was compared to the yield of a wild-type or transgenic null. The test used a randomized complete block design with six replications. Statistical analysis was conducted using ASReml to assess differences in yield, taking into account row and column spatial effects and autoregressive (AR1) adjustments.

Table 2 provides yield data in bushels/acre for plants representing 19 transformation events under nitrogen-stress conditions in two geographic locations. Yields marked with an asterisk are significantly greater than the control at P<0.1.

TABLE 2

| Event | Location 1 | Location 2 |
|---|---|---|
| 2.12 | 121 | 202* |
| 2.29 | 124* | 199 |
| 2.32 | 123 | 211* |
| 113.2.7 | 124* | 206* |
| 4.3 | 124* | 204* |
| 4.8 | 125* | 203* |
| 1.23 | 127* | 208* |
| 1.44 | 126* | 207* |
| 2.15 | 124* | 205* |
| 2.2 | 124 | 201 |
| 2.24 | 124* | 198 |
| 2.38 | 125* | 204* |
| 2.49 | 123 | 202* |
| 1.14 | 125* | 210* |
| 2.18 | 126* | 206* |
| 2.22 | 124* | 208* |
| 2.8 | 125* | 205* |
| 2.1 | 125* | 206* |
| 66.2.7 | 124* | 202* |
| Control | 120 | 197 |

Additional measurements were taken at Location 2, as follows. Average yield of the transgenic plants under normal-nitrogen conditions was 232 bushels per acre; under nitrogen-stress conditions, the average yield was 203 bushels per acre. Under nitrogen stress, growing-degree-units to pollen shed was 1273, compared to 1330 under normal-nitrogen conditions. In addition, plants grown in the nitrogen-stress environment showed a reduction in anthesis-silking interval (ASI) of 18. Barren count in the low-nitrogen environment was 1 on a 1 to 10 scale, where 10 is least favorable.

Example 4

Low Nitrogen Seedling Assay Protocol

Seeds produced by transgenic plants are separated into transgene (heterozygous) and null seed using a seed color marker. Two different random assignments of treatments are made to each block of 54 pots, arranged as 6 rows of 9 columns and using 9 replicates of all treatments. In one case, null seed of 5 events of the same construct are mixed and used as control for comparison of the 5 positive events in this block, making up 6 treatment combinations in each block. In the second case, 3 transgenic positive treatments and their corresponding nulls are randomly assigned to the 54 pots of the block, making 6 treatment combinations for each block, containing 9 replicates of all treatment combinations. In the first case transgenic parameters are compared to a bulked construct null; in the second case, transgenic parameters are compared to the corresponding event null. In cases where there are 10, 15 or 20 events in a construct, the events are assigned in groups of 5 events, the variances calculated for each block of 54 pots, but the block null means are pooled across blocks before mean comparisons are made.

Two seeds of each treatment are planted in 4-inch-square pots containing TURFACE®-MVP on 8-inch, staggered centers and watered four times each day with a solution containing the following nutrients:

| | | | |
|---|---|---|---|
| 1 mM CaCl2 | 2 mM MgSO4 | 0.5 mM KH2PO4 | 83 ppm Sprint330 |
| 3 mM KCl | 1 mM KNO3 | 1 uM ZnSO4 | 1 uM MnCl2 |
| 3 uM H3BO4 | 1 uM MnCl2 | 0.1 uM CuSO4 | 0.1 uM NaMoO4 |

After emergence the plants are thinned to one seed per pot. Treatments routinely are planted on a Monday, emerge the following Friday and are harvested 18 days after planting. At harvest, plants are removed from the pots and the Turface® washed from the roots. The roots are separated from the shoot, placed in a paper bag and dried at 70° C. for 70 hr. The dried plant parts (roots and shoots) are weighed and placed in a 50 ml conical tube with approximately 20 5/32 inch steel balls and ground by shaking in a paint shaker. Approximately, 30 mg of the ground tissue (weight recorded for later adjustment) is hydrolyzed in 2 ml of 20% $H_2O_2$ and 6M $H_2SO_4$ for 30 min at 170° C. After cooling, water is added to 20 ml, mixed thoroughly, and a 50 μl aliquot removed and added to 950 μl 1M $Na_2CO_3$. The ammonia in this solution is used to estimate total reduced plant nitrogen by placing 100 μl of this solution in individual wells of a 96 well plate followed by adding 50 μl of OPA solution. Fluorescence, excitation=360 nM/emission=530 nM, is determined and compared to $NH_4Cl$ standards dissolved in a similar solution and treated with OPA solution.

OPA solution—5 ul Mercaptoethanol+1 ml OPA stock solution (make fresh, daily) OPA stock—50 mg o-phthadialdehyde (OPA—Sigma #P0657) dissolved in 1.5 ml methanol+4.4 ml 1M Borate buffer pH9.5 (3.09 g $H_3BO_4$+1 g NaOH in 50 ml water)+0.55 ml 20% SDS (make fresh weekly)

Using these data the following parameters are measured and means are compared to null mean parameters using a Student's t test:

Total Plant Biomass
Root Biomass
Shoot Biomass

Root/Shoot Ratio

Plant N concentration

Total Plant N

Variance is calculated within each block using a nearest neighbor calculation as well as by Analysis of Variance (ANOV) using a completely random design (CRD) model. An overall treatment effect for each block was calculated using an F statistic by dividing overall block treatment mean square by the overall block error mean square.

Example 5

Screening of Gaspe Bay Flint Derived Maize Lines Under Nitrogen Limiting Conditions Transgenic plants will contain two or three doses of Gaspe Flint-3 with one dose of GS3 (GS3/(Gaspe-3)2× or GS3/(Gaspe-3)3×) and will segregate 1:1 for a dominant transgene. Plants will be planted in TURFACE®, a commercial potting medium and watered four times each day with 1 mM $KNO_3$ growth medium and with 2 mM $KNO_3$ or higher, growth medium. Control plants grown in 1 mM $KNO_3$ medium will be less green, produce less biomass and have a smaller ear at anthesis. Results are analyzed for statistical significance.

Expression of a transgene will result in plants with improved plant growth in 1 mM $KNO_3$ when compared to a transgenic null. Thus biomass and greenness will be monitored during growth and compared to a transgenic null. Improvements in growth, greenness and ear size at anthesis will be indications of increased nitrogen utilization efficiency.

Example 6

Assays to Determine Alterations of Root Architecture in Maize

Transgenic maize plants are assayed for changes in root architecture at seedling stage, flowering time or maturity. Assays to measure alterations of root architecture of maize plants include, but are not limited to the methods outlined below. To facilitate manual or automated assays of root architecture alterations, corn plants can be grown in clear pots.

1) Root mass (dry weights). Plants are grown in Turface®, a growth medium that allows easy separation of roots. Oven-dried shoot and root tissues are weighed and a root/shoot ratio calculated.
2) Levels of lateral root branching. The extent of lateral root branching (e.g., lateral root number, lateral root length) is determined by sub-sampling a complete root system, imaging with a flat-bed scanner or a digital camera and analyzing with WinRHIZO™ software (Regent Instruments Inc.).
3) Root band width measurements. The root band is the band or mass of roots that forms at the bottom of greenhouse pots as the plants mature. The thickness of the root band is measured in mm at maturity as a rough estimate of root mass.
4) Nodal root count. The number of crown roots coming off the upper nodes can be determined after separating the root from the support medium (e.g., potting mix). In addition the angle of crown roots and/or brace roots can be measured. Digital analysis of the nodal roots and amount of branching of nodal roots form another extension to the aforementioned manual method.

All data taken on root phenotype are subjected to statistical analysis, normally a t-test to compare the transgenic roots with those of non-transgenic sibling plants. One-way ANOVA may also be used in cases where multiple events and/or constructs are involved in the analysis.

Example 7

NUE Assay of Plant Growth

Seeds of *Arabidopsis thaliana* (control and transgenic line), ecotype Columbia, are surface sterilized (Sanchez, et al., 2002) and then plated on to Murashige and Skoog (MS) medium containing 0.8% (w/v) Bacto™-Agar (Difco). Plates are incubated for 3 days in darkness at 4° C. to break dormancy (stratification) and transferred thereafter to growth chambers (Conviron, Manitoba, Canada) at a temperature of 20° C. under a 16-h light/8-h dark cycle. The average light intensity is 120 μE/m2/s. Seedling are grown for 12 days and then transferred to soil based pots. Potted plants are grown on a nutrient-free soil LB2 Metro-Mix® 200 (Scott's Sierra Horticultural Products, Marysville, Ohio, USA) in individual 1.5-in pots (*Arabidopsis* system; Lehle Seeds, Round Rock, Tex., USA) in growth chambers, as described above. Plants are watered with 0.6 or 6.5 mM potassium nitrate in the nutrient solution based on Murashige and Skoog (MS free Nitrogen) medium. The relative humidity is maintained around 70%. 16-18 days later plant shoots are collected for evaluation of biomass and SPAD readings.

Example 8

*Agrobacterium* Mediated Transformation into Maize

Maize plants can be transformed to overexpress a nucleic acid sequence of interest in order to examine the resulting phenotype.

*Agrobacterium*-mediated transformation of maize is performed essentially as described by Zhao, et al., (2006) *Meth. Mol. Biol.* 318:315-323 (see also, Zhao, et al., (2001) *Mol. Breed.* 8:323-333 and U.S. Pat. No. 5,981,840 issued Nov. 9, 1999, incorporated herein by reference). The transformation process involves bacterium inoculation, co-cultivation, resting, selection and plant regeneration.

1. Immature Embryo Preparation

Immature embryos are dissected from caryopses and placed in a 2 mL microtube containing 2 mL PHI-A medium.

2. *Agrobacterium* Infection and Co-Cultivation of Embryos 2.1 Infection Step

PHI-A medium is removed with 1 mL micropipettor and 1 mL *Agrobacterium* suspension is added. Tube is gently inverted to mix. The mixture is incubated for 5 min at room temperature.

2.2 Co-Culture Step

The *Agrobacterium* suspension is removed from the infection step with a 1 mL micropipettor. Using a sterile spatula the embryos are scraped from the tube and transferred to a plate of PHI-B medium in a 100×15 mm Petri dish. The embryos are oriented with the embryonic axis down on the surface of the medium. Plates with the embryos are cultured at 20° C., in darkness, for 3 days. L-Cysteine can be used in the co-cultivation phase. With the standard binary vector, the co-cultivation medium supplied with 100-400 mg/L L-cysteine is critical for recovering stable transgenic events.

3. Selection of Putative Transgenic Events

To each plate of PHI-D medium in a 100×15 mm Petri dish, 10 embryos are transferred, maintaining orientation, and the dishes are sealed with Parafilm®. The plates are incubated in darkness at 28° C. Actively growing putative events, as pale yellow embryonic tissue are expected to be visible in 6-8 weeks. Embryos that produce no events may be brown and necrotic, and little friable tissue growth is evident. Putative transgenic embryonic tissue is subcultured to fresh PHI-D plates at 2-3 week intervals, depending on growth rate. The events are recorded.

4. Regeneration of T0 Plants

Embryonic tissue propagated on PHI-D medium is subcultured to PHI-E medium (somatic embryo maturation medium); in 100×25 mm Petri dishes and incubated at 28° C., in darkness, until somatic embryos mature, for about 10-18 days. Individual, matured somatic embryos with well-defined scutellum and coleoptile are transferred to PHI-F embryo germination medium and incubated at 28° C. in the light (about 80 µE from cool white or equivalent fluorescent lamps). In 7-10 days, regenerated plants, about 10 cm tall, are potted in horticultural mix and hardened-off using standard horticultural methods.

Media for Plant Transformation

1. PHI-A: 4 g/L CHU basal salts, 1.0 mL/L 1000× Eriksson's vitamin mix, 0.5 mg/L thiamin HCL, 1.5 mg/L 2,4-D, 0.69 g/L L-proline, 68.5 g/L sucrose, 36 g/L glucose, pH 5.2. Add 100 µM acetosyringone, filter-sterilized before using.
2. PHI-B: PHI-A without glucose, increased 2,4-D to 2 mg/L, reduced sucrose to 30 g/L and supplemented with 0.85 mg/L silver nitrate (filter-sterilized), 3.0 g/L Gelrite®, 100 µM acetosyringone (filter-sterilized), pH 5.8.
3. PHI-C: PHI-B without Gelrite® and acetosyringone, reduced 2,4-D to 1.5 mg/L and supplemented with 8.0 g/L agar, 0.5 g/L Ms-morpholino ethane sulfonic acid (MES) buffer, 100 mg/L carbenicillin (filter-sterilized).
4. PHI-D: PHI-C supplemented with 3 mg/L bialaphos (filter-sterilized).
5. PHI-E: 4.3 g/L of Murashige and Skoog (MS) salts, (Gibco, BRL 11117-074), 0.5 mg/L nicotinic acid, 0.1 mg/L thiamine HCl, 0.5 mg/L pyridoxine HCl, 2.0 mg/L glycine, 0.1 g/L myo-inositol, 0.5 mg/L zeatin (Sigma, cat. no. Z-0164), 1 mg/L indole acetic acid (IAA), 26.4 µg/L abscisic acid (ABA), 60 g/L sucrose, 3 mg/L bialaphos (filter-sterilized), 100 mg/L carbenicillin (filter-sterilized), 8 g/L agar, pH 5.6.
6. PHI-F: PHI-E without zeatin, IAA, ABA; sucrose reduced to 40 g/L; replacing agar with 1.5 g/L Gelrite®; pH 5.6.

Plants can be regenerated from the transgenic callus by first transferring clusters of tissue to N6 medium supplemented with 0.2 mg per liter of 2,4-D. After two weeks the tissue can be transferred to regeneration medium (Fromm, et al., (1990) *Bio/Technology* 8:833-839).

Phenotypic analysis of transgenic T0 plants and T1 plants can be performed.

T1 plants can be analyzed for phenotypic changes. Using image analysis T1 plants can be analyzed for phenotypical changes in plant area, volume, growth rate and color analysis at multiple times during growth of the plants. Alteration in root architecture can be assayed as described herein.

Subsequent analysis of alterations in agronomic characteristics can be done to determine whether plants containing the nucleic acid sequence of interest have an improvement of at least one agronomic characteristic, when compared to the control (or reference) plants that have not been so transformed. The alterations may also be studied under various environmental conditions.

Expression constructs containing the nucleic acid sequence of interest that result in a significant alteration in root and/or shoot biomass, improved green color, larger ear at anthesis or yield will be considered evidence that the nucleic acid sequence of interest functions in maize to alter nitrogen use efficiency.

Example 9

Electroporation of *Agrobacterium tumefaciens* LBA4404

Electroporation competent cells (40 µl), such as *Agrobacterium tumefaciens LBA*4404 (containing PHP10523), are thawed on ice (20-30 min). PHP10523 contains VIR genes for T-DNA transfer, an *Agrobacterium* low copy number plasmid origin of replication, a tetracycline resistance gene and a cos site for in vivo DNA biomolecular recombination. Meanwhile the electroporation cuvette is chilled on ice. The electroporator settings are adjusted to 2.1 kV.

A DNA aliquot (0.5 µL (U.S. Pat. No. 7,087,812) parental DNA at a concentration of 0.2 µg-1.0 µg in low salt buffer or twice distilled $H_2O$) is mixed with the thawed *Agrobacterium* cells while still on ice. The mix is transferred to the bottom of electroporation cuvette and kept at rest on ice for 1-2 min. The cells are electroporated (Eppendorf electroporator 2510) by pushing "Pulse" button twice (ideally achieving a 4.0 msec pulse). Subsequently 0.5 ml 2×YT medium (or SOC medium) are added to cuvette and transferred to a 15 ml Falcon tube. The cells are incubated at 28-30° C., 200-250 rpm for 3 h.

Aliquots of 250 µl are spread onto #30B (YM+50 µg/mL Spectinomycin) plates and incubated 3 days at 28-30° C. To increase the number of transformants one of two optional steps can be performed:

Option 1: overlay plates with 30 µl of 15 mg/ml Rifampicin. LBA4404 has a chromosomal resistance gene for Rifampicin. This additional selection eliminates some contaminating colonies observed when using poorer preparations of LBA4404 competent cells.

Option 2: Perform two replicates of the electroporation to compensate for poorer electrocompetent cells.

Identification of Transformants:

Four independent colonies are picked and streaked on AB minimal medium plus 50 mg/mL Spectinomycin plates (#12S medium) for isolation of single colonies. The plates are incubated at 28° C. for 2-3 days.

A single colony for each putative co-integrate is picked and inoculated with 4 ml #60A with 50 mg/l Spectinomycin. The mix is incubated for 24 h at 28° C. with shaking Plasmid DNA from 4 ml of culture is isolated using Qiagen Miniprep+ optional PB wash. The DNA is eluted in 30 µl. Aliquots of 2 µl are used to electroporate 20 µl of DH10b+20 µl of dd $H_2O$ as per above.

Optionally a 15 µl aliquot can be used to transform 75-100 µl of Invitrogen™ Library Efficiency DH5α. The cells are spread on LB medium plus 50 mg/mL Spectinomycin plates (#34T medium) and incubated at 37° C. overnight.

Three to four independent colonies are picked for each putative co-integrate and inoculated 4 ml of 2×YT (#60A) with 50 µg/ml Spectinomycin. The cells are incubated at 37° C. overnight with shaking The plasmid DNA is isolated from 4 ml of culture using QIAprep® Miniprep with optional PB wash (elute in 50 µl) and 8 µl are used for digestion with SalI (using JT parent and PHP10523 as controls).

Three more digestions using restriction enzymes BamHI, EcoRI and HindIII are performed for 4 plasmids that represent 2 putative co-integrates with correct SalI digestion pattern (using parental DNA and PHP10523 as controls). Electronic gels are recommended for comparison.

Example 10

Particle-Mediated Bombardment for Transformation of Maize

A vector can be transformed into embryogenic maize callus by particle bombardment, generally as described by Tomes, et al., Plant Cell, Tissue and Organ Culture: Fundamental Methods, Eds. Gamborg and Phillips, Chapter 8, pgs. 197-213 (1995) and as briefly outlined below. Transgenic maize plants can be produced by bombardment of embryogenically responsive immature embryos with tungsten particles associated with DNA plasmids. The plasmids typically comprise or consist of a selectable marker and an unselected structural gene, or a selectable marker and an ACC synthase polynucleotide sequence or subsequence, or the like.

Preparation of Particles

Fifteen mg of tungsten particles (General Electric), 0.5 to 1.8μ, preferably 1 to 1.8μ, and most preferably 1μ, are added to 2 ml of concentrated nitric acid. This suspension is sonicated at 0° C. for 20 minutes (Branson Sonifier Model 450, 40% output, constant duty cycle). Tungsten particles are pelleted by centrifugation at 10000 rpm (Biofuge) for one minute and the supernatant is removed. Two milliliters of sterile distilled water are added to the pellet, and brief sonication is used to resuspend the particles. The suspension is pelleted, one milliliter of absolute ethanol is added to the pellet and brief sonication is used to resuspend the particles. Rinsing, pelleting and resuspending of the particles are performed two more times with sterile distilled water and finally the particles are resuspended in two milliliters of sterile distilled water. The particles are subdivided into 250-μl aliquots and stored frozen.

Preparation of Particle-Plasmid DNA Association

The stock of tungsten particles are sonicated briefly in a water bath sonicator (Branson Sonifier Model 450, 20% output, constant duty cycle) and 50 μl is transferred to a microfuge tube. The vectors are typically cis: that is, the selectable marker and the gene (or other polynucleotide sequence) of interest are on the same plasmid.

Plasmid DNA is added to the particles for a final DNA amount of 0.1 to 10 μg in 10 μL total volume and briefly sonicated. Preferably, 10 μg (1 μg/μL in TE buffer) total DNA is used to mix DNA and particles for bombardment. Fifty microliters (50 μL) of sterile aqueous 2.5 M $CaCl_2$ are added and the mixture is briefly sonicated and vortexed. Twenty microliters (20 μL) of sterile aqueous 0.1 M spermidine are added and the mixture is briefly sonicated and vortexed. The mixture is incubated at room temperature for 20 minutes with intermittent brief sonication. The particle suspension is centrifuged and the supernatant is removed. Two hundred fifty microliters (250 μL) of absolute ethanol are added to the pellet, followed by brief sonication. The suspension is pelleted, the supernatant is removed and 60 μl of absolute ethanol are added. The suspension is sonicated briefly before loading the particle-DNA agglomeration onto macrocarriers.

Preparation of Tissue

Immature embryos of maize are the target for particle bombardment-mediated transformation. Ears from F1 plants are selfed or sibbed and embryos are aseptically dissected from developing caryopses when the scutellum first becomes opaque. This stage occurs about 9 13 days post-pollination and most generally about 10 days post-pollination, depending on growth conditions. The embryos are about 0.75 to 1.5 millimeters long. Ears are surface sterilized with 20 50% Clorox® for 30 minutes, followed by three rinses with sterile distilled water.

Immature embryos are cultured with the scutellum oriented upward, on embryogenic induction medium comprised of N6 basal salts, Eriksson vitamins, 0.5 mg/l thiamine HCl, 30 gm/l sucrose, 2.88 gm/l L-proline, 1 mg/l 2,4-dichlorophenoxyacetic acid, 2 gm/l Gelrite® and 8.5 mg/l $AgNO_3$. Chu, et al., (1975) *Sci. Sin.* 18:659; Eriksson, (1965) *Physiol. Plant* 18:976. The medium is sterilized by autoclaving at 121° C. for 15 minutes and dispensed into 100×25 mm Petri dishes. $AgNO_3$ is filter-sterilized and added to the medium after autoclaving. The tissues are cultured in complete darkness at 28° C. After about 3 to 7 days, most usually about 4 days, the scutellum of the embryo swells to about double its original size and the protuberances at the coleorhizal surface of the scutellum indicate the inception of embryogenic tissue. Up to 100% of the embryos display this response, but most commonly, the embryogenic response frequency is about 80%.

When the embryogenic response is observed, the embryos are transferred to a medium comprised of induction medium modified to contain 120 gm/l sucrose. The embryos are oriented with the coleorhizal pole, the embryogenically responsive tissue, upwards from the culture medium. Ten embryos per Petri dish are located in the center of a Petri dish in an area about 2 cm in diameter. The embryos are maintained on this medium for 3 to 16 hours, preferably 4 hours, in complete darkness at 28° C. just prior to bombardment with particles associated with plasmid DNAs containing the selectable and unselectable marker genes.

To effect particle bombardment of embryos, the particle-DNA agglomerates are accelerated using a DuPont PDS-1000 particle acceleration device. The particle-DNA agglomeration is briefly sonicated and 10 μl are deposited on macrocarriers and the ethanol is allowed to evaporate. The macrocarrier is accelerated onto a stainless-steel stopping screen by the rupture of a polymer diaphragm (rupture disk). Rupture is effected by pressurized helium. The velocity of particle-DNA acceleration is determined based on the rupture disk breaking pressure. Rupture disk pressures of 200 to 1800 psi are used, with 650 to 1100 psi being preferred and about 900 psi being most highly preferred. Multiple disks are used to effect a range of rupture pressures.

The shelf containing the plate with embryos is placed 5.1 cm below the bottom of the macrocarrier platform (shelf #3). To effect particle bombardment of cultured immature embryos, a rupture disk and a macrocarrier with dried particle-DNA agglomerates are installed in the device. The He pressure delivered to the device is adjusted to 200 psi above the rupture disk breaking pressure. A Petri dish with the target embryos is placed into the vacuum chamber and located in the projected path of accelerated particles. A vacuum is created in the chamber, preferably about 28 in Hg. After operation of the device, the vacuum is released and the Petri dish is removed.

Bombarded embryos remain on the osmotically-adjusted medium during bombardment, and 1 to 4 days subsequently. The embryos are transferred to selection medium comprised of N6 basal salts, Eriksson vitamins, 0.5 mg/l thiamine HCl, 30 gm/l sucrose, 1 mg/l 2,4-dichlorophenoxyacetic acid, 2 gm/l Gelrite®, 0.85 mg/l Ag $NO_3$ and 3 mg/l bialaphos (Herbiace, Meiji). Bialaphos is added filter-sterilized. The embryos are subcultured to fresh selection medium at 10 to 14 day intervals. After about 7 weeks, embryogenic tissue, putatively transformed for both selectable and unselected marker genes, proliferates from a fraction of the bombarded embryos. Putative transgenic tissue is rescued and that tissue derived from individual embryos is considered to be an event and is propagated independently on selection medium. Two cycles of clonal propagation are achieved by visual selection for the smallest contiguous fragments of organized embryogenic tissue.

A sample of tissue from each event is processed to recover DNA. The DNA is restricted with a restriction endonuclease and probed with primer sequences designed to amplify DNA sequences overlapping the ACC synthase and non-ACC synthase portion of the plasmid. Embryogenic tissue with amplifiable sequence is advanced to plant regeneration.

For regeneration of transgenic plants, embryogenic tissue is subcultured to a medium comprising MS salts and vitamins (Murashige and Skoog, (1962) *Physiol. Plant* 15:473), 100 mg/l myo-inositol, 60 gm/l sucrose, 3 gm/l Gelrite®, 0.5 mg/l zeatin, 1 mg/l indole-3-acetic acid, 26.4 ng/l cis-trans-abscissic acid and 3 mg/l bialaphos in 100×25 mm Petri dishes and is incubated in darkness at 28° C. until the development of well-formed, matured somatic embryos is seen. This requires about 14 days. Well-formed somatic embryos are opaque and cream-colored and are comprised of an identifiable scutellum and coleoptile. The embryos are individually subcultured to a germination medium comprising MS salts and vitamins, 100 mg/l myo-inositol, 40 gm/l sucrose and 1.5 gm/l Gelrite® in 100×25 mm Petri dishes and incubated under a 16 hour light:8 hour dark photoperiod and 40 meinsteinsm$^{-2}$sec$^{-1}$ from cool-white fluorescent tubes. After about 7 days, the somatic embryos germinate and produce a well-defined shoot and root. The individual plants are subcultured to germination medium in 125×25 mm glass tubes to allow further plant development. The plants are maintained under a 16 hour light:8 hour dark photoperiod and 40 meinsteinsm$^{-2}$sec$^{-1}$ from cool-white fluorescent tubes. After about 7 days, the plants are well-established and are transplanted to horticultural soil, hardened off and potted into commercial greenhouse soil mixture and grown to sexual maturity in a greenhouse. An elite inbred line is used as a male to pollinate regenerated transgenic plants.

Example 11

Soybean Embryo Transformation

Soybean embryos are bombarded with a plasmid comprising a preferred promoter operably linked to a heterologous nucleotide sequence comprising an ACC synthase polynucleotide sequence or subsequence (e.g., SEQ ID NOS: 1 and 2), as follows. To induce somatic embryos, cotyledons of 3 5 mm in length are dissected from surface-sterilized, immature seeds of the soybean cultivar A2872, then cultured in the light or dark at 26° C. on an appropriate agar medium for six to ten weeks. Somatic embryos producing secondary embryos are then excised and placed into a suitable liquid medium. After repeated selection for clusters of somatic embryos that multiply as early, globular-staged embryos, the suspensions are maintained as described below.

Soybean embryogenic suspension cultures can be maintained in 35 ml liquid media on a rotary shaker, 150 rpm, at 26° C. with fluorescent lights on a 16:8 hour day/night schedule. Cultures are sub-cultured every two weeks by inoculating approximately 35 mg of tissue into 35 ml of liquid medium.

Soybean embryogenic suspension cultures may then be transformed by the method of particle gun bombardment (Klein, et al., (1987) *Nature* (*London*) 327:70-73, U.S. Pat. No. 4,945,050). A DuPont Biolistic™ PDS1000/HE instrument (helium retrofit) can be used for these transformations.

A selectable marker gene that can be used to facilitate soybean transformation is a transgene composed of the 35S promoter from Cauliflower Mosaic Virus (Odell, et al., (1985) *Nature* 313:810-812), the hygromycin phosphotransferase gene from plasmid pJR225 (from *E. coli*; Gritz, et al., (1983) *Gene* 25:179-188) and the 3' region of the nopaline synthase gene from the T-DNA of the Ti plasmid of *Agrobacterium tumefaciens*. The expression cassette of interest, comprising the preferred promoter and a heterologous ACC synthase polynucleotide, can be isolated as a restriction fragment. This fragment can then be inserted into a unique restriction site of the vector carrying the marker gene.

To 50 μl of a 60 mg/ml 1 μm gold particle suspension is added (in order): 5 μl DNA (1 μg/μl), 20 μl spermidine (0.1 M) and 50 μl $CaCl_2$ (2.5 M). The particle preparation is then agitated for three minutes, spun in a microfuge for 10 seconds and the supernatant removed. The DNA-coated particles are then washed once in 400 μl 70% ethanol and resuspended in 40 μl of anhydrous ethanol. The DNA/particle suspension can be sonicated three times for one second each. Five microliters of the DNA-coated gold particles are then loaded on each macro carrier disk.

Approximately 300 400 mg of a two-week-old suspension culture is placed in an empty 60×5 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 12

Composition of cDNA Libraries; Isolation and Sequencing of cDNA Clones cDNA libraries representing mRNAs from various tissues of *Canna edulis* (*Canna*), *Momordica charantia* (balsam pear), *Brassica* (mustard), *Cyamopsis tetragonoloba* (guar), *Zea mays* (maize), *Oryza sativa* (rice), *Glycine max* (soybean), *Helianthus annuus* (sunflower) and *Triticum aestivum* (wheat) are prepared. cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.).

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke, (1994) *Nucleic Acids Res.* 22:3765-3772). The in vitro transposition system places unique binding sites randomly throughout a population of large DNA molecules. Multiple subclones are randomly selected from each transposition reaction, plasmid DNAs are prepared via alkaline lysis and templates are sequenced (ABI Prism dye-terminator ReadyReaction mix) outward from the transposition event site, utilizing unique primers specific to the binding sites within the transposon.

Sequence data is collected (ABI Prism Collections) and assembled using Phred and Phrap (Ewing, et al., (1998) *Genome Res.* 8:175-185; Ewing and Green, (1998) *Genome Res.* 8:186-194). The resulting DNA fragment is ligated into a pBluescript vector using a commercial kit and following the manufacturer's protocol. This kit is selected from many available from several vendors including Invitrogen™ (Carlsbad, Calif.), Promega Biotech (Madison, Wis.) and Gibco-BRL (Gaithersburg, Md.). The plasmid DNA is isolated by alkaline lysis method and submitted for sequencing and assembly using Phred/Phrap, as above.

Example 13

Identification of cDNA Clones cDNA clones encoding ACC synthase-like polypeptides were identified by conducting BLAST (Basic Local Alignment Search Tool; Altschul, et al., (1993) *J. Mol. Biol.* 215: 403-410; see also, the explanation of the BLAST algorithm on the world wide web site for the National Center for Biotechnology Information at the National Library of Medicine of the National Institutes of Health) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL and DDBJ databases). The cDNA sequences obtained as described in Example 11 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States, (1993) *Nat. Genet.* 3:266-272) provided by the NCBI. For convenience, the P-values (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

ESTs submitted for analysis are compared to the Genbank database as described above. ESTs that contain sequences more 5- or 3-prime can be found by using the BLASTn algorithm (Altschul, et al., (1997) *Nucleic Acids Res.* 25:3389-3402.) against the Du Pont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5- or 3-prime direction. Once the most 5-prime EST is identified, its complete sequence can be determined by Full Insert Sequencing. Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species and for codon degeneracy.

Example 14

Preparation of a Plant Expression Vector

A PCR product obtained using methods that are known by one skilled in the art can be combined with the Gateway® donor vector, such as pDONR™/Zeo (Invitrogen™). Using the Invitrogen™ Gateway® Clonase™ technology, the homologous gene can then be transferred to a suitable destination vector to obtain a plant expression vector for use with *Arabidopsis* and corn.

Example 15

Variants of ACC Synthase Sequences

A. Variant Nucleotide Sequences of ACC Synthase Proteins that do not Alter the Encoded Amino Acid Sequence The ACC synthase nucleotide sequences are used to generate variant nucleotide sequences having the nucleotide sequence of the open reading frame with about 70%, 75%, 80%, 85%, 90% and 95% nucleotide sequence identity when compared to the starting unaltered ORF nucleotide sequence of the corresponding SEQ ID NO. These functional variants are generated using a standard codon table. While the nucleotide sequences of the variants are altered, the amino acid sequence encoded by the open reading frames does not change.

B. Variant Amino Acid Sequences of ACC Synthase Polypeptides

Variant amino acid sequences of the ACC synthase polypeptides are generated. In this example, one amino acid is altered. Specifically, the open reading frames are reviewed to determine the appropriate amino acid alteration. The selection of the amino acid to change is made by consulting the protein alignment (with the other orthologs and other gene family members from various species). An amino acid is selected that is deemed not to be under high selection pressure (not highly conserved) and which is rather easily substituted by an amino acid with similar chemical characteristics (i.e., similar functional side-chain). Using the protein alignment, an appropriate amino acid can be changed. Once the targeted amino acid is identified, the procedure outlined in the following section C is followed. Variants having about 70%, 75%, 80%, 85%, 90% and 95% nucleic acid sequence identity are generated using this method.

C. Additional Variant Amino Acid Sequences of ACC Synthase Polypeptides

In this example, artificial protein sequences are created having 80%, 85%, 90% and 95% identity relative to the reference protein sequence. This latter effort requires identifying conserved and variable regions from the alignment and then the judicious application of an amino acid substitutions table. These parts will be discussed in more detail below.

Largely, the determination of which amino acid sequences are altered is made based on the conserved regions among ACC synthase protein or among the other ACC synthase polypeptides. It is recognized that conservative substitutions can be made in the conserved regions below without altering function. In addition, one of skill will understand that functional variants of the ACC synthase sequence of the invention can have minor non-conserved amino acid alterations in the conserved domain.

Artificial protein sequences are then created that are different from the original in the intervals of 80-85%, 85-90%, 90-95% and 95-100% identity. Midpoints of these intervals are targeted, with liberal latitude of plus or minus 1%, for example. The amino acids substitutions will be effected by a custom Perl script. The substitution table is provided below in Table 3.

TABLE 3

Substitution Table

| Amino Acid | Strongly Similar and Optimal Substitution | Rank of Order to Change | Comment |
|---|---|---|---|
| I | L, V | 1 | 50:50 substitution |
| L | I, V | 2 | 50:50 substitution |
| V | I, L | 3 | 50:50 substitution |
| A | G | 4 | |
| G | A | 5 | |
| D | E | 6 | |
| E | D | 7 | |
| W | Y | 8 | |
| Y | W | 9 | |
| S | T | 10 | |
| T | S | 11 | |
| K | R | 12 | |
| R | K | 13 | |
| N | Q | 14 | |
| Q | N | 15 | |
| F | Y | 16 | |
| M | L | 17 | First methionine cannot change |
| H | | Na | No good substitutes |
| C | | Na | No good substitutes |
| P | | Na | No good substitutes |

First, any conserved amino acids in the protein that should not be changed is identified and "marked off" for insulation from the substitution. The start methionine will of course be added to this list automatically. Next, the changes are made.

H, C and P are not changed in any circumstance. The changes will occur with isoleucine first, sweeping N-terminal to C-terminal. Then leucine, and so on down the list until the desired target it reached. Interim number substitutions can be made so as not to cause reversal of changes. The list is ordered 1-17, so start with as many isoleucine changes as needed before leucine, and so on down to methionine. Clearly many amino acids will in this manner not need to be changed. L, I and V will involve a 50:50 substitution of the two alternate optimal substitutions.

The variant amino acid sequences are written as output. Perl script is used to calculate the percent identities. Using this procedure, variants of the ACC synthase polypeptides are generating having about 80%, 85%, 90% and 95% amino acid identity to the starting unaltered ORF nucleotide sequence of SEQ ID NO: 1, 2 or 3.

Example 16

ACS Sequences from Genbank

The following are examples of publicly available ACS genes from Genbank which may be used for various crop species according to the invention.

TABLE 4

| Crop | Genbank Accession Number | SEQ ID NO |
|---|---|---|
| *Arabidopsis* | NM_116016-ACS1 | 16 |
| *Arabidopsis* | NM_100030-ACS2 | 17 |
| *Arabidopsis* | NM_179241-ACS2 | 18 |
| *Arabidopsis* | AF334719-ACS2 | 19 |
| *Arabidopsis* | NM_122719-ACS-3 | 20 |
| *Arabidopsis* | NM_127846-ACS4 | 21 |
| *Arabidopsis* | AF332404-ACS4 | 22 |
| *Arabidopsis* | AK229087-ACS5 | 23 |
| *Arabidopsis* | AF334720-ACS5 | 24 |
| *Arabidopsis* | NM_125977-ACS5 | 25 |
| *Arabidopsis* | NM_117199-ACS6 | 26 |
| *Arabidopsis* | NM_118753-ACS7 | 27 |
| *Arabidopsis* | NM_119939-ACS8 | 28 |
| *Arabidopsis* | AF334712-ACS8 | 29 |
| *Arabidopsis* | AF332391-ACS9 | 30 |
| *Arabidopsis* | NM_104974-ACS10 | 31 |
| *Arabidopsis* | NM_116873-ACS11 | 32 |
| *Oryza sativa* | Z27244-ACC synthase | 33 |
| *Oryza sativa* | Z27243-ACC synthase | 34 |
| *Oryza sativa* | Z27242-ACC synthase | 35 |
| *Oryza sativa* | Z27241-ACC synthase | 36 |
| *Oryza sativa* | U65704-ACS5 | 37 |
| *Oryza sativa* | U65703-ACS4 | 38 |
| *Oryza sativa* | U65702-ACS3 | 39 |
| *Oryza sativa* | U65701-ACS2 | 40 |
| *Oryza sativa* | M96673-(ACC1 synthase) | 41 |
| *Oryza sativa* | M96672-(ACC1 synthase) | 42 |
| *Glycine max* | EU604829-ACS | 43 |
| *Glycine max* | X67100-ACC synthase | 44 |
| *Glycine max* | DQ273841-ACS | 45 |
| *Glycine max* | DQ273840-ACS | 46 |
| Potato | Z27235-ACS2 | 47 |
| Potato | Z27234-ACS | 48 |
| Potato | L20634-ACS | 49 |
| Potato | U70842-ACS | 50 |

TABLE 5

Sequence Listing Summary

| SEQ ID NO | NT or PP | DESCRIPTION |
|---|---|---|
| 1 | nucleotide | maize ACS 2 (genomic) |
| 2 | nucleotide | maize ACS 6 (genomic) |
| 3 | nucleotide | maize ACS 7 (genomic) |
| 4 | nucleotide | maize ACS 2(cDNA) |
| 5 | nucleotide | maize ACS 6(cDNA) |
| 6 | nucleotide | maize ACS 7(cDNA) |
| 7 | polypeptide | maize ACS 2 |
| 8 | polypeptide | maize ACS 6 |
| 9 | polypeptide | maize ACS 7 |
| 10 | nucleotide | maize ACC |
| 11 | polypeptide | maize ACC |
| 12 | nucleotide | ACS 2 RNAi hairpin TR1 |
| 13 | nucleotide | ACS 2 RNAi hairpin TR2 |
| 14 | nucleotide | ACS 6 RNAi hairpin TR1 |
| 15 | nucleotide | ACS 6 RNAi hairpin TR2 |

TABLE 5-continued

Sequence Listing Summary

| SEQ ID NO | NT or PP | DESCRIPTION |
|---|---|---|
| 16 | nucleotide | NM_116016-ACS1 |
| 17 | nucleotide | NM_100030ACS2 |
| 18 | nucleotide | NM179241-ACS2 |
| 19 | nucleotide | AF334719ACS2 |
| 20 | nucleotide | NM_122719ACS3 |
| 21 | nucleotide | NM_127846-ACS4 |
| 22 | nucleotide | AF332404-ACS4 |
| 23 | nucleotide | AK229087ACS5 |
| 24 | nucleotide | AF334720ACS5 |
| 25 | nucleotide | NM_125977-ACS5 |
| 26 | nucleotide | NM_117199-ACS6 |
| 27 | nucleotide | NM_118753ACS7 |
| 28 | nucleotide | NM_119939-ACS8 |
| 29 | nucleotide | AF334712-ACS8 |
| 30 | nucleotide | AF332391-ACS9 |
| 31 | nucleotide | NM_104974-ACS10 |
| 32 | nucleotide | NM_116873ACS11 |
| 33 | nucleotide | Z27244 ACC synthase |
| 34 | nucleotide | Z27243 ACC synthase |
| 35 | nucleotide | Z27242 ACC synthase |
| 36 | nucleotide | Z27241-ACC synthase |
| 37 | nucleotide | U65704-ACS5 |
| 38 | nucleotide | U65703ACS4 |
| 39 | nucleotide | U65702ACS3 |
| 40 | nucleotide | U65701ACS2 |
| 41 | nucleotide | M96673 (ACC1synthase) |
| 42 | nucleotide | M96672 (ACC1synthase) |
| 43 | nucleotide | EU604829-ACS |
| 44 | nucleotide | X67100-ACC synthase |
| 45 | nucleotide | DQ273841-ACS |
| 46 | nucleotide | DQ273840-ACS |
| 47 | nucleotide | Z27235-ACS2 |
| 48 | nucleotide | Z27234-ACS |
| 49 | nucleotide | L20634-ACS |
| 50 | nucleotide | U70842-ACS |
| 51 | nucleotide | improved ACS 6 RNAi hairpin TR3 (3272-3776 of SEQ ID NO: 54) |
| 52 | nucleotide | improved ACS 6 RNAi hairpin TR4 (4332-4874 of SEQ ID NO: 54) |
| 53 | nucleotide | Entire improved ACS6 inhibition plasmid construct |
| 54 | nucleotide | Fragment of improved ACS6 inhibition construct comprising TR3, ADH1 intron 1, and TR4 (3272-4874 of SEQ ID NO: 53) |
| 55 | nucleotide | Fragment of improved ACS6 inhibition construct comprising UBIZm promoter, UBIZm 5' UTR, UBI1Zm Intron 1, TR3, ADH1 intron 1, and TR4 (1218-4874 of SEQ ID NO: 53) |
| 56 | nucleotide | Fragment of improved ACS6 inhibition construct comprising UBIZm promoter, UBIZm 5'UTR, UBIZm Intron 1, TR3, ADH1 intron 1, TR4, ATTB2, FRT12, UBIZm promoter, UBIZm 5'UTR, UBIZm Intron 1, MO-PAT, and PinII terminator (1218-7989 of SEQ ID NO: 53) |
| 57 | nucleotide | Complete improved ACS6 inhibition expression cassette (1-8350 of SEQ ID NO: 53) |

All publications and patent applications in this specification are indicative of the level of ordinary skill in the art to which this invention pertains. All publications and patent applications are herein incorporated by reference to the same extent as if each individual publication or patent application was specifically and individually indicated by reference.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method of improving nitrogen stress tolerance in a maize plant comprising:

a) inhibiting ethylene synthesis in a plant by introducing into a maize plant a heterologous polynucleotide that reduces the activity of 1-aminocyclopropane-1-carboxcylic acid (ACC) synthase 6 (ACS6) upon expression of said heterologous polynucleotide;

wherein said heterologous polynucleotide comprises a nucleic acid selected from the group consisting of:

i) a nucleic acid comprising a maize ACS6 nucleic acid;

ii) a nucleic acid comprising at least 15 contiguous nucleotides of the complement of a maize ACS6 nucleic acid; and iii) a nucleic acid encoding a transcript that is capable of forming a double-stranded RNA and mediating RNA interference of a maize ACS6 nucleic acid, wherein said nucleic acid comprises:

(1) a first nucleotide sequence comprising at least 21 contiguous nucleotides of a maize ACS6 nucleic acid; and (2) a second nucleotide sequence comprising the complement of said first nucleotide sequence;

b) growing said plant under nitrogen limiting conditions; and c) selecting plants exhibiting greater tolerance to low nitrogen levels whereby said heterologous polynucleotide is expressed and said plant demonstrates improved nitrogen stress tolerance comprising increased grain yield compared to a control plant.

2. The method of claim 1, wherein said heterologous polynucleotide comprises a nucleotide sequence selected from the group consisting of:

a) the nucleotide sequence set forth in SEQ ID NO:2 or 5, or a complete complement thereof;

b) a nucleotide sequence having at least 90% sequence identity to SEQ ID NO:2 or 5, or a complete complement thereof;

c) a nucleotide sequence encoding the polypeptide sequence of SEQ ID NO:8 or a complete complement thereof;

d) a nucleotide sequence encoding a polypeptide sequence having at least 95% identity to SEQ ID NO:8 or a complete complement thereof;

e) a nucleotide sequence comprising at least 15 contiguous nucleotides of the complement of SEQ ID NO:2 or 5; and f) a nucleotide sequence encoding a transcript that is capable of forming a double-stranded RNA and mediating RNA interference of an ACS6 nucleic acid, wherein said nucleotide sequence comprises at least 21 contiguous nucleotides of SEQ ID NO:2 or 5 and the complement thereof.

3. The method of claim 2, wherein said plant comprises an mRNA transcribed from a polynucleotide having the sequence set forth in SEQ ID NO: 2 or 5, wherein expression of said heterologous polynucleotide inhibits the expression of the mRNA.

4. The method of claim 1, wherein said heterologous polynucleotide is operably linked to a promoter that functions in plants.

5. The method of claim 4, wherein the promoter that functions in plants is a tissue-preferred promoter, tissue-specific promoter, or an inducible promoter.

6. The method of claim 1, wherein the heterologous polynucleotide is introduced by a method selected from one of the following: electroporation, micro-projectile bombardment and *Agrobacterium*-mediated transfer.

7. A method for improving nitrogen stress tolerance under low nitrogen conditions, said method comprising:

a) evaluating environmental conditions of an area of cultivation for nitrogen limiting conditions;

b) selecting a transgenic maize seed or transgenic maize plant exhibiting greater tolerance to low nitrogen levels, said transgenic maize seed or transgenic maize plant having a reduced activity of ACS6 and comprising the heterologous polynucleotide of claim 1;

c) planting said selected transgenic maize seed or transgenic maize plant in an area of cultivation having nitrogen limiting conditions; and d) harvesting seed from said selected transgenic maize plants or harvesting said selected transgenic maize plants, wherein said selected transgenic maize plants have increased grain yield, relative to a control.

8. The method of claim 7, wherein said plant comprises an mRNA transcribed from a polynucleotide having the sequence set forth in SEQ ID NO: 2 or 5, wherein expression of said heterologous polynucleotide inhibits the expression of the mRNA.

9. The method of claim 7, wherein said heterologous polynucleotide comprises a nucleotide sequence selected from the group consisting of:

a) the nucleotide sequence set forth in SEQ ID NO:2 or 5, or a complete complement thereof;

b) a nucleotide sequence having at least 90% sequence identity to SEQ ID NO:2 or 5, or a complete complement thereof;

c) a nucleotide sequence encoding the polypeptide sequence of SEQ ID NO:8 or a complete complement thereof;

d) a nucleotide sequence encoding a polypeptide sequence having at least 95% identity to SEQ ID NO:8;

e) a nucleotide sequence comprising at least 15 contiguous nucleotides of the complement of SEQ ID NO:2 or 5; and f) a nucleotide sequence encoding a transcript that is capable of forming a double-stranded RNA and mediating RNA interference of an ACC synthase nucleic acid, wherein said nucleotide sequence comprises at least 21 contiguous nucleotides of SEQ ID NO:2 or 5 and the complement thereof.

10. The method of claim 7, wherein said heterologous polynucleotide is operably linked to a promoter that functions in plants.

11. The method of claim 10, wherein the promoter that functions in plants is a tissue-preferred promoter, tissue-specific promoter, or an inducible promoter.

* * * * *

SEQUENCE LISTING

```
<160> NUMBER OF SEQ ID NOS: 57

<210> SEQ ID NO 1
<211> LENGTH: 5115
<212> TYPE: DNA
<213> ORGANISM: Zea mays

<400> SEQUENCE: 1

aaacttcata ccggtcggtg ccttacgttc tctggcgttc ttatcctttc ctccgctttt      60

agtcgatgat tatagtagtt tctacaacaa gctttcaacg ccattgacta ttttttcccc     120

cattgaaaac gaacaccacc attgacactg ataaatgtag tacagcattt gacaacatac     180

tttcctagaa agtaaccagc agagactgga cgctacgtac taccacacca ttggagcagc     240

caatttaatc gtgtatagaa ctccgtatcg aaatttgtct gtgaatggac cttcatttgc     300

atctaggtct agtacaatgg atttcgaaca ggacagcgcc gatctggcaa tacacacacg     360

cacgacgtag cacagctgtt cttcgttcca cgcgttaatt gaaggcaaag cgactgtagt     420
```

-continued

```
tgctgttggt ggccaagttg tttaatgcta tagtagcagc cagtcactcc tagggcaaat    480
tttaggactt ttgcattgca ttgccgccat gtagaggttg actgcacacc gagaatatcg    540
agcattcatt aggctccttg acttgttgct gtgaactccg gccatctgtc acagtacgta    600
tatgaccaga tcggcaccat ttgtctcggc ctgacaatct cgcgcgccat tggccatgca    660
aagctgtcct gccgttcgga gagactagag agccagttgg caaattgaca tttgcgatag    720
gtggggcggc tttgactatg acatgatgac agatccagat ggtcctccgc tagtcccccc    780
gagcccgagg acagcacact agctcacacg aactgacagc gcggaggagg acacgtaccg    840
ggatgacacc gccacccatt tgctggcaag ccggggtgcg ccggcggttc aggttgaatc    900
cttcctaatg gtcgtgctag caaaccccgc aagctcagtg cgggtccaaa acccattaat    960
tatcccacaa agccgccgtt agacgtagaa tcgacgccgc gcgccacggc cggcggcggc   1020
tacctggctc ttaccaccat cattcgcttg tccgttccgt cgcccccgcc accctctcag   1080
agatggaggc ggttaagtgc ctgtcgacta ttgcagaacg tcgtcaggct cgctagttcg   1140
accgagcatc ctagatacat aatccaaatt ccgctcggcg attataggag ggtgatagta   1200
ctgagtacag ggcgaaaaac gttgaaaagg tcagcgaggc ccccacatgt ctcccccggt   1260
cgcgttcgca ttcaacaccc tctgcgctgc gtttcatgga agtttccagc agccacgccc   1320
acgcgcatgg acgcggctga tcttataaag gtggcgcgcg tcccaacctc gggagccatc   1380
atttcaccag aagctgcaaa ttgcaagctc tcctccctag ctagcctctc cagcagccca   1440
accacagcct gcagctgcag ctcgcgttgg cacagcgccg cctgaacgcg tgctaattta   1500
agctctgtcg tagctcaacg cggccgccgg gctttcgccg acgacgtcaa aatggccggt   1560
ggtagcagtg ccgagcagct cctatccagg atcgcctccg gcgatggcca cggcgagaac   1620
tcgtcctact tcgacgggtg gaaggcctac gacatggacc ctttcgacct gcgccacaac   1680
cgcgacggcg tcatccagat gggcctcgcc gagaaccaag tacgtgacgt agccctgccg   1740
catgcagcta cagctacacc ctttcgacct gcgcaacaac cgcgacggcg tcatccagat   1800
gggcctgctg tcgatggaat gctcatgtaa ttaaaccacc ggccggggcg tgttttgcag   1860
ctgtccctgg acctgatcga gcaatggagc atggagcacc cggaggcgtc catctgcacg   1920
gcgcagggag cgtcgcagtt caggaggata gccaacttcc aggactacca cggcctgccg   1980
gagttcagag aggtattaat taagttaact aacagctcgg ctaaggaaac gccagaatca   2040
ttgattaggt ttgctgctct ctaatggcga ctgcgaaaac gacggagcag ctaccggcca   2100
gccggccggc ggttagctag cactagcagc cgccttcctg acagatcatc catgacgttt   2160
tgattgttgc aggcgatggc caagttcatg ggccaggtga gggccgggaa ggtgacgttc   2220
gaccccgacc gcgtcgtcat gtgcggaggc gccaccggcg cgcaggacac tctcgccttc   2280
tgcctcgctg acccgggcga cgcctacctc gtgccgacgc catactaccc agcgtatgtc   2340
tcgaccaacg tcatccttgt acttgtacca aaattagtca cccgttgaca cgaaagttgg   2400
taagagggta agagcaggga aaggcagagc taaggccctg tttggtttga ggtgactaaa   2460
gtttagtgac taatatttag tcacttttag tctctaaaga agtaaacatg gtgactaaag   2520
tgaagtgact aaattttagt tctttagtca ctaagaggct gactaaaagg gactaaagta   2580
gtatttttac cttatttgtc ctctccactt tcttcttata gcaaacatct attaattaat   2640
agggataaaa taatcattat tcacagcaat taatgccctt tagtccggtt tagtcactgg   2700
aaccaaacgg gatactttag cgactaaact ttagtcacta aaatttagtc tagtgactaa   2760
gggaaccaaa caggacctaa ttcgagtgtg atgtcaacaa gacaacaaat aatagccaat   2820
```

tgtagcccct cgccatcttt ccttgtttgg gtaacgtttc aaaatttagg gggtgtttgg 2880
tttctaggga ctaatgttta gtcccttcat tttattccat tttagtatat aaattgtcaa 2940
atataaaaac caaaatagag ttttagtttc tatatttgac aattttagaa ctaaaatgaa 3000
ataaaatgta gggactaaag tataaactaa acaccccctt acctcgatca cgaacctcta 3060
aaagtaagta gcaccctcct cccccacagt caaatcaaca taatacagta caatagacct 3120
tgttagtcgc atggatgatt gtcgtcaagt gggcaacgca atctagtcac gtaaggaaaa 3180
ccatgcacgt tgttcataca cggtctgttt ccatgcgact ttaatttcca cgcacgtttg 3240
catcgttgac caaccaactg aacgtgcctg taggtcccgc acagcaacgt aagcatatgc 3300
atgcacgtac gacgtacggc acgggaaaaa aattctgcac accgtatttt acagctcttc 3360
atatccacca catgtagcgg ccccacaaaa aacagattaa aatttgcaac ttaatcctta 3420
agtaatttgt ttttcttcta tttatataga ttatcagttg atggatgtgt gaagttgtaa 3480
aagagattat ttgtatccag gattaaaata attttccgta cggcacgcct gcagtactca 3540
ttctcgccag ccctgagccc ctgatatatg acacgctttt cattgttcac acagtttcga 3600
ccgtgactgt tgctggaggt caggcgtgaa gctgctgccc atcgaatgcc acagctcaaa 3660
caacttcacc ctcacacggg aggcgctcgt gtcggcctac gacggcgcgc ggaggcaggg 3720
cgtccgcgtc aagggcgtcc tcatcaccaa cccctccaac ccgctgggca ccaccatgga 3780
ccgcgccacg ctggcgatgc tcgccaggtt cgccacggag caccgtgtcc acctcatctg 3840
cgacgagatc tacgcgggct ccgtcttcgc caagccggac ttcgtgagca tcgccgaggt 3900
catcgagcgc gacgtcccgg gctgcaacag ggacctcatc cacatcgcgt acagcctctc 3960
caaggacttc ggcctcccgg gcttccgcgt cggcatcgtc tactcgtaca acgacgacgt 4020
cgtggcctgc gcgcgcaaga tgtccagctt cggcctcgtc tcctcgcaga cgcagcactt 4080
cctggcgaag atgctgtcgg acgcggagtt catggcccgc ttcctcgcgg agagcgcgcg 4140
gcggctggcg gcgcgccacg accgcttcgt cgcgggactc cgcgaggtcg gcatcgcgtg 4200
cctgcccggc aacgcggggc tcttctcgtg gatggacctg cggggcatgc tccgggacaa 4260
gacgcacgac gcggagctgg agctgtggcg ggtcatcgta cacaaggtga agctcaacgt 4320
gtcgcccggc acgtcgttcc actgcaacga gcccggctgg ttccgcgtct gccacgctaa 4380
catggacgac gagaccatgg aggtcgcgct cgacaggatc cgccgcttcg tgcgccagca 4440
ccagcacaag gccaaggccg agcgctgggc ggccacgcgg cccatgcgcc tcagcttgcc 4500
gcgccgggga ggcgccaccg cttcgcacct ccccatctcc agccccatgg cgttgctgtc 4560
gccgcagtcc ccgatggttc acgccagcta gtcaccgagc atccggcaag actggctgta 4620
gggtgtgccc gtacatccgt acgtacacct ttttttccca ttcacgtgac tgcaatcaag 4680
tctatgggat ggttgacaaa agactatcta gacaagagtg ggcgtagtac gtaactagtt 4740
tgacgttgta caggcgtcag caggtatcgg taagcagcta gtcaaaagca cgcaagcagg 4800
acgcatttgt cctcgatact ttcgtgtaaa tctctctcta ttttttttg cgaaattcgc 4860 gtgtatggtt tgttttgacg ttggtataaa gtatggtaga ataacgatgg gaaatggcaa 4920
tttagtcctc ccgatcaatt gttattgtaa accactgacg aaagttaaga acagaagctg 4980
taccagaagg gtgaataaaa ataccacata ggtattgaat taataatcta tgtatttcga 5040
gttactcctg caagatatct attttttcat gctgtgctgg ccacatttgc ctcttcttca 5100
aactagtttc tcgca 5115

<210> SEQ ID NO 2
<211> LENGTH: 3749
<212> TYPE: DNA
<213> ORGANISM: Zea mays

<400> SEQUENCE: 2

```
cggctagttt tgatagttag acgatgttct gacagcgcac cagacagtaa ccagtgacag     60

tccggtgcct ggctaaatat cgagccagcg aacagcgcgc tctcgggttt ctacgggggc    120

agagggttgc tctcggggca ttcttgtgct cactgtcagg gggagcacca gacagtccgg    180

tgcacagcga acagtctgat gcccctaggt cagcaagtca aagttctctt ccttagattt    240

ttctaaaccg ttttcgtttt aacttgtgag tgagttatcg agtgacacct agcactagtt    300

gtgagtatga acaccaacac tatattagat ttctcttggt caaactactc atccacaacc    360

actctttata gtacggctaa aataaaaata gaagtcctaa ctttatacca agtgtcaaca    420

actccttcgg acacttagaa tataaagtcc ttcatctttt gtttcgcctt tttccgccgt    480

cgcttcaagt tctcatccga gggattgttt tatcgttgta gtgcaacttc atgcaatgtg    540

acctaacttg ccatttgctc ttcaaaacac acgttagtca tataatatta cgttgtcatt    600

aatctctatc gatatttttc acccattacg ttgtcactag atgctttcac ccatttcgat    660

ttcagacgat gtcttcggac gttgcgggcc atgtgtccaa acgtggttaa gtgtggtcgg    720

gaaatacccg atcgaggttg agttcggcct tcgctccgac acccagccgt gtcattactg    780

tcatatatat tgtagcaatg tcaaaaaaaa tcaaaacatt gagtatgacg tatagggcac    840

atatgtcatt aaacttattc agtgtaatga tatattatca tcacgggact tttttttaat    900

gtatgtatta gattacctct gccatgcact atacaaacag ctacgccgca gtcgcaagca    960

aacaggctct aaaaggcttc agtcggagaa ggatatgaga gcggtgagta ccaaacgggt   1020

atcttcccct tccaaatgat ataagcctac ttgtttgacc ccagcccgca ggcagtcatc   1080

tgctataata ggctaataca acttgtgtac tctagtctgc tctcgccgcg ttgtccgcat   1140

gctgaacccg cgatgttaac acctccctga acgagtcctc tgttcctcaa ctgaaattca   1200

gcaataaaag gaaaaatccg cggtccctgt ccctgtccag caccgcactc tcgcacttgt   1260

gctgcaggct tctgagctcg gcacctgctg ctagctgctg ctatatatag acgcgttttg   1320

gggtcaccaa aaccaccagc tgatcaacag ctagcttcat tcctctgcct ctctctccct   1380

ccttcgccaa ctggccatct ctgttgtctc tcgctagcta gctcgctcgc tcgctcgcca   1440

gtcaccacac acacacacac acactgtgtg tctgtgcctg acgccgcccc ccagtttcaa   1500

acgaacgacc cagccagaaa cgcgcgcgcg ccaaagctac gtgagtgacg tggcagcatg   1560

gtgagcatga tcgccgacga gaagccgcag ccgcagctgc tgtccaagaa ggccgcctgc   1620

aacagccacg gccaggactc gtcctacttc ctggggtggg aggagtatga gaaaaaccca   1680

tacgaccccg tcgccaaccc cggcggcatc atccagatgg gcctcgccga gaaccagctg   1740

tccttcgacc tgctggaggc gtggctggag gccaacccgg acgcgctcgg cctccgccgg   1800

ggaggcgcct ctgtattccg cgagctcgcg ctcttccagg actaccacgg catgccggcc   1860

ttcaagaatg tgagtgcctg ctagcttact cattcccagg caggcaggca gccagccacg   1920

gcatgccgaa ccagtctgac ctctctcgcg cacatgaatg cgtgattccc gcaggcattg   1980

gcgaggttca tgtcggagca acgtgggtac cgggtgacct tcgaccccag caacatcgtg   2040

ctcaccgccg gagccacctc ggccaacgag gccctcatgt tctgcctcgc cgaccacgga   2100

gacgcctttc tcatccccac gccatactac ccagggtatg tgtgtgtgtt gccttgtact   2160
```

```
tactcgtcgc cgcaagtact tgcagtaggg aacgtgcaag tggcggcggg gcggcgtctg   2220
ggtgtcgccg cgatgcacgt tactgctatt aaagtagtag tagtacacta atagctaggc   2280
ccaccacagc acacgatgac atgacgaacg atggatggga acggctgctg actgggcctg   2340
cttgctcttg tctgcaggtt cgaccgtgac ctcaagtggc gcaccggcgc ggagatcgtc   2400
cccgtgcact gcacgagcgg caacggcttc cggctgacgc gcgccgcgct ggacgacgcg   2460
taccggcgcg cgcagaagct gcggctgcgc gtcaagggcg tgctcatcac caacccttcc   2520
aacccgctgg gcaccacgtc gccgcgcgcc gacctggaga tgctggtgga cttcgtggcc   2580
gccaagggca tccacctggt gagcgacgag atatactcgg gcacggtctt cgcggacccg   2640
ggcttcgtga gcgtcctcga ggtggtggcc gcgcgcgccg ccacggacga cggcgtcgtc   2700
ggcgttgggc cgctgtcgga ccgcgtgcac gtggtgtaca gcctgtccaa ggacctgggc   2760
ctcccggggt tccgcgtggg cgccatctac tcgtccaacg ccggcgtggt ctccgcggcc   2820
accaagatgt cgagcttcgg cctggtgtcg tcccagacgc agcacctcct ggcgtcgctc   2880
ctgggcgaca gggacttcac gcggaggtac atcgcggaga acacgcggcg gatcagggag   2940
cggcgcgagc agctggcgga gggcctggcg gccgtgggca tcgagtgcct ggagagcaac   3000
gcggggctct tctgctgggt caacatgcgg cgcctgatgc ggagccggtc gttcgagggc   3060
gagatggagc tgtggaagaa ggtggtcttc gaggtggggc tcaacatctc cccgggctcc   3120
tcctgccact gccgggagcc cggctggttc cgcgtctgct tcgccaacat gtccgccaag   3180
acgctcgacg tcgcgctcca gcgcctgggc gccttcgcgg aggccgccac cgcggggcgc   3240
cgcgtgcttg cccccgccag gagcatcagc ctcccggtcc gcttcagctg ggctaaccgc   3300
ctcaccccgg gctccgccgc cgaccggaag gccgagcggt agccggtccc cgtccgcgcc   3360
gaccgcacgt gctcagctca gcagcttcac agctcaccac cagtcaccac caccaccacc   3420
accaccacct ggggtggagg cgtggagcaa gcaatgttca tagaaaccac ggtcacgtac   3480
tatacaatac tactaccgta ccacaccaca cggcagcatc attagcagta ggagattagt   3540
agtaatcatt aattccttat tgggttcttg taatttcgta tataccacgc cgccattttt   3600
ccttggggcc aggccagccg ataggtgccc gagggccact gcactgcact gctgtattag   3660
gtaggagcag gagtggtggg tagcgaatcc accttccagc agcaggcatc acatttgtgt   3720
atttttcgac tgggtctccc ggttgtttt                                     3749
```

<210> SEQ ID NO 3
<211> LENGTH: 5105
<212> TYPE: DNA
<213> ORGANISM: Zea mays

<400> SEQUENCE: 3

```
gctggtagct tctttaactg atctcaatgg ggcatttcgg tggctagcaa ttcacattaa     60
taatttaaaa gtgaatttca ggtgtacatt tgatggcctc cgatatggtg cagccttcaa    120
tcctctacaa tgtgcgagaa tgttgctccg gagggtagag gcgattaacg gctgaacaca    180
gatgacctcc tcggagtcat gtttctaatt atctacacta cgattctctt tccgttgata    240
aaatatttgt tttattgtcc tgtgagctaa tgataacatt gatggtaagt aaatatagtc    300
catgcatatt ctcatcacag atggctgaaa aactcccggt gctgctacac tactagagtc    360
ttcatgtgca tacttacttc aagaactcaa ggtacacaaa gttttctcaa cagaagaatg    420
tgtatctgtt tgattccagc tgaaatgctt actaaactca gtgtgtcgct ttagatgata    480
```

-continued

```
tgagatgaag ttgggcaaga ccaaagtgaa agggagagaa taacggaaga acttgttcgc    540
caacttggag aaaccaatac taaaactcag tgaatatatg tgtggatttg gaagcaagtg    600
aattttacag aaaagttttt tgagagtgtt tatatgaatc gtactcatct gtttattttg    660
atgactgcaa tataactact tgtatttata gtttgagatc aagaaaataa gttattattt    720
agaaataata aaaaattata gtgatgtttg ttgttccgta tcaatgtttc atacaaatgt    780
tttacttccg tcgcaacaca cggaatata cctataaatat atattgttat catgttatta    840
tacggttccg ttgcaacgca cgggcacata cctagtacaa aaataattac gcatcccgca    900
gttgacatct gggagcgcta caaataatga aggcagctgg tccaccacac gaactgacag    960
cgcggagaag ggagtgcacc ggcccaccgg gatggcaccg cgaatcagcc tcggcagcgc   1020
catactgccc acccattttt tctggcgaat ccgggtgcgg cgggcggttg aggatgaatt   1080
gaataatact ctacttccta atggtcgtgc tagcagaccc tggaagctca gtgtggctcc   1140
aaaacccatt aattaattaa accacaaagc cgccgccgtt agacctagaa ccaccgctgc   1200
gctcgccggg cgccggctac ccggcgtaac tgccgtcacc atccaccacc tggccgctcc   1260
gttctttcct ccaccccaag atggagccgg ttaacctgtc caatcttacc tcatatgcgt   1320
aatcaactat tttaactttc actatatata tatgttaata tttataatat ataatttgta   1380
gtataagata aatatttgaa tttgttttta taataaacgt attttgacat ataaatattg   1440
gtaatatttt tttttacaa atctgactag attttaaatc tgtaacgagg agtacatagt   1500
acgaaatgtt gaaaagtcag cgtgtctttg gtcgcgttcg cattcattct ttctttacct   1560
cagccaccca cctgccacac cctgtgggcc gtggcgcctt cacggaaggt tcgccggcca   1620
cgcatggagg cggctcttta taaagctggt gcgcgggcgg gaggggagag ggcaccagaa   1680
gcagccagca agctcatgcc cttcaaaagc ctccggcagc ccagcgcccc agccagctag   1740
tggtgatctc tcatctcagc agcgcgcctg aacgtgtgct ccctgctaag ctctgcgcct   1800
cgataggcaa aggaaaatca aaccgatcgt cgtcagatta aatggccggt agcagcgcgg   1860
agcagctcct ctccaggatc gccgccggcg acggccacgg cgagaactcg tcctacttcg   1920
acgggtggaa ggcctacgac atgaaccctt tcgacctgcg ccacaaccgc gacggcgtca   1980
tccagatggg cctcgccgag aaccaagtac gtacctatag cgtgtaccta cccttccgat   2040
ctgtagtact gcccacactt gctgcatgct gctgccgatc caagtccaat gctcatgtaa   2100
actggcgtgc tgcagctgtc gttggacctg atcgagcaat ggagcgtgga ccacccggag   2160
gcgtccatct gcacggcgca gggcgcgccg cagttccgga ggatagccaa cttccaggac   2220
taccacggcc tgccggagtt cagagaggta actaactagt agtgattaac aagcaaataa   2280
acgccaggat cactgcatcg attagctagg tttgctgctg ctgctgctgc tgtctaatat   2340
aatggcgact gcacgcgaaa agcgacggag cagctaccgg ccggcggcta gctagctagc   2400
tggcactggc agcgcagtcg ccttcatgag tccacgcacg cgcggctacg tcttaatgat   2460
cgatcggctc gtcgtttgtt gcaggcgatg gccaagttca tggggcaggt gaggggcggc   2520
aaggtgacgt tcgaccccga ccgcgtcgtc atgtgcggag gagccaccgg cgcgcaggac   2580
actctcgcct tctgcctcgc tgacccgggc gacgcctacc tcgtgccgac gccttattac   2640
ccagcgtatg ttctgacgtc acccttgtac tgccaaacta ctactcaggt cctagtcata   2700
tccgtagaca cgaaagggtg ggtgggtctg ggttgttggt tggtcaagag cacgcaaaat   2760
tgagctaatt cgactacgta cgtgtcaatg tcaactagcc acttatcttt ccttgtttgg   2820
gtaaagtttc aaaacttatt aactcgatca ggaacctctc taaaaagcat tcacctattt   2880
```

ttcccccgta aggcggtaac caaatctaaa cgatataccc ttgttagtcg cactgatgac 2940
tgcattgtcg tcaagtggac aacgcaatct agtcacgcga cctctaagga aaaccacgca 3000
cgtatacgca cttcgtgcac ggtctgttcc acgcgacttt agtttccatg cacgtttaca 3060
tcgttgacca tccgcagtcc gcacagcaac gtaagcataa acatgcacgc acgacgtacg 3120
gcacaccgta cctgttcctc tcgagggctg agaccctgac acgttttttt cgttgtgtgg 3180
tgatcacagt ttcgaccgcg actgttgctg gaggtcagga gtgaagctgc tgcccatcga 3240
atgccacagc tcgaacaact tcaccctcac cagggaggcg ctcgtgtcgg cctacgacgg 3300
cgcgcggagg cagggcgtcc gcgtcagggg catcctcatc accaacccct ccaacccgct 3360
gggcaccacc atggaccgcg gcacgctggc gatgctcgcc gcgttcgcca cagagcgccg 3420
cgtccacctc atctgcgacg agatctacgc gggctccgtc ttcgccaagc cgggcttcgt 3480
gagcatcgcc gaggtcatcg agcgcggcga cgcccccggc tgcaacaggg acctcgtcca 3540
catcgcgtac agcctctcca aggacttcgg cctcccgggc ttccgcgtcg gcatcgtcta 3600
ctcctacaac gacgacgtgg tggcctgcgc gcgcaagatg tccagcttcg gcctcgtctc 3660
gtcgcagacg cagcacttcc tggcgatgat gctcgccgac gcggagttca tggcacgctt 3720
cctcgcggag agcgcgcggc ggctggcggc gcgccacgac cgcttcgtcg cgggcctccg 3780
cgaggtcggc atcgcgtgcc tgccgggcaa cgcgggcctc ttctcgtgga tggacctgcg 3840
gggcatgctc cgggagaaga cgcacgacgc ggagctcgag ctgtggcggg tcatcgtaca 3900
cagggtgaag ctcaacgtgt cgcccggcac gtcgttccac tgcaacgagc ccggctggtt 3960
ccgcgtctgc tacgccaaca tggacgacga caccatggag gtcgcgctcg accggatccg 4020
ccgcttcgtg cgccagcacc agcacagcaa ggccaaggcc gagcgctggg cggccacgcg 4080
gccccttcgc ctcagcttgc cgcgccgggg agcaaccacc gcttcgcatc tcgccatctc 4140
cagccccttg gcgttgctgt cgccgcagtc cccgatggtc cacgccagct aggtagtcac 4200
cgagcgttcg gtaagactgg ctgtaggttg tgccctcaca tgactgcaaa caagtggaca 4260
aaaaaaaaga caagactaat aaagggcgta cgtagctagc ttgacattac acagagtgac 4320
agagacgttg cacaggcgtc agcaggcgtc ggcggtaagc agctagtcaa gtaggacgca 4380
tttgtcctcg atttttttcgt gtttttttttt tgacgaaggg gcgaagcccc ctatttcatt 4440
aagaaatagg aaagtatgaa acaaccgcac ccacgcggta ggacctccaa aaagaacagc 4500
cacggccaga aagtaatcta gactctaaac actatcgcta gatcagtgaa gagactatga 4560
taacagggaa agttttggcc tacgaagagc tacataagac tttcttatat acaaccaacc 4620
aagacaggca gaagccacaa aagacctgaa cagaatggcc aacaaaagac agacaactat 4680
cccaacaagg tttcacagct tcagcatctt tgtcatccag aaatccgcct gtcaagagga 4740
caccacccca aggccctccc gaaagcttca cttgccgtct ttcggattaa cctgcttcct 4800
agcaccacca ttctttgctc cttctttttc tgacgaatcg cccaagaatc caaccagaag 4860
cagcaaagaa aaatgatgtt agatgggtca agtaaatgac tattcccaaa acaccaatca 4920
ttcctagtgc gccaaatagc ccagaataaa gcaccacaac caaataacac caactgagcc 4980
atcgtgtctt ttggtttaca aaaccaattg tcatacaaat ctttgatatt ttttggaata 5040
gatctcaaat tcagggccac ttgaataact ctccacatgt attgagcaat ggggcaatag 5100
aaaaa 5105

<210> SEQ ID NO 4

<211> LENGTH: 1455
<212> TYPE: DNA
<213> ORGANISM: Zea mays

<400> SEQUENCE: 4
atggccggtg gtagcagtgc cgagcagctc ctatccagga tcgcctccgg cgatggccac 60
ggcgagaact cgtcctactt cgacgggtgg aaggcctacg acatggaccc tttcgacctg 120
cgccacaacc gcgacggcgt catccagatg ggcctcgccg agaaccaact gtccctggac 180
ctgatcgagc aatggagcat ggagcacccg gaggcgtcca tctgcacggc gcagggagcg 240
tcgcagttca ggaggatagc caacttccag gactaccacg gcctgccgga gttcagagag 300
gcgatggcca agttcatggg ccaggtgagg gccgggaagg tgacgttcga ccccgaccgc 360
gtcgtcatgt gcggaggcgc caccggcgcg caggacactc tcgccttctg cctcgctgac 420
ccgggcgacg cctacctcgt gccgacgcca tactacccag cgttcgaccg tgactgttgc 480
tggaggtcag gcgtgaagct gctgcccatc gaatgccaca gctcaaacaa cttcaccctc 540
acacgggagg cgctcgtgtc ggcctacgac ggcgcgcgga ggcagggcgt ccgcgtcaag 600
ggcgtcctca tcaccaaccc ctccaacccg ctgggcacca ccatggaccg cgccacgctg 660
gcgatgctcg ccaggttcgc cacggagcac cgtgtccacc tcatctgcga cgagatctac 720
gcgggctccg tcttcgccaa gccggacttc gtgagcatcg ccgaggtcat cgagcgcgac 780
gtcccgggct gcaacaggga cctcatccac atcgcgtaca gcctctccaa ggacttcggc 840
ctcccgggct tccgcgtcgg catcgtctac tcgtacaacg acgacgtcgt ggcctgcgcg 900
cgcaagatgt ccagcttcgg cctcgtctcc tcgcagacgc agcacttcct ggcgaagatg 960
ctgtcggacg cggagttcat ggcccgcttc ctcgcggaga gcgcgcggcg gctggcggcg 1020
cgccacgacc gcttcgtcgc gggactccgc gaggtcggca tcgcgtgcct gcccggcaac 1080
gcggggctct tctcgtggat ggacctgcgg ggcatgctcc gggacaagac gcacgacgcg 1140
gagctggagc tgtggcgggt catcgtacac aaggtgaagc tcaacgtgtc gcccggcacg 1200
tcgttccact gcaacgagcc cggctggttc cgcgtctgcc acgctaacat ggacgacgag 1260
accatggagg tcgcgctcga caggatccgc cgcttcgtgc gccagcacca gcacaaggcc 1320
aaggccgagc gctgggcggc cacgcggccc atgcgcctca gcttgccgcg ccggggaggc 1380
gccaccgctt cgcacctccc catctccagc cccatggcgt tgctgtcgcc gcagtccccg 1440
atggttcacg ccagc 1455

<210> SEQ ID NO 5
<211> LENGTH: 1446
<212> TYPE: DNA
<213> ORGANISM: Zea mays

<400> SEQUENCE: 5
atgatcgccg acgagaagcc gcagccgcag ctgctgtcca agaaggccgc ctgcaacagc 60
cacggccagg actcgtccta cttcctgggg tgggaggagt atgagaaaaa cccatacgac 120
cccgtcgcca accccggcgg catcatccag atgggcctcg ccgagaacca gctgtccttc 180
gacctgctgg aggcgtggct ggaggccaac ccggacgcgc tcggcctccg ccggggaggc 240
gcctctgtat tccgcgagct cgcgctcttc caggactacc acggcatgcc ggccttcaag 300
aatgcattgg cgaggttcat gtcggagcaa cgtgggtacc gggtgacctt cgaccccagc 360
aacatcgtgc tcaccgccgg agccacctcg gccaacgagg ccctcatgtt ctgcctcgcc 420
gaccacggag acgcctttct catccccacg ccatactacc cagggttcga ccgtgacctc 480

-continued

```
aagtggcgca ccggcgcgga gatcgtcccc gtgcactgca cgagcggcaa cggcttccgg    540
ctgacgcgcg ccgcgctgga cgacgcgtac cggcgcgcgc agaagctgcg gctgcgcgtc    600
aagggcgtgc tcatcaccaa cccttccaac ccgctgggca ccacgtcgcc gcgcgccgac    660
ctggagatgc tggtggactt cgtggccgcc aagggcatcc acctggtgag cgacgagata    720
tactcgggca cggtcttcgc ggacccgggc ttcgtgagcg tcctcgaggt ggtggccgcg    780
cgcgccgcca cggacgacgg cgtcgtcggc gttgggccgc tgtcggaccg cgtgcacgtg    840
gtgtacagcc tgtccaagga cctgggcctc ccggggttcc gcgtgggcgc catctactcg    900
tccaacgccg gcgtggtctc cgcggccacc aagatgtcga gcttcggcct ggtgtcgtcc    960
cagacgcagc acctcctggc gtcgctcctg ggcgacaggg acttcacgcg gaggtacatc   1020
gcggagaaca cgcggcggat cagggagcgg cgcgagcagc tggcggaggg cctggcggcc   1080
gtgggcatcg agtgcctgga gagcaacgcg gggctcttct gctgggtcaa catgcggcgc   1140
ctgatgcgga gccggtcgtt cgagggcgag atggagctgt ggaagaaggt ggtcttcgag   1200
gtggggctca acatctcccc gggctcctcc tgccactgcc gggagcccgg ctggttccgc   1260
gtctgcttcg ccaacatgtc cgccaagacg ctcgacgtcg cgctccagcg cctgggcgcc   1320
ttcgcggagg ccgccaccgc ggggcgccgc gtgcttgccc ccgccaggag catcagcctc   1380
ccggtccgct tcagctgggc taaccgcctc accccgggct ccgccgccga ccggaaggcc   1440
gagcgg                                                              1446
```

<210> SEQ ID NO 6
<211> LENGTH: 1458
<212> TYPE: DNA
<213> ORGANISM: Zea mays

<400> SEQUENCE: 6

```
atggccggta gcagcgcgga gcagctcctc tccaggatcg ccgccggcga cggccacggc     60
gagaactcgt cctacttcga cgggtggaag gcctacgaca tgaacccttt cgacctgcgc    120
cacaaccgcg acggcgtcat ccagatgggc ctcgccgaga accaactgtc gttggacctg    180
atcgagcaat ggagcgtgga ccacccggag gcgtccatct gcacggcgca gggcgcgccg    240
cagttccgga ggatagccaa cttccaggac taccacggcc tgccggagtt cagagaggcg    300
atggccaagt tcatggggca ggtgaggggc ggcaaggtga cgttcgaccc cgaccgcgtc    360
gtcatgtgcg gaggagccac cggcgcgcag gacactctcg ccttctgcct cgctgacccg    420
ggcgacgcct acctcgtgcc gacgccttat tacccagcgt tcgaccgcga ctgttgctgg    480
aggtcaggag tgaagctgct gcccatcgaa tgccacagct cgaacaactt caccctcacc    540
agggaggcgc tcgtgtcggc ctacgacggc gcgcggaggc agggcgtccg cgtcaggggc    600
atcctcatca ccaacccctc caacccgctg ggcaccacca tggaccgcgg cacgctggcg    660
atgctcgccg cgttcgccac agagcgccgc gtccacctca tctgcgacga gatctacgcg    720
ggctccgtct tcgccaagcc gggcttcgtg agcatcgccg aggtcatcga gcgcggcgac    780
gccccgggct gcaacaggga cctcgtccac atcgcgtaca gcctctccaa ggacttcggc    840
ctcccgggct tccgcgtcgg catcgtctac tcctacaacg acgacgtggt ggcctgcgcg    900
cgcaagatgt ccagcttcgg cctcgtctcg tcgcagacgc agcacttcct ggcgatgatg    960
ctcgccgacg cggagttcat ggcacgcttc ctcgcggaga gcgcgcggcg gctggcggcg   1020
cgccacgacc gcttcgtcgc gggcctccgc gaggtcggca tcgcgtgcct gccgggcaac   1080
```

-continued

```
gcgggcctct tctcgtggat ggacctgcgg ggcatgctcc gggagaagac gcacgacgcg   1140

gagctcgagc tgtggcgggt catcgtacac agggtgaagc tcaacgtgtc gcccggcacg   1200

tcgttccact gcaacgagcc cggctggttc cgcgtctgct acgccaacat ggacgacgac   1260

accatggagg tcgcgctcga ccggatccgc cgcttcgtgc gccagcacca gcacagcaag   1320

gccaaggccg agcgctgggc ggccacgcgg ccccttcgcc tcagcttgcc gcgccgggga   1380

gcaaccaccg cttcgcatct cgccatctcc agccccttgg cgttgctgtc gccgcagtcc   1440

ccgatggtcc acgccagc                                                 1458
```

<210> SEQ ID NO 7
<211> LENGTH: 485
<212> TYPE: PRT
<213> ORGANISM: Zea mays

<400> SEQUENCE: 7

```
Met Ala Gly Gly Ser Ser Ala Glu Gln Leu Leu Ser Arg Ile Ala Ser
 1               5                  10                  15

Gly Asp Gly His Gly Glu Asn Ser Ser Tyr Phe Asp Gly Trp Lys Ala
            20                  25                  30

Tyr Asp Met Asp Pro Phe Asp Leu Arg His Asn Arg Asp Gly Val Ile
        35                  40                  45

Gln Met Gly Leu Ala Glu Asn Gln Leu Ser Leu Asp Leu Ile Glu Gln
    50                  55                  60

Trp Ser Met Glu His Pro Glu Ala Ser Ile Cys Thr Ala Gln Gly Ala
65                  70                  75                  80

Ser Gln Phe Arg Arg Ile Ala Asn Phe Gln Asp Tyr His Gly Leu Pro
                85                  90                  95

Glu Phe Arg Glu Ala Met Ala Lys Phe Met Gly Gln Val Arg Ala Gly
            100                 105                 110

Lys Val Thr Phe Asp Pro Asp Arg Val Val Met Cys Gly Gly Ala Thr
        115                 120                 125

Gly Ala Gln Asp Thr Leu Ala Phe Cys Leu Ala Asp Pro Gly Asp Ala
    130                 135                 140

Tyr Leu Val Pro Thr Pro Tyr Tyr Pro Ala Phe Asp Arg Asp Cys Cys
145                 150                 155                 160

Trp Arg Ser Gly Val Lys Leu Leu Pro Ile Glu Cys His Ser Ser Asn
                165                 170                 175

Asn Phe Thr Leu Thr Arg Glu Ala Leu Val Ser Ala Tyr Asp Gly Ala
            180                 185                 190

Arg Arg Gln Gly Val Arg Val Lys Gly Val Leu Ile Thr Asn Pro Ser
        195                 200                 205

Asn Pro Leu Gly Thr Thr Met Asp Arg Ala Thr Leu Ala Met Leu Ala
    210                 215                 220

Arg Phe Ala Thr Glu His Arg Val His Leu Ile Cys Asp Glu Ile Tyr
225                 230                 235                 240

Ala Gly Ser Val Phe Ala Lys Pro Asp Phe Val Ser Ile Ala Glu Val
                245                 250                 255

Ile Glu Arg Asp Val Pro Gly Cys Asn Arg Asp Leu Ile His Ile Ala
            260                 265                 270

Tyr Ser Leu Ser Lys Asp Phe Gly Leu Pro Gly Phe Arg Val Gly Ile
        275                 280                 285

Val Tyr Ser Tyr Asn Asp Asp Val Val Ala Cys Ala Arg Lys Met Ser
    290                 295                 300
```

```
Ser Phe Gly Leu Val Ser Ser Gln Thr Gln His Phe Leu Ala Lys Met
305                 310                 315                 320

Leu Ser Asp Ala Glu Phe Met Ala Arg Phe Leu Ala Glu Ser Ala Arg
                325                 330                 335

Arg Leu Ala Ala Arg His Asp Arg Phe Val Ala Gly Leu Arg Glu Val
            340                 345                 350

Gly Ile Ala Cys Leu Pro Gly Asn Ala Gly Leu Phe Ser Trp Met Asp
        355                 360                 365

Leu Arg Gly Met Leu Arg Asp Lys Thr His Asp Ala Glu Leu Glu Leu
    370                 375                 380

Trp Arg Val Ile Val His Lys Val Lys Leu Asn Val Ser Pro Gly Thr
385                 390                 395                 400

Ser Phe His Cys Asn Glu Pro Gly Trp Phe Arg Val Cys His Ala Asn
                405                 410                 415

Met Asp Asp Glu Thr Met Glu Val Ala Leu Asp Arg Ile Arg Arg Phe
            420                 425                 430

Val Arg Gln His Gln His Lys Ala Lys Ala Glu Arg Trp Ala Ala Thr
        435                 440                 445

Arg Pro Met Arg Leu Ser Leu Pro Arg Arg Gly Gly Ala Thr Ala Ser
    450                 455                 460

His Leu Pro Ile Ser Ser Pro Met Ala Leu Leu Ser Pro Gln Ser Pro
465                 470                 475                 480

Met Val His Ala Ser
                485
```

<210> SEQ ID NO 8
<211> LENGTH: 482
<212> TYPE: PRT
<213> ORGANISM: Zea mays

<400> SEQUENCE: 8

```
Met Ile Ala Asp Glu Lys Pro Gln Pro Gln Leu Leu Ser Lys Lys Ala
 1               5                  10                  15

Ala Cys Asn Ser His Gly Gln Asp Ser Ser Tyr Phe Leu Gly Trp Glu
            20                  25                  30

Glu Tyr Glu Lys Asn Pro Tyr Asp Pro Val Ala Asn Pro Gly Gly Ile
        35                  40                  45

Ile Gln Met Gly Leu Ala Glu Asn Gln Leu Ser Phe Asp Leu Leu Glu
    50                  55                  60

Ala Trp Leu Glu Ala Asn Pro Asp Ala Leu Gly Leu Arg Arg Gly Gly
65                  70                  75                  80

Ala Ser Val Phe Arg Glu Leu Ala Leu Phe Gln Asp Tyr His Gly Met
                85                  90                  95

Pro Ala Phe Lys Asn Ala Leu Ala Arg Phe Met Ser Glu Gln Arg Gly
            100                 105                 110

Tyr Arg Val Thr Phe Asp Pro Ser Asn Ile Val Leu Thr Ala Gly Ala
        115                 120                 125

Thr Ser Ala Asn Glu Ala Leu Met Phe Cys Leu Ala Asp His Gly Asp
    130                 135                 140

Ala Phe Leu Ile Pro Thr Pro Tyr Tyr Pro Gly Phe Asp Arg Asp Leu
145                 150                 155                 160

Lys Trp Arg Thr Gly Ala Glu Ile Val Pro Val His Cys Thr Ser Gly
                165                 170                 175

Asn Gly Phe Arg Leu Thr Arg Ala Ala Leu Asp Asp Ala Tyr Arg Arg
            180                 185                 190
```

Ala Gln Lys Leu Arg Leu Arg Val Lys Gly Val Leu Ile Thr Asn Pro
195 200 205

Ser Asn Pro Leu Gly Thr Thr Ser Pro Arg Ala Asp Leu Glu Met Leu
210 215 220

Val Asp Phe Val Ala Ala Lys Gly Ile His Leu Val Ser Asp Glu Ile
225 230 235 240

Tyr Ser Gly Thr Val Phe Ala Asp Pro Gly Phe Val Ser Val Leu Glu
245 250 255

Val Val Ala Ala Arg Ala Ala Thr Asp Asp Gly Val Val Gly Val Gly
260 265 270

Pro Leu Ser Asp Arg Val His Val Val Tyr Ser Leu Ser Lys Asp Leu
275 280 285

Gly Leu Pro Gly Phe Arg Val Gly Ala Ile Tyr Ser Ser Asn Ala Gly
290 295 300

Val Val Ser Ala Ala Thr Lys Met Ser Ser Phe Gly Leu Val Ser Ser
305 310 315 320

Gln Thr Gln His Leu Leu Ala Ser Leu Leu Gly Asp Arg Asp Phe Thr
325 330 335

Arg Arg Tyr Ile Ala Glu Asn Thr Arg Arg Ile Arg Glu Arg Arg Glu
340 345 350

Gln Leu Ala Glu Gly Leu Ala Ala Val Gly Ile Glu Cys Leu Glu Ser
355 360 365

Asn Ala Gly Leu Phe Cys Trp Val Asn Met Arg Arg Leu Met Arg Ser
370 375 380

Arg Ser Phe Glu Gly Glu Met Glu Leu Trp Lys Lys Val Val Phe Glu
385 390 395 400

Val Gly Leu Asn Ile Ser Pro Gly Ser Ser Cys His Cys Arg Glu Pro
405 410 415

Gly Trp Phe Arg Val Cys Phe Ala Asn Met Ser Ala Lys Thr Leu Asp
420 425 430

Val Ala Leu Gln Arg Leu Gly Ala Phe Ala Glu Ala Ala Thr Ala Gly
435 440 445

Arg Arg Val Leu Ala Pro Ala Arg Ser Ile Ser Leu Pro Val Arg Phe
450 455 460

Ser Trp Ala Asn Arg Leu Thr Pro Gly Ser Ala Ala Asp Arg Lys Ala
465 470 475 480

Glu Arg

<210> SEQ ID NO 9
<211> LENGTH: 486
<212> TYPE: PRT
<213> ORGANISM: Zea mays

<400> SEQUENCE: 9

Met Ala Gly Ser Ser Ala Glu Gln Leu Leu Ser Arg Ile Ala Ala Gly
1 5 10 15

Asp Gly His Gly Glu Asn Ser Ser Tyr Phe Asp Gly Trp Lys Ala Tyr
20 25 30

Asp Met Asn Pro Phe Asp Leu Arg His Asn Arg Asp Gly Val Ile Gln
35 40 45

Met Gly Leu Ala Glu Asn Gln Leu Ser Leu Asp Leu Ile Glu Gln Trp
50 55 60

Ser Val Asp His Pro Glu Ala Ser Ile Cys Thr Ala Gln Gly Ala Pro
65 70 75 80

-continued

```
Gln Phe Arg Arg Ile Ala Asn Phe Gln Asp Tyr His Gly Leu Pro Glu
                85                  90                  95

Phe Arg Glu Ala Met Ala Lys Phe Met Gly Gln Val Arg Gly Gly Lys
            100                 105                 110

Val Thr Phe Asp Pro Asp Arg Val Val Met Cys Gly Gly Ala Thr Gly
        115                 120                 125

Ala Gln Asp Thr Leu Ala Phe Cys Leu Ala Asp Pro Gly Asp Ala Tyr
    130                 135                 140

Leu Val Pro Thr Pro Tyr Tyr Pro Ala Phe Asp Arg Asp Cys Cys Trp
145                 150                 155                 160

Arg Ser Gly Val Lys Leu Leu Pro Ile Glu Cys His Ser Ser Asn Asn
                165                 170                 175

Phe Thr Leu Thr Arg Glu Ala Leu Val Ser Ala Tyr Asp Gly Ala Arg
            180                 185                 190

Arg Gln Gly Val Arg Val Arg Gly Ile Leu Ile Thr Asn Pro Ser Asn
        195                 200                 205

Pro Leu Gly Thr Thr Met Asp Arg Gly Thr Leu Ala Met Leu Ala Ala
    210                 215                 220

Phe Ala Thr Glu Arg Arg Val His Leu Ile Cys Asp Glu Ile Tyr Ala
225                 230                 235                 240

Gly Ser Val Phe Ala Lys Pro Gly Phe Val Ser Ile Ala Glu Val Ile
                245                 250                 255

Glu Arg Gly Asp Ala Pro Gly Cys Asn Arg Asp Leu Val His Ile Ala
            260                 265                 270

Tyr Ser Leu Ser Lys Asp Phe Gly Leu Pro Gly Phe Arg Val Gly Ile
        275                 280                 285

Val Tyr Ser Tyr Asn Asp Asp Val Val Ala Cys Ala Arg Lys Met Ser
    290                 295                 300

Ser Phe Gly Leu Val Ser Ser Gln Thr Gln His Phe Leu Ala Met Met
305                 310                 315                 320

Leu Ala Asp Ala Glu Phe Met Ala Arg Phe Leu Ala Glu Ser Ala Arg
                325                 330                 335

Arg Leu Ala Ala Arg His Asp Arg Phe Val Ala Gly Leu Arg Glu Val
            340                 345                 350

Gly Ile Ala Cys Leu Pro Gly Asn Ala Gly Leu Phe Ser Trp Met Asp
        355                 360                 365

Leu Arg Gly Met Leu Arg Glu Lys Thr His Asp Ala Glu Leu Glu Leu
    370                 375                 380

Trp Arg Val Ile Val His Arg Val Lys Leu Asn Val Ser Pro Gly Thr
385                 390                 395                 400

Ser Phe His Cys Asn Glu Pro Gly Trp Phe Arg Val Cys Tyr Ala Asn
                405                 410                 415

Met Asp Asp Asp Thr Met Glu Val Ala Leu Asp Arg Ile Arg Arg Phe
            420                 425                 430

Val Arg Gln His Gln His Ser Lys Ala Lys Ala Glu Arg Trp Ala Ala
        435                 440                 445

Thr Arg Pro Leu Arg Leu Ser Leu Pro Arg Arg Gly Ala Thr Thr Ala
    450                 455                 460

Ser His Leu Ala Ile Ser Ser Pro Leu Ala Leu Leu Ser Pro Gln Ser
465                 470                 475                 480

Pro Met Val His Ala Ser
                485
```

<210> SEQ ID NO 10
<211> LENGTH: 2120
<212> TYPE: DNA
<213> ORGANISM: Zea mays

<400> SEQUENCE: 10

```
atgaccatga ttacgccaag ctctaatacg actcactata gggaaagctg gtacgcctgc      60
aggtaccggt ccggaattcc cgggtcgacc cacgcgtccg cagcaagctc atccccttca     120
aaaccctccg gcagcccagc cagctagtgg tgatctctca gcagcgcgcc tgaacgtgtg     180
ctccctgcta aactctgcgc ctcggtaggc aaggaaaatt aaaccggtcg tcgtcagatt     240
aaatggccgg tagcagcgcg gagcagctcc tctccaggat cgccgccggc gatggccacg     300
gcgagaactc gtcctacttc gacgggtgga aggcctacga cacgaaccct ttcgacctgc     360
gccacaaccg cgacggcgtc atccagatgg gactcgccga gaaccaactg tcgctggacc     420
tgatcgagca atggagcgtg gaccacccgg aggcgtccat ctgcacggcg cagggcgcgc     480
cgcagttccg gaggatagcc aacttccagg actaccacgg cctgccggag ttcagagagg     540
cgatggccaa gttcatgggg caggtgaggg gcggcaaggt gacgttcgac cccgaccgcg     600
tcgtcatgtg cgggggagcc accggcgcgc aggacactct cgccttctgc ctcgctgacc     660
cgggcgacgc ctacctcgtg ccgacgcctt attacccagc tttcgaccgc gactgttgct     720
ggaggtcagg agtgaagctg ctgcccatcg aatgccacag ctcgaacaac ttcaccctca     780
ccagggaggc gctcgtgtcg gcctacgacg gcgcgcggag gcagggcgtc cgcgtcaggg     840
gcatcctcat caccaacccc tccaacccgc tgggcaccac aatggaccgc ggcacgctgg     900
cgatgctcgc cgcgttcgcc acagagcgcc gcgtccacct catctgcgac gagatctacg     960
cgggctccgt cttcgccaag ccgggcttcg tgagcatcgc cgaggtcatc gagcgcggcg    1020
acgccccggg ctgcaacagg gacctcgtcc acatcgcgta cagcctctcc aaggacttcg    1080
gcctcccggg cttccgcgtc ggcatcgtct actcctacaa cgacgacgtg gtggcctgcg    1140
cgcgcaagat gtccagcttc ggcctcgtct cgtcgcagac gcagcacttc ctggcgatga    1200
tgctcgccga cgcggagttc atggcacgct tcctcgcgga gagcgcgcgg cggctggcgg    1260
cgcgccacga ccgcttcgtc gcgggcctcc gcgaggtcgg catcgcgtgc ctgccgggca    1320
acgcgggcct cttctcgtgg atggacctgc ggggcatgct ccgggagagg acgcacgacg    1380
cggagctgga gctgtggcgg gtcatcgtac acagggtgaa gctcaacgtg tcgcccggca    1440
cgtcgttcca ctgcaacgag cccggctggt tccgcgtctg ctacgccaac atggacgacg    1500
acaccatgga ggtcgcgctc gaccggatcc gccgcttcgt gcgccagcac cagcacagca    1560
aggccaaggc cgagcgctgg gcggccacgc ggcccctccg cctcagcttg ccgcgccggg    1620
gagcaaccac cgcttcgcac ctcgccatcc ccagcccctt ggcgttgctg tcgccgcagt    1680
ccccgatggt ccacgccagc tagctagtca ccgagcgttc ggtaagactg gctgtagggt    1740
gtgccctcac ataactgcaa acaagtggac aaaaaaatatt agacaagact aataaagggc    1800
attagtagct agcttgacat tacacagaga cgttgcacag gcgtcagcag gcgtcggcgg    1860
taagcagcta gtcaagcagg acgcatttgt cctcgatttt ttcgtgtata tatgttcttt    1920
tttctgtttt gccaaatcgc atgtatggtt tggtttaacg ttagtacacg gtagaataac    1980
gatcgggtat ggtaatttag acctcccgat caattgttgt tgaaaacctg tcacgtaact    2040
tcaggacaca gaaggcgtag ctcaagggtg aataaaagac cagtttacat atcaaaaaaa    2100
aaaaaaaaaa aaaaaaaaaa                                                 2120
```

<210> SEQ ID NO 11
<211> LENGTH: 486
<212> TYPE: PRT
<213> ORGANISM: Zea mays

<400> SEQUENCE: 11

```
Met Ala Gly Ser Ser Ala Glu Gln Leu Leu Ser Arg Ile Ala Ala Gly
 1               5                  10                  15

Asp Gly His Gly Glu Asn Ser Ser Tyr Phe Asp Gly Trp Lys Ala Tyr
            20                  25                  30

Asp Thr Asn Pro Phe Asp Leu Arg His Asn Arg Asp Gly Val Ile Gln
        35                  40                  45

Met Gly Leu Ala Glu Asn Gln Leu Ser Leu Asp Leu Ile Glu Gln Trp
    50                  55                  60

Ser Val Asp His Pro Glu Ala Ser Ile Cys Thr Ala Gln Gly Ala Pro
65                  70                  75                  80

Gln Phe Arg Arg Ile Ala Asn Phe Gln Asp Tyr His Gly Leu Pro Glu
                85                  90                  95

Phe Arg Glu Ala Met Ala Lys Phe Met Gly Gln Val Arg Gly Gly Lys
            100                 105                 110

Val Thr Phe Asp Pro Asp Arg Val Val Met Cys Gly Gly Ala Thr Gly
        115                 120                 125

Ala Gln Asp Thr Leu Ala Phe Cys Leu Ala Asp Pro Gly Asp Ala Tyr
    130                 135                 140

Leu Val Pro Thr Pro Tyr Tyr Pro Ala Phe Asp Arg Asp Cys Cys Trp
145                 150                 155                 160

Arg Ser Gly Val Lys Leu Leu Pro Ile Glu Cys His Ser Ser Asn Asn
                165                 170                 175

Phe Thr Leu Thr Arg Glu Ala Leu Val Ser Ala Tyr Asp Gly Ala Arg
            180                 185                 190

Arg Gln Gly Val Arg Val Arg Gly Ile Leu Ile Thr Asn Pro Ser Asn
        195                 200                 205

Pro Leu Gly Thr Thr Met Asp Arg Gly Thr Leu Ala Met Leu Ala Ala
    210                 215                 220

Phe Ala Thr Glu Arg Arg Val His Leu Ile Cys Asp Glu Ile Tyr Ala
225                 230                 235                 240

Gly Ser Val Phe Ala Lys Pro Gly Phe Val Ser Ile Ala Glu Val Ile
                245                 250                 255

Glu Arg Gly Asp Ala Pro Gly Cys Asn Arg Asp Leu Val His Ile Ala
            260                 265                 270

Tyr Ser Leu Ser Lys Asp Phe Gly Leu Pro Gly Phe Arg Val Gly Ile
        275                 280                 285

Val Tyr Ser Tyr Asn Asp Asp Val Val Ala Cys Ala Arg Lys Met Ser
    290                 295                 300

Ser Phe Gly Leu Val Ser Ser Gln Thr Gln His Phe Leu Ala Met Met
305                 310                 315                 320

Leu Ala Asp Ala Glu Phe Met Ala Arg Phe Leu Ala Glu Ser Ala Arg
                325                 330                 335

Arg Leu Ala Ala Arg His Asp Arg Phe Val Ala Gly Leu Arg Glu Val
            340                 345                 350

Gly Ile Ala Cys Leu Pro Gly Asn Ala Gly Leu Phe Ser Trp Met Asp
        355                 360                 365

Leu Arg Gly Met Leu Arg Glu Arg Thr His Asp Ala Glu Leu Glu Leu
```

```
    370                 375                 380

Trp Arg Val Ile Val His Arg Val Lys Leu Asn Val Ser Pro Gly Thr
385                 390                 395                 400

Ser Phe His Cys Asn Glu Pro Gly Trp Phe Arg Val Cys Tyr Ala Asn
                405                 410                 415

Met Asp Asp Asp Thr Met Glu Val Ala Leu Asp Arg Ile Arg Arg Phe
            420                 425                 430

Val Arg Gln His Gln His Ser Lys Ala Lys Ala Glu Arg Trp Ala Ala
        435                 440                 445

Thr Arg Pro Leu Arg Leu Ser Leu Pro Arg Arg Gly Ala Thr Thr Ala
    450                 455                 460

Ser His Leu Ala Ile Pro Ser Pro Leu Ala Leu Leu Ser Pro Gln Ser
465                 470                 475                 480

Pro Met Val His Ala Ser
                485
```

<210> SEQ ID NO 12
<211> LENGTH: 1173
<212> TYPE: DNA
<213> ORGANISM: Zea mays

<400> SEQUENCE: 12

```
ggccgccctt ttttttttt ttttttttt ttttttgata tgtaaactgg tcttttattc     60

acccttgagc tacgccttct gtgtcctgaa gttacgtgac aggttttcaa caacaattga    120

tcgggaggtc taaattacca tacccgatcg ttattctacc gtgtactaac gttaaaccaa    180

accatacatg cgatttggca aaacagaaaa aagaacatat atacacgaaa aaatcgagga    240

caaatgcgtc ctgcttgact agctgcttac cgccgacgcc tgctgacgcc tgtgcaacgt    300

ctctgtgtaa tgtcaagcta gctactaatg ccctttatta gtcttgtcta atattttttg    360

tccacttgtt tgcagttatg tgagggcaca ccctacagcc agtcttaccg aacgctcggt    420

gactagctag ctggcgtgga ccatcgggga ctgcggcgac agcaacgcca aggggctggg    480

gatggcgagg tgcgaagcgg tggttgctcc ccggcgcggc aagctgaggc ggaggggccg    540

cgtggccgcc cagcgctcgg ccttggcctt gctgtgctgg tgctggcgca cgaagcggcg    600

gatccggtcg agcgcgacct ccatggtgtc gtcgtccatg ttggcgtagc agacgcggaa    660

ccagccgggc tcgttgcagt ggaacgacgt gccgggcgac acgttgagct tcaccctgtg    720

tacgatgacc cgccacagct ccagctccgc gtcgtgcgtc ctctcccgga gcatgccccg    780

caggtccatc cacgagaaga ggcccgcgtt gcccggcagg cacgcgatgc cgacctcgcg    840

gaggcccgcg acgaagcggt cgtggcgcgc cgccagccgc cgcgcgctct ccgcgaggaa    900

gcgtgccatg aactccgcgt cggcgagcat catcgccagg aagtgctgcg tctgcgacga    960

gacgaggccg aagctggaca tcttgcgcgc gcaggccacc acgtcgtcgt tgtaggagta   1020

gacgatgccg acgcggaagc ccgggaggcc gaagtccttg gagaggctgt acgcgatgtg   1080

gacgaggtcc ctgttgcagc ccggggcgtc gccgcgctcg atgacctcgg cgatgctcac   1140

gaagcccggc ttggcgaaga cggagcccgc gta                                1173
```

<210> SEQ ID NO 13
<211> LENGTH: 600
<212> TYPE: DNA
<213> ORGANISM: Zea mays

<400> SEQUENCE: 13
gatccgccgc ttcgtgcgcc agcaccagca cagcaaggcc aaggccgagc gctgggcggc 60
cacgcggccc ctccgcctca gcttgccgcg ccggggagca accaccgctt cgcacctcgc 120
catccccagc cccttggcgt tgctgtcgcc gcagtccccg atggtccacg ccagctagct 180
agtcaccgag cgttcggtaa gactggctgt agggtgtgcc ctcacataac tgcaaacaag 240
tggacaaaaa atattagaca agactaataa agggcattag tagctagctt gacattacac 300
agagacgttg cacaggcgtc agcaggcgtc ggcggtaagc agctagtcaa gcaggacgca 360
tttgtcctcg attttttcgt gtatatatgt tctttttct gttttgccaa atcgcatgta 420
tggtttggtt taacgttagt acacggtaga ataacgatcg ggtatggtaa tttagacctc 480
ccgatcaatt gttgttgaaa acctgtcacg taacttcagg acacagaagg cgtagctcaa 540
gggtgaataa aagaccagtt tacatatcaa aaaaaaaaaa aaaaaaaaaa aaaaaagggc 600

<210> SEQ ID NO 14
<211> LENGTH: 701
<212> TYPE: DNA
<213> ORGANISM: Zea mays

<400> SEQUENCE: 14
tagcagacgc ggaaccagcc gggctcccgg cagtggcagg aggagcccgg ggagatgttg 60
agccccacct cgaagaccac cttcttccac agctccatct cgccctcgaa cgaccggctc 120
cgcatcaggc gccgcatgtt gacccagcag aagagccccg cgttgctctc caggcactcg 180
atgcccacgg ccgccaggcc ctccgccagc tgctcgcgcc gctccctgat ccgccgcgtg 240
ttctccgcga tgtacctccg cgtgaagtcc ctgtcgccca ggagcgacgc caggaggtgc 300
tgcgtctggg acgacaccag gccgaagctc gacatcttgg tggccgcgga gaccacgccg 360
gcgttggacg agtagatggc gcccacgcgg aaccccggga ggcccaggtc cttggacagg 420
ctgtacacca cgtgcacgcg gtccgacagc ggcccaacgc cgacgacgcc gtcgtccgtg 480
gcggcgcgcg cggccaccac ctcgaggacg ctcacgaagc ccgggtccgc gaagaccgtg 540
cccgagtata tctcgtcgct caccaggtgg atgcccttgg cggccacgaa gtccaccagc 600
atctccaggt cggcgcgcgg cgacgtggtg cccagcgggt tggaagggtt ggtgatgagc 660
acgcccttga cgcgcagccg cagcttctgc gcgcgccggt a 701

<210> SEQ ID NO 15
<211> LENGTH: 489
<212> TYPE: DNA
<213> ORGANISM: Zea mays

<400> SEQUENCE: 15
cgcgccgcca cggacgacgg cgtcgtcggc gttgggccgc tgtcggaccg cgtgcacgtg 60
gtgtacagcc tgtccaagga cctgggcctc ccggggttcc gcgtgggcgc catctactcg 120
tccaacgccg gcgtggtctc cgcggccacc aagatgtcga gcttcggcct ggtgtcgtcc 180
cagacgcagc acctcctggc gtcgctcctg ggcgacaggg acttcacgcg gaggtacatc 240
gcggagaaca cgcggcggat cagggagcgg cgcgagcagc tggcggaggg cctggcggcc 300
gtgggcatcg agtgcctgga gagcaacgcg gggctcttct gctgggtcaa catgcggcgc 360
ctgatgcgga gccggtcgtt cgagggcgag atggagctgt ggaagaaggt ggtcttcgag 420
gtggggctca acatctcccc gggctcctcc tgccactgcc gggagcccgg ctggttccgc 480
gtctgctaa 489

<210> SEQ ID NO 16
<211> LENGTH: 1467
<212> TYPE: DNA
<213> ORGANISM: Arabidopsis thaliana

<400> SEQUENCE: 16
atgtctcagg gtgcatgtga gaatcaactt ctatccaaat tagctttgag tgacaaacat 60
ggagaagctt cgccgtactt ccatggctgg aaagcttacg acaataatcc ttttcatcca 120
actcataatc cacaaggagt tattcaaatg ggtctcgccg aaaatcaact ttgttcagat 180
ttgatcaaag aatggataaa ggaaaatcca caggcatcta tttgtacggc ggagggaatt 240
gactctttct ccgacattgc tgtttttcaa gattatcacg gtctcaaaca atttagacag 300
gcgattgcga cgtttatgga gagagcgaga ggcgggcggg tgaggtttga ggcggagagg 360
gtggtgatga gcggaggagc caccggagca aatgagacga tcatgttctg tcttgctgat 420
cccggcgacg cttttctcgt ccctactcct tattatgctg cattcgatag agacttaagg 480
tggagaactg gagttagaat aatccctgtg gagtgtagca gctcaaacaa tttccagatt 540
acaaaacaag ccctagaatc agcgtacctt aaggcccaag aaaccggtat caagatcaaa 600
ggcctgatca tctcaaaccc tcttggaaca tctctcgatc gagaaactct tgaaagcctt 660
gtcagcttca tcaacgacaa gcaaattcac ttagtatgcg acgaaatata cgcagcaacg 720
gtttttgcgg aaccgggatt catcagtgtt gcagagatca tccaagagat gtattatgtt 780
aaccgtgatc tgattcatat cgtctacagt ctttcaaagg acatgggtct tcccggtttc 840
cgggttggag tggtttactc ttacaacgat gttgttgtgt cctgcgcaag gaggatgtcg 900
agttttggat tggtctcgtc gcagacacaa agttttctag ctgctatgtt gtctgatcag 960
agttttgtcg ataactttct tgttgaggtt tcgaaaagag tagcgaagag acaccatatg 1020
ttcacggaag ggcttgaaga gatggggatt tcttgcttga gaagcaacgc gggtttattc 1080
gttttgatgg atttgaggca tatgcttaag gatcagacat ttgattccga aatggcgctt 1140
tggcgagtta ttatcaataa ggtcaagatt aatgtctctc ctggctcgtc gtttcactgc 1200
tctgagcctg gttggttccg agtctgcttt gctaatatgg acgaagacac actccaaatt 1260
gcacttgaac gaatcaaaga ctttgtggtt ggagacagag ccaacaagaa caagaactgt 1320
aactgcattt gcaacaacaa aagggagaac aagaaacgta agagttttca aaagaatctc 1380
aagctgagtt tatcttcgat gaggtacgag gaacatgtta ggtcaccaaa gttgatgtct 1440
cctcattcac cattgcttcg agcttaa 1467

<210> SEQ ID NO 17
<211> LENGTH: 1920
<212> TYPE: DNA
<213> ORGANISM: Arabidopsis thaliana

<400> SEQUENCE: 17
aaaacttgtc ataagatcaa tatcgatacc cccaaaaaaa aaaaaaaaca gctacaaaga 60
agtgagaatt gacacagcaa atgggtcttc cgggaaaaaa taaaggtgca gttttgtcga 120
agatagcgac taacaatcaa cacggagaga actcagagta ctttgatgga tggaaagctt 180
acgacaaaga tccttttcat ctttcccgta acccccatgg gatcatccaa atgggtcttg 240
cagagaatca gctttgctta gatttgatca aagattgggt caaagagaac ccagaagctt 300
ctatttgcac ccttgaaggt attcatcagt ttagcgacat cgctaatttc caagactacc 360
atggtcttaa gaagtttaga caggcaattg cacatttcat gggaaaagct agaggtggaa 420

```
gagtgacttt tgatccggag agggtggtta tgagcggagg agccaccgga gccaatgaaa    480
caatcatgtt ctgccttgcg gatcccggcg acgttttcct cattccctcc ccgtactatg    540
ccgcatttga tagagacttg aggtggcgga caggtgtcga gataatcccg gttccttgtt    600
caagctccga caatttcaaa ttaaccgttg acgccgcgga atgggcttat aaaaaagccc    660
aagagtccaa taaaaaagtc aaaggtctga ttttgaccaa cccatcaaat ccactcggta    720
caatgttgga taaggacaca ctcacgaact tggtccggtt tgtcacgagg aagaacattc    780
acctagtcgt cgacgagatc tacgccgcca cagtcttcgc cggaggagat ttcgtgagcg    840
ttgctgaggt ggtcaatgat gtggacatct ccgaagtcaa cgttgacttg attcacattg    900
tctatagtct ttctaaagat atgggacttc ctggttttag agtcgggata gtctattctt    960
tcaatgactc ggtcgtgtct tgcgcaagaa aaatgtcaag tttcggactt gtttcgtctc   1020
agacacaact catgcttgct tcgatgttgt ccgatgatca gtttgtggat aatttctaa   1080
tggaaagctc gagaaggttg gggataaggc ataaagtttt taccacgggg atcaagaaag   1140
cagatattgc ttgtttgaca agcaacgctg gtttatttgc gtggatggat ttgagacatc   1200
tactgagaga tcgtaactcg tttgaatctg agatcgagct ttggcatata atcatcgata   1260
gagttaagct caatgtgtct cctggctctt ccttccgttg cacggaacct ggatggttta   1320
ggatttgctt tgccaacatg gacgatgata ctctccatgt ggcgcttgga cggatccaag   1380
atttcgtgtc taagaacaag aacaagatcg tcgagaaagc atctgaaaat gatcaggtaa   1440
tccagaacaa gagtgctaaa aagctgaaat ggacgcagac caatcttcga ctaagtttcc   1500
gacgacttta cgaggatggt ctctcgtctc cagggataat gtcaccacac tcacctcttc   1560
tccgagcatg aaaatcttaa ggcataacgt ctgagagatt ggattaactc gtccgcgttt   1620
cactccgtgt taattaatct taaattagta agtgattaag taaatgtttt ttctttcatt   1680
gtaagattgg aataattcaa tttcgacatt agggttgttt ttgacggcca gctttttttcc   1740
tggggtcaaa tggtaacttt taagatttta tgtgtttgat tctgtttctt ttttccgctt   1800
aggattttaa tcgatggatt gtcctagtgg tgctggtgtg tagcatatat gcttttctta   1860
tatgtttttg tgtgtaataa atgaaacatt gtcttttgat aaggatcacc agagtttatt   1920
```

<210> SEQ ID NO 18
<211> LENGTH: 1735
<212> TYPE: DNA
<213> ORGANISM: Arabidopsis thaliana

<400> SEQUENCE: 18

```
accttttttt cttcttttca agtcaagtta aatacttaat aacacatttt tctaaacttc     60
ttacagcttt gcttagattt gatcaaagat tgggtcaaag agaacccaga agcttctatt    120
tgcacccttg aaggtattca tcagtttagc gacatcgcta atttccaaga ctaccatggt    180
cttaagaagt ttagacaggc aattgcacat ttcatgggaa aagctagagg tggaagagtg    240
acttttgatc cggagagggt ggttatgagc ggaggagcca ccggagccaa tgaaacaatc    300
atgttctgcc ttgcggatcc cggcgacgtt ttcctcattc cctccccgta ctatgccgca    360
tttgatagag acttgaggtg gcggacaggt gtcgagataa tcccggttcc ttgttcaagc    420
tccgacaatt tcaaattaac cgttgacgcc gcggaatggg cttataaaaa agcccaagag    480
tccaataaaa aagtcaaagg tctgattttg accaacccat caaatccact cggtacaatg    540
ttggataagg acacactcac gaacttggtc cggtttgtca cgaggaagaa cattcaccta    600
gtcgtcgacg agatctacgc cgccacagtc ttcgccggag gagatttcgt gagcgttgct    660
```

gaggtggtca atgatgtgga catctccgaa gtcaacgttg acttgattca cattgtctat 720
agtctttcta aagatatggg acttcctggt tttagagtcg ggatagtcta ttctttcaat 780
gactcggtcg tgtcttgcgc aagaaaaatg tcaagtttcg gacttgtttc gtctcagaca 840
caactcatgc ttgcttcgat gttgtccgat gatcagtttg tggataattt tctaatggaa 900
agctcgagaa ggttggggat aaggcataaa gtttttacca cggggatcaa gaaagcagat 960
attgcttgtt tgacaagcaa cgctggttta tttgcgtgga tggatttgag acatctactg 1020
agagatcgta actcgtttga atctgagatc gagctttggc atataatcat cgatagagtt 1080
aagctcaatg tgtctcctgg ctcttccttc cgttgcacgg aacctggatg gtttaggatt 1140
tgctttgcca acatggacga tgatactctc catgtggcgc ttggacggat ccaagatttc 1200
gtgtctaaga acaagaacaa gatcgtcgag aaagcatctg aaaatgatca ggtaatccag 1260
aacaagagtg ctaaaaagct gaaatggacg cagaccaatc ttcgactaag tttccgacga 1320
ctttacgagg atggtctctc gtctccaggg ataatgtcac cacactcacc tcttctccga 1380
gcatgaaaat cttaaggcat aacgtctgag agattggatt aactcgtccg cgtttcactc 1440
cgtgttaatt aatcttaaat tagtaagtga ttaagtaaat gtttttttctt tcattgtaag 1500 attggaataa ttcaatttcg acattagggt tgtttttgac ggccagcttt tttcctgggg 1560
tcaaatggta acttttaaga ttttatgtgt ttgattctgt ttcttttttc cgcttaggat 1620
tttaatcgat ggattgtcct agtggtgctg gtgtgtagca tatatgcttt tcttatatgt 1680
ttttgtgtgt aataaatgaa acattgtctt ttgataagga tcaccagagt ttatt 1735

<210> SEQ ID NO 19
<211> LENGTH: 2003
<212> TYPE: DNA
<213> ORGANISM: Arabidopsis thaliana
<220> FEATURE:
<221> NAME/KEY: misc_feature
<222> LOCATION: 1492
<223> OTHER INFORMATION: n = A,T,C or G

<400> SEQUENCE: 19
atgggtcttc cgggaaaaaa taaaggtgca gttttgtcga agatagcgac taacaatcaa 60
cacggagaga actcagagta ctttgatgga tggaaagctt acgacaaaga tccttttcat 120
ctttcccgta acccccatgg gatcatccaa atgggtcttg cagagaatca gctttgctta 180
gatttgatca aagattgggt caaagagaac ccagaagctt ctatttgcac ccttgaaggt 240
attcatcagt ttagcgacat cgctaatttc caagactacc atggtcttaa gaagtttaga 300
caggcaattg cacatttcat gggaaaagct agaggtggaa gagtgacttt tgatccggag 360
agggtggtta tgagcggagg agccaccgga gccaatgaaa caatcatgtt ctgccttgcg 420
gatcccggcg acgttttcct cattccctcc ccgtactatg ccgcatttga tagagacttg 480
aggtggcgga caggtgtcga gataatcccg gttccttgtt caagctccga caatttcaaa 540
ttaaccgttg acgccgcgga atgggcttat aaaaaagccc aagagtccaa taaaaaagtc 600
aaaggtctga ttttgaccaa cccatcaaat ccactcggta caatgttgga taaggacaca 660
ctcacgaact tggtccggtt tgtcacgagg aagaacattc acctagtcgt cgacgagatc 720
tacgccgcca cagtcttcgc cggaggagat ttcgtgagcg ttgctgaggt ggtcaatgat 780
gtggacatct ccgaagtcaa cgttgacttg attcacattg tctatagtct ttctaaagat 840
atgggacttc ctggttttag agtcgggata gtctattctt tcaatgactc ggtcgtgtct 900

```
tgcgcaagaa aaatgtcaag tttcggactt gtttcgtctc agacacaact catgcttgct    960
tcgatgttgt ccgatgatca gtttgtggat aattttctaa tggaaagctc gagaaggttg   1020
gggataaggc ataaagtttt taccacgggg atcaagaaag cagatattgc ttgtttgaca   1080
agcaacgctg gtttatttgc gtggatggat ttgagacatc tactgagaga tcgtaactcg   1140
tttgaatctg agatcgagct ttggcatata atcatcgata gagttaagct caatgtgtct   1200
cctggctctt ccttccgttg cacggaacct ggatggttta ggatttgctt tgccaacatg   1260
gacgatgata ctctccatgt ggcgcttgga cggatccaag atttcgtgtc taagaacaag   1320
aacaagatcg tcgagaaagc atctgaaaat gatcaggtaa tccagaacaa gagtgctaaa   1380
aagctgaaat ggacgcagac caatcttcga ctaagtttcc gacgacttta cgaggatggt   1440
ctctcgtctc cagggataat gtcaccacac tcacctcttc tccgagcatg anmacsatgt   1500
ctcagggtgc atgtgagaat caacttctat ccaaattagc tttgagtgac aaacatggag   1560
aagcttcgcc gtacttccat ggctggaaag cttacgacaa taatcctttt catccaactc   1620
ataatccaca aggagttatt caaatgggtc tcgccgaaaa tcaactttgt tcagatttga   1680
tcaaagaatg gataaaggaa aatccacatg catctatttg tacggcggag ggaattgact   1740
ctttctccga cattgctgtt tttcaagatt atcacggtct caaacaattt agacaggcga   1800
ttgcgacgtt tatggagaga gcgagaggcg ggcgggtgag gtttgaggcg gagagggtgg   1860
tgatgagcgg aggagccacc ggagcaaatg agacgatcat gttctgtctt gctgatcccg   1920
gcgacgcttt tctcgtccct actccttatt atgctgcgta cagagagaaa gagaattact   1980
tgagacttgt gagccctttg tga                                           2003
```

```
<210> SEQ ID NO 20
<211> LENGTH: 1425
<212> TYPE: DNA
<213> ORGANISM: Arabidopsis thaliana

<400> SEQUENCE: 20

atggttcaat tgtcaagaaa agctacatgc aacagccatg gccaagtctc ttcgtatttc     60
cttggttggg aagagtacga gaagaatcct tacgacgtta ccaagaaccc tcaaggcatt    120
atccagatgg gtcttgcgga aaatcagcta tgctttgatc tactagagtc atggcttgca    180
caaaacacag acgcagcctg tttcaagaga gatggccagt ctgttttccg ggaactcgct    240
ctctttcaag actaccatgg cctctcttcc ttcaaaaatg cctttgctga tttcatgtca    300
gaaaatagag gaaatcgagt ttcttttgat tcaaacaacc ttgtgctcac tgctggagcc    360
acttccgcaa acgagactct aatgttttgt cttgcagatc ccggtgacgc tttcttgctt    420
cccacgccat attatccagg gtttgatagg gatctaaaat ggcgaaccgg ggttgagatt    480
gtaccaatcc aaagctcaag tactaacggg tttcgcataa cgaaacttgc actcgaagaa    540
gcctacgagc aagccaagaa gcttgaccta aacgtcaaag gaatactcat caccaaccca    600
tctaaccctt tgggtacgac aacaacccaa accgaactca acattctatt tgatttcatc    660
accaagaata agaatataca tttagtaagt gacgagatat attcgggcac agtattcaac    720
tcttcagaat tcatcagcgt catggagatt ctaaaaaata atcaactcga aaacaccgat    780
gttttgaacc gagtccacat tgtttgtagc ttatctaaag atctaggcct ccctggtttt    840
agagttggag ccatttactc caatgacaaa gatgtcatct ctgccgctac aaaaatgtca    900
agtttcggcc ttgtctcctc ccagacacaa tacctactat cctcattatt atctgacaag    960
aagttcacta agaactacct tagagagaac caaaaacggc tcaagaacag acagagaaag   1020
```

-continued ctcgtgttgg gtctagaggc catcgggatc aaatgtctga agagtaatgc gggactcttt 1080
tgttgggtcg acatgagacc tctccttaga tctaaaacgt tcgaagcgga aatggatctt 1140
tggaagaaga ttgtttacga agtgaagctc aacatctctc ctggttcgtc gtgccattgt 1200
gaagaaccgg gttggtttag agtttgtttc gcgaacatga ttgatgagac attaaagctt 1260
gctttaaaga gattgaagat gttggttgat gatgaaaact caagtagaag atgccaaaag 1320
agtaaaagcg aaagactaaa cggttcgagg aagaagacga tgtcaaatgt ctctaactgg 1380
gttttccgac tatcgtttca cgaccgtgag gctgaggaac gatag 1425

<210> SEQ ID NO 21
<211> LENGTH: 1425
<212> TYPE: DNA
<213> ORGANISM: Arabidopsis thaliana

<400> SEQUENCE: 21
atggttcaat tgtcaagaaa agctacatgc aacagccatg gccaagtctc ttcgtatttc 60
cttggttggg aagagtacga gaagaatcct tacgacgtta ccaagaaccc tcaaggcatt 120
atccagatgg gtcttgcgga aaatcagcta tgctttgatc tactagagtc atggcttgca 180
caaaacacag acgcagcctg tttcaagaga gatggccagt ctgttttccg ggaactcgct 240
ctctttcaag actaccatgg cctctcttcc ttcaaaaatg cctttgctga tttcatgtca 300
gaaaatagag gaaatcgagt ttcttttgat tcaaacaacc ttgtgctcac tgctggagcc 360
acttccgcaa acgagactct aatgttttgt cttgcagatc ccggtgacgc tttcttgctt 420
cccacgccat attatccagg gtttgatagg gatctaaaat ggcgaaccgg ggttgagatt 480
gtaccaatcc aaagctcaag tactaacggg tttcgcataa cgaaacttgc actcgaagaa 540
gcctacgagc aagccaagaa gcttgaccta aacgtcaaag gaatactcat caccaaccca 600
tctaaccctt tgggtacgac aacaacccaa accgaactca acattctatt tgatttcatc 660
accaagaata agaatataca tttagtaagt gacgagatat attcgggcac agtattcaac 720
tcttcagaat tcatcagcgt catggagatt ctaaaaaata atcaactcga aaacaccgat 780
gttttgaacc gagtccacat tgtttgtagc ttatctaaag atctaggcct ccctggtttt 840
agagttggag ccatttactc caatgacaaa gatgtcatct ctgccgctac aaaaatgtca 900
agtttcggcc ttgtctcctc ccagacacaa tacctactat cctcattatt atctgacaag 960
aagttcacta agaactacct tagagagaac caaaaacggc tcaagaacag acagagaaag 1020
ctcgtgttgg gtctagaggc catcgggatc aaatgtctga agagtaatgc gggactcttt 1080
tgttgggtcg acatgagacc tctccttaga tctaaaacgt tcgaagcgga aatggatctt 1140
tggaagaaga ttgtttacga agtgaagctc aacatctctc ctggttcgtc gtgccattgt 1200
gaagaaccgg gttggtttag agtttgtttc gcgaacatga ttgatgagac attaaagctt 1260
gctttaaaga gattgaagat gttggttgat gatgaaaact caagtagaag atgccaaaag 1320
agtaaaagcg aaagactaaa cggttcgagg aagaagacga tgtcaaatgt ctctaactgg 1380
gttttccgac tatcgtttca cgaccgtgag gctgaggaac gatag 1425

<210> SEQ ID NO 22
<211> LENGTH: 1888
<212> TYPE: DNA
<213> ORGANISM: Arabidopsis thaliana

<400> SEQUENCE: 22

-continued

```
acatctcact cttcaccaac ttaaacccta attcaagatc tcttcttttc gttctctcct     60
tcacccacat tagtcttctc tacgaccaaa atctcttgac tttaaaaaca gagaatgaaa    120
cagctttcga caaaagtgac aagcaatggt catggacaag actcatccta cttcttggga    180
tgggaagagt acgagaagaa tccttatgat gagatcaaga accctaatgg gatgatccag    240
atgggtctag ccgaaaacca gctatgtttc gatctaatcg agtcatggtt aactaagaac    300
ccagacgcgg caagtctcaa gaggaacggt caatccattt tcagagagct tgctctattt    360
caagactatc atggcatgcc tgaattcaaa aaagctatgg ctgagtttat ggaagagata    420
agaggaaacc gtgtcacgtt cgatccaaaa aagattgttt tagcggctgg ttcgacatct    480
gcgaatgaga ctctcatgtt ttgccttgca gagcctggcg atgctttcct tttgcctact    540
ccttactatc ctggatttga tagagatctt aaatggagaa ccggagcaga gatagtaccc    600
attcactgct caagctctaa tggcttccaa atcacggaat cagctctgca acaagcttac    660
caacaagccc agaaacttga tctcaaagtc aaaggagttc ttgtcacgaa tccatctaac    720
ccacttggca ctgcgttgac cagacgtgaa cttaaccttc tcgttgactt catcacttcc    780
aagaacattc atctcattag cgacgagatc tattcaggca ctatgttcgg gtttgaacag    840
ttcataagcg taatggatgt cttgaaagac aagaaactcg aagacacgga ggtttcaaaa    900
cgagtccacg tcgtttatag cctttctaaa gatctgggac ttcctggttt ccgtgtggga    960
gcgatctact ccaacgacga aatgatcgtt tcagcagcta caaaaatgtc aagttttggt   1020
cttgtttctt ctcagacaca ataccttctc tctgcattgc tctccgacaa gaagttcact   1080
agccaatacc tcgaagagaa ccagaaacga ctcaagtcca gacagagacg cctcgtgtct   1140
ggtcttgagt ctgcagggat tacttgcctg agaagcaacg cgggtttgtt ctgttgggtc   1200
gacatgagac accttttgga cacaaacaca tttgaagcag agcttgacct ctggaaaaag   1260
attgtttaca acgtgaaact aaacatatca cccggttctt catgtcactg caccgaaccg   1320
ggttggttta gggtttgttt cgctaatatg agcgaggaca cactcgattt ggccttgaag   1380
aggctcaaaa ctttcgtaga atccacagac tgtggacgaa tgatatcaag aagcagccat   1440
gaaaggctca agagtttgag gaagaagaca gtctctaact gggttttccg ggtttcatgg   1500
accgatcgtg tacctgatga acgatgaaat tattcatctc cctaagtttg agacgacgaa   1560
caaaagaaaa cttcacggtt ttttcttctt ctttatttcc ttcatttttt atattttggg   1620
aaagtatttt taattttcca agatatctat aatcatatca ttatatatgt aatatttttt   1680
ttaatgtttg ggtgagtctt taatttatgc aatttttcgg gtgtaaaatt gttactatgt   1740
gttattatat gtttttaatg cactcaatcc gaatgtggat ttgcagtggc tatatatata   1800
aataaatata tatcccgttg taattttagt gaaacgtttg tgtgtattgt acccatatat   1860
aaaaatgtaa ttcactcgaa aaaaaaaa                                      1888
```

<210> SEQ ID NO 23
<211> LENGTH: 1888
<212> TYPE: DNA
<213> ORGANISM: Arabidopsis thaliana

<400> SEQUENCE: 23

```
acatctcact cttcaccaac ttaaacccta attcaagatc tcttcttttc gttctctcct     60
tcacccacat tagtcttctc tacgaccaaa atctcttgac tttaaaaaca gagaatgaaa    120
cagctttcga caaaagtgac aagcaatggt catggacaag actcatccta cttcttggga    180
tgggaagagt acgagaagaa tccttatgat gagatcaaga accctaatgg gatgatccag    240
```

```
atgggtctag ccgaaaacca gctatgtttc gatctaatcg agtcatggtt aactaagaac    300
ccagacgcgg caagtctcaa gaggaacggt caatccattt tcagagagct tgctctattt    360
caagactatc atggcatgcc tgaattcaaa aaagctatgg ctgagtttat ggaagagata    420
agaggaaacc gtgtcacgtt cgatccaaaa aagattgttt tagcggctgg ttcgacatct    480
gcgaatgaga ctctcatgtt ttgccttgca gagcctggcg atgctttcct tttgcctact    540
ccttactatc ctggatttga tagagatctt aaatggagaa ccggagcaga gatagtaccc    600
attcactgct caagctctaa tggcttccaa atcacggaat cagctctgca acaagcttac    660
caacaagccc agaaacttga tctcaaagtc aaaggagttc ttgtcacgaa tccatctaac    720
ccacttggca ctgcgttgac cagacgtgaa cttaaccttc tcgttgactt catcacttcc    780
aagaacattc atctcattag cgacgagatc tattcaggca ctatgttcgg gtttgaacag    840
ttcataagcg taatggatgt cttgaaagac aagaaactcg aagacacgga ggtttcaaaa    900
cgagtccacg tcgtttatag cctttctaaa gatctgggac ttcctggttt ccgtgtggga    960
gcgatctact ccaacgacga aatgatcgtt tcagcagcta caaaaatgtc aagttttggt   1020
cttgtttctt ctcagacaca ataccttctc tctgcattgc tctccgacaa gaagttcact   1080
agccaatacc tcgaagagaa ccagaaacga ctcaagtcca gacagagacg cctcgtgtct   1140
ggtcttgagt ctgcagggat tacttgcctg agaagcaacg cgggtttgtt ctgttgggtc   1200
gacatgagac accttttgga cacaaacaca tttgaagcag agcttgacct ctggaaaaag   1260
attgtttaca acgtgaaact aaacatatca cccggttctt catgtcactg caccgaaccg   1320
ggttggttta gggtttgttt cgctaatatg agcgaggaca cactcgattt ggccttgaag   1380
aggctcaaaa ctttcgtaga atccacagac tgtggacgaa tgatatcaag aagcagccat   1440
gaaaggctca agagtttgag gaagaagaca gtctctaact gggttttccg ggtttcatgg   1500
accgatcgtg tacctgatga acgatgaaat tattcatctc cctaagtttg agacgacgaa   1560
caaaagaaaa cttcacggtt ttttcttctt ctttatttcc ttcatttttt atattttggg   1620
aaagtatttt taattttcca agatatctat aatcatatca ttatatatgt aatatttttt   1680
ttaatgtttg ggtgagtctt taatttatgc aatttttcgg gtgtaaaatt gttactatgt   1740
gttattatat gtttttaatg cactcaatcc gaatgtggat ttgcagtggc tatatatata   1800
aataaatata tatcccgttg taattttagt gaaacgtttg tgtgtattgt acccatatat   1860
aaaaatgtaa ttcactcgaa aaaaaaaa                                      1888
```

<210> SEQ ID NO 24
<211> LENGTH: 1413
<212> TYPE: DNA
<213> ORGANISM: Arabidopsis thaliana

<400> SEQUENCE: 24

```
atgaaacagc tttcgacaaa agtgacaagc aatggtcatg gacaagactc atcctacttc     60
ttgggatggg aagagtacga gaagaatcct tatgatgaga tcaagaaccc taatgggatg    120
atccagatgg gtctagccga aaaccagcta tgtttcgatc taatcgagtc atggttaact    180
aagaacccag acgcggcaag tctcaagagg aacggtcaat ccattttcag agagcttgct    240
ctatttcaag actatcatgg catgcctgaa ttcaaaaaag ctatggctga gtttatggaa    300
gagataagag gaaaccgtgt cacgttcgat ccaaaaaaga ttgttttagc ggctggttcg    360
acatctgcga atgagactct catgttttgc cttgcagagc ctggcgatgc tttccttttg    420
```

-continued

```
cctactcctt actatcctgg atttgataga gatcttaaat ggagaaccgg agcagagata    480

gtacccattc actgctcaag ctctaatggc ttccaaatca cggaatcagc tctgcaacaa    540

gcttaccaac aagcccagaa acttgatctc aaagtcaaag gagttcttgt cacgaatcca    600

tctaacccac ttggcactgc gttgaccaga cgtgaactta accttctcgt tgacttcatc    660

acttccaaga acattcatct cattagcgac gagatctatt caggcactat gttcgggttt    720

gaacagttca taagcgtaat ggatgtcttg aaagacaaga aactcgaaga cacggaggtt    780

tcaaaacgag tccacgtcgt ttatagcctt tctaaagatc tgggacttcc tggtttccgt    840

gtgggagcga tctactccaa cgacgaaatg atcgtttcag cagctacaaa aatgtcaagt    900

tttggtcttg tttcttctca gacacaatac cttctctctg cattgctctc cgacaagaag    960

ttcactagcc aatacctcga agagaaccag aaacgactca agtccagaca gagacgcctc   1020

gtgtctggtc ttgagtctgc agggattact tgcctgagaa gcaacgcggg tttgttctgt   1080

tgggtcgaca tgagacacct tttggacaca aacacatttg aagcagagct tgacctctgg   1140

aaaaagattg tttacaacgt gaaactaaac atatcacccg gttcttcatg tcactgcacc   1200

gaaccgggtt ggtttagggt ttgtttcgct aatatgagcg aggacacact cgatttggcc   1260

ttgaagaggc tcaaaacttt cgtagaatcc acagactgtg gacgaatgat atcaagaagc   1320

agccatgaaa ggctcaagag tttgaggaag aagacagtct ctaactgggt tttccgggtt   1380

tcatggaccg atcgtgtacc tgatgaacga tga                                1413
```

<210> SEQ ID NO 25
<211> LENGTH: 1877
<212> TYPE: DNA
<213> ORGANISM: Arabidopsis thaliana

<400> SEQUENCE: 25

```
acatctcact cttcaccaac ttaaacccta attcaagatc tcttcttttc gttctctcct     60

tcacccacat tagtcttctc tacgaccaaa atctcttgac tttaaaaaca gagaatgaaa    120

cagctttcga caaaagtgac aagcaatggt catggacaag actcatccta cttcttggga    180

tgggaagagt acgagaagaa tccttatgat gagatcaaga accctaatgg gatgatccag    240

atgggtctag ccgaaaacca gctatgtttc gatctaatcg agtcatggtt aactaagaac    300

ccagacgcgg caagtctcaa gaggaacggt caatccattt tcagagagct tgctctattt    360

caagactatc atggcatgcc tgaattcaaa aaagctatgg ctgagtttat ggaagagata    420

agaggaaacc gtgtcacgtt cgatccaaaa aagattgttt tagcggctgg ttcgacatct    480

gcgaatgaga ctctcatgtt ttgccttgca gagcctggcg atgctttcct tttgcctact    540

ccttactatc ctggatttga tagagatctt aaatggagaa ccggagcaga gatagtaccc    600

attcactgct caagctctaa tggcttccaa atcacggaat cagctctgca acaagcttac    660

caacaagccc agaaacttga tctcaaagtc aaaggagttc ttgtcacgaa tccatctaac    720

ccacttggca ctgcgttgac cagacgtgaa cttaaccttc tcgttgactt catcacttcc    780

aagaacattc atctcattag cgacgagatc tattcaggca ctatgttcgg gtttgaacag    840

ttcataagcg taatggatgt cttgaaagac aagaaactcg aagacacgga ggtttcaaaa    900

cgagtccacg tcgtttatag cctttctaaa gatctgggac ttcctggttt ccgtgtggga    960

gcgatctact ccaacgacga aatgatcgtt tcagcagcta caaaaatgtc aagttttggt   1020

cttgtttctt ctcagacaca ataccttctc tctgcattgc tctccgacaa gaagttcact   1080

agccaatacc tcgaagagaa ccagaaacga ctcaagtcca gacagagacg cctcgtgtct   1140
```

```
ggtcttgagt ctgcagggat tacttgcctg agaagcaacg cgggtttgtt ctgttgggtc   1200

gacatgagac accttttgga cacaaacaca tttgaagcag agcttgacct ctggaaaaag   1260

attgtttaca acgtgaaact aaacatatca cccggttctt catgtcactg caccgaaccg   1320

ggttggttta gggtttgttt cgctaatatg agcgaggaca cactcgattt ggccttgaag   1380

aggctcaaaa ctttcgtaga atccacagac tgtggacgaa tgatatcaag aagcagccat   1440

gaaaggctca agagtttgag gaagaagaca gtctctaact gggttttccg ggtttcatgg   1500

accgatcgtg tacctgatga acgatgaaat tattcatctc cctaagtttg agacgacgaa   1560

caaaagaaaa cttcacggtt ttttcttctt ctttatttcc ttcatttttt atattttggg   1620

aaagtatttt taattttcca agatatctat aatcatatca ttatatatgt aatatttttt   1680

ttaatgtttg ggtgagtctt taatttatgc aatttttcgg gtgtaaaatt gttactatgt   1740

gttattatat gtttttaatg cactcaatcc gaatgtggat ttgcagtggc tatatatata   1800

aataaatata tatcccgttg taattttagt gaaacgtttg tgtgtattgt acccatatat   1860

aaaaatgtaa ttcactc                                                   1877
```

<210> SEQ ID NO 26
<211> LENGTH: 1753
<212> TYPE: DNA
<213> ORGANISM: Arabidopsis thaliana

<400> SEQUENCE: 26

```
atcaaaccat aacttccaaa tctcaacaga accaaaaaca aaagaaacct atattaaaga     60

agaaacaaaa aatggtggct tttgcaacag agaagaagca agatctgaat ctattgtcta    120

aaatcgcctc cggtgacggt cacggcgaga attcctctta tttcgatggt tggaaagctt    180

atgaagaaaa cccatttcac ccaattgata gacctgacgg agttattcaa atgggtctcg    240

ctgaaaatca gctttgtgga gatttgatgc gtaaatgggt tttaaaacat ccagaagctt    300

cgatttgtac atcagaaggt gtgaatcaat tcagtgacat tgccattttt caagattatc    360

atggcttgcc tgaattcaga caagctgtag cgaaatttat ggagaagact agaaataaca    420

aagttaagtt tgatcctgac cggattgtta tgagcggcgg cgcaaccgga gcacacgaga    480

cggttgcttt ctgtttagct aatcccggcg atggtttctt agttccaacc ccttattatc    540

cagggtttga tagagatttg agatggagaa ccggagtgaa tcttgtaccg gttacttgtc    600

atagctctaa tgggttcaag attacggtgg aagccttgga agctgcttac gaaaacgcga    660

gaaaatcgaa tattccggtt aagggtttac ttgtaaccaa tccttcaaac ccgcttggta    720

cgacgttaga ccgggaatgt ttgaagtctc ttgttaactt cactaatgac aaagggattc    780

atcttattgc tgatgagatt tatgctgcta ctacttttgg tcaatccgag ttcataagtg    840

ttgcggaagt aatcgaggag atcgaagatt gtaaccgcga tttgatacat attgtgtata    900

gtctatctaa agatatgggt ctgcctggtt taagagttgg tatagtatac tcttacaatg    960

acagggtggt tcagatcgca aggaaaatgt cgagtttcgg tcttgtttcg tcacaaacgc   1020

agcatttgat cgctaaaatg ttatccgatg aagagtttgt agacgagttt atccgcgaga   1080

gcaaattgcg gttagctgca aggcacgctg agataaccac cggtttagat ggtttaggga   1140

ttggttggtt aaaggccaaa gccggtttgt tcttgtggat ggatttaaga aatcttttga   1200

agacagcaac gtttgattcg gaaaccgaac tatggcgtgt gattgttcac caagtgaagc   1260

tcaacgtgtc tccaggcggt tcgttccatt gccatgaacc gggatggttt agagtatgtt   1320
```

-continued

```
ttgcgaatat ggaccataag acgatggaga cagctctaga gaggattaga gtgttcacta   1380

gccaacttga ggaggagact aaaccgatgg ctgcaacaac tatgatggct aaaaagaaga   1440

agaagtgttg gcagagtaac ctcaggttaa gctttagtga cacgaggcgg ttcgatgatg   1500

gcttcttctc gcctcattcg cctgtgccgc cttctccgct agtccgtgca cagacttaag   1560

accgtctcat attttgacta gaccagtcgt cgttaattaa aaagtcaatt ctttagattg   1620

attttgacac atttatctga ttaaatcaaa tgtatagcta cgactatcaa gttgattttt   1680

tctttctttt aattttgtat ctcatgtaat tttaaccggg tgaataatat gaatttgaaa   1740

tcagaatttg ttt                                                      1753


<210> SEQ ID NO 27
<211> LENGTH: 1586
<212> TYPE: DNA
<213> ORGANISM: Arabidopsis thaliana

<400> SEQUENCE: 27

atgggtcttc ctctaatgat ggagagatca tcaaacaaca acaacgtcga gctttctcga     60

gtggcggttt cagacactca cggcgaagac tcaccgtact tcgccggctg gaaagcttac    120

gacgaaaatc cttacgacga atctcataac ccttccggtg tcatccaaat gggtctcgct    180

gagaatcagg tctcgtttga tcttcttgaa acttacttgg agaagaagaa tccagaaggt    240

tcgatgtggg gatcaaaagg agctcctggg ttccgtgaaa acgcattgtt tcaagactac    300

cacggtctca aaactttcag acaagccatg gctagtttca tggaacagat tcgaggaggc    360

aaagctagat ttgatcctga ccggatcgtc ctcaccgccg gagccaccgc cgctaacgaa    420

ctcttaactt tcattctcgc cgatcctaac gacgcccttc tagttcccac accgtattat    480

ccaggattcg atagagattt gagatggaga accggagtga aaatagtacc catccactgc    540

gacagctcga accatttcca gataaccccg gaggcgctag agtcggcgta ccaaacggct    600

cgtgacgcga acattagagt ccgaggagtg ctcataacca acccatcgaa cccattaggg    660

gcgacggtcc aaaagaaggt tctagaagat ctccttgact tctgcgtacg caagaatatt    720

cacttggtct cagacgagat ctactccggc tccgtcttcc atgcctccga gttcacaagc    780

gttgccgaga tcgtagaaaa catagatgac gtgtcagtaa aggaacgagt tcacatcgtc    840

tacagtctct ccaaggatct tggtcttcct ggtttccgcg tgggaactat atactcgtac    900

aacgataatg ttgttcggac agcgagaagg atgtcgagct tcacgcttgt ctcgtctcag    960

acacaacata tgctggcttc tatgttgtcg gatgaggagt ttacggagaa gtacattagg   1020

ataaaccggg aaagacttag aagacggtac gataccattg tggaagggct taagaaggca   1080

gggattgagt gtttgaaagg gaacgcaggg ctattttgtt ggatgaattt gggtttcttg   1140

ctcgaaaaga aaactaaaga cggcgagctc cagctttggg atgtgatctt aaaggagctg   1200

aacctgaata tatctccggg atcttcgtgc cactgctcgg aggtcggatg gtttagggtt   1260

tgttttgcta atatgagtga gaacactttg gagattgcgt tgaagagaat acatgagttc   1320

atggaccgac gaaggaggtt ttgaaatgtt aaaaaaaaaa gtaaagtaaa tccgtttttt   1380

tggtggttaa atatatgggg gaggggtaat taattttta ggaaagagaa gataattaat   1440

ttaaacccat tgatgtaaaa tgggttttga tttgtttctc ttttctagat attattgttt   1500

gttttcttgc ttggacaaag caagttaatt tcatgttcat caaggttgat ttgtaatatt   1560

tattgttata aacgaatttt ttaaaa                                        1586
```

<210> SEQ ID NO 28
<211> LENGTH: 1780
<212> TYPE: DNA
<213> ORGANISM: Arabidopsis thaliana

<400> SEQUENCE: 28

```
gatcgtagct tacctacaaa caacactcac aatccaatca aaacaaaaca ctttttattc     60
tctctcaaaa tcttcatatc tactttattc tcctactcat ccatctctgt ctctctatct    120
ctagagctaa ttaagaaaat gggtctcttg tcaaagaaag ctagttgcaa cacgcacggc    180
caagattctt cgtatttttg gggttgggaa gagtatgaaa aaaatcctta cgacgagatc    240
aagaacccag acggcattat ccaaatgggt ctagcagaaa atcagttgtc tttcgatctc    300
attgagtcat ggcttgctaa gaaccccgac gcagccaatt tccaaagaga aggccaatcc    360
atatttcggg aattagctct ctttcaagat tatcatggcc ttccttcctt caagaatgct    420
atggcggatt tcatgtcgga aaatagagga aatcgagttt ctttcaatcc aaacaagctt    480
gtcctcaccg ctggtgctac tccggctaac gagactctca tgttttgtct cgctgatcct    540
ggagatgctt tcttgctccc tacgccgtat tatccaggat ttgataggga tttgaaatgg    600
agaaccggag ctgagattgt accgatccag tgtaagagtg caaacggttt ccgcatcaca    660
aaagtagcac ttgaagaagc ctacgagcaa gctcaaaagc ttaacctaaa agttaaagga    720
gtccttataa ccaacccatc taacccgttg ggcactacaa cgacacgaac cgaactaaac    780
catctcttgg acttcatctc acgtaagaag atacatttga taagcgacga gatctattcg    840
ggtaccgttt tcaccaatcc cggattcatt agcgtaatgg aagtcctcaa agacagaaag    900
ctcgaaaaca ccgatgtttt cgaccgtgtc cacattgttt acagtttgtc taaagatcta    960
ggcctacctg gttttcgcgt tggggtgatt tactccaacg atgattttgt tgtctccgca   1020
gcgacaaaaa tgtccagttt cggtctaatc tcttctcaaa cacaatacct cttgtccgca   1080
ttgttatcag acaagacctt caccaaaaac tacctcgaag aaaaccaaat ccggctcaag   1140
aacagacaca agaagctcgt ctcgggtcta gaggctgcag gcatcgagtg tctcaagagc   1200
aacgccggac tcttctgttg ggttgacatg agacacctat taaaatcaaa cacgttcgaa   1260
gccgagattg agctatggaa aaagatcgtt tacgaggtta agctcaatat ctctcccggt   1320
tcttcgtgcc attgcaacga accgggttgg tttagggttt gttttgcgaa tttgagcgaa   1380
gagacattaa aggtagcgtt ggatagattg aagaggttcg ttgatggacc gtcgcctact   1440
agaagaagtc aaagtgaaca tcaaagacta aagaatctaa ggaagatgaa agtctctaat   1500
tgggttttcc ggctatcgtt tcacgaccgt gaacccgagg aacgatagtc tgtttttaaa   1560
aaaaagttaa agtgtaataa gtatgttttt ttggtcatta tttacaagtg attgttgggc   1620
aaatgtatat ttttttaat atcagaattt gatattttgg tatagttttt tttagggaga    1680
aagttcactc attccgtaag tgtaacggat aatgcagtgt ggcttttctt atgtataatt   1740
tactgtcact ttctaatgat atttaaaagt aataattgtc                         1780
```

<210> SEQ ID NO 29
<211> LENGTH: 1410
<212> TYPE: DNA
<213> ORGANISM: Arabidopsis thaliana

<400> SEQUENCE: 29

```
atgggtctct tgtcaaagaa agctagttgc aacacgcacg gccaagattc ttcgtatttt     60
tggggttggg aagagtatga aaaaaatcct tacgacgaga tcaagaaccc agacggcatt    120
```

```
atccaaatgg gtctagcaga aaatcagttg tctttcgatc tcattgagtc atggcttgct    180

aagaaccccg acgcagccaa tttccaaaga gaaggccaat ccatatttcg ggaattagct    240

ctctttcaag attatcatgg ccttccttcc ttcaagaatg ctatggcgga tttcatgtcg    300

gaaaatagag gaaatcgagt ttctttcaat ccaaacaagc ttgtcctcac cgctggtgct    360

actccggcta acgagactct catgttttgt ctcgctgatc ctggagatgc tttcttgctc    420

cctacgccgt attatccagg atttgatagg gatttgaaat ggagaaccgg agctgagatt    480

gtaccgatcc agtgtaagag tgcaaacggt ttccgcatca caaaagtagc acttgaagaa    540

gcctacgagc aagctcaaaa gcttaaccta aaagttaaag gagtccttat aaccaaccca    600

tctaacccgt tgggcactac aacgacacga accgaactaa accatctctt ggacttcatc    660

tcacgtaaga agatacattt gataagcgac gagatctatt cgggtaccgt tttcaccaat    720

cccggattca ttagcgtaat ggaagtcctc aaagacagaa agctcgaaaa caccgatgtt    780

ttcgaccgtg tccacattgt ttacagtttg tctaaagatc taggcctacc tggttttcgc    840

gttggggtga tttactccaa cgatgatttt gttgtctccg cagcgacaaa aatgtccagt    900

ttcggtctaa tctcttctca aacacaatac ctcttgtccg cattgttatc agacaagacc    960

ttcaccaaaa actacctcga agaaaaccaa atccggctca agaacagaca caagaagctc   1020

gtctcgggtc tagaggctgc aggcatcgag tgtctcaaga gcaacgccgg actcttctgt   1080

tgggttgaca tgagacacct attaaaatca aacacgttcg aagccgagat tgagctatgg   1140

aaaaagatcg tttacgaggt taagctcaat atctctcccg gttcttcgtg ccattgcaac   1200

gaaccgggtt ggtttagggt ttgttttgcg aatttgagcg aagagacatt aaaggtagcg   1260

ttggatagat tgaagaggtt cgttgatgga ccgtcgccta ctagaagaag tcaaagtgaa   1320

catcaaagac taaagaatct aaggaagatg aaagtctcta attgggtttt ccggctatcg   1380

tttcacgacc gtgaacccga ggaacgatag                                    1410
```

<210> SEQ ID NO 30
<211> LENGTH: 1413
<212> TYPE: DNA
<213> ORGANISM: Arabidopsis thaliana

<400> SEQUENCE: 30

```
atgaaacaac tgtcgagaaa agtgacaagc aatgctcatg gacaagactc ttcctacttc     60

ttgggatggg aagaatacga gaagaaccct tacgacgaaa tcaagaaccc taatgggatt    120

attcaaatgg gtcttgccga aaatcagcta tgttttgatc tcatagagac atggttagct    180

aagaatccgg acgcagccgg actaaaaaag gacggccaat ccattttcaa agagcttgct    240

ctctttcaag actatcatgg cctacccgaa ttcaagaaag ctttggcaga gtttatggag    300

gaaatcagag gaaatagagt aacatttgat ccaagcaaga ttgtcctagc tgctggttca    360

acatctgcca acgaaactct catgttttgt ctcgccgaac ccggggacgc tttcctttta    420

ccaactcctt actatccagg attcgataga gacttgaaat ggagaacggg agcagagatc    480

gtacctattc attgctcaag ctctaatggg ttccaaataa cagagtcagc tcttcaacaa    540

gcttatcaac aagctcaaaa gcttgatctt aaggtcaaag gagttcttgt taccaacccg    600

tctaaccctc ttggcacaat gttgaccaga agagaactta accttctcgt tgacttcatt    660

acttccaaaa acattcatct cataagcgac gagatctatt caggtaccgt tttgggttt    720

gaacagtttg taagtgtcat ggatgtctta aaagacaaga acctcgagaa cagcgaagtc    780

tccaaacgag ttcatattgt ttatagtctt tccaaagatc tcggtttacc aggttttcgc    840
```

```
gtaggagcaa tttactccaa cgacgaaatg gttgtttccg ctgcaacaaa aatgtcaagt    900
ttcggtctcg tgtcttctca aacacagtac cttctctctg cattgctttc agacaagaag    960
ttcacaagta catacctcga cgaaaaccag aaaagactca agattcgtca gaagaaactc   1020
gtgtccggtc tagaagctgc agggattact tgtcttaaaa gcaacgctgg tttgttctgt   1080
tgggttgaca tgagacatct tttggacaca aacacattcg aagcagaact tgagctatgg   1140
aagaagattg tatatgacgt caagctgaat atttcacctg gttcatcgtg ccattgtact   1200
gaaccgggtt ggtttagggt ttgtttcgcc aacatgagtg aagatacgct tgatttggcg   1260
atgaagaggc tcaaagagta cgtagagtca acagatagta gaagagtgat ttcaaaaagc   1320
agtcatgata ggatcaagag tttgaggaag agaactgtct ccaactgggt tttccgggtt   1380
tcatggaccg accgtgtacc tgatgaacga tga                                1413
```

<210> SEQ ID NO 31
<211> LENGTH: 1845
<212> TYPE: DNA
<213> ORGANISM: Arabidopsis thaliana

<400> SEQUENCE: 31

```
cgacccgtta aaaaaccttc aaagtggctc cgattttgat ttcaaacact aaaatattta     60
tttacctaaa aacatgagtt cactacaatg acccgtaccg aaccaaaccg gagccggagc    120
tccaattccg attccgataa gaattccggt aacgtcggcg gaggtagaac caccgggatg    180
agggttattg ttccgttaca aggtgtggta caaggtcgtg gtggtttatt cttaggctct    240
gtgattcctt gtgctttctt ctactttctt cagttttacc taaaacgaaa tcgtaaaaac    300
gacgaatcag ataattccgg tgaacaaaac tcctcagctt cttcttcttc ttctcctaat    360
tcgggtttac cggatcccac ccggtcacaa tccgctggtc atctcacgga gcttactggt    420
ttacctcgtt ctctctctcg tattctcctc tcgccgagaa attccggtgg agctgtttcg    480
gtttcgggtc gggttaattg tgtactcaaa ggtggagatt cttcgcctta ctacgttggt    540
caaaaacggg tcgaggatga tccgtatgat gagttgggta acccggacgg agttatccaa    600
cttggtttag ctcaaaacaa caagttgagt ttggatgatt gggttttaga gaatccaaaa    660
gaagcaattt cagatggatt gagtattagt ggcattgctt cttatgagcc ttctgatgga    720
cttttggaac tgaaaatggc tgtggcagga tttatgactg aagctaccaa aaactcggtg    780
acttttgatc catcacagtt agtgttaact tctggtgcat catctgctat tgagattctt    840
tccttctgct tagctgattc gggaaacgcc ttccttgttc caactccgtg ttctcccgga    900
tatgataggg atgttaaatg gcgaacagga gttgacatta tacacgttcc atgtagaagt    960
gcggataatt tcaatatgtc gatggtcgtg cttgatcgag cattctatca agctaagaaa   1020
cgaggtgtaa gaatccgcgg cattataatc tcgaatcctt caaatcccat gggaagccta   1080
ctgagcagag agaatctcta tgcgcttttg gactttgccc gtgagaggaa cattcatatt   1140
atatcaaacg aaatctttgc tgggtcagtc cacggagaag aaggagagtt tgttagcatg   1200
gctgaaatag ttgacacgga agagaatatc gacagggaaa gagttcatat cgtgtatgac   1260
ctttcgaaag acttgtcttt ccgggggctt agatccgctg ctatctactc gttcaacgag   1320
agtgttttat ccgcttcaag aaagctcacg acgctctcac ctgtctcatc tccaacccaa   1380
catttgctga tatccgcaat ctccaatcca aaaaatgttc agagatttgt gaaaaccaac   1440
aggcagagat tgcagagtat ctacacggag ctcgtggagg ggttgaaaga gttagggatc   1500
```

gagtgcacaa gaagcaatgg agggttctac tgttgggctg atatgcgagg attgatttca 1560
tcttacagcg aaaaaggcga gattgagctg tggaacaagc tcttgaacat tggcaagatc 1620
aatgtcatac caggatcttg ttgtcactgt atcgaaccag gatggttccg tatctgtttc 1680
agtaatttgt ctgagagaga tgtgccagta gttatgaacc gcattagaaa agtttgtgaa 1740
acatgtaaat ctcaaaattg attacaattt gattatttgg tttattctga atcagactct 1800
ttatatcagt aaaccggata atatcaatcc agaatcggtt taagg 1845

<210> SEQ ID NO 32
<211> LENGTH: 1383
<212> TYPE: DNA
<213> ORGANISM: Arabidopsis thaliana

<400> SEQUENCE: 32
atgttgtcaa gcaaagttgt tggcgactct catggacaag actcatccta cttccttgga 60
tggcaagaat acgagaagaa tcctttccac gagtcgttta acactagtgg gattgttcaa 120
atgggtcttg ctgaaaacca gctttctttt gacctaatag agaaatggct tgaagagcat 180
ccagaagtct tgggtttgaa gaaaaatgat gagtcggtgt ttagacaatt agctctgttc 240
caagattacc atggcttgcc agctttcaag gatgccatgg cgaagttcat ggggaaaatc 300
agagagaaca aagtgaaatt cgatacgaac aagatggttc ttacagctgg atcaacctcg 360
gctaacgaga ctctaatgtt ctgtcttgct aatccaggag atgcctttct tatccctgca 420
ccttattatc cagggtttga tagagatctc aaatggagga caggagtaga gattgttcct 480
atccattgcg taagctcaaa tgggtacaag ataaccgagg atgcattaga agatgcctac 540
gaacgagctc tcaaacataa cctaaatgtt aaaggagttc tcataaccaa cccttcaaac 600
ccacttggaa cctctaccac ccgtgaagag cttgatcttc ttctgacctt cacatcaacc 660
aagaaaatcc atatggttag cgatgagatc tactcgggaa cggttttcga ctctcctgag 720
ttcaccagcg ttctagaagt ggctaaggac aagaacatgg gtttagatgg taaaatccat 780
gttgtttaca gcttgtccaa agatctaggc ctccccggat ttcgtgttgg cttgatttac 840
tcaaacaatg agaaagtggt gtcagccgcg actaaaatgt cgagttttgg actcatttct 900
tcccaaactc aacatttgct agccaatttg ctgtctgatg aaagattcac gaccaactat 960
ttggaagaga acaagaagag gctgagagag agaaaggata ggctggtttc gggtctaaag 1020
gaagcgggta tcagttgttt gaagagtaac gcaggtttgt tctgttgggt tgacttaaga 1080
cacctcttga aatccaacac ttttgaggcc gagcattctt tatggacaaa gattgtgtgt 1140
gaagttggtc ttaacatctc tccaggctca tcgtgtcatt gcgatgaacc tggttggttt 1200
agagtttgtt tcgcgaatat gtcggaccaa acgatggagg ttgctatgga ccgtgttaaa 1260
ggttttgttg acaacaataa tggtggtaaa caaaagagaa ccatgtggga tacaaggaga 1320
agatctctta tcaacaaatg ggtctccaag ctttcctctg ttacttgtga atcagaacgt 1380
tga 1383

<210> SEQ ID NO 33
<211> LENGTH: 372
<212> TYPE: DNA
<213> ORGANISM: Oryza sativa

<400> SEQUENCE: 33
gttggtatag tatactctta caatgaccgg gtggttcaga tcgcaaggaa aatgtcgagt 60
ttcggtcttg tttcgtcaca aacgcagcat ttgatcgcta aaatgttatc cgatgaagag 120
tttgtagacg agtttatccg cgagagcaaa ttgcggttag ctgcaaggca cgctgagata 180
accaccggtt tagatggttt agggattggt tggttaaagg ccaaagccgg tttgttcttg 240
tggatggatt taagaaatct tttgaagaca gcaacgtttg attcggaaac cgaactatgg 300
cgtgtgattg ttcaccaagt gaagctcaac gtgtctccag gcggttcgtt ccattgccat 360
gaaccgggat gg 372

<210> SEQ ID NO 34
<211> LENGTH: 372
<212> TYPE: DNA
<213> ORGANISM: Oryza sativa

<400> SEQUENCE: 34
gttggagtgg tttactctta caacgatgtt gttgtgtcct gcgcaaggag gatgtcgagt 60
tttggattgg tctcgtcgca gacacaaagt tttctagctg ctatgttgtc tgatcagagt 120
tttgtcgata actttcttgt tgaggtttcg aaaagagtag cgaagagaca ccatatgttc 180
acggaagggc ttgaagagat ggggatttct tgcttgagaa gcaacgcggg tttattcgtt 240
ttgatggatt tgaggcatat gcttaaggat cagacatttg attccgaaat ggcgctttgg 300
cgagttacta tcaataaggt caagattaat gtctctcctg gctcgtcgtt tcactgctct 360
gagcctggtt gg 372

<210> SEQ ID NO 35
<211> LENGTH: 735
<212> TYPE: DNA
<213> ORGANISM: Oryza sativa

<400> SEQUENCE: 35
ctttctctgg acctgatcga gaatgagcaa gaccaccccg aggcatccat ttgcacaccg 60
gagggcgtct cgcagttcaa gaggatcgcc aattttcagg actatcatgg cctcccggag 120
ttcagaaagg cgatggccca gtttatgggg caggtgaggg gaggcaaggc aacgtttgac 180
cccgaccgtg tcgtcatgag cggcggcgcc accggcgccc aggagacgct cgccttctgc 240
ctcgccaacc ccggcgaggc cttcctcgtg cccacgccat actacccagc tttcgaccgc 300
gactgttgct ggaggtcagg aataaagctg ctgccgatcg agtgccacag cttcaacgac 360
ttcaggctca ccaaggaggc cctcgtgtcg gcgtacgacg gcgcacggag gcagggcatc 420
tccgtcaagg ggatcctcat caccaacccg tccaacccgc tcggcaccat caccgaccgc 480
gacacgctgg ccatgctcgc caccttcgcc accgagcacc gcgtccacct cgtctgcgac 540
gagatctacg cggggtcggt gttcgccacg ccggagtacg tgagcatcgc cgaggtcatc 600
gagcgcgacg tgccgtggtg caacagggac ctgatccacg tcgtgtacag cctctctaag 660
gacatcggcc tccccggctt ccgcgtcggc atcatctact cgtacaacga cgccgtcgtg 720
gcggccgcgc gcagg 735

<210> SEQ ID NO 36
<211> LENGTH: 192
<212> TYPE: DNA
<213> ORGANISM: Oryza sativa

<400> SEQUENCE: 36
acgacgttag accgggaatg tttgaagtct cttgttaact tcactaatga caaagggatt 60
catcttattg ctgatgagat ttatgctgct actacttttg gtcaatccga gttcataagt 120
gttgcggaag taatcgagga gatcgaagat tgtaaccgcg atttgatcca tattgtgtat 180
agtctatcta aa 192

<210> SEQ ID NO 37
<211> LENGTH: 102
<212> TYPE: DNA
<213> ORGANISM: Oryza sativa

<400> SEQUENCE: 37
gtctccttcg acctcctcga ggcctacctc cgtgaccacc cggaggccgc cggctggagc 60
accggcggcg ccggcgccgg tagcttcagg gacaacgcgc tg 102

<210> SEQ ID NO 38
<211> LENGTH: 105
<212> TYPE: DNA
<213> ORGANISM: Oryza sativa

<400> SEQUENCE: 38
gtctccatcg acctcctcga gggctacctc cgggagcacc cggaggccgc cgcctggggc 60
gtcgccggcg acggcggcgg cgacagcttc agggacaatg cgctg 105

<210> SEQ ID NO 39
<211> LENGTH: 208
<212> TYPE: DNA
<213> ORGANISM: Oryza sativa

<400> SEQUENCE: 39
gtgatcttag ttgctaaaat cttaattgtt cttacttcaa actaatcgaa aacgcgttaa 60
tgcgttatat atatcatgtg tatcgatcgt taagacgcaa taacttttac gtttcctgtg 120
ttaggtttcc tttgatcttc tagaggaata catgagggag cacccggagg cgtcggattg 180
cggcgccggg tttcgagaga acgccctc 208

<210> SEQ ID NO 40
<211> LENGTH: 189
<212> TYPE: DNA
<213> ORGANISM: Oryza sativa

<400> SEQUENCE: 40
gtacgcgcac agacctgtgt atactcattt ctgaattaag gatcgttctc gacaaagtgc 60
taatccgtct ttgttgccct gtaaatgtca cagctttctc tggacctgat cgaggaatgg 120
agcaagaacc accccgaggc atccatttgc acaccggagg gcgtctcgca gttcaagagg 180
atcgccaac 189

<210> SEQ ID NO 41
<211> LENGTH: 2778
<212> TYPE: DNA
<213> ORGANISM: Oryza sativa

<400> SEQUENCE: 41
gaattcgaag cagcagcagc agcagaagga gaagcttctt aattcgttcg cgtttaacaa 60
ccccatcccc gtagacgacg acgaggagga gaacgatggc atggcatggc atccctgtcg 120
gcgtgcagta acacctcact ctgctgctgt cccgacgtta acctctcccc tcactgacgc 180
taagcacact ggcagtcgcg tactacacgc ggttagagcg agcttccatt agcccccgag 240
aaattaacaa aaagcaaaag cagaaggaaa aaaaaagaaa aacgtcactc gcatcacagc 300
actagccgcg ctctctctct ctcctcacca gattctatat aagcagctcg tccaaccttg 360

```
ggaggcaccc agcagcagcc agctagctag ctactcctac tcagcagcag cagcagctca    420
ggtctctcca gtgttcttcg agctatacac tagctctcac agatttttgc tccgactcat    480
caagcggatt gattcgatcg gctgttagag agagaaaaaa ggagagttgg agatggtgag    540
ccaagtggtc gccgaggaga agccgcagct gctgtccaag aaggccgggt gcaacagcca    600
cggccaggac tcgtcctact tcctggggtg gcaggagtac gagaaaaacc cgttcgaccc    660
cgtctccaac ccttccggca tcatccagat gggcctcgcc gagaaccagg tacgcacacg    720
cgcgtgccac acctgcatgt acacacttgt acatgtgtgt acactgtctc tgacgacatg    780
gttgctctgc cttggctgtt gcagctgtcg ttcgacctgc ttgaggagtg gctggagaag    840
aacccccacg cgctcggcct ccggcgagag ggcggcggcg cctccgtctt ccgcgagctc    900
gcgctgttcc aggactacca cggcctcccg gctttcaaaa atgtaattaa ttaaatcaac    960
tgtactctgg ttcgcgtaca cggtcgtcaa aagttacagt tggctaaccc cccgagcata   1020
tgcgcacgtg gattgcacag gcattggcgc ggttcatgtc ggagcagaga gggtacaagg   1080
tggtgttcga ccccagcaac atcgtgctca ccgccggcgc cacctcggct aacgaggcgc   1140
tcatgttctg cctcgccgac cacggcgacg ccttcctcat ccccacccca tactacccag   1200
ggtacgcact ggcactgccg ctgctgctac accttttac catacgcgac aacgtgcatg    1260
gtggcgcatg gctaacggtg gatggatggg tggatgcagg ttcgaccgcg acctcaagtg   1320
gcgcaccggc gcggagatcg tacccgtgca ctgcgcgagc gcgaacgggt tccgggtgac   1380
gcgcgccgcg ctggacgacg cgtaccgccg cgcgcagaag cgccggctgc gcgtcaaggg   1440
ggtgctgatc accaacccgt ccaacccgct cggcaccgcg tcgccgcgcg ccgacctcga   1500
gacgatcgtc gacttcgtcg ccgccaaggg catccacctc atcagcgacg agatctacgc   1560
cggcacggcg ttcgccgagc cgcccgcggg cttcgtcagc gcgctcgagg tcgtggccgg   1620
gcgcgacggc ggcggcgctg acgtgtccga ccgcgtgcac gtcgtgtaca gcctgtccaa   1680
ggacctcggc ctcccggggt tccgcgtcgg cgccatctac tccgccaacg ccgccgtcgt   1740
gtccgcggcg accaagatgt ccagcttcgg cctcgtgtcg tcccagacgc agtacctcct   1800
cgcggcgctg ctcggcgaca gggacttcac ccggagctac gtcgcggaga acaagcggcg   1860
gatcaaggag cggcacgacc agctcgtgga cgggctcagg gagatcggca ttgggtgcct   1920
gcccagcaac gccggcctct tctgctgggt ggacatgagc cacctgatgc ggagccggtc   1980
gttcgccggc gagatggagc tctggaagaa ggtggtgttc gaggtcggcc tcaacatctc   2040
ccccgggtcg tcgtgccact gccgcgagcc cggctggttc cgcgtctgct tcgccaacat   2100
gtcggccaag accctcgacg tcgccatgca gcgcctcagg tcgttcgtcg actccgccac   2160
cggcggcggc gacaacgccg ccctccgccg cgccgccgtc cccgtcagga gcgtcagctg   2220
cccgctcgcc atcaagtggg cgctccgcct caccccgtcc atcgccgacc ggaaggccga   2280
gagataatcg ccaagaacaa aaccacacca tgtccattac tattaccagt agtagcacat   2340
actagtacat tactacgtca cagtacacta tactagtagc agcagtagca gattcctttc   2400
gtttcttgta atcttttggc gccatttttt tttcctcgga tcgaggcgtg catgcccgat   2460
ggtctcggat gatcacatat cgatccattc catcagccgg catcggatcg atcccgtatt   2520
tttcactggg aattttcagt tttcccccga cactgaattt ctcccagttg ttgtaaccta   2580
tggaaagtat tattgctcgt caataaaagc tagtgcccac cacttgtagt tcacgactac   2640
cactcccaca tttgggctcg gtcgcatcca tccatcgcgt gttttcgccg ccgctgtcat   2700
```

-continued ataaaagtca accgttgcag cgaaaccact tgggccaatg gcgtttttta acccccatct 2760
gctccgtatt gcatgcga 2778

<210> SEQ ID NO 42
<211> LENGTH: 1485
<212> TYPE: DNA
<213> ORGANISM: Oryza sativa

<400> SEQUENCE: 42
gatggtgagc caagtggtcg ccgaggagaa gccgcagctg ctgtccaaga aggccgggtg 60
caacagccac ggccaggact cgtcctactt cctggggtgg caggagtacg agaaaaaccc 120
gttcgacccc gtctccaacc cttccggcat catccagatg ggcctcgccg agaaccagct 180
gtcgttcgac ctgcttgagg agtggctgga gaagaacccc cacgcgctcg gcctccggcg 240
agagggcggc ggcgcctccg tcttccgcga gctcgcgctg ttccaggact accacggcct 300
cccggctttc aaaaatgcat tggcgcggtt catgtcggag cagagagggt acaaggtggt 360
gttcgacccc agcaacatcg tgctcaacgc cggcgccacc tcggctaacg aggcgctcat 420
gttctgcctc gccgaccacg gcgacgcctt cttcatcccc accccatact acccagggtt 480
cgaccgcgac ctcaagtggc gcaccggcgc ggagatcgta cccgtgcact gcgcgagcgc 540
gaacgggttc cgggtgacgc gcgccgcgct ggacgacgcg taccgccgcg cgcagaagcg 600
ccggctgcgc gtcaaggggg tgctgatcac caacccgtcc aacccgctcg gcaccgcgtc 660
gccgcgcgcc gacctcgaga cgatcgtcga cttcgtcgcc gccaagggca tccacctcat 720
cagcgacgag atctacgccg gcacggcgtt cgccgagccg cccgcgggct tcgtcagcgc 780
gctcgaggtc gtggccgggc gcgacggcgg cggcgctggc gtgtccgacc gcgtgcacgt 840
cgtgtacagc ctgtccaagg acctcggcct cccggggttc cgcgtcggcg ccatctactc 900
cgccaacgcc gccgtcgtgt ccgcggcgac caagatgtcc agcttcggcc tcgtgtcgtc 960
ccagacgcag tacctcctcg cggcgctgct cggcgacagg gacttcaccc ggagctacgt 1020
cgcggagaac aagcggcgga tcaaggagcg gcacgaccag ctcgtggacg ggctcaggga 1080
gatcggcatt gggtgcctgc ccagcaacgc cggcctcttc tgctgggtgg acatgagcca 1140
cctgatgcgg agccggtcgt tcgccggcga gatggagctc tggaagaagg tggtgttcga 1200
ggtcggcctc aacatctccc ccgggtcgtc gtgccactgc cgcgagcccg gctggttccg 1260
cgtctgcttc gccaacatgt cggccaagac cctcgacgtc gccatgcagc gcctcaggtc 1320
gttcgtcgac tccgccaccg gcggcggcga caacgccgcc ctccgccgcg ccgccgtccc 1380
cgtcaggagc gtcagctgcc cgctcgccat caagtgggcg ctccgcctca ccccgtccat 1440
cgccgaccgg aaggccgaga gataatcgcc aagaacaaaa ccaca 1485

<210> SEQ ID NO 43
<211> LENGTH: 4303
<212> TYPE: DNA
<213> ORGANISM: Glycine max
<220> FEATURE:
<221> NAME/KEY: misc_feature
<222> LOCATION: 1550, 1742, 1776, 1838, 2351, 2992, 3113, 3233, 3267, 3335, 3353, 3540, 3624, 3625, 3631, 3640, 3645, 3661, 3662, 3684, 3699, 3727, 3766, 3809, 3814, 3824, 3830, 3839, 3856, 3868, 3875, 3879, 3881, 3906
<223> OTHER INFORMATION: n = A,T,C or G

<400> SEQUENCE: 43
ccagtttgca cgcctgccgt tcgacgatca taagtgtggt tttgtgggct cctgtctatg 60

-continued

```
acaggataat tgttcccatt acaaggaaat tcaccggcaa tgaaaggaga atttcagtgc    120
tgcaaagagt aagcattggc tacttcattt cagtcctgtc catgttgtag tgttggtgag    180
gaagtttagt ttttctttgg ggcttgaatt ttgtccattc aatgttctgt tgtgctttgt    240
cttctctgta gatgttgagg attggatctt ctatcttgca tttcattgac gaaaaatata    300
tccttttgtt tgttagtttg tttttacata ttgaataact aaaatcaaga agatattttg    360
ctgtgcttta cccctttctt tctcttggac tcataatgag cattagagct ataattccct    420
tatgattatt ttctcttttg aattgatagc atgacggttt gaaagttgaa agtacagaat    480
cctgctaact cccccattgc tttaatctcc tcgaaagttc ttttcaattt ctgttatggc    540
tatagtatgc ttttatttta ctttgagctt ttgtaaaaat gatattttga ttattttctg    600
tttgtatttc tacttgatat ttttttgtc tttgatttta ttgtagaagt tgcctgacat    660
ggcttcgtac accccaaaga atatcctcat tactggggcg gctggattta ttgcgtctca    720
tgttgccaac cggcttgtcc ggagctaccc tgactacaaa attgttgtgc ttgacaaact    780
tgattattgt tctagtctga agaacctcct tccttcaaaa tcatctccta acttcaaatt    840
tgtgaagggg gatattggta gtgctgatct tgtcaactac cttctcatca ccgaatccat    900
tgacactata atgcatttcg ctgcccaaac ccatgttgac aactcgtttg gtaatagctt    960
tgagttcacc aagaacaaca tatacggaac tcatgtccta ttagaagcct gcaaggttac   1020
tggccagatc agaaggttca ttcatgtgag cactgatgag gtctatggag agacggaaga   1080
ggatgctgtt gttggaaacc atgaggcctc tcaacttctt cccactaacc cgtactctgc   1140
tacaaaagct ggggctgaaa tgcttgtcat ggcttatggt aggtcatatg ggctacctgt   1200
tattacaact cgtggaaaca atgtttatgg gcccaatcag tttcctgaga agttaattcc   1260
aaagttcatc ctcctggcta tgcagggaaa gaatcttcca attcatgggg atggttcaaa   1320
tgtgaggagt tatttatatt gtgaagatgt tgctgaggct tttgaagttg tcctgcacaa   1380
gggtgaggtt ggccatgttt acaatatcgg gacaaagaag gaaaggagag ttgtcgatgt   1440
agccaaagat atatgcagac ttttctcaat ggacccagaa acttgtataa aatttgtaga   1500
gaacagacca tttaacgacc agagatactt tcttgatgat caaaagctgn aggacttggg   1560
ttggtctgag aggaccactt gggaagaagg cttgaagaaa accatggatt ggtatatcaa   1620
taaccctgat tggtggggtg atgttactgg ggcattgctt cctcatccta ggatgctgat   1680
gatgcctggt gggttggaga ggcatttcga gggatctgaa gagggaaaac ctgcatcttt   1740
tngctcaagt aataccagga tagtggttcc atcatncaag aacaccagct ctcaacagaa   1800
acatcctttt atgttcttga tctatggtag aacagggngg attgggggtt tgctggggaa   1860
attgtgtgaa aagcaaggaa ttccgtatga atatggaaag ggtcgcctag aggaccgctc   1920
ctcactcttg gctgatcttc agaatgtgaa gcctacacat gtttttaatg ctgcaggagt   1980
gaccggcaga cccaatgttg attggtgtga atcccataaa acagaaacca tccgcaccaa   2040
tgttgctggt accttaacaa tggctgatgt ctgcagagag catgggatct tgatgataaa   2100
ttatgctact gggtgcatat tcgagtacaa tgcaacacat cccgagggct ctggcattgg   2160
ttttaaggag gaagacaagc ccaatttcat tggctctttc tattccaaaa ctaaagctat   2220
ggtaagtttc ttacatgtta tggattaatt atatctgttc ataatgaatt atcataataa   2280
tttttatgtg aacattgaca ggttgaggag ctcttgagag actatgacaa tgtatgcaca   2340
ctcagggttc ncatgccaat ttcgtcagac ctgagcaacc cgcgcaactt cataacaaag   2400
atttctcgtt ataacaaagt ggtcaacatt ccaaacagta tgactatttt ggatgaactt   2460
```

```
ctgcctatct caattgagat ggcaaagagg aacttgaagg gaatctggaa cttcacaaat   2520

ccaggggttg tgagccacaa tgagatcctt gagatgtaca gggattacat tgacccaaac   2580

ttcaagtggt ctaacttcac ccttgaagag caagcaaagg tgattgttgc tcctcgaagc   2640

aacaatgaga tggacgcatc aaaattgaag acagaattcc cagaattgct ttccatcaag   2700

gaatcactca tcaaatatgt ctttgagcca aacaagaaaa cataagcagg tttatgttat   2760

tcagacaagg cagttatgtg ttcaggctat atagaccagt gaaattggat tttctaacta   2820

agttattgta aaaaaaaaaa aactgatgaa agggaagaac atcattagat attgttgata   2880

aattccatta ctattagtac accaaatgtg gcaaatatgt tctgctcata tgttatccat   2940

tgacctttct cacctcatcc gtatatattt tttggacttg tgttgatgag cnacttttct   3000

gccggtagtt cgttctcctt ggtttttggt tcccgttaat caaacacaat gaacataaaa   3060

aaaatcaaaa tttctaattt tttttagccc aaataatctg atgtcattta cancttatat   3120

atgtgatttt tgcactgtac agaacgtgtc atttacaact tatatatgag gatgtatatc   3180

cctttgtact agtacctctg gtactgtttt gatcatatat atataatata ttnagttttg   3240

ctgatcaaaa aaaaaactaa caatttncct atatcactat atgtgtagta agcaacctga   3300

tcagaacatg cttcaactca taatagatgt ctganaaatc ttaagaagtc ttngtctgct   3360

tgtacctttt ggcagcaaca atgtatacca acatatttaa gaagctaagt ccagctaaaa   3420

gcaagaaaaa ataatcgaga tgacccttgt tcaaattatc aggaatccag ccaagctttc   3480

caccttgtgt ggtgaagtaa gtcaccatag taagaatgaa agagctcaag taatttcccn   3540

acgcaaaata caaaggtgac agtgctgtac ctaaagtctt catagtatct ggagattgat   3600

catagaagaa ctcaagcagt cccnngaatg ngaatacttn tgctnccccc aataagaagt   3660

nntgagggat ttgccaaagt atantgagtg gtacagcanc aggttcatca acaagatcaa   3720

ggtctcntgc aagccgcaga cgcataatct ccacaacaac agctgntaac atggacagga   3780

ctgaaatgaa gtagccaatg cttactctnt gcancactga aatncccctn tcattgccng   3840

tgaatttcct tgtaanggga acaattancc tgtcntagnc nggagcccac aaaaccacac   3900

ttatgncatc aacagttgcc agggaagctg gggtatttc aaaggagcca atgtgtgtgt   3960

tcatcactgt tccttgctcc acaaacaatg ttgacatctg ggtataaaca gcagaaaaaa   4020

cggccccagt agcccacatt ggaaacatgc agatcaagat tttcaattcc tctcactcac   4080

taggacaatc attatttcta attaatagtg gggctagtct gcgtaccaac tactgcctaa   4140

ttttcaaacc aaagaagcat catagctgat gttgaactct tctctctttc gtgggaacct   4200

tcatttaatt tgaactaaag agattcctgt ctctgaaggt caaggtgaat ttgtgcacta   4260

cattataaat aagcacccct ctcggtgttg ttcattgcta gac                     4303
```

<210> SEQ ID NO 44
<211> LENGTH: 1789
<212> TYPE: DNA
<213> ORGANISM: Glycine max

<400> SEQUENCE: 44

```
gaattcggca cgagatttcc tctgaaaatt attcatagca tatttctaac cacactcaaa     60

aggcttccct tcctgacttg gatttcatta cattgctaaa ctatattatt tttattggtg    120

aattgctaca ctatattcta aggacaatta aacatagact atatggggtt gatggatgtg    180

gaccaaactc aattgttgtc taagatggtc atcggagatg gacatggtga agcatcacca    240
```

```
tactttgatg gatggaaggc ttatgatgaa aacccctttc atcccaaaga gaatcctaac    300
ggggttatcc aaatgggtct tgctgagaat cagcttactt ctgatttggt tgaagattgg    360
atactgaata acccagaggc ctccatttgc acaccagaag gaataaatga tttcagggcc    420
atagctaact ttcaggatta tcatggtctg cccgagttca gaaatgctgt ggctaaattc    480
atgggtagaa caagaggaaa cagagtcacg tttgatcctg accgtattgt catgagcggt    540
ggagcaactg gagcacacga agtcactacc ttttgtttgg cagaccctgg tgacgcattt    600
ttggtgccca ttccttatta tccaggtttt gaccgggatt tgaggtggag aacaggaatt    660
aaacttgttc cagttatgtg cgatagctca aacaatttca agttgacaaa gcaagcattg    720
gaagatgcgt atgagaaggc caaagaggat aatataagag taaagggctt gctcatcacc    780
aatccatcaa acccattagg cacagtcatg gacagaaaca cactaagaac cgtgatgagc    840
ttcatcaacg agaagcgtat ccaccttgta tctgatgaaa tatactctgc aacagttttt    900
agccacccca gtttcataag cattgctgag atattagagg aagacacaga catcgaatgt    960
gaccgcaacc tcgttcacat tgtttatagt ctttcaaagg atatggggtt ccctggcttc   1020
agagttggca tcatatactc ttacaatgat gctgtggtcc attgtgcacg caaaatgtca   1080
agctttggat tggtgtcaac acagactcag tatcttttag catcaatgct aaatgatgat   1140
gagtttgtgg aaagttttct ggtagagagt gcaaaaaggc tggcacaaag gcatagagtt   1200
ttcactgggg ggttggccaa agttggcata aagtgcttgc aaagcaatgc tggtctcttt   1260
gtgtggatgg atttaaggca acttctcaag aagccaacgc ttgactctga aatggagctt   1320
tggagagtga tcattgatga ggttaagatc aatgtttcac ctggctcctc tttccattgc   1380
actgagccag ggtggtttag ggtgtgctat gccaacatgg atgatatggc tgtgcaaatt   1440
gcattgcaaa gaattcgtaa ctttgtgctt caaaacaagg agatcatggt gcctaacaag   1500
aaacattgtt ggcacagtaa cttgaggttg agcctcaaaa ccagaaggtt tgatgatatc   1560
atgatgtcac ctcactcccc catacctcag tcacctctgg ttaaagccac aatttgagtt   1620
ggcatatttc tctgaaccct ctagaagaag taactgatat atgatgatta tttggctctt   1680
tgacttgttg ttttggcaag gtacataaag tgcttgagtt tgttattttt aacagcagta   1740
acaggcaatg cctgatattg tttttgttac caaaaaaaaa aaaaaaaaa              1789
```

<210> SEQ ID NO 45
<211> LENGTH: 1473
<212> TYPE: DNA
<213> ORGANISM: Glycine max
<220> FEATURE:
<221> NAME/KEY: misc_feature
<222> LOCATION: 1400
<223> OTHER INFORMATION: n = A,T,C or G

<400> SEQUENCE: 45

```
caattaaaca tagactatat ggggttgatg gctgcgaacc aaactcaatt gttgtctaag     60
atggccatcg gagatggaca tggtgaagca tccccatatt ttgatggatg gaaggcttat    120
gatgaaaacc cctttcatcc caaagagaat cctaacgggg ttattcaaat gggtcttgct    180
gagaatcagc ttacttctga tttggttgaa gattggatac tgaataaccc agaggcctcc    240
atttgcactc cagaaggaat aaatgatttc agggcaatag ctaactttca ggattatcat    300
ggtctacccg agttcagaaa tgctgtggct aaattcatgg gtagaacaag aggaaacaga    360
gtcacgtttg atcctgatcg tattgtcatg agcggtggag caactggagc acacgaagtc    420
actacctttt gtttggcaga ccccggtgac gcatttttgg tgccaattcc ttattatcca    480
```

```
ggttttgacc gggatttgag gtggagaaca ggaattaaac ttgttccagt tatgtgcgat    540

agctcaaaca atttcaagtt gacaaagcaa gcattggaag atgcgtatgt gaaagccaaa    600

gaggataaca ttagagtgaa gggcatgctc atcaccaatc cttcaaaccc attaggcaca    660

gtcatggaca gaaacacact aagaaccgtg gtgagcttca tcaatgagaa gcgtatccat    720

cttgtatctc atgaaatata ctctgcaaca gtttttagcc gtcccagttt cataagcatt    780

gctgagatac tagaggaaga cacagacatc gaatgtgacc gcaacctcgt tcacattgtt    840

tatagtcttt caaaggatat ggggttccct ggcttcagag ttggcatcat atactcttac    900

aatgatgctg tggtcaattg tgcacgcaaa atgtcaagct ttgggttggt gtcaacacag    960

actcagcatc ttttagcatc aatgctaaat gatgatgagt ttgtggaaag gtttctggaa   1020

gagagtgcaa aaaggttggc acaaaggcat agagttttca cttcggggtt ggccaaagta   1080

ggcataaagt gcttgcaaag caatgctggt ctctttgtgt ggatggattt aaggcaactt   1140

ctcaagaagc caacgcttga ctctgaaatg gagctttgga gagtgatcat tcatgaggtt   1200

aagatcaatg tttcacctgg ctcttctttc cattgcactg agccagggtg gtttagggtg   1260

tgctatgcca acatggatga tatggctgtg caaattgcat tgcaaagaat tcgaaccttc   1320

gtgcttcaaa acaaggaggt catggttcct aacaagaaac attgctggca cagtaacttg   1380

aggttgagcc tcaaaaccan aaggtttgat gatatcatga tgtcacctca ctcccctata   1440

cctcagtccc ctttggttaa agccacaatt tga                                1473
```

<210> SEQ ID NO 46
<211> LENGTH: 2161
<212> TYPE: DNA
<213> ORGANISM: Glycine max

<400> SEQUENCE: 46

```
gggttgatgg atgtggacca aactcaattg ttgtctaaga tggtcatcgg agatggacat     60

ggtgaagcat caccatactt tgatggatgg aaggcttatg atgaaaaccc ctttcatccc    120

aaagagaatc ctaacggggt tatccaaatg ggtcttgctg agaatcaggt atatagcata    180

taaagtttct ttccaaagtc atgcaatttt gactacttac tacaattgca taaatttgga    240

gaataatagt atatgtacat attatttaat tattttccca tgttaattag ttctaattaa    300

ttcaattatc ttaaattttt gcagcttact tctgatttgg ttgaagattg gatactgaat    360

aacccagagg cctccatttg cacaccagaa ggaataaatg atttcagggc catagctaac    420

tttcaggatt atcatggtct gcccgagttc agaaatgtga gtacaataat aatatgtgaa    480

atttgatcat atcactcatt ttatccataa attaacaagt tgagttcaac tagtgataat    540

attttataca caaattaaag gtgaattgaa aacttgcaca ggctgtggct aaattcatgg    600

gtagaacaag aggaaacaga gtcacgtttg atcctgaccg tattgtcatg agcggtggag    660

caactggagc acacgaagtc actacctttt gtttggcaga ccctggtgac gcatttttgg    720

tgcccattcc ttattatcca gggtcagtat tcaattcaat ttcaccctcc tttttcattt    780

ttcattaatt tagaatacaa tgatgaagta tggcttacgt gcgtcattac gtttttcaat    840

taaagtaaat ttgatctccc ctgagttgcc tttctattaa tttaacattc cattagggcg    900

tatagccccc acaaagtgga attctggatt agaaaccagg ataatgagat ttgatggcac    960

tactttgcaa tttcaacctt catctattgc agtagtcaac gatcatatca aacataaaaa   1020

aatccttaaa taaaagtcaa attcacccca caattgaata gcaatttggc catgaatatt   1080
```

```
atttgattta atcatgttat tgtatgatat ttagccatat agtatatatt aaattttttt   1140
tgcatctaca tgttaatatt tgtttctaat aagaagctga atttccttgt gcagttttga   1200
ccgggatttg aggtggagaa caggaattaa acttgttcca gttatgtgcg atagctcaaa   1260
caatttcaag ttgacaaagc aagcattgga agatgcgtat gagaaggcca aagaggataa   1320
tataagagta aagggcttgc tcatcaccaa tccatcaaac ccattaggca cagtcatgga   1380
cagaaacaca ctaagaaccg tgatgagctt catcaacgag aagcgtatcc accttgtatc   1440
tgatgaaata tactctgcaa cagtttttag ccacccagt ttcataagca ttgctgagat   1500
attagaggaa gacacagaca tcgaatgtga ccgcaacctc gttcacattg tttatagtct   1560
ttcaaaggat atggggttcc ctggcttcag agttggcatc atatactctt acaatgatgc   1620
tgtggtccat tgtgcacgca aaatgtcaag ctttggattg gtgtcaacac agactcagta   1680
tcttttagca tcaatgctaa atgatgatga gtttgtggaa agttttctgg tagagagtgc   1740
aaaaaggctg gcacaaaggc atagagtttt cactgggggg ttggccaaag ttggcataaa   1800
gtgcttgcaa agcaatgctg gtctctttgt gtggatggat ttaaggcaac ttctcaagaa   1860
gccaacgctt gactctgaaa tggagctttg gagagtgatc attgatgagg ttaagatcaa   1920
tgtttcacct ggctcctctt tccattgcac tgagccaggg tggtttaggg tgtgctatgc   1980
caacatggat gatatggctg tgcaaattgc attgcaaaga attcgtaact ttgtgcttca   2040
aaacaaggag atcatggtgc ctaacaagaa acattgttgg cacagtaact tgaggttgag   2100
cctcaaaacc agaaggtttg atgatatcat gatgtcacct cactccccca tacctcagtc   2160
a                                                                   2161
```

<210> SEQ ID NO 47
<211> LENGTH: 4036
<212> TYPE: DNA
<213> ORGANISM: Solanum tuberosum

<400> SEQUENCE: 47

```
gaattccacc taactcatcc tgagctagaa tttatggctg ttcaaagttg gccaaaaatt     60
cacattttcc atacttagcc aaaatttcca aaactttaaa attcttccca aaaatgaaaa    120
tttcaaattc taagcctctt ccaagctatt tcaaattgtc ggatgttaca aaattttaga    180
tatgaaattc tctcgatgtt tcgaatttaa aaaaaaatat aatttgatta aaacaattca    240
tgtttgcggt acgtcgaatt tcttttaaga agaagaagaa gaagaagagt agtaaatata    300
aaaaattgga gtaagaaaag gtaactaaag tttatgggct gatattttgt ataatatttc    360
ctaaaagttt tacaataata atttattttg acatgctata acaaattaat taacatctct    420
ttttattcaa ttactcaaat aatgtgtgag tggagtattt gtcaattttg acatctttct    480
gcatgcacaa aatcttcgta tgaaaattac cacaagccat gtatgaacag ttatcactat    540
atatatccaa ttctcttcat caactacgca cgtgtttgat aggtggacaa ggcaagcata    600
ctattacttt ttaaatggcc gtggtactca agtaatacta gttacttata ataaaattgg    660
tataattcca aaaggccagg agataatgac tttcatttgt ccataagagt tatgtttaat    720
tttaaatgca ttcatgtcgt tcgttttatg caatgcccct gttatatgta tatttcaaaa    780
gtgtatggag gattttgttg aaaatactta tgaatgactt tgaatctttt tttctcgtta    840
tggttctttt cagaagtgaa gagactataa tttggtcctt aattgggaaa aagtcacttc    900
ttagtaaggg aagatattgt cttgggattc aaggtgtcaa aaagggccta cgacaacttc    960
tcctttcttt gagcatcact ttctcaatct tggataacaa ttcctactgt agtatcacta   1020
```

```
cggtacgcgg cgcctgacac gtgtccctta tattaataag aattgattct aataacaata   1080
ctataaaata atatttaaaa gatgtatttg tgtaaaaata taaaaattta aaaataaaat   1140
tataaattat aaatttcaat tgacaaatga tcagttatat tactatgttc atatataatg   1200
tagccttagt atttagagtg tgctttcgtg catcaataca aacataattt ttattttaat   1260
caatgataaa attttgttca ttacatttaa tttttatcct taattgttag tgtgttggtg   1320
agttatcata ttccttttta agtacactta tttcttgaaa attttaagtt atatttttta   1380
caagtctatc gagagtactg taaaagaatc tgaatggaga gggataatta ataaagtaag   1440
tttgcatgtt taaaaattgg aggtagttaa gttaaaattt taagagccac ccagatcaac   1500
caccccattt gatttgggga tcttttggag attgagaata tacaaaaact ctgaataaga   1560
tgacagaaac taacagttgt caccagccat ttaaacaata gttgtaaaag gtgagcgttg   1620
atcttgcttc atctatataa tcaatcattg gttcctttat tttttgtga gaaatttatc   1680
atcttgttga gggcccttt attaaactac tttctatata agttgctctt tgccaaaaaa   1740
agttcatatt caaacactaa ttctttcttc attttttccc ccactattca catttatatt   1800
atcttccata gcctctttct tgattaagag taccctaatt agccaaaaac aaattaaaac   1860
aataagttaa ttatggccat agagattgag caacgtccaa cagtagttcg tctatcaaac   1920
gttgcaacgt ctgacactca tggagaagac tcaccttact ttgctggatg gaaagcatat   1980
gatgaaaatc catttgatga agttcacaac ccatctggag ttattcaaat ggcattagcc   2040
gaaaatcaag taagttttcg atcatcatta ttggccatgc taaacttaac attaaatatt   2100
gaacttgaaa atcatttctt gtactgtatt gtattgtatt gtaggtgtca tttgatttgc   2160
tggaagagta cttggaaaag aagaaagacg atggcattgc tgaaatttct agattcaggg   2220
aaaatgcttt gttccaagat tatcatggac ttgtttgttt tagaaaggca atggctacct   2280
tcatggaaca agtaagaggt ggaagggcaa gatttgatcc tgatagagtt gttattacag   2340
ctggtgccac tgcagctaat gagttgttaa ctttcatttt agctgatcct ggtgatgctt   2400
tgcttgttcc aactccttac tatcctgggt aagtaccata tatatatttt gtcttctaat   2460
tacatgggga aaggaaatat gagtatgagt ggtggtgaga ttcgatctca acacttctgc   2520
ctgctctgat atttcatgtt caagtgtgtg aacactttta ttagttaatt atattctcaa   2580
caattactaa atattttttt tacagatttg acagagactt gaggtggaga acgggtgtga   2640
aaatcattcc agtccattgt gacagttcaa ataatttcca agtcactcta caggccttgg   2700
aagaagccta caaggatgca gaatccaaca acatcaaagt gagaggggtt cttataacaa   2760
accccctcaaa ccctttgggt accacagttc aaagatgtgt tcttgaggaa attcttgaat   2820
tcgtcgcaag aaaaaacatc catcttgtat ctgatgaaat ctactcaggt tcagcctttt   2880
gttgctccga atttgtcagt attgctgaaa tacttgaatc gagaaactac aaggattcag   2940
agagggtaca cattgtgtac agcctctcta aagacttggg actccccggg tttcgagttg   3000
gtacaatcta ctcatacaat gacaaagtag tcacaacggc aagaagaatg tcaagtttta   3060
cattgatttc ttctcagaca caacaactct tggcttccat gttgtctgat gagaaattca   3120
ctgagaatta cataaagaag aatcgcgaaa ggctgagaag gagatatgaa atgatgattg   3180
aagggctgag gagtgctggg attgagtgct tgagagggaa tgcgggattg ttttgctgga   3240
tgaatttaag tactttgttg gaaaagccta caaaggaatg tgaattggaa gtgtggaaca   3300
caatattgca tgaagtgaaa ctgaatattt ctccaggttc ttcttgtcat tgctcagagc   3360
```

caggctggtt cagggtttgt tttgctaaca tgagtgaaaa taccctagaa attgcactca 3420
aaagaataca ccatttcatg gaaacaaggg gcatacttca aaaatactaa ttactcatca 3480
tcattattta caaaaaaaat taattttttg atttgttttt ttttgtcttt tttggtttgg 3540
ggattttttt tttccagtta ggattggcta ctggattatt cttcaattat acccattcca 3600
agtattggat ttttccctcg agccttgtac ctcggattga gtggttcata gtttaagatg 3660
aatgtttgat tttgtttttt catatttgtc ttttccttta ttaaaatttt atattttcta 3720
aggtataaat tgactattta tacagtgata tttatgattt cacaaacaat aatgaaaatt 3780
atggttaaaa ttatgtcttt aaatgttttt ctaattaata ggtgtgtatt gcctcacaaa 3840
ttcacttaat atggaataga ggaagtacta tatatatata tatatatact agttttgatg 3900
cacgtgtgtt gcacgtgaat atcaaatcat gcattacatt aataataatg tgaatattat 3960
taaattaaaa aattatgtaa acaattataa aatgaatgat aaagcataag ttcctatgaa 4020
tagtggatgt aagctt 4036

<210> SEQ ID NO 48
<211> LENGTH: 4153
<212> TYPE: DNA
<213> ORGANISM: Solanum tuberosum

<400> SEQUENCE: 48
taacttttta atggaattat ttctatgtct cttcttcact tccctaatcg acatgtaatg 60
tattaagcta atcaaacata agttacatat tttgttcatt ccaaaactat gataagattt 120
caagttccct atatgatcta catttctaat ttcaaacatt tactttgaat agagagtggg 180
ccttttactt tcattacact atcatattga tatggcttgc ttcgtgaaat agataaaaaa 240
gaattattag aacttggatt taaaaaaatt atttttccta tgagttggat aacatatgtt 300
tatacgtatt cctatatatt gtgatcactt atctaattat aaaaagatta tcaaggatta 360
ttgtgggtat gaatagaatt tctttaatct taaattaaag gtatattttt caagtctttg 420
aatgtatttt ctttttttggt aagaaacaat ttttccttta ataaatttta cacaactcga 480
atttgaatta gataggacca caaaaaatgt ccacacatct agtgagaaac taaaaaaaat 540
gcccatttaa taatttaaat taaattatta gagatgatcg actcactttt atttgtttag 600
ataaattata tatttgttaa tatatgcctt cattagaagc gtgattactt cattttagtt 660
taagttgtta catatctagg gcccactctt aatatattca atcataaatt taatcaattg 720
gacttaaata taccccgatt ttgtcatatg agtgaaatat accctaaaat tctcgccaag 780
tttatgatgt tttcaacatt ctcttgactt tttattaaga gttttatttt cgagtgtgag 840
accacttaat atgtcatgtg gtagatcata agtatatcta aatttagtta gtcaaataaa 900
aatgtatttt taagactgta aataatcgag aataacacta ataatttgtg gcaagtgtat 960
aaccaatact tctctcaaat agaaaatatt ggtactaatt cagcgcagta ttatactagc 1020
agactaacag catcaacatt gacagtaggc agtagcatca ccattcacca agagtccaag 1080
acatcacttg ttatgttttt cgaagtgttt ttttaccaaa aatgttgatg gatttgacat 1140
tagtcccacc cttttgttac acccttagac aaggcagtac aaaattgatc cctaaatgtc 1200
cctatgacaa ataaaacatt caattataat atacgactaa aaaagcgcgt ccaattagtg 1260
tatacatccc aaacacagta aaattaattg ttttattttg gggacaaaaa agtagaaaaa 1320
aacaaaaatt gtatagtcaa agtttgaaaa catatggtga tatgtttggt tcttcattgc 1380
taatctctta tacatatata tatatatacc tcaccatgat atatgccaga cacatagcaa 1440

```
caatctccat tcaatatttt ctttcttctt atttctgcct ctcaaaacaa acataaaatt   1500
caagtgctta ctcagaaaaa atgaagctcc tatcgaagaa agccatgtgt aactcacatg   1560
gacaagattc ttcctacttc ctaggatggg aagagtatga gaaaaaccca tacgatgaaa   1620
ctcgtaatcc taaaggaatc attcagatgg gtctcgcaga gaatcagctc tctttcgatt   1680
tattagagtc atggcttact caaaatccag atgcagctgc atttaaaaga aatggtgact   1740
caatatttag agaccttgcc ttatttcaag attaccatgg tcttcccgct ttcaaagatg   1800
taagttggtc attacaatag aatttaactt atatacactg actaacgtaa ctgactcatc   1860
atatatttat cattaacttc acaatctcac attgtaatgt atatttttgt gcaggcattg   1920
gttcaattca tgtctgaaat cagagggaac aaagtgagtt ttgattcaaa caagcttgta   1980
cttacagctg gtgctacttc tgcaaatgag acactcatgt tttgccttgc tgatcctggc   2040
gatgcttttc tccttcctac tccatactac cctgggtacg tttagtttaa tttatatgca   2100
ctgactatta gtcatgtatt tttaacttgtt ataacagatg aactatgttc cttactaatt   2160
atatatgata ttgtgtaata atgcagattt gatagagacc taaaatggag aaccggagct   2220
gagattgttc caatacaatg tacaagttca aacggcttta gaatcacaga atcagctctt   2280
gaagaagctt acaaagaagc cgaaaggcgg aaccttagag tgaaaggggt tttagtcact   2340
aacccttcga acccattagg cacaacatta accaaaaaag aactccaact tcttctaacc   2400
ttcgtatcta caaaacaaat ccatctcatc agtgacgaga tatattctgg cactgttttt   2460
aactcgccta aattcgttag tgtcatggaa gtattaatcg aaaataacta catgtacact   2520
gaagtatggg atcgagttca cattgtctat agtctttcta aagatttggg tcttccagga   2580
tttcgagttg gtgccattta ttccaacgac gttatgatcg tctctgcagc cacaaaaatg   2640
tctagttttg gattaatttc atctcaaact caatacctcc tttccgcttt gctatcagac   2700
aaaaaattca cgaaaaaata cgtgtctgaa aatcaaaaga ggcttaagaa acgtcatgaa   2760
atgctagttg gtggtcttaa acaaattgga atcagatgcc ttgagagcaa tgctggattg   2820
ttttgttggg tggatatgag acatcttcta agttcaaaca catttgatgg agaaatggaa   2880
ttatggaaga aaatagtgta cgaagtaggc ctaaatattt cacctggatc gtcatgccac   2940
tgtacagaac cgggttggtt tcgtgcatgt tttgctaaca tgtccgaaga taccctaaat   3000
atcgctatac aacgtttgaa ggcttttgtt gattcaaggg ataacaagga tgatattcaa   3060
aatcagaagc attctaataa gaagaagtca ttttccaagt gggtttttcg actatcgttc   3120
aatgaacgtc aaagagaacg atagtctaga catgtgaaag ttcctaaatg attctttttt   3180
ttttatctct acatttagtt agatcaatgt tgagtttcta aatttttgta tcatatataa   3240
tacatacatt ttgtagaggg gcactccgtc catgtgatcg atataggacg agaagtgctt   3300
atcatacata ttgtaatgaa tccacattat caatattctt cacaaaatgt tcaattaatt   3360
ctattactcc atttcaatta catttgtctg taccatataa ctttccatat ctaatttaat   3420
atgtaaacta aacatagagt gataatctat tattacggtt aaattacatt aataaatataa   3480
tttattttt taactgaaag ttgggtgttg gtatatttaa cctctgaaaa tgatattctt   3540
aagtagaaaa agatacgatg ttgttatgta gcacacaaag tgtcaacaga cacatgtgtc   3600
atgtgttgcc catagccagc tagtccagaa tgtgattgtt ttattcgaag tgttaattat   3660
taaaaaaata tttttattca tttaattatg tttttaacat ttatttttaa aaaaatcatc   3720
aactatgcaa gtgggtagag cctttttttc ccgaggagat attactaagt tacaatttac   3780
```

```
aaacattaga aattaaactt gatcatttgc aagtaaaatg attgggttta cttcacaggg   3840
agcaagatta gttcaaatag cactataact catttatctt actttgatgt caattttcta   3900
attagcaatt ataattgttt catgttaata aagaatttga aatgtgaaat ttaatcacaa   3960
ttaagattac gtacataaga aaagaaacct gcattttaaa ccacaattga attgtacatt   4020
agtattatac tagtatagaa tgaacaataa tatatacaca cactaacata gttttttggg   4080
ttctttaatt tccatattgt ttaattatgt ttgagtaagt actctatgta tgtgcccgaa   4140
aataaaatct aga                                                       4153
```

<210> SEQ ID NO 49
<211> LENGTH: 1571
<212> TYPE: DNA
<213> ORGANISM: Solanum tuberosum

<400> SEQUENCE: 49

```
aaagcatacg atagcgatcc tttccaccct ctaaagaacc caaatggagt tatccaaatg     60
ggacttgctg aaaatcagct ttgtttagac ttgatagagg attggattaa gagaaaccca    120
aaagcttcaa tttgttccaa tgaaggaatc aaatcattca gggccattgc caactttcaa    180
gattatcatg gcttgcctga attcagaaga gcgattgcga aatttatgga gaaaacaaga    240
ggaggaagag ttagatttga tccagaaaga gttgttatgg ctggtggtgc cactggagct    300
aatgagacaa ttatattttg tttggctgat ccaggcgatg catttttagt accttcacca    360
tattacccag catttaacag agatctaaga tggagaactg gagtacaact tcttccaatt    420
cactgtgaga gctccaacaa tttcaaaatt acttcaaaag cagtaaaaga agcatatgaa    480
aatgcacaaa aatcaaacat caaagtaaga ggtttgattt tgaccaatcc atcaaatcca    540
ttgggtacca ctttggacaa atacacactg aaaagtctct tgagtttcac caaccaacac    600
aacatccacc ttgtttgcga cgaaatctac gcagccacgg tcttcgacac gcctcaattc    660
gtcagcatag ctgaagtcct cgatgaaaag gaaatgactt attgcaacaa agatttagtt    720
cacatcgtct atagtctttc aaaagacatg ggttaccag gatttagaat cggaatcgta    780
tattctttta acgatgacgt cgttaattgc gctagaaaaa tgtcgagttt cggtttagtg    840
tcaactcaaa cgcaatattt tttagccgct atgctatcgg acgaaaaatt cgtcgataat    900
tttctgacag aaagtgcgat aaggttagct aaaagacaca aacattttac caatggactc    960
gaagaagtgg gaattaaatg cttgaaaaat aatgcggggc tttttgttg gatggatttg   1020
cgtccgcttt taagggaatc gactttcgat agtgaaatgt cgttatggag agttattata   1080
aacgacgtaa agctcaacgt ctcgcctgga tcatcgtttg aatgtcaaga gccagggtgg   1140
ttccgagttt gttttgcgaa tatggatgat ggaacggtgg atatcgcgct agcgcggatt   1200
cggaggtttg tacgtgttga gaaaagtgga gatgaatcga gcgcgatgga aaagaagcaa   1260
caatggaaga agaataattt aagacttagt ttttcgaaaa gaatgtatga tgaaagtgtt   1320
ttgtcaccac tttcgtctcc tattccaccc tcaccactag ttcgatagga cttaattaaa   1380
agggaagaat ttaatttatg tttttttata tttgaaaaat atttgtaaga ataagattat   1440
agaaggaaat ctaggaggag tattttcaga aatagttgtt agcgtatgta ttgacaactg   1500
atctatgtac tttgacatca taatttgtct atctaattaa ttaatgaaat gtaaaagtaa   1560
agttatgtta a                                                        1571
```

<210> SEQ ID NO 50
<211> LENGTH: 1098

<212> TYPE: DNA
<213> ORGANISM: Solanum tuberosum

<400> SEQUENCE: 50
cagatgggtc tagccgagaa tcagctttgt tttgatttaa ttcaagaatg gatagtcaac 60
aacccaaaag cctcaatttg tacctatgaa ggagttcaag attttcaaga tattgctatt 120
ttccaagact atcatggctt gccagaattt agaaaggcag ttgcaagatt catggagaaa 180
gtgagaggag atagagtcac atttgatcca gaaagaatag ttatgagtgg aggagcaaca 240
ggagctcatg aaagtttggc cttttgtttg gctgatcctg gtgatgcatt tctagttcct 300
acaccatatt atccaggatt tgatagagat ttgaggtgga gaacaggagt acaacttttt 360
cctgttgttt gtgagagttc taacaacttc aaggtgacaa aagaagcctt agaagaagca 420
tataaaaaag ctcaagaatc aaatatcaaa gtaaaaggat tacttataaa caatccatca 480
aatccattag gtacaatttt ggacaaggaa acattaaaag acatacttag attcatcaat 540
gacaaaaaca tacatctagt atgtgatgaa atctatgcag caaccgcgtt ttgtcaacct 600
tcattcatca gtatatcaga agtcatgaat gaagttgttg gatgcaacga tgatttagta 660
catatagtgt atagtctctc caaagatcta gggttccctg gatttagggt tgggattatt 720
tactcgtaca atgatgttgt tgtcaatatt gcacgtcaga tgtcaagttt tggacttgtt 780
tcaacacaaa cacaacggtt aattgcttcc atgctatcag acactatctt tgttgaaaat 840
ttcatcgcga agagcgcgat gaaattgtca caaagacatg atttgttcac taaaggatta 900
ggacaagttg gaattacaac attgaagagt aatgctggcc tatttatttg gatggatttg 960
agaaggtttc ttgaaaattc aacatttgat aatgaattga aactttggca tataattatt 1020
aataaagtga aacttaatgt ttcacctggt tgttcatttc attgctcaga gccaggttgg 1080
tttagagtat gcttcgct 1098

<210> SEQ ID NO 51
<211> LENGTH: 505
<212> TYPE: DNA
<213> ORGANISM: Zea mays

<400> SEQUENCE: 51
tagcagacgc ggaaccagcc gggctcccgg cagtggcagg aggagcccgg ggagatgttg 60
agccccacct cgaagaccac cctcttccac agctccatct cgccctcgaa cgaccggctc 120
cgcatcaggc gccgcatgtt gacccagcag aagagccccg cgttgctctc caggcactcg 180
atgcccacgg ccgccaggcc ctccgccagc tgctcgcgcc gctccctgat ccgccgcgtg 240
ttctccgcga tgtacctccg cgtgaagtcc ctgtcgccca ggagcgacgc caggaggtgc 300
tgcgtctggg acgacaccag gccgaagctc gacatcttgg tggccgcgga gaccacgccg 360
gcgttggacg agtagatggc gcccacgcgg aaccccggga ggcccaggtc cttggacagg 420
ctgtacacca cgtgcacgcg gtccgacagc ggcccaacgc cgacgacgcc gtcgtccgtg 480
gcggcgcgcg cggccaccac ctgca 505

<210> SEQ ID NO 52
<211> LENGTH: 543
<212> TYPE: DNA
<213> ORGANISM: Zea mays

<400> SEQUENCE: 52
cccggtacgc gccgccacgg acgacggcgt cgtcggcgtt gggccgctgt cggaccgcgt 60

-continued gcacgtggtg tacagcctgt ccaaggacct gggcctcccg gggttccgcg tgggcgccat 120
ctactcgtcc aacgccggcg tggtctccgc ggccaccaag atgtcgagct tcggcctggt 180
gtcgtcccag acgcagcacc tcctggcgtc gctcctgggc gacagggact tcacgcggag 240
gtacatcgcg gagaacacgc ggcggatcag ggagcggcgc gagcagctgg cggagggcct 300
ggcggccgtg ggcatcgagt gcctggagag caacgcgggg ctcttctgct gggtcaacat 360
gcggcgcctg atgcggagcc ggtcgttcga gggcgagatg gagctgtgga agagggtggt 420
cttcgaggtg gggctcaaca tctccccggg ctcctcctgc cactgccggg agcccggctg 480
gttccgcgtc tgctaaaggg cgaattccag cacactggcg gccgttacta gtggatccga 540
gct 543

<210> SEQ ID NO 53
<211> LENGTH: 51280
<212> TYPE: DNA
<213> ORGANISM: Artificial Sequence
<220> FEATURE:
<223> OTHER INFORMATION: improved ACS6 inhibition plasmid

<400> SEQUENCE: 53
gtttacccgc caatatatcc tgtcaaacac tgatagttta aactgaaggc gggaaacgac 60
aatctgatca tgagcggaga attaagggag tcacgttatg acccccgccg atgacgcggg 120
acaagccgtt ttacgtttgg aactgacaga accgcaacgt tgaaggagcc actcagcaag 180
ctggtacgat tgtaatacga ctcactatag ggcgaattga gcgctgttta aacgctcttc 240
aactggaaga gcggttacta ccggctggat ggcggggcct tgatcgtgca ccgccggcgt 300
ccggataagt gactagggtc acgtgaccct agtcacttat cgagctagtt accctatgag 360
gtgacatgaa gcgctcacgg ttactatgac ggttagcttc acgactgttg gtggcagtag 420
cgtacgactt agctatagtt ccggtagatc tgaagttcct attccgaagt tcctattctt 480
caaaaggtat aggaacttcc tcgaattgtt gtggtggggt atagaggttt gatataggtg 540
gaactgctgt agagcgtgga gatatagggg gaaagagaac gctgatgtga caagtgagtg 600
agatataggg ggagaaattt aggggggaacg ccgaacacag tctaaagaag cttgggaccc 660
aaagcactct gttcgggggt tttttttttt gtctttcaac tttttgctgt aatgttattc 720
aaaataagaa aagcacttgg catggctaag aaatagagtt caacaactga acagtacagt 780
gtattatcaa tggcataaaa aacaaccctt acagcattgc cgtattttat tgatcaaaca 840
ttcaactcaa cactgacgag tggtcttcca ccgatcaacg gactaatgct gctttgtcag 900
atcaccggtt aagtgactag ggtcacgtga ccctagtcac ttaggttacc agagctggtc 960
acctttgtcc accaagatgg aactgcggcc gctcattaat taagtcaggc gcgcctctag 1020
ttgaagacac gttcatgtct tcatcgtaag aagacactca gtagtcttcg gccagaatgg 1080
ccatctggat tcagcaggcc tagaaggcca tttaaatcct gaggatctgg tcttcctaag 1140
gacccgggat atcacaagtt tgtacaaaaa agcaggctcc ggccagagtt acccggaccg 1200
aagcttgcat gcctgcagtg cagcgtgacc cggtcgtgcc cctctctaga gataatgagc 1260
attgcatgtc taagttataa aaaattacca catatttttt ttgtcacact tgtttgaagt 1320
gcagtttatc tatctttata catatattta aactttactc tacgaataat ataatctata 1380
gtactacaat aatatcagtg ttttagagaa tcatataaat gaacagttag acatggtcta 1440
aaggacaatt gagtattttg acaacaggac tctacagttt tatcttttta gtgtgcatgt 1500
gttctccttt ttttttgcaa atagcttcac ctatataata cttcatccat tttattagta 1560

```
catccattta gggtttaggg ttaatggttt ttatagacta atttttttag tacatctatt   1620
ttattctatt ttagcctcta aattaagaaa actaaaactc tattttagtt tttttattta   1680
ataatttaga tataaaatag aataaaataa agtgactaaa aattaaacaa ataccettta   1740
agaaattaaa aaaactaagg aaacattttt cttgtttcga gtagataatg ccagcctgtt   1800
aaacgccgtc gacgagtcta acggacacca accagcgaac cagcagcgtc gcgtcgggcc   1860
aagcgaagca gacggcacgg catctctgtc gctgcctctg gacccctctc gagagttccg   1920
ctccaccgtt ggacttgctc cgctgtcggc atccagaaat tgcgtggcgg agcggcagac   1980
gtgagccggc acggcaggcg gcctcctcct cctctcacgg caccggcagc tacgggggat   2040
tcctttccca ccgctccttc gctttccctt cctcgcccgc cgtaataaat agacaccccc   2100
tccacaccct ctttccccaa cctcgtgttg ttcggagcgc acacacacac aaccagatct   2160
cccccaaatc cacccgtcgg cacctccgct tcaaggtacg ccgctcgtcc tccccccccc   2220
ccctctctac cttctctaga tcggcgttcc ggtccatgca tggttagggc ccggtagttc   2280
tacttctgtt catgtttgtg ttagatccgt gtttgtgtta gatccgtgct gctagcgttc   2340
gtacacggat gcgacctgta cgtcagacac gttctgattg ctaacttgcc agtgtttctc   2400
tttggggaat cctgggatgg ctctagccgt tccgcagacg ggatcgattt catgattttt   2460
tttgtttcgt tgcatagggt ttggtttgcc cttttccttt atttcaatat atgccgtgca   2520
cttgtttgtc gggtcatctt ttcatgcttt tttttgtctt ggttgtgatg atgtggtctg   2580
gttgggcggt cgttctagat cggagtagaa ttctgtttca aactacctgg tggatttatt   2640
aattttggat ctgtatgtgt gtgccataca tattcatagt tacgaattga agatgatgga   2700
tggaaatatc gatctaggat aggtatacat gttgatgcgg gttttactga tgcatataca   2760
gagatgcttt ttgttcgctt ggttgtgatg atgtggtgtg gttgggcggt cgttcattcg   2820
ttctagatcg gagtagaata ctgtttcaaa ctacctggtg tatttattaa ttttggaact   2880
gtatgtgtgt gtcatacatc ttcatagtta cgagtttaag atggatggaa atatcgatct   2940
aggataggta tacatgttga tgtgggtttt actgatgcat atacatgatg gcatatgcag   3000
catctattca tatgctctaa ccttgagtac ctatctatta taataaacaa gtatgtttta   3060
taattatttt gatcttgata tacttggatg atggcatatg cagcagctat atgtggattt   3120
ttttagccct gccttcatac gctatttatt tgcttggtac tgtttctttt gtcgatgctc   3180
accctgttgt ttggtgttac ttctgcaggt cgactttaac ttagcctagg atccactagt   3240
aacggccgcc agtgtgctgg aattcgccct ttagcagacg cggaaccagc cgggctcccg   3300
gcagtggcag gaggagcccg gggagatgtt gagccccacc tcgaagacca ccctcttcca   3360
cagctccatc tcgccctcga acgaccggct ccgcatcagg cgccgcatgt tgacccagca   3420
gaagagcccc gcgttgctct ccaggcactc gatgcccacg gccgccaggc cctccgccag   3480
ctgctcgcgc cgctccctga tccgccgcgt gttctccgcg atgtacctcc gcgtgaagtc   3540
cctgtcgccc aggagcgacg ccaggaggtg ctgcgtctgg gacgacacca ggccgaagct   3600
cgacatcttg gtggccgcgg agaccacgcc ggcgttggac gagtagatgg cgcccacgcg   3660
gaaccccggg aggcccaggt ccttggacag gctgtacacc acgtgcacgc ggtccgacag   3720
cggcccaacg ccgacgacgc cgtcgtccgt ggcggcgcgc gcggccacca cctgcagtcg   3780
acgtgcaaag gtccgccttg tttctcctct gtctcttgat ctgactaatc ttggtttatg   3840
attcgttgag taattttggg gaaagcttcg tccacagttt tttttcgatg aacagtgccg   3900
```

-continued cagtggcgct gatcttgtat gctatcctgc aatcgtggtg aacttatttc ttttatatcc 3960
tttactccca tgaaaaggct agtaatcttt ctcgatgtaa catcgtccag cactgctatt 4020
accgtgtggt ccatccgaca gtctggctga acacatcata cgatctatgg agcaaaaatc 4080
tatcttccct gttctttaat gaaggacgtc attttcatta gtatgatcta ggaatgttgc 4140
aacttgcaag gaggcgtttc tttctttgaa tttaactaac tcgttgagtg gccctgtttc 4200
tcggacgtaa ggcctttgct gctccacaca tgtccattcg aattttaccg tgtttagcaa 4260
gggcgaaaag tttgcatctt gatgatttag cttgactatg cgattgcttt cctggacccg 4320
tgcagctgga tcccggtacg cgccgccacg gacgacggcg tcgtcggcgt tgggccgctg 4380
tcggaccgcg tgcacgtggt gtacagcctg tccaaggacc tgggcctccc ggggttccgc 4440
gtgggcgcca tctactcgtc caacgccggc gtggtctccg cggccaccaa gatgtcgagc 4500
ttcggcctgg tgtcgtccca gacgcagcac ctcctggcgt cgctcctggg cgacagggac 4560
ttcacgcgga ggtacatcgc ggagaacacg cggcggatca gggagcggcg cgagcagctg 4620
gcggagggcc tggcggccgt gggcatcgag tgcctggaga gcaacgcggg gctcttctgc 4680
tgggtcaaca tgcggcgcct gatgcggagc cggtcgttcg agggcgagat ggagctgtgg 4740
aagagggtgg tcttcgaggt ggggctcaac atctccccgg gctcctcctg ccactgccgg 4800
gagcccggct ggttccgcgt ctgctaaagg gcgaattcca gcacactggc ggccgttact 4860
agtggatccg agctcgaatt ccggtccggg tcacccggtc cgggcctaga aggccgatct 4920
cccgggcacc cagctttctt gtacaaagtg gtgatatcgg accgattaaa ctttaattcg 4980
gtccgatgca tgtatacgaa gttcctattc cgaagttcct attctacata gagtatagga 5040
acttcacctg gtggcgccgc tagtggatcc cccgggctgc agtgcagcgt gacccggtcg 5100
tgcccctctc tagagataat gagcattgca tgtctaagtt ataaaaaatt accacatatt 5160
ttttttgtca cacttgtttg aagtgcagtt tatctatctt tatacatata tttaaacttt 5220
actctacgaa taatataatc tatagtacta caataatatc agtgttttag agaatcatat 5280
aaatgaacag ttagacatgg tctaaaggac aattgagtat tttgacaaca ggactctaca 5340
gttttatctt tttagtgtgc atgtgttctc cttttttttt gcaaatagct tcacctatat 5400
aatacttcat ccattttatt agtacatcca tttagggttt agggttaatg gtttttatag 5460
actaattttt ttagtacatc tattttattc tattttagcc tctaaattaa gaaaactaaa 5520
actctatttt agttttttta tttaataatt tagatataaa atagaataaa ataaagtgac 5580
taaaaattaa acaaataccc tttaagaaat taaaaaaact aaggaaacat ttttcttgtt 5640
tcgagtagat aatgccagcc tgttaaacgc cgtcgacgag tctaacggac accaaccagc 5700
gaaccagcag cgtcgcgtcg ggccaagcga agcagacggc acggcatctc tgtcgctgcc 5760
tctggacccc tctcgagagt tccgctccac cgttggactt gctccgctgt cggcatccag 5820
aaattgcgtg gcggagcggc agacgtgagc cggcacggca ggcggcctcc tcctcctctc 5880
acggcaccgg cagctacggg ggattccttt cccaccgctc cttcgctttc ccttcctcgc 5940 ccgcccgtaat aaatagacac cccctccaca ccctctttcc ccaacctcgt gttgttcgga 6000
gcgcacacac acacaaccag atctccccca aatccacccg tcggcacctc cgcttcaagg 6060
tacgccgctc gtcctccccc cccccccctct ctaccttctc tagatcggcg ttccggtcca 6120
tgcatggtta gggcccggta gttctacttc tgttcatgtt tgtgttagat ccgtgtttgt 6180
gttagatccg tgctgctagc gttcgtacac ggatgcgacc tgtacgtcag acacgttctg 6240
attgctaact tgccagtgtt tctctttggg gaatcctggg atggctctag ccgttccgca 6300

-continued

```
gacgggatcg atttcatgat ttttttgtt tcgttgcata gggtttggtt tgcccttttc   6360
ctttatttca atatatgccg tgcacttgtt tgtcgggtca tcttttcatg cttttttttg   6420
tcttggttgt gatgatgtgg tctggttggg cggtcgttct agatcggagt agaattctgt   6480
ttcaaactac ctggtggatt tattaatttt ggatctgtat gtgtgtgcca tacatattca   6540
tagttacgaa ttgaagatga tggatggaaa tatcgatcta ggataggtat acatgttgat   6600
gcgggtttta ctgatgcata tacagagatg ctttttgttc gcttggttgt gatgatgtgg   6660
tgtggttggg cggtcgttca ttcgttctag atcggagtag aatactgttt caaactacct   6720
ggtgtattta ttaattttgg aactgtatgt gtgtgtcata catcttcata gttacgagtt   6780
taagatggat ggaaatatcg atctaggata ggtatacatg ttgatgtggg ttttactgat   6840
gcatatacat gatggcatat gcagcatcta ttcatatgct ctaaccttga gtacctatct   6900
attataataa acaagtatgt tttataatta ttttgatctt gatatacttg gatgatggca   6960
tatgcagcag ctatatgtgg attttttag ccctgccttc atacgctatt tatttgcttg   7020
gtactgtttc ttttgtcgat gctcaccctg ttgtttggtg ttacttctgc aggtcgactt   7080
taacttagcc taggatccac acgacaccat gtcccccgag cgccgccccg tcgagatccg   7140
cccggccacc gccgccgaca tggccgccgt gtgcgacatc gtgaaccact acatcgagac   7200
ctccaccgtg aacttccgca ccgagccgca gaccccgcag gagtggatcg acgacctgga   7260
gcgcctccag gaccgctacc cgtggctcgt ggccgaggtg gagggcgtgg tggccggcat   7320
cgcctacgcc ggcccgtgga aggcccgcaa cgcctacgac tggaccgtgg agtccaccgt   7380
gtacgtgtcc caccgccacc agcgcctcgg cctcggctcc accctctaca cccacctcct   7440
caagagcatg gaggcccagg gcttcaagtc cgtggtggcc gtgatcggcc tcccgaacga   7500
cccgtccgtg cgcctccacg aggccctcgg ctacaccgcc cgcggcaccc tccgcgccgc   7560
cggctacaag cacggcggct ggcacgacgt cggcttctgg cagcgcgact tcgagctgcc   7620
ggccccgccg cgcccggtgc gcccggtgac gcagatctga gtcgaaacct agacttgtcc   7680
atcttctgga ttggccaact taattaatgt atgaaataaa aggatgcaca catagtgaca   7740
tgctaatcac tataatgtgg gcatcaaagt tgtgtgttat gtgtaattac tagttatctg   7800
aataaaagag aaagagatca tccatatttc ttatcctaaa tgaatgtcac gtgtctttat   7860
aattctttga tgaaccagat gcatttcatt aaccaaatcc atatacatat aaatattaat   7920
catatataat taatatcaat tgggttagca aaacaaatct agtctaggtg tgttttgcga   7980
attgcggccg ctctagcgta tacgaagttc ctattccgaa gttcctattc tctagaaagt   8040
ataggaactt ctgattccga tgacttcgta ggttcctagc tcaagccgct cgtgtccaag   8100
cgtcacttac gattagctaa tgattacggc atctaggacc gactagtaag tgactagggt   8160
cacgtgaccc tagtcactta tacgtagaat taattcattc cgattaatcg tggcctcttg   8220
ctcttcagga tgaagagcta tgtttaaacg tgcaagcgct actagacaat tcagtacatt   8280
aaaaacgtcc gcaatgtgtt attaagttgt ctaagcgtca atttgtttac accacaatat   8340
atcctgccac cagccagcca acagctcccc gaccggcagc tcggcacaaa atcaccactc   8400
gatacaggca gcccatcagt ccgggacggc gtcagcggga gagccgttgt aaggcggcag   8460
actttgctca tgttaccgat gctattcgga agaacggcaa ctaagctgcc gggtttgaaa   8520
cacggatgat ctcgcggagg gtagcatgtt gattgtaacg atgacagagc gttgctgcct   8580
gtgatcaaat atcatctccc tcgcagagat ccgaattatc agccttctta ttcatttctc   8640
```

-continued

```
gcttaaccgt gacaggctgt cgatcttgag aactatgccg acataatagg aaatcgctgg   8700
ataaagccgc tgaggaagct gagtggcgct atttctttag aagtgaacgt tgacgatcgt   8760
cgaccgtacc ccgatgaatt aattcggacg tacgttctga acacagctgg atacttactt   8820
gggcgattgt catacatgac atcaacaatg tacccgtttg tgtaaccgtc tcttggaggt   8880
tcgtatgaca ctagtggttc ccctcagctt gcgactagat gttgaggcct aacattttat   8940
tagagagcag gctagttgct tagatacatg atcttcaggc cgttatctgt cagggcaagc   9000
gaaaattggc catttatgac gaccaatgcc ccgcagaagc tcccatcttt gccgccatag   9060
acgccgcgcc cccttttgg ggtgtagaac atcctttgc cagatgtgga aaagaagttc   9120
gttgtcccat tgttggcaat gacgtagtag ccggcgaaag tgcgagaccc atttgcgcta   9180
tatataagcc tacgatttcc gttgcgacta ttgtcgtaat tggatgaact attatcgtag   9240
ttgctctcag agttgtcgta atttgatgga ctattgtcgt aattgcttat ggagttgtcg   9300
tagttgcttg gagaaatgtc gtagttggat ggggagtagt catagggaag acgagcttca   9360
tccactaaaa caattggcag gtcagcaagt gcctgccccg atgccatcgc aagtacgagg   9420
cttagaacca ccttcaacag atcgcgcata gtcttcccca gctctctaac gcttgagtta   9480
agccgcgccg cgaagcggcg tcggcttgaa cgaattgtta gacattattt gccgactacc   9540
ttggtgatct cgcctttcac gtagtgaaca aattcttcca actgatctgc gcgcgaggcc   9600
aagcgatctt cttgtccaag ataagcctgc ctagcttcaa gtatgacggg ctgatactgg   9660
gccggcaggc gctccattgc ccagtcggca gcgacatcct tcggcgcgat tttgccggtt   9720
actgcgctgt accaaatgcg ggacaacgta agcactacat ttcgctcatc gccagcccag   9780
tcgggcggcg agttccatag cgttaaggtt tcatttagcg cctcaaatag atcctgttca   9840
ggaaccggat caaagagttc ctccgccgct ggacctacca aggcaacgct atgttctctt   9900
gcttttgtca gcaagatagc cagatcaatg tcgatcgtgg ctggctcgaa gatacctgca   9960
agaatgtcat tgcgctgcca ttctccaaat tgcagttcgc gcttagctgg ataacgccac  10020
ggaatgatgt cgtcgtgcac aacaatggtg acttctacag cgcggagaat ctcgctctct  10080
ccaggggaag ccgaagtttc caaaaggtcg ttgatcaaag ctcgccgcgt tgtttcatca  10140
agccttacag tcaccgtaac cagcaaatca atatcactgt gtggcttcag gccgccatcc  10200
actgcggagc cgtacaaatg tacggccagc aacgtcggtt cgagatggcg ctcgatgacg  10260
ccaactacct ctgatagttg agtcgatact tcggcgatca ccgcttccct catgatgttt  10320
aactcctgaa ttaagccgcg ccgcgaagcg gtgtcggctt gaatgaattg ttaggcgtca  10380
tcctgtgctc ccgagaacca gtaccagtac atcgctgttt cgttcgagac ttgaggtcta  10440
gttttatacg tgaacaggtc aatgccgccg agagtaaagc cacattttgc gtacaaattg  10500
caggcaggta cattgttcgt ttgtgtctct aatcgtatgc caaggagctg tctgcttagt  10560
gcccactttt tcgcaaattc gatgagactg tgcgcgactc ctttgcctcg gtgcgtgtgc  10620
gacacaacaa tgtgttcgat agaggctaga tcgttccatg ttgagttgag ttcaatcttc  10680
ccgacaagct cttggtcgat gaatgcgcca tagcaagcag agtcttcatc agagtcatca  10740
tccgagatgt aatccttccg gtaggggctc acacttctgg tagatagttc aaagccttgg  10800
tcggataggt gcacatcgaa cacttcacga acaatgaaat ggttctcagc atccaatgtt  10860
tccgccacct gctcagggat caccgaaatc ttcatatgac gcctaacgcc tggcacagcg  10920
gatcgcaaac ctggcgcggc ttttggcaca aaaggcgtga caggtttgcg aatccgttgc  10980
tgccacttgt taacccttt gccagatttg gtaactataa tttatgttag aggcgaagtc  11040
```

-continued

```
ttgggtaaaa actggcctaa aattgctggg gatttcagga aagtaaacat caccttccgg  11100
ctcgatgtct attgtagata tatgtagtgt atctacttga tcgggggatc tgctgcctcg  11160
cgcgtttcgg tgatgacggt gaaaacctct gacacatgca gctcccggag acggtcacag  11220
cttgtctgta agcggatgcc gggagcagac aagcccgtca gggcgcgtca gcgggtgttg  11280
gcgggtgtcg gggcgcagcc atgacccagt cacgtagcga tagcggagtg tatactggct  11340
taactatgcg gcatcagagc agattgtact gagagtgcac catatgcggt gtgaaatacc  11400
gcacagatgc gtaaggagaa aataccgcat caggcgctct tccgcttcct cgctcactga  11460
ctcgctgcgc tcggtcgttc ggctgcggcg agcggtatca gctcactcaa aggcggtaat  11520
acggttatcc acagaatcag gggataacgc aggaaagaac atgtgagcaa aaggccagca  11580
aaaggccagg aaccgtaaaa aggccgcgtt gctggcgttt ttccataggc tccgcccccc  11640
tgacgagcat cacaaaaatc gacgctcaag tcagaggtgg cgaaacccga caggactata  11700
aagataccag gcgtttcccc ctggaagctc cctcgtgcgc tctcctgttc cgaccctgcc  11760
gcttaccgga tacctgtccg cctttctccc ttcgggaagc gtggcgcttt ctcatagctc  11820
acgctgtagg tatctcagtt cggtgtaggt cgttcgctcc aagctgggct gtgtgcacga  11880
accccccgtt cagcccgacc gctgcgcctt atccggtaac tatcgtcttg agtccaaccc  11940
ggtaagacac gacttatcgc cactggcagc agccactggt aacaggatta gcagagcgag  12000
gtatgtaggc ggtgctacag agttcttgaa gtggtggcct aactacggct acactagaag  12060
gacagtattt ggtatctgcg ctctgctgaa gccagttacc ttcggaaaaa gagttggtag  12120
ctcttgatcc ggcaaacaaa ccaccgctgg tagcggtggt ttttttgttt gcaagcagca  12180
gattacgcgc agaaaaaaag gatctcaaga agatcctttg atcttttcta cggggtctga  12240
cgctcagtgg aacgaaaact cacgttaagg gattttggtc atgagattat caaaaaggat  12300
cttcacctag atccttttaa attaaaaatg aagttttaaa tcaatctaaa gtatatatga  12360
gtaaacttgg tctgacagtt accaatgctt aatcagtgag gcacctatct cagcgatctg  12420
tctatttcgt tcatccatag ttgcctgact ccccgtcgtg tagataacta cgatacggga  12480
gggcttacca tctggcccca gtgctgcaat gataccgcga gacccacgct caccggctcc  12540
agatttatca gcaataaacc agccagccgg aagggccgag cgcagaagtg gtcctgcaac  12600
tttatccgcc tccatccagt ctattaattg ttgccgggaa gctagagtaa gtagttcgcc  12660
agttaatagt ttgcgcaacg ttgttgccat tgctgcaggg gggggggggg ggggggactt  12720
ccattgttca ttccacggac aaaaacagag aaaggaaacg acagaggcca aaaagcctcg  12780
ctttcagcac ctgtcgtttc ctttcttttc agagggtatt ttaaataaaa acattaagtt  12840
atgacgaaga agaacggaaa cgccttaaac cggaaaattt tcataaatag cgaaaacccg  12900
cgaggtcgcc gccccgtaac acctgtcgga tcaccggaaa ggacccgtaa agtgataatg  12960
attatcatct acatatcaca acgtgcgtgg aggccatcaa accacgtcaa ataatcaatt  13020
atgacgcagg tatcgtatta attgatctgc atcaacttaa cgtaaaaaca acttcagaca  13080
atacaaatca gcgacactga atacggggca acctcatgtc cccccccccc ccccccctgc  13140
aggcatcgtg gtgtcacgct cgtcgtttgg tatggcttca ttcagctccg gttcccaacg  13200
atcaaggcga gttacatgat cccccatgtt gtgcaaaaaa gcggttagct ccttcggtcc  13260
tccgatcgtt gtcagaagta agttggccgc agtgttatca ctcatggtta tggcagcact  13320
gcataattct cttactgtca tgccatccgt aagatgcttt tctgtgactg gtgagtactc  13380
```

-continued aaccaagtca ttctgagaat agtgtatgcg gcgaccgagt tgctcttgcc cggcgtcaac 13440
acgggataat accgcgccac atagcagaac tttaaaagtg ctcatcattg gaaaacgttc 13500
ttcggggcga aaactctcaa ggatcttacc gctgttgaga tccagttcga tgtaacccac 13560
tcgtgcaccc aactgatctt cagcatcttt tactttcacc agcgtttctg ggtgagcaaa 13620
aacaggaagg caaaatgccg caaaaaaggg aataagggcg acacggaaat gttgaatact 13680
catactcttc ctttttcaat attattgaag catttatcag ggttattgtc tcatgagcgg 13740
atacatattt gaatgtattt agaaaaataa acaaataggg gttccgcgca catttccccg 13800
aaaagtgcca cctgacgtct aagaaaccat tattatcatg acattaacct ataaaaatag 13860
gcgtatcacg aggccctttc gtcttcaaga attcggagct tttgccattc tcaccggatt 13920
cagtcgtcac tcatggtgat ttctcacttg ataaccttat ttttgacgag gggaaattaa 13980
taggttgtat tgatgttgga cgagtcggaa tcgcagaccg ataccaggat cttgccatcc 14040
tatggaactg cctcggtgag ttttctcctt cattacagaa acggcttttt caaaaatatg 14100
gtattgataa tcctgatatg aataaattgc agtttcattt gatgctcgat gagtttttct 14160
aatcagaatt ggttaattgg ttgtaacact ggcagagcat tacgctgact tgacgggacg 14220
gcggctttgt tgaataaatc gaacttttgc tgagttgaag gatcagatca cgcatcttcc 14280
cgacaacgca gaccgttccg tggcaaagca aaagttcaaa atcaccaact ggtccaccta 14340
caacaaagct ctcatcaacc gtggctccct cactttctgg ctggatgatg gggcgattca 14400
ggcctggtat gagtcagcaa caccttcttc acgaggcaga cctcagcgcc agaaggccgc 14460
cagagaggcc gagcgcggcc gtgaggcttg gacgctaggg cagggcatga aaaagcccgt 14520
agcgggctgc tacgggcgtc tgacgcggtg gaaaggggga ggggatgttg tctacatggc 14580
tctgctgtag tgagtgggtt gcgctccggc agcggtcctg atcaatcgtc accctttctc 14640
ggtccttcaa cgttcctgac aacgagcctc cttttcgcca atccatcgac aatcaccgcg 14700
agtccctgct cgaacgctgc gtccggaccg gcttcgtcga aggcgtctat cgcggcccgc 14760
aacagcggcg agagcggagc ctgttcaacg gtgccgccgc gctcgccggc atcgctgtcg 14820
ccggcctgct cctcaagcac ggccccaaca gtgaagtagc tgattgtcat cagcgcattg 14880
acggcgtccc cggccgaaaa acccgcctcg cagaggaagc gaagctgcgc gtcggccgtt 14940
tccatctgcg gtgcgcccgg tcgcgtgccg gcatggatgc gcgcgccatc gcggtaggcg 15000
agcagcgcct gcctgaagct gcgggcattc ccgatcagaa atgagcgcca gtcgtcgtcg 15060
gctctcggca ccgaatgcgt atgattctcc gccagcatgg cttcggccag tgcgtcgagc 15120
agcgcccgct tgttcctgaa gtgccagtaa agcgccggct gctgaacccc caaccgttcc 15180
gccagtttgc gtgtcgtcag accgtctacg ccgacctcgt tcaacaggtc cagggcggca 15240
cggatcactg tattcggctg caactttgtc atgcttgaca ctttatcact gataaacata 15300
atatgtccac caacttatca gtgataaaga atccgcgcgt tcaatcggac cagcggaggc 15360
tggtccggag gccagacgtg aaacccaaca tacccctgat cgtaattctg agcactgtcg 15420
cgctcgacgc tgtcggcatc ggcctgatta tgccggtgct gccgggcctc ctgcgcgatc 15480
tggttcactc gaacgacgtc accgcccact atggcattct gctggcgctg tatgcgttgg 15540
tgcaatttgc ctgcgcacct gtgctgggcg cgctgtcgga tcgtttcggg cggcggccaa 15600
tcttgctcgt ctcgctggcc ggcgccactg tcgactacgc catcatggcg acagcgcctt 15660
tcctttgggt tctctatatc gggcggatcg tggccggcat caccggggcg actggggcgg 15720
tagccggcgc ttatattgcc gatatcactg atggcgatga gcgcgcgcgg cacttcggct 15780

```
tcatgagcgc ctgtttcggg ttcgggatgg tcgcgggacc tgtgctcggt gggctgatgg  15840
gcggtttctc cccccacgct ccgttcttcg ccgcggcagc cttgaacggc ctcaatttcc  15900
tgacgggctg tttccttttg ccggagtcgc acaaaggcga acgccggccg ttacgccggg  15960
aggctctcaa cccgctcgct tcgttccggt gggcccgggg catgaccgtc gtcgccgccc  16020
tgatggcggt cttcttcatc atgcaacttg tcggacaggt gccggccgcg ctttgggtca  16080
ttttcggcga ggatcgcttt cactgggacg cgaccacgat cggcatttcg cttgccgcat  16140
ttggcattct gcattcactc gcccaggcaa tgatcaccgg ccctgtagcc gcccggctcg  16200
gcgaaaggcg ggcactcatg ctcggaatga ttgccgacgg cacaggctac atcctgcttg  16260
ccttcgcgac acggggatgg atggcgttcc cgatcatggt cctgcttgct tcgggtggca  16320
tcggaatgcc ggcgctgcaa gcaatgttgt ccaggcaggt ggatgaggaa cgtcaggggc  16380
agctgcaagg ctcactggcg gcgctcacca gcctgacctc gatcgtcgga cccctcctct  16440
tcacggcgat ctatgcggct tctataacaa cgtggaacgg gtgggcatgg attgcaggcg  16500
ctgccctcta cttgctctgc ctgccggcgc tgcgtcgcgg gctttggagc ggcgcagggc  16560
aacgagccga tcgctgatcg tggaaacgat aggcctatgc catgcgggtc aaggcgactt  16620
ccggcaagct atacgcgccc taggagtgcg gttggaacgt tggcccagcc agatactccc  16680
gatcacgagc aggacgccga tgatttgaag cgcactcagc gtctgatcca agaacaacca  16740
tcctagcaac acggcggtcc ccgggctgag aaagcccagt aaggaaacaa ctgtaggttc  16800
gagtcgcgag atcccccgga accaaaggaa gtaggttaaa cccgctccga tcaggccgag  16860
ccacgccagg ccgagaacat tggttcctgt aggcatcggg attggcggat caaacactaa  16920
agctactgga acgagcagaa gtcctccggc cgccagttgc caggcggtaa aggtgagcag  16980
aggcacggga ggttgccact tgcgggtcag cacggttccg aacgccatgg aaaccgcccc  17040
cgccaggccc gctgcgacgc cgacaggatc tagcgctgcg tttggtgtca acaccaacag  17100
cgccacgccc gcagttccgc aaatagcccc caggaccgcc atcaatcgta tcgggctacc  17160
tagcagagcg gcagagatga acacgaccat cagcggctgc acagcgccta ccgtcgccgc  17220
gaccccgccc ggcaggcggt agaccgaaat aaacaacaag ctccagaata gcgaaatatt  17280
aagtgcgccg aggatgaaga tgcgcatcca ccagattccc gttggaatct gtcggacgat  17340
catcacgagc aataaacccg ccggcaacgc ccgcagcagc ataccggcga cccctcggcc  17400
tcgctgttcg ggctccacga aaacgccgga cagatgcgcc ttgtgagcgt ccttggggcc  17460
gtcctcctgt ttgaagaccg acagcccaat gatctcgccg tcgatgtagg cgccgaatgc  17520
cacggcatct cgcaaccgtt cagcgaacgc ctccatgggc tttttctcct cgtgctcgta  17580
aacggacccg aacatctctg gagctttctt cagggccgac aatcggatct cgcggaaatc  17640
ctgcacgtcg gccgctccaa gccgtcgaat ctgagcctta atcacaattg tcaattttaa  17700
tcctctgttt atcggcagtt cgtagagcgc gccgtgcgtc ccgagcgata ctgagcgaag  17760
caagtgcgtc gagcagtgcc cgcttgttcc tgaaatgcca gtaaagcgct ggctgctgaa  17820
cccccagccg gaactgaccc cacaaggccc tagcgtttgc aatgcaccag gtcatcattg  17880
acccaggcgt gttccaccag gccgctgcct cgcaactctt cgcaggcttc gccgacctgc  17940
tcgcgccact tcttcacgcg ggtggaatcc gatccgcaca tgaggcggaa ggtttccagc  18000
ttgagcgggt acggctcccg gtgcgagctg aaatagtcga acatccgtcg ggccgtcggc  18060
gacagcttgc ggtacttctc ccatatgaat ttcgtgtagt ggtcgccagc aaacagcacg  18120
```

-continued

```
acgatttcct cgtcgatcag gacctggcaa cgggacgttt tcttgccacg gtccaggacg  18180
cggaagcggt gcagcagcga caccgattcc aggtgcccaa cgcggtcgga cgtgaagccc  18240
atcgccgtcg cctgtaggcg cgacaggcat tcctcggcct tcgtgtaata ccggccattg  18300
atcgaccagc ccaggtcctg gcaaagctcg tagaacgtga aggtgatcgg ctcgccgata  18360
ggggtgcgct tcgcgtactc caacacctgc tgccacacca gttcgtcatc gtcggcccgc  18420
agctcgacgc cggtgtaggt gatcttcacg tccttgttga cgtggaaaat gaccttgttt  18480
tgcagcgcct cgcgcgggat tttcttgttg cgcgtggtga acagggcaga gcgggccgtg  18540
tcgtttggca tcgctcgcat cgtgtccggc cacggcgcaa tatcgaacaa ggaaagctgc  18600
atttccttga tctgctgctt cgtgtgtttc agcaacgcgg cctgcttggc ctcgctgacc  18660
tgttttgcca ggtcctcgcc ggcggttttt cgcttcttgg tcgtcatagt tcctcgcgtg  18720
tcgatggtca tcgacttcgc caaacctgcc gcctcctgtt cgagacgacg cgaacgctcc  18780
acggcggccg atggcgcggg cagggcaggg ggagccagtt gcacgctgtc gcgctcgatc  18840
ttggccgtag cttgctggac catcgagccg acggactgga aggtttcgcg gggcgcacgc  18900
atgacggtgc ggcttgcgat ggtttcggca tcctcggcgg aaaaccccgc gtcgatcagt  18960
tcttgcctgt atgccttccg gtcaaacgtc cgattcattc accctccttg cgggattgcc  19020
ccgactcacg ccggggcaat gtgcccttat tcctgatttg acccgcctgg tgccttggtg  19080
tccagataat ccaccttatc ggcaatgaag tcggtcccgt agaccgtctg gccgtccttc  19140
tcgtacttgg tattccgaat cttgccctgc acgaatacca gcgacccctt gcccaaatac  19200
ttgccgtggg cctcggcctg agagccaaaa cacttgatgc ggaagaagtc ggtgcgctcc  19260
tgcttgtcgc cggcatcgtt gcgccactct tcattaaccg ctatatcgaa aattgcttgc  19320
ggcttgttag aattgccatg acgtacctcg gtgtcacggg taagattacc gataaactgg  19380
aactgattat ggctcatatc gaaagtctcc ttgagaaagg agactctagt ttagctaaac  19440
attggttccg ctgtcaagaa ctttagcggc taaaattttg cgggccgcga ccaaaggtgc  19500
gaggggcggc ttccgctgtg tacaaccaga tatttttcac caacatcctt cgtctgctcg  19560
atgagcgggg catgacgaaa catgagctgt cggagagggc aggggtttca atttcgtttt  19620
tatcagactt aaccaacggt aaggccaacc cctcgttgaa ggtgatggag gccattgccg  19680
acgccctgga aactccccta cctcttctcc tggagtccac cgaccttgac cgcgaggcac  19740
tcgcggagat tgcgggtcat cctttcaaga gcagcgtgcc gcccggatac gaacgcatca  19800
gtgtggtttt gccgtcacat aaggcgttta tcgtaaagaa atggggcgac gacacccgaa  19860
aaaagctgcg tggaaggctc tgacgccaag ggttagggct tgcacttcct tctttagccg  19920
ctaaaacggc cccttctctg cgggccgtcg gctcgcgcat catatcgaca tcctcaacgg  19980
aagccgtgcc gcgaatggca tcgggcgggt gcgctttgac agttgttttc tatcagaacc  20040
cctacgtcgt gcggttcgat tagctgtttg tcttgcaggc taaacacttt cggtatatcg  20100
tttgcctgtg cgataatgtt gctaatgatt tgttgcgtag ggttactgga aaagtgagcg  20160
ggaaagaaga gtttcagacc atcaaggagc gggccaagcg caagctggaa cgcgacatgg  20220
gtgcggacct gttggccgcg ctcaacgacc cgaaaaccgt tgaagtcatg ctcaacgcgg  20280
acggcaaggt gtggcacgaa cgccttggcg agccgatgcg gtacatctgc gacatgcggc  20340
ccagccagtc gcaggcgatt atagaaacgg tggccggatt ccacggcaaa gaggtcacgc  20400
ggcattcgcc catcctggaa ggcgagttcc ccttggatgg cagccgcttt gccggccaat  20460
tgccgccggt cgtggccgcg ccaacctttg cgatccgcaa gcgcgcggtc gccatcttca  20520
```

cgctggaaca gtacgtcgag gcgggcatca tgacccgcga gcaatacgag gtcattaaaa 20580
gcgccgtcgc ggcgcatcga aacatcctcg tcattggcgg tactggctcg ggcaagacca 20640
cgctcgtcaa cgcgatcatc aatgaaatgg tcgccttcaa cccgtctgag cgcgtcgtca 20700
tcatcgagga caccggcgaa atccagtgcg ccgcagagaa cgccgtccaa taccacacca 20760
gcatcgacgt ctcgatgacg ctgctgctca agacaacgct gcgtatgcgc cccgaccgca 20820
tcctggtcgg tgaggtacgt ggccccgaag cccttgatct gttgatggcc tggaacaccg 20880
ggcatgaagg aggtgccgcc accctgcacg caaacaaccc caaagcgggc ctgagccggc 20940
tcgccatgct tatcagcatg cacccggatt caccgaaacc cattgagccg ctgattggcg 21000
aggcggttca tgtggtcgtc catatcgcca ggacccctag cggccgtcga gtgcaagaaa 21060
ttctcgaagt tcttggttac gagaacggcc agtacatcac caaaaccctg taaggagtat 21120
ttccaatgac aacggctgtt ccgttccgtc tgaccatgaa tcgcggcatt ttgttctacc 21180
ttgccgtgtt cttcgttctc gctctcgcgt tatccgcgca tccggcgatg gcctcggaag 21240
gcaccggcgg cagcttgcca tatgagagct ggctgacgaa cctgcgcaac tccgtaaccg 21300
gcccggtggc cttcgcgctg tccatcatcg gcatcgtcgt cgccggcggc gtgctgatct 21360
tcggcggcga actcaacgcc ttcttccgaa ccctgatctt cctggttctg gtgatggcgc 21420
tgctggtcgg cgcgcagaac gtgatgagca ccttcttcgg tcgtggtgcc gaaatcgcgg 21480
ccctcggcaa cggggcgctg caccaggtgc aagtcgcggc ggcggatgcc gtgcgtgcgg 21540
tagcggctgg acggctcgcc taatcatggc tctgcgcacg atccccatcc gtcgcgcagg 21600
caaccgagaa aacctgttca tgggtggtga tcgtgaactg gtgatgttct cgggcctgat 21660
ggcgtttgcg ctgattttca gcgcccaaga gctgcgggcc accgtggtcg gtctgatcct 21720
gtggttcggg gcgctctatg cgttccgaat catggcgaag gccgatccga agatgcggtt 21780
cgtgtacctg cgtcaccgcc ggtacaagcc gtattacccg gcccgctcga ccccgttccg 21840
cgagaacacc aatagccaag ggaagcaata ccgatgatcc aagcaattgc gattgcaatc 21900
gcgggcctcg gcgcgcttct gttgttcatc ctctttgccc gcatccgcgc ggtcgatgcc 21960
gaactgaaac tgaaaaagca tcgttccaag gacgccggcc tggccgatct gctcaactac 22020
gccgctgtcg tcgatgacgg cgtaatcgtg ggcaagaacg gcagctttat ggctgcctgg 22080
ctgtacaagg gcgatgacaa cgcaagcagc accgaccagc agcgcgaagt agtgtccgcc 22140
cgcatcaacc aggccctcgc gggcctggga agtgggtgga tgatccatgt ggacgccgtg 22200
cggcgtcctg ctccgaacta cgcggagcgg ggcctgtcgg cgttccctga ccgtctgacg 22260
gcagcgattg aagaagagcg ctcggtcttg ccttgctcgt cggtgatgta cttcaccagc 22320
tccgcgaagt cgctcttctt gatggagcgc atggggacgt gcttggcaat cacgcgcacc 22380
ccccggccgt tttagcggct aaaaaagtca tggctctgcc ctcgggcgga ccacgcccat 22440
catgaccttg ccaagctcgt cctgcttctc ttcgatcttc gccagcaggg cgaggatcgt 22500
ggcatcaccg aaccgcgccg tgcgcgggtc gtcggtgagc cagagtttca gcaggccgcc 22560
caggcggccc aggtcgccat tgatgcgggc cagctcgcgg acgtgctcat agtccacgac 22620
gcccgtgatt ttgtagccct ggccgacggc cagcaggtag gccgacaggc tcatgccggc 22680
cgccgccgcc ttttcctcaa tcgctcttcg ttcgtctgga aggcagtaca ccttgatagg 22740
tgggctgccc ttcctggttg gcttggtttc atcagccatc cgcttgccct catctgttac 22800
gccggcggta gccggccagc ctcgcagagc aggattcccg ttgagcaccg ccaggtgcga 22860

-continued

```
ataagggaca gtgaagaagg aacacccgct cgcgggtggg cctacttcac ctatcctgcc  22920
cggctgacgc cgttggatac accaaggaaa gtctacacga accctttggc aaaatcctgt  22980
atatcgtgcg aaaaaggatg gatataccga aaaaatcgct ataatgaccc cgaagcaggg  23040
ttatgcagcg gaaaagcgct gcttccctgc tgttttgtgg aatatctacc gactggaaac  23100
aggcaaatgc aggaaattac tgaactgagg ggacaggcga gagacgatgc caaagagcta  23160
caccgacgag ctggccgagt gggttgaatc ccgcgcggcc aagaagcgcc ggcgtgatga  23220
ggctgcggtt gcgttcctgg cggtgagggc ggatgtcgag gcggcgttag cgtccggcta  23280
tgcgctcgtc accatttggg agcacatgcg ggaaacgggg aaggtcaagt tctcctacga  23340
gacgttccgc tcgcacgcca ggcggcacat caaggccaag cccgccgatg tgcccgcacc  23400
gcaggccaag gctgcggaac ccgcgccggc acccaagacg ccggagccac ggcggccgaa  23460
gcagggggc aaggctgaaa agccggcccc cgctgcggcc ccgaccggct tcaccttcaa  23520
cccaacaccg gacaaaaagg atctactgta atggcgaaaa ttcacatggt tttgcagggc  23580
aagggcgggg tcggcaagtc ggccatcgcc gcgatcattg cgcagtacaa gatggacaag  23640
gggcagacac ccttgtgcat cgacaccgac ccggtgaacg cgacgttcga gggctacaag  23700
gccctgaacg tccgccggct gaacatcatg gccggcgacg aaattaactc gcgcaacttc  23760
gacaccctgg tcgagctgat tgcgccgacc aaggatgacg tggtgatcga caacggtgcc  23820
agctcgttcg tgcctctgtc gcattacctc atcagcaacc aggtgccggc tctgctgcaa  23880
gaaatggggc atgagctggt catccatacc gtcgtcaccg gcggccaggc tctcctggac  23940
acggtgagcg gcttcgccca gctcgccagc cagttcccgg ccgaagcgct tttcgtggtc  24000
tggctgaacc cgtattgggg gcctatcgag catgagggca agagctttga gcagatgaag  24060
gcgtacacgg ccaacaaggc ccgcgtgtcg tccatcatcc agattccggc cctcaaggaa  24120
gaaacctacg gccgcgattt cagcgacatg ctgcaagagc ggctgacgtt cgaccaggcg  24180
ctggccgatg aatcgctcac gatcatgacg cggcaacgcc tcaagatcgt gcggcgcggc  24240
ctgtttgaac agctcgacgc ggcggccgtg ctatgagcga ccagattgaa gagctgatcc  24300
gggagattgc ggccaagcac ggcatcgccg tcggccgcga cgacccggtg ctgatcctgc  24360
ataccatcaa cgcccggctc atggccgaca gtgcggccaa gcaagaggaa atccttgccg  24420
cgttcaagga agagctggaa gggatcgccc atcgttgggg cgaggacgcc aaggccaaag  24480
cggagcggat gctgaacgcg gccctggcgg ccagcaagga cgcaatggcg aaggtaatga  24540
aggacagcgc cgcgcaggcg gccgaagcga tccgcaggga aatcgacgac ggccttggcc  24600
gccagctcgc ggccaaggtc gcggacgcgc ggcgcgtggc gatgatgaac atgatcgccg  24660
gcggcatggt gttgttcgcg gccgccctgg tggtgtgggc ctcgttatga atcgcagagg  24720
cgcagatgaa aaagcccggc gttgccgggc tttgtttttg cgttagctgg gcttgtttga  24780
caggcccaag ctctgactgc gcccgcgctc gcgctcctgg gcctgtttct tctcctgctc  24840
ctgcttgcgc atcagggcct ggtgccgtcg ggctgcttca cgcatcgaat cccagtcgcc  24900
ggccagctcg ggatgctccg cgcgcatctt gcgcgtcgcc agttcctcga tcttgggcgc  24960
gtgaatgccc atgccttcct tgatttcgcg caccatgtcc agccgcgtgt gcagggtctg  25020
caagcgggct tgctgttggg cctgctgctg ctgccaggcg gcctttgtac gcggcaggga  25080
cagcaagccg ggggcattgg actgtagctg ctgcaaacgc gcctgctgac ggtctacgag  25140
ctgttctagg cggtcctcga tgcgctccac ctggtcatgc tttgcctgca cgtagagcgc  25200
aagggtctgc tggtaggtct gctcgatggg cgcggattct aagagggcct gctgttccgt  25260
```

ctcggcctcc tgggccgcct gtagcaaatc ctcgccgctg ttgccgctgg actgctttac 25320
tgccggggac tgctgttgcc ctgctcgcgc cgtcgtcgca gttcggcttg cccccactcg 25380
attgactgct tcatttcgag ccgcagcgat gcgatctcgg attgcgtcaa cggacggggc 25440
agcgcggagg tgtccggctt ctccttgggt gagtcggtcg atgccatagc caaaggtttc 25500
cttccaaaat gcgtccattg ctggaccgtg tttctcattg atgcccgcaa gcatcttcgg 25560
cttgaccgcc aggtcaagcg cgccttcatg ggcggtcatg acggacgccg ccatgacctt 25620
gccgccgttg ttctcgatgt agccgcgtaa tgaggcaatg gtgccgccca tcgtcagcgt 25680
gtcatcgaca acgatgtact tctggccggg gatcacctcc ccctcgaaag tcgggttgaa 25740
cgccaggcga tgatctgaac cggctccggt tcgggcgacc ttctcccgct gcacaatgtc 25800
cgtttcgacc tcaaggccaa ggcggtcggc cagaacgacc gccatcatgg ccggaatctt 25860
gttgttcccc gccgcctcga cggcgaggac tggaacgatg cggggcttgt cgtcgccgat 25920
cagcgtcttg agctgggcaa cagtgtcgtc cgaaatcagg cgctcgacca aattaagcgc 25980
cgcttccgcg tcgccctgct tcgcagcctg gtattcaggc tcgttggtca aagaaccaag 26040
gtcgccgttg cgaaccacct tcgggaagtc tccccacggt gcgcgctcgg ctctgctgta 26100
gctgctcaag acgcctccct ttttagccgc taaaactcta acgagtgcgc ccgcgactca 26160
acttgacgct ttcggcactt acctgtgcct tgccacttgc gtcataggtg atgcttttcg 26220
cactcccgat ttcaggtact ttatcgaaat ctgaccgggc gtgcattaca aagttcttcc 26280
ccacctgttg gtaaatgctg ccgctatctg cgtggacgat gctgccgtcg tggcgctgcg 26340
acttatcggc cttttgggcc atatagatgt tgtaaatgcc aggtttcagg gccccggctt 26400
tatctacctt ctggttcgtc catgcgcctt ggttctcggt ctggacaatt ctttgcccat 26460
tcatgaccag gaggcggtgt ttcattgggt gactcctgac ggttgcctct ggtgttaaac 26520
gtgtcctggt cgcttgccgg ctaaaaaaaa gccgacctcg gcagttcgag gccggctttc 26580
cctagagccg ggcgcgtcaa ggttgttcca tctattttag tgaactgcgt tcgatttatc 26640
agttactttc ctcccgcttt gtgtttcctc ccactcgttt ccgcgtctag ccgacccctc 26700
aacatagcgg cctcttcttg ggctgccttt gcctcttgcc gcgcttcgtc acgctcggct 26760
tgcaccgtcg taaagcgctc ggcctgcctg gccgcctctt gcgccgccaa cttcctttgc 26820
tcctggtggg cctcggcgtc ggcctgcgcc ttcgctttca ccgctgccaa ctccgtgcgc 26880
aaactctccg cttcgcgcct ggtggcgtcg cgctcgccgc gaagcgcctg catttcctgg 26940
ttggccgcgt ccagggtctt gcggctctct tctttgaatg cgcgggcgtc ctggtgagcg 27000
tagtccagct cggcgcgcag ctcctgcgct cgacgctcca cctcgtcggc ccgctgcgtc 27060
gccagcgcgg cccgctgctc ggctcctgcc agggcggtgc gtgcttcggc cagggcttgc 27120
cgctggcgtg cggccagctc ggccgcctcg gcggcctgct gctctagcaa tgtaacgcgc 27180
gcctgggctt cttccagctc gcgggcctgc gcctcgaagg cgtcggccag ctccccgcgc 27240
acggcttcca actcgttgcg ctcacgatcc cagccggctt gcgctgcctg caacgattca 27300
ttggcaaggg cctgggcggc ttgccagagg gcggccacgg cctggttgcc ggcctgctgc 27360
accgcgtccg gcacctggac tgccagcggg gcggcctgcg ccgtgcgctg gcgtcgccat 27420
tcgcgcatgc cggcgctggc gtcgttcatg ttgacgcggg cggccttacg cactgcatcc 27480
acggtcggga agttctcccg gtcgccttgc tcgaacagct cgtccgcagc cgcaaaaatg 27540
cggtcgcgcg tctctttgtt cagttccatg ttggctccgg taattggtaa gaataataat 27600
actcttacct accttatcag cgcaagagtt tagctgaaca gttctcgact taacggcagg 27660
ttttttagcg gctgaagggc aggcaaaaaa agccccgcac ggtcggcggg ggcaaagggt 27720
cagcgggaag gggattagcg ggcgtcgggc ttcttcatgc gtcggggccg cgcttcttgg 27780
gatggagcac gacgaagcgc gcacgcgcat cgtcctcggc cctatcggcc cgcgtcgcgg 27840
tcaggaactt gtcgcgcgct aggtcctccc tggtgggcac caggggcatg aactcggcct 27900
gctcgatgta ggtccactcc atgaccgcat cgcagtcgag gccgcgttcc ttcaccgtct 27960
cttgcaggtc gcggtacgcc cgctcgttga gcggctggta acgggccaat tggtcgtaaa 28020
tggctgtcgg ccatgagcgg cctttcctgt tgagccagca gccgacgacg aagccggcaa 28080
tgcaggcccc tggcacaacc aggccgacgc cgggggcagg ggatggcagc agctcgccaa 28140
ccaggaaccc cgccgcgatg atgccgatgc cggtcaacca gcccttgaaa ctatccggcc 28200
ccgaaacacc cctgcgcatt gcctggatgc tgcgccggat agcttgcaac atcaggagcc 28260
gtttcttttg ttcgtcagtc atggtccgcc ctcaccagtt gttcgtatcg gtgtcggacg 28320
aactgaaatc gcaagagctg ccggtatcgg tccagccgct gtccgtgtcg ctgctgccga 28380
agcacggcga ggggtccgcg aacgccgcag acggcgtatc cggccgcagc gcatcgccca 28440
gcatggcccc ggtcagcgag ccgccggcca ggtagcccag catggtgctg ttggtcgccc 28500
cggccaccag ggccgacgtg acgaaatcgc cgtcattccc tctggattgt tcgctgctcg 28560
gcggggcagt gcgccgcgcc ggcggcgtcg tggatggctc gggttggctg gcctgcgacg 28620
gccggcgaaa ggtgcgcagc agctcgttat cgaccggctg cggcgtcggg gccgccgcct 28680
tgcgctgcgg tcggtgttcc ttcttcggct cgcgcagctt gaacagcatg atcgcggaaa 28740
ccagcagcaa cgccgcgcct acgcctcccg cgatgtagaa cagcatcgga ttcattcttc 28800
ggtcctcctt gtagcggaac cgttgtctgt gcggcgcggg tggcccgcgc cgctgtcttt 28860
ggggatcagc cctcgatgag cgcgaccagt ttcacgtcgg caaggttcgc ctcgaactcc 28920
tggccgtcgt cctcgtactt caaccaggca tagccttccg ccggcggccg acggttgagg 28980
ataaggcggg cagggcgctc gtcgtgctcg acctggacga tggccttttt cagcttgtcc 29040
gggtccggct ccttcgcgcc cttttccttg gcgtccttac cgtcctggtc gccgtcctcg 29100
ccgtcctggc cgtcgccggc ctccgcgtca cgctcggcat cagtctggcc gttgaaggca 29160
tcgacggtgt tgggatcgcg gcccttctcg tccaggaact cgcgcagcag cttgaccgtg 29220
ccgcgcgtga tttcctgggt gtcgtcgtca agccacgcct cgacttcctc cgggcgcttc 29280
ttgaaggccg tcaccagctc gttcaccacg gtcacgtcgc gcacgcggcc ggtgttgaac 29340
gcatcggcga tcttctccgg caggtccagc agcgtgacgt gctgggtgat gaacgccggc 29400
gacttgccga tttccttggc gatatcgcct ttcttcttgc ccttcgccag ctcgcggcca 29460
atgaagtcgg caatttcgcg cggggtcagc tcgttgcgtt gcaggttctc gataacctgg 29520
tcggcttcgt tgtagtcgtt gtcgatgaac gccgggatgg acttcttgcc ggcccacttc 29580
gagccacggt agcggcgggc gccgtgattg atgatatagc ggcccggctg ctcctggttc 29640
tcgcgcaccg aaatgggtga cttcaccccg cgctctttga tcgtggcacc gatttccgcg 29700
atgctctccg gggaaaagcc ggggttgtcg gccgtccgcg gctgatgcgg atcttcgtcg 29760
atcaggtcca ggtccagctc gatagggccg gaaccgccct gagacgccgc aggagcgtcc 29820
aggaggctcg acaggtcgcc gatgctatcc aaccccaggc cggacggctg cgccgcgcct 29880
gcggcttcct gagcggccgc agcggtgttt ttcttggtgg tcttggcttg agccgcagtc 29940
attgggaaat ctccatcttc gtgaacacgt aatcagccag ggcgcgaacc tctttcgatg 30000

```
ccttgcgcgc ggccgttttc ttgatcttcc agaccggcac accggatgcg agggcatcgg  30060
cgatgctgct gcgcaggcca acggtggccg gaatcatcat cttggggtac gcggccagca  30120
gctcggcttg gtggcgcgcg tggcgcggat tccgcgcatc gaccttgctg ggcaccatgc  30180
caaggaattg cagcttggcg ttcttctggc gcacgttcgc aatggtcgtg accatcttct  30240
tgatgccctg gatgctgtac gcctcaagct cgatgggggga cagcacatag tcggccgcga  30300
agagggcggc cgccaggccg acgccaaggg tcggggccgt gtcgatcagg cacacgtcga  30360
agccttggtt cgccagggcc ttgatgttcg ccccgaacag ctcgcgggcg tcgtccagcg  30420
acagccgttc ggcgttcgcc agtaccgggt tggactcgat gagggcgagg cgcgcggcct  30480
ggccgtcgcc ggctgcgggt gcggtttcgg tccagccgcc ggcagggaca gcgccgaaca  30540
gcttgcttgc atgcaggccg gtagcaaagt ccttgagcgt gtaggacgca ttgccctggg  30600
ggtccaggtc gatcacggca acccgcaagc cgcgctcgaa aaagtcgaag gcaagatgca  30660
caagggtcga agtcttgccg acgccgcctt tctggttggc cgtgaccaaa gttttcatcg  30720
tttggtttcc tgtttttttct tggcgtccgc ttcccacttc cggacgatgt acgcctgatg  30780
ttccggcaga accgccgtta cccgcgcgta cccctcgggc aagttcttgt cctcgaacgc  30840
ggcccacacg cgatgcaccg cttgcgacac tgcgcccctg gtcagtccca gcgacgttgc  30900
gaacgtcgcc tgtggcttcc catcgactaa gacgccccgc gctatctcga tggtctgctg  30960
ccccacttcc agcccctgga tcgcctcctg gaactggctt tcggtaagcc gtttcttcat  31020
ggataacacc cataatttgc tccgcgcctt ggttgaacat agcggtgaca gccgccagca  31080
catgagagaa gtttagctaa acatttctcg cacgtcaaca cctttagccg ctaaaactcg  31140
tccttggcgt aacaaaacaa aagcccggaa accgggcttt cgtctcttgc cgcttatggc  31200
tctgcacccg gctccatcac caacaggtcg cgcacgcgct tcactcggtt gcggatcgac  31260
actgccagcc caacaaagcc ggttgccgcc gccgccagga tcgcgccgat gatgccggcc  31320
acaccggcca tcgcccacca ggtcgccgcc ttccggttcc attcctgctg gtactgcttc  31380
gcaatgctgg acctcggctc accataggct gaccgctcga tggcgtatgc cgcttctccc  31440
cttggcgtaa aacccagcgc cgcaggcggc attgccatgc tgcccgccgc tttcccgacc  31500
acgacgcgcg caccaggctt gcggtccaga ccttcggcca cggcgagctg cgcaaggaca  31560
taatcagccg ccgacttggc tccacgcgcc tcgatcagct cttgcactcg cgcgaaatcc  31620
ttggcctcca cggccgccat gaatcgcgca cgcggcgaag gctccgcagg gccggcgtcg  31680
tgatcgccgc cgagaatgcc cttcaccaag ttcgacgaca cgaaaatcat gctgacggct  31740
atcaccatca tgcagacgga tcgcacgaac ccgctgaatt gaacacgagc acggcacccg  31800
cgaccactat gccaagaatg cccaaggtaa aaattgccgg ccccgccatg aagtccgtga  31860
atgccccgac ggccgaagtg aagggcaggc cgccacccag gccgccgccc tcactgcccg  31920
gcacctggtc gctgaatgtc gatgccagca cctgcggcac gtcaatgctt ccgggcgtcg  31980
cgctcgggct gatcgcccat cccgttactg ccccgatccc ggcaatggca aggactgcca  32040
gcgctgccat ttttggggtg aggccgttcg cggccgaggg gcgcagcccc tggggggatg  32100
ggaggcccgc gttagcgggc cgggagggtt cgagaagggg gggcaccccc cttcggcgtg  32160
cgcggtcacg cgcacagggc gcagccctgg ttaaaaacaa ggtttataaa tattggttta  32220
aaagcaggtt aaaagacagg ttagcggtgg ccgaaaaacg ggcggaaacc cttgcaaatg  32280
ctggattttc tgcctgtgga cagcccctca aatgtcaata ggtgcgcccc tcatctgtca  32340
```

-continued

```
gcactctgcc cctcaagtgt caaggatcgc gcccctcatc tgtcagtagt cgcgcccctc  32400
aagtgtcaat accgcagggc acttatcccc aggcttgtcc acatcatctg tgggaaactc  32460
gcgtaaaatc aggcgttttc gccgatttgc gaggctggcc agctccacgt cgccggccga  32520
aatcgagcct gcccctcatc tgtcaacgcc gcgccgggtg agtcggcccc tcaagtgtca  32580
acgtccgccc ctcatctgtc agtgagggcc aagttttccg cgaggtatcc acaacgccgg  32640
cggccgcggt gtctcgcaca cggcttcgac ggcgtttctg gcgcgtttgc agggccatag  32700
acggccgcca gcccagcggc gagggcaacc agcccggtga gcgtcggaaa ggcgctggaa  32760
gccccgtagc gacgcggaga ggggcgagac aagccaaggg cgcaggctcg atgcgcagca  32820
cgacatagcc ggttctcgca aggacgagaa tttccctgcg gtgcccctca agtgtcaatg  32880
aaagtttcca acgcgagcca ttcgcgagag ccttgagtcc acgctagatg agagctttgt  32940
tgtaggtgga ccagttggtg attttgaact tttgctttgc cacggaacgg tctgcgttgt  33000
cgggaagatg cgtgatctga tccttcaact cagcaaaagt tcgatttatt caacaaagcc  33060
acgttgtgtc tcaaaatctc tgatgttaca ttgcacaaga taaaaatata tcatcatgaa  33120
caataaaact gtctgcttac ataaacagta atacaagggg tgttatgagc catattcaac  33180
gggaaacgtc ttgctcgact ctagagctcg ttcctcgagg cctcgaggcc tcgaggaacg  33240
gtacctgcgg ggaagcttac aataatgtgt gttgttaagt cttgttgcct gtcatcgtct  33300
gactgacttt cgtcataaat cccggcctcc gtaacccagc tttgggcaag ctcacggatt  33360
tgatccggcg gaacgggaat atcgagatgc cgggctgaac gctgcagttc cagctttccc  33420
tttcgggaca ggtactccag ctgattgatt atctgctgaa gggtcttggt tccacctcct  33480
ggcacaatgc gaatgattac ttgagcgcga tcgggcatcc aattttctcc cgtcaggtgc  33540
gtggtcaagt gctacaaggc acctttcagt aacgagcgac cgtcgatccg tcgccgggat  33600
acggacaaaa tggagcgcag tagtccatcg agggcggcga aagcctcgcc aaaagcaata  33660
cgttcatctc gcacagcctc cagatccgat cgagggtctt cggcgtaggc agatagaagc  33720
atggatacat tgcttgagag tattccgatg gactgaagta tggcttccat cttttctcgt  33780
gtgtctgcat ctatttcgag aaagccccg atgcggcgca ccgcaacgcg aattgccata  33840
ctatccgaaa gtcccagcag gcgcgcttga taggaaaagg tttcatactc ggccgatcgc  33900
agacgggcac tcacgacctt gaacccttca actttcaggg atcgatgctg gttgatggta  33960
gtctcactcg acgtggctct ggtgtgtttt gacatagctt cctccaaaga aagcggaagg  34020
tctggatact ccagcacgaa atgtgcccgg gtagacggat ggaagtctag ccctgctcaa  34080
tatgaaatca acagtacatt tacagtcaat actgaatata cttgctacat ttgcaattgt  34140
cttataacga atgtgaaata aaaatagtgt aacaacgctt ttactcatcg ataatcacaa  34200
aaacatttat acgaacaaaa atacaaatgc actccggttt cacaggatag gcgggatcag  34260
aatatgcaac ttttgacgtt ttgttctttc aaagggggtg ctggcaaaac caccgcactc  34320
atgggccttt gcgctgcttt ggcaaatgac ggtaaacgag tggccctctt tgatgccgac  34380
gaaaaccggc ctctgacgcg atggagagaa aacgccttac aaagcagtac tgggatcctc  34440
gctgtgaagt ctattccgcc gacgaaatgc cccttcttga agcagcctat gaaaatgccg  34500
agctcgaagg atttgattat gcgttggccg atacgcgtgg cggctcgagc gagctcaaca  34560
acacaatcat cgctagctca aacctgcttc tgatccccac catgctaacg ccgctcgaca  34620
tcgatgaggc actatctacc taccgctacg tcatcgagct gctgttgagt gaaaatttgg  34680
caattcctac agctgttttg cgccaacgcg tcccggtcgg ccgattgaca acatcgcaac  34740
```

gcaggatgtc agagacgcta gagagccttc cagttgtacc gtctcccatg catgaaagag 34800
atgcatttgc cgcgatgaaa gaacgcggca tgttgcatct tacattacta aacacgggaa 34860
ctgatccgac gatgcgcctc atagagagga atcttcggat tgcgatggag gaagtcgtgg 34920
tcatttcgaa actgatcagc aaaatcttgg aggcttgaag atggcaattc gcaagcccgc 34980
attgtcggtc ggcgaagcac ggcggcttgc tggtgctcga cccgagatcc accatcccaa 35040
cccgacactt gttccccaga agctggacct ccagcacttg cctgaaaaag ccgacgagaa 35100
agaccagcaa cgtgagcctc tcgtcgccga tcacatttac agtcccgatc gacaacttaa 35160
gctaactgtg gatgccctta gtccacctcc gtccccgaaa aagctccagg tttttctttc 35220
agcgcgaccg cccgcgcctc aagtgtcgaa aacatatgac aacctcgttc ggcaatacag 35280
tccctcgaag tcgctacaaa tgattttaag gcgcgcgttg gacgatttcg aaagcatgct 35340
ggcagatgga tcatttcgcg tggccccgaa aagttatccg atcccttcaa ctacagaaaa 35400
atccgttctc gttcagacct cacgcatgtt cccggttgcg ttgctcgagg tcgctcgaag 35460
tcattttgat ccgttggggt tggagaccgc tcgagctttc ggccacaagc tggctaccgc 35520
cgcgctcgcg tcattctttg ctggagagaa gccatcgagc aattggtgaa gagggaccta 35580
tcggaacccc tcaccaaata ttgagtgtag gtttgaggcc gctggccgcg tcctcagtca 35640
ccttttgagc cagataatta agagccaaat gcaattggct caggctgcca tcgtcccccc 35700
gtgcgaaacc tgcacgtccg cgtcaaagaa ataaccggca cctcttgctg tttttatcag 35760
ttgagggctt gacggatccg cctcaagttt gcggcgcagc cgcaaaatga gaacatctat 35820
actcctgtcg taaacctcct cgtcgcgtac tcgactggca atgagaagtt gctcgcgcga 35880
tagaacgtcg cggggtttct ctaaaaacgc gaggagaaga ttgaactcac ctgccgtaag 35940
tttcacctca ccgccagctt cggacatcaa gcgacgttgc ctgagattaa gtgtccagtc 36000
agtaaaacaa aaagaccgtc ggtctttgga gcggacaacg ttggggcgca cgcgcaaggc 36060
aacccgaatg cgtgcaagaa actctctcgt actaaacggc ttagcgataa aatcacttgc 36120
tcctagctcg agtgcaacaa ctttatccgt ctcctcaagg cggtcgccac tgataattat 36180
gattggaata tcagactttg ccgccagatt tcgaacgatc tcaagcccat cttcacgacc 36240
taaatttaga tcaacaacca cgacatcgac cgtcgcggaa gagagtactc tagtgaactg 36300
ggtgctgtcg gctaccgcgg tcactttgaa ggcgtggatc gtaaggtatt cgataataag 36360
atgccgcata gcgacatcgt catcgataag aagaacgtgt ttcaacggct cacctttcaa 36420
tctaaaatct gaacccttgt tcacagcgct tgagaaattt tcacgtgaag gatgtacaat 36480
catctccagc taaatgggca gttcgtcaga attgcggctg accgcggatg acgaaaatgc 36540
gaaccaagta tttcaatttt atgacaaaag ttctcaatcg ttgttacaag tgaaacgctt 36600
cgaggttaca gctactattg attaaggaga tcgcctatgg tctcgccccg gcgtcgtgcg 36660
tccgccgcga gccagatctc gcctacttca taaacgtcct cataggcacg gaatggaatg 36720
atgacatcga tcgccgtaga gagcatgtca atcagtgtgc gatcttccaa gctagcacct 36780
tgggcgctac ttttgacaag ggaaaacagt ttcttgaatc cttggattgg attcgcgccg 36840
tgtattgttg aaatcgatcc cggatgtccc gagacgactt cactcagata agcccatgct 36900
gcatcgtcgc gcatctcgcc aagcaatatc cggtccggcc gcatacgcag acttgcttgg 36960
agcaagtgct cggcgctcac agcacccagc ccagcaccgt tcttggagta gagtagtcta 37020
acatgattat cgtgtggaat gacgagttcg agcgtatctt ctatggtgat tagcctttcc 37080

-continued

```
tggggggga tggcgctgat caaggtcttg ctcattgttg tcttgccgct tccggtaggg  37140
ccacatagca acatcgtcag tcggctgacg acgcatgcgt gcagaaacgc ttccaaatcc  37200
ccgttgtcaa aatgctgaag gatagcttca tcatcctgat tttggcgttt ccttcgtgtc  37260
tgccactggt tccacctcga agcatcataa cgggaggaga cttctttaag accagaaaca  37320
cgcgagcttg gccgtcgaat ggtcaagctg acggtgcccg agggaacggt cggcggcaga  37380
cagatttgta gtcgttcacc accaggaagt tcagtggcgc agagggggtt acgtggtccg  37440
acatcctgct ttctcagcgc gcccgctaaa atagcgatat cttcaagatc atcataagag  37500
acgggcaaag gcatcttggt aaaaatgccg gcttggcgca caaatgcctc tccaggtcga  37560
ttgatcgcaa tttcttcagt cttcgggtca tcgagccatt ccaaaatcgg cttcagaaga  37620
aagcgtagtt gcggatccac ttccatttac aatgtatcct atctctaagc ggaaatttga  37680
attcattaag agcggcggtt cctcccccgc gtggcgccgc cagtcaggcg gagctggtaa  37740
acaccaaaga aatcgaggtc ccgtgctacg aaaatggaaa cggtgtcacc ctgattcttc  37800
ttcagggttg gcggtatgtt gatggttgcc ttaagggctg tctcagttgt ctgctcaccg  37860
ttattttgaa agctgttgaa gctcatcccg ccacccgagc tgccggcgta ggtgctagct  37920
gcctggaagg cgccttgaac aacactcaag agcatagctc cgctaaaacg ctgccagaag  37980
tggctgtcga ccgagcccgg caatcctgag cgaccgagtt cgtccgcgct tggcgatgtt  38040
aacgagatca tcgcatggtc aggtgtctcg gcgcgatccc acaacacaaa aacgcgccca  38100
tctccctgtt gcaagccacg ctgtatttcg ccaacaacgg tggtgccacg atcaagaagc  38160
acgatattgt tcgttgttcc acgaatatcc tgaggcaaga cacactttac atagcctgcc  38220
aaatttgtgt cgattgcggt ttgcaagatg cacggaatta ttgtcccttg cgttaccata  38280
aaatcggggt gcggcaagag cgtggcgctg ctgggctgca gctcggtggg tttcatacgt  38340
atcgacaaat cgttctcgcc ggacacttcg ccattcggca aggagttgtc gtcacgcttg  38400
ccttcttgtc ttcggcccgt gtcgccctga atggcgcgtt tgctgacccc ttgatcgccg  38460
ctgctatatg caaaaatcgg tgtttcttcc ggccgtggct catgccgctc cggttcgccc  38520
ctcggcggta gaggagcagc aggctgaaca gcctcttgaa ccgctggagg atccggcggc  38580
acctcaatcg gagctggatg aaatggcttg gtgtttgttg cgatcaaagt tgacggcgat  38640
gcgttctcat tcaccttctt ttggcgccca cctagccaaa tgaggcttaa tgataacgcg  38700
agaacgacac ctccgacgat caatttctga gaccccgaaa gacgccggcg atgtttgtcg  38760
gagaccaggg atccagatgc atcaacctca tgtgccgctt gctgactatc gttattcatc  38820
ccttcgcccc cttcaggacg cgtttcacat cgggcctcac cgtgcccgtt tgcggccttt  38880
ggccaacggg atcgtaagcg gtgttccaga tacatagtac tgtgtggcca tccctcagac  38940
gccaacctcg ggaaaccgaa gaaatctcga catcgctccc tttaactgaa tagttggcaa  39000
cagcttcctt gccatcagga ttgatggtgt agatggaggg tatgcgtaca ttgcccggaa  39060
agtggaatac cgtcgtaaat ccattgtcga agacttcgag tggcaacagc gaacgatcgc  39120
cttgggcgac gtagtgccaa ttactgtccg ccgcaccaag ggctgtgaca ggctgatcca  39180
ataaattctc agctttccgt tgatattgtg cttccgcgtg tagtctgtcc acaacagcct  39240
tctgttgtgc ctcccttcgc cgagccgccg catcgtcggc ggggtaggcg aattggacgc  39300
tgtaatagag atcgggctgc tctttatcga ggtgggacag agtcttggaa cttatactga  39360
aaacataacg gcgcatcccg gagtcgcttg cggttagcac gattactggc tgaggcgtga  39420
ggacctggct tgccttgaaa aatagataat ttccccgcgg tagggctgct agatctttgc  39480
```

```
tatttgaaac ggcaaccgct gtcaccgttt cgttcgtggc gaatgttacg accaaagtag  39540
ctccaaccgc cgtcgagagg cgcaccactt gatcgggatt gtaagccaaa taacgcatgc  39600
gcggatctag cttgcccgcc attggagtgt cttcagcctc cgcaccagtc gcagcggcaa  39660
ataaacatgc taaaatgaaa agtgcttttc tgatcatggt tcgctgtggc ctacgtttga  39720
aacggtatct tccgatgtct gataggaggt gacaaccaga cctgccgggt tggttagtct  39780
caatctgccg ggcaagctgg tcaccttttc gtagcgaact gtcgcggtcc acgtactcac  39840
cacaggcatt ttgccgtcaa cgacgagggt ccttttatag cgaatttgct gcgtgcttgg  39900
agttacatca tttgaagcga tgtgctcgac ctccaccctg ccgcgtttgc caagaatgac  39960
ttgaggcgaa ctgggattgg gatagttgaa gaattgctgg taatcctggc gcactgttgg  40020
ggcactgaag ttcgatacca ggtcgtaggc gtactgagcg gtgtcggcat cataactctc  40080
gcgcaggcga acgtactccc acaatgaggc gttaacgacg gcctcctctt gagttgcagg  40140
caatcgcgag acagacacct cgctgtcaac ggtgccgtcc ggccgtatcc atagatatac  40200
gggcacaagc ctgctcaacg gcaccattgt ggctatagcg aacgcttgag caacatttcc  40260
caaaatcgcg atagctgcga cagctgcaat gagtttggag agacgtcgcg ccgatttcgc  40320
tcgcgcggtt tgaaaggctt ctacttcctt atagtgctcg gcaaggcttt cgcgcgccac  40380
tagcatggca tattcaggcc ccgtcatagc gtccacccga attgccgagc tgaagatctg  40440
acggagtagg ctgccatcgc cccacattca gcgggaagat cgggcctttg cagctcgcta  40500
atgtgtcgtt tgtctggcag ccgctcaaag cgacaactag gcacagcagg caatacttca  40560
tagaattctc cattgaggcg aatttttgcg cgacctagcc tcgctcaacc tgagcgaagc  40620
gacggtacaa gctgctggca gattgggttg cgccgctcca gtaactgcct ccaatgttgc  40680
cggcgatcgc cggcaaagcg acaatgagcg catcccctgt cagaaaaaac atatcgagtt  40740
cgtaaagacc aatgatcttg gccgcggtcg taccggcgaa ggtgattaca ccaagcataa  40800
gggtgagcgc agtcgcttcg gttaggatga cgatcgttgc cacgaggttt aagaggagaa  40860
gcaagagacc gtaggtgata agttgcccga tccacttagc tgcgatgtcc cgcgtgcgat  40920
caaaaatata tccgacgagg atcagaggcc cgatcgcgag aagcactttc gtgagaattc  40980
caacggcgtc gtaaactccg aaggcagacc agagcgtgcc gtaaaggacc cactgtgccc  41040
cttggaaagc aaggatgtcc tggtcgttca tcggaccgat ttcggatgcg attttctgaa  41100
aaacggcctg ggtcacggcg aacattgtat ccaactgtgc cggaacagtc tgcagaggca  41160
agccggttac actaaactgc tgaacaaagt ttgggaccgt cttttcgaag atggaaacca  41220
catagtcttg gtagttagcc tgcccaacaa ttagagcaac aacgatggtg accgtgatca  41280
cccgagtgat accgctacgg gtatcgactt cgccgcgtat gactaaaata ccctgaacaa  41340
taatccaaag agtgacacag gcgatcaatg gcgcactcac cgcctcctgg atagtctcaa  41400
gcatcgagtc caagcctgtc gtgaaggcta catcgaagat cgtatgaatg gccgtaaacg  41460
gcgccggaat cgtgaaattc atcgattgga cctgaacttg actggtttgt cgcataatgt  41520
tggataaaat gagctcgcat tcggcgagga tgcgggcgga tgaacaaatc gcccagcctt  41580
aggggagggc accaaagatg acagcggtct tttgatgctc cttgcgttga gcggccgcct  41640
cttccgcctc gtgaaggccg gcctgcgcgg tagtcatcgt taataggctt gtcgcctgta  41700
cattttgaat cattgcgtca tggatctgct tgagaagcaa accattggtc acggttgcct  41760
gcatgatatt gcgagatcgg gaaagctgag cagacgtatc agcattcgcc gtcaagcgtt  41820
```

-continued tgtccatcgt ttccagattg tcagccgcaa tgccagcgct gtttgcggaa ccggtgatct 41880
gcgatcgcaa caggtccgct tcagcatcac tacccacgac tgcacgatct gtatcgctgg 41940
tgatcgcacg tgccgtggtc gacattggca ttcgcggcga aaacatttca ttgtctaggt 42000
ccttcgtcga aggatactga tttttctggt tgagcgaagt cagtagtcca gtaacgccgt 42060
aggccgacgt caacatcgta accatcgcta tagtctgagt gagattctcc gcagtcgcga 42120
gcgcagtcgc gagcgtctca gcctccgttg ccgggtcgct aacaacaaac tgcgcccgcg 42180
cgggctgaat atatagaaag ctgcaggtca aaactgttgc aataagttgc gtcgtcttca 42240
tcgtttccta ccttatcaat cttctgcctc gtggtgacgg gccatgaatt cgctgagcca 42300
gccagatgag ttgccttctt gtgcctcgcg tagtcgagtt gcaaagcgca ccgtgttggc 42360
acgccccgaa agcacggcga catattcacg catatcccgc agatcaaatt cgcagatgac 42420
gcttccactt tctcgtttaa gaagaaactt acggctgccg accgtcatgt cttcacggat 42480
cgcctgaaat tccttttcgg tacatttcag tccatcgaca taagccgatc gatctgcggt 42540
tggtgatgga tagaaaatct tcgtcataca ttgcgcaacc aagctggctc ctagcggcga 42600
ttccagaaca tgctctggtt gctgcgttgc cagtattagc atcccgttgt tttttcgaac 42660
ggtcaggagg aatttgtcga cgacagtcga aaatttaggg tttaacaaat aggcgcgaaa 42720
ctcatcgcag ctcatcacaa aacggcggcc gtcgatcatg gctccaatcc gatgcaggag 42780
atatgctgca gcgggagcgc atacttcctc gtattcgaga agatgcgtca tgtcgaagcc 42840
ggtaatcgac ggatctaact ttacttcgtc aacttcgccg tcaaatgccc agccaagcgc 42900
atggccccgg caccagcgtt ggagccgcgc tcctgcgcct tcggcgggcc catgcaacaa 42960
aaattcacgt aaccccgcga ttgaacgcat ttgtggatca aacgagagct gacgatggat 43020
accacggacc agacggcggt tctcttccgg agaaatccca ccccgaccat cactctcgat 43080
gagagccacg atccattcgc gcagaaaatc gtgtgaggct gctgtgtttt ctaggccacg 43140
caacggcgcc aacccgctgg gtgtgcctct gtgaagtgcc aaatatgttc ctcctgtggc 43200
gcgaaccagc aattcgccac cccggtcctt gtcaaagaac acgaccgtac ctgcacggtc 43260
gaccatgctc tgttcgagca tggctagaac aaacatcatg agcgtcgtct taccccctccc 43320 gataggcccg aatattgccg tcatgccaac atcgtgctca tgcgggatat agtcgaaagg 43380
cgttccgcca ttggtacgaa atcgggcaat cgcgttgccc cagtggcctg agctggcgcc 43440
ctctggaaag ttttcgaaag agacaaaccc tgcgaaattg cgtgaagtga ttgcgccagg 43500
gcgtgtgcgc cacttaaaat tccccggcaa ttgggaccaa taggccgctt ccataccaat 43560
accttcttgg acaaccacgg cacctgcatc cgccattcgt gtccgagccc gcgcgcccct 43620
gtccccaaga ctattgagat cgtctgcata gacgcaaagg ctcaaatgat gtgagcccat 43680
aacgaattcg ttgctcgcaa gtgcgtcctc agcctcggat aatttgccga tttgagtcac 43740
ggctttatcg ccggaactca gcatctggct cgatttgagg ctaagtttcg cgtgcgcttg 43800
cgggcgagtc aggaacgaaa aactctgcgt gagaacaagt ggaaaatcga gggatagcag 43860
cgcgttgagc atgcccggcc gtgtttttgc agggtattcg cgaaacgaat agatggatcc 43920
aacgtaactg tcttttggcg ttctgatctc gagtcctcgc ttgccgcaaa tgactctgtc 43980
ggtataaatc gaagcgccga gtgagccgct gacgaccgga accggtgtga accgaccagt 44040
catgatcaac cgtagcgctt cgccaatttc ggtgaagagc acaccctgct tctcgcggat 44100
gccaagacga tgcaggccat acgctttaag agagccagcg acaacatgcc aaagatcttc 44160
catgttcctg atctggcccg tgagatcgtt ttcccttttt ccgcttagct tggtgaacct 44220

-continued cctctttacc ttccctaaag ccgcctgtgg gtagacaatc aacgtaagga agtgttcatt 44280
gcggaggagt tggccggaga gcacgcgctg ttcaaaagct tcgttcaggc tagcggcgaa 44340
aacactacgg aagtgtcgcg gcgccgatga tggcacgtcg gcatgacgta cgaggtgagc 44400
atatattgac acatgatcat cagcgatatt gcgcaacagc gtgttgaacg cacgacaacg 44460
cgcattgcgc atttcagttt cctcaagctc gaatgcaacg ccatcaattc tcgcaatggt 44520
catgatcgat ccgtcttcaa gaaggacgat atggtcgctg aggtggccaa tataagggag 44580
atagatctca ccggatcttt cggtcgttcc actcgcgccg agcatcacac cattcctctc 44640
cctcgtgggg gaaccctaat tggatttggg ctaacagtag cgcccccccca aactgcacta 44700 tcaatgcttc ttcccgcggt ccgcaaaaat agcaggacga cgctcgccgc attgtagtct 44760
cgctccacga tgagccgggc tgcaaaccat aacggcacga gaacgacttc gtagagcggg 44820
ttctgaacga taacgatgac aaagccggcg aacatcatga ataaccctgc caatgtcagt 44880
ggcaccccaa gaaacaatgc gggccgtgtg gctgcgaggt aaagggtcga ttcttccaaa 44940
cgatcagcca tcaactaccg ccagtgagcg tttggccgag gaagctcgcc ccaaacatga 45000
taacaatgcc gccgacgacg ccggcaacca gcccaagcga agcccgcccg aacatccagg 45060
agatcccgat agcgacaatg ccgagaacag cgagtgactg gccgaacgga ccaaggataa 45120
acgtgcatat attgttaacc attgtggcgg ggtcagtgcc gccacccgca gattgcgctg 45180
cggcgggtcc ggatgaggaa atgctccatg caattgcacc gcacaagctt ggggcgcagc 45240
tcgatatcac gcgcatcatc gcattcgaga gcgagaggcg atttagatgt aaacggtatc 45300
tctcaaagca tcgcatcaat gcgcacctcc ttagtataag tcgaataaga cttgattgtc 45360
gtctgcggat ttgccgttgt cctggtgtgg cggtggcgga gcgattaaac cgccagcgcc 45420
atcctcctgc gagcggcgct gatatgaccc ccaaacatcc cacgtctctt cggattttag 45480
cgcctcgtga tcgtcttttg gaggctcgat taacgcgggc accagcgatt gagcagctgt 45540
ttcaactttt cgcacgtagc cgtttgcaaa accgccgatg aaattaccgg tgttgtaagc 45600
ggagatcgcc cgacgaagcg caaattgctt ctcgtcaatc gtttcgccgc ctgcataacg 45660
acttttcagc atgtttgcag cggcagataa tgatgtgcac gcctggagcg caccgtcagg 45720
tgtcagaccg agcatagaaa aatttcgaga gtttatttgc atgaggccaa catccagcga 45780
atgccgtgca tcgagacggt gcctgacgac ttgggttgct tggctgtgat cttgccagtg 45840
aagcgtttcg ccggtcgtgt tgtcatgaat cgctaaagga tcaaagcgac tctccacctt 45900
agctatcgcc gcaagcgtag atgtcgcaac tgatggggca cacttgcgag caacatggtc 45960
aaactcagca gatgagagtg gcgtggcaag gctcgacgaa cagaaggaga ccatcaaggc 46020
aagagaaagc gaccccgatc tcttaagcat accttatctc cttagctcgc aactaacacc 46080
gcctctcccg ttggaagaag tgcgttgttt tatgttgaag attatcggga gggtcggtta 46140
ctcgaaaatt ttcaattgct tctttatgat ttcaattgaa gcgagaaacc tcgcccggcg 46200
tcttggaacg caacatggac cgagaaccgc gcatccatga ctaagcaacc ggatcgacct 46260
attcaggccg cagttggtca ggtcaggctc agaacgaaaa tgctcggcga ggttacgctg 46320
tctgtaaacc cattcgatga acgggaagct tccttccgat tgctcttggc aggaatattg 46380
gcccatgcct gcttgcgctt tgcaaatgct cttatcgcgt tggtatcata tgccttgtcc 46440
gccagcagaa acgcactcta agcgattatt tgtaaaaatg tttcggtcat gcggcggtca 46500
tgggcttgac ccgctgtcag cgcaagacgg atcggtcaac cgtcggcatc gacaacagcg 46560
tgaatcttgg tggtcaaacc gccacgggaa cgtcccatac agccatcgtc ttgatcccgc 46620
tgtttcccgt cgccgcatgt tggtggacgc ggacacagga actgtcaatc atgacgacat 46680
tctatcgaaa gccttggaaa tcacactcag aatatgatcc cagacgtctg cctcacgcca 46740
tcgtacaaag cgattgtagc aggttgtaca ggaaccgtat cgatcaggaa cgtctgccca 46800
gggcgggccc gtccggaagc gccacaagat gacattgatc acccgcgtca acgcgcggca 46860
cgcgacgcgg cttatttggg aacaaaggac tgaacaacag tccattcgaa atcggtgaca 46920
tcaaagcggg gacgggttat cagtggcctc caagtcaagc ctcaatgaat caaaatcaga 46980
ccgatttgca aacctgattt atgagtgtgc ggcctaaatg atgaaatcgt ccttctagat 47040
cgcctccgtg gtgtagcaac acctcgcagt atcgccgtgc tgaccttggc cagggaattg 47100
actggcaagg gtgctttcac atgaccgctc ttttggccgc gatagatgat ttcgttgctg 47160
ctttgggcac gtagaaggag agaagtcata tcggagaaat tcctcctggc gcgagagcct 47220
gctctatcgc gacggcatcc cactgtcggg aacagaccgg atcattcacg aggcgaaagt 47280
cgtcaacaca tgcgttatag gcatcttccc ttgaaggatg atcttgttgc tgccaatctg 47340
gaggtgcggc agccgcaggc agatgcgatc tcagcgcaac ttgcggcaaa acatctcact 47400
cacctgaaaa ccactagcga gtctcgcgat cagacgaagg ccttttactt aacgacacaa 47460
tatccgatgt ctgcatcaca ggcgtcgcta tcccagtcaa tactaaagcg gtgcaggaac 47520
taaagattac tgatgactta ggcgtgccac gaggcctgag acgacgcgcg tagacagttt 47580
tttgaaatca ttatcaaagt gatggcctcc gctgaagcct atcacctctg cgccggtctg 47640
tcggagagat gggcaagcat tattacggtc ttcgcgcccg tacatgcatt ggacgattgc 47700
agggtcaatg gatctgagat catccagagg attgccgccc ttaccttccg tttcgagttg 47760
gagccagccc ctaaatgaga cgacatagtc gacttgatgt gacaatgcca agagagagat 47820
ttgcttaacc cgattttttt gctcaagcgt aagcctattg aagcttgccg gcatgacgtc 47880
cgcgccgaaa gaatatccta caagtaaaac attctgcaca ccgaaatgct tggtgtagac 47940
atcgattatg tgaccaagat ccttagcagt ttcgcttggg gaccgctccg accagaaata 48000
ccgaagtgaa ctgacgccaa tgacaggaat cccttccgtc tgcagatagg taccatcgat 48060
agatctgctg cctcgcgcgt ttcggtgatg acggtgaaaa cctctgacac atgcagctcc 48120
cggagacggt cacagcttgt ctgtaagcgg atgccgggag cagacaagcc cgtcagggcg 48180
cgtcagcggg tgttggcggg tgtcggggcg cagccatgac ccagtcacgt agcgatagcg 48240
gagtgtatac tggcttaact atgcggcatc agagcagatt gtactgagag tgcaccatat 48300
gcggtgtgaa ataccgcaca gatgcgtaag gagaaaatac cgcatcaggc gctcttccgc 48360
ttcctcgctc actgactcgc tgcgctcggt cgttcggctg cggcgagcgg tatcagctca 48420
ctcaaaggcg gtaatacggt tatccacaga atcaggggat aacgcaggaa agaacatgtg 48480
agcaaaaggc cagcaaaagg ccaggaaccg taaaaaggcc gcgttgctgg cgtttttcca 48540
taggctccgc ccccctgacg agcatcacaa aaatcgacgc tcaagtcaga ggtggcgaaa 48600
cccgacagga ctataaagat accaggcgtt tccccctgga agctccctcg tgcgctctcc 48660
tgttccgacc ctgccgctta ccggatacct gtccgccttt ctcccttcgg gaagcgtggc 48720
gctttctcat agctcacgct gtaggtatct cagttcggtg taggtcgttc gctccaagct 48780
gggctgtgtg cacgaacccc ccgttcagcc cgaccgctgc gccttatccg gtaactatcg 48840
tcttgagtcc aacccggtaa gacacgactt atcgccactg gcagcagcca ctggtaacag 48900
gattagcaga gcgaggtatg taggcggtgc tacagagttc ttgaagtggt ggcctaacta 48960
cggctacact agaaggacag tatttggtat ctgcgctctg ctgaagccag ttaccttcgg 49020
aaaaagagtt ggtagctctt gatccggcaa acaaaccacc gctggtagcg gtggtttttt 49080
tgtttgcaag cagcagatta cgcgcagaaa aaaaggatct caagaagatc ctttgatctt 49140
ttctacgggg tctgacgctc agtggaacga aaactcacgt taagggattt tggtcatgag 49200
attatcaaaa aggatcttca cctagatcct tttaaattaa aaatgaagtt ttaaatcaat 49260
ctaaagtata tatgagtaaa cttggtctga cagttaccaa tgcttaatca gtgaggcacc 49320
tatctcagcg atctgtctat ttcgttcatc catagttgcc tgactccccg tcgtgtagat 49380
aactacgata cgggagggct taccatctgg ccccagtgct gcaatgatac cgcgagaccc 49440
acgctcaccg gctccagatt tatcagcaat aaaccagcca gccggaaggg ccgagcgcag 49500
aagtggtcct gcaactttat ccgcctccat ccagtctatt aattgttgcc gggaagctag 49560
agtaagtagt tcgccagtta atagtttgcg caacgttgtt gccattgctg caggggggggg 49620
gggggggggg ttccattgtt cattccacgg acaaaaacag agaaaggaaa cgacagaggc 49680
caaaaagctc gctttcagca cctgtcgttt cctttctttt cagagggtat tttaaataaa 49740
aacattaagt tatgacgaag aagaacggaa acgccttaaa ccggaaaatt ttcataaata 49800
gcgaaaaccc gcgaggtcgc cgccccgtac tgtcggatca ccggaaagga cccgtaaagt 49860
gataatgatt atcatctaca tatcacaacg tgcgtggagg ccatcaaacc acgtcaaata 49920
atcaattatg acgcaggtat cgtattaatt gatctgcatc aacttaacgt aaaaacaact 49980
tcagacaata caaatcagcg acactgaata cggggcaacc tcatgtcccc cccccccccc 50040
cccctgcagg catcgtggtg tcacgctcgt cgtttggtat ggcttcattc agctccggtt 50100
cccaacgatc aaggcgagtt acatgatccc ccatgttgtg caaaaaagcg gttagctcct 50160
tcggtcctcc gatcgttgtc agaagtaagt tggccgcagt gttatcactc atggttatgg 50220
cagcactgca taattctctt actgtcatgc catccgtaag atgcttttct gtgactggtg 50280
agtactcaac caagtcattc tgagaatagt gtatgcggcg accgagttgc tcttgcccgg 50340
cgtcaacacg ggataatacc gcgccacata gcagaacttt aaaagtgctc atcattggaa 50400
aacgttcttc ggggcgaaaa ctctcaagga tcttaccgct gttgagatcc agttcgatgt 50460
aacccactcg tgcacccaac tgatcttcag catcttttac tttcaccagc gtttctgggt 50520
gagcaaaaac aggaaggcaa aatgccgcaa aaaagggaat aagggcgaca cggaaatgtt 50580
gaatactcat actcttcctt tttcaatatt attgaagcat ttatcagggt tattgtctca 50640
tgagcggata catatttgaa tgtatttaga aaaataaaca aataggggtt ccgcgcacat 50700
ttccccgaaa agtgccacct gacgtctaag aaaccattat tatcatgaca ttaacctata 50760
aaaataggcg tatcacgagg ccctttcgtc ttcaagaatt ggtcgacgat cttgctgcgt 50820
tcggatattt tcgtggagtt cccgccacag acccggattg aaggcgagat ccagcaactc 50880
gcgccagatc atcctgtgac ggaactttgg cgcgtgatga ctggccagga cgtcggccga 50940
aagagcgaca agcagatcac gcttttcgac agcgtcggat ttgcgatcga ggatttttcg 51000
gcgctgcgct acgtccgcga ccgcgttgag ggatcaagcc acagcagccc actcgacctt 51060
ctagccgacc cagacgagcc aagggatctt tttggaatgc tgctccgtcg tcaggctttc 51120
cgacgtttgg gtggttgaac agaagtcatt atcgtacgga atgccaagca ctcccgaggg 51180
gaaccctgtg gttggcatgc acatacaaat ggacgaacgg ataaaccttt tcacgccctt 51240
ttaaatatcc gttattctaa taaacgctct tttctcttag 51280

<210> SEQ ID NO 54
<211> LENGTH: 1603
<212> TYPE: DNA
<213> ORGANISM: Artificial Sequence
<220> FEATURE:
<223> OTHER INFORMATION: Fragment of improved ACS6 inhibition plasmid comprising TR3, ADH1 intron 1, and TR4

<400> SEQUENCE: 54
tagcagacgc ggaaccagcc gggctcccgg cagtggcagg aggagcccgg ggagatgttg 60
agccccacct cgaagaccac cctcttccac agctccatct cgccctcgaa cgaccggctc 120
cgcatcaggc gccgcatgtt gacccagcag aagagccccg cgttgctctc caggcactcg 180
atgcccacgg ccgccaggcc ctccgccagc tgctcgcgcc gctccctgat ccgccgcgtg 240
ttctccgcga tgtacctccg cgtgaagtcc ctgtcgccca ggagcgacgc caggaggtgc 300
tgcgtctggg acgacaccag gccgaagctc gacatcttgg tggccgcgga gaccacgccg 360
gcgttggacg agtagatggc gcccacgcgg aaccccggga ggcccaggtc cttggacagg 420
ctgtacacca cgtgcacgcg gtccgacagc ggcccaacgc cgacgacgcc gtcgtccgtg 480
gcggcgcgcg cggccaccac ctgcagtcga cgtgcaaagg tccgccttgt ttctcctctg 540
tctcttgatc tgactaatct tggtttatga ttcgttgagt aattttgggg aaagcttcgt 600
ccacagtttt ttttcgatga acagtgccgc agtggcgctg atcttgtatg ctatcctgca 660
atcgtggtga acttatttct tttatatcct ttactcccat gaaaaggcta gtaatctttc 720
tcgatgtaac atcgtccagc actgctatta ccgtgtggtc catccgacag tctggctgaa 780
cacatcatac gatctatgga gcaaaaatct atcttccctg ttctttaatg aaggacgtca 840
ttttcattag tatgatctag gaatgttgca acttgcaagg aggcgtttct ttctttgaat 900
ttaactaact cgttgagtgg ccctgtttct cggacgtaag gcctttgctg ctccacacat 960
gtccattcga attttaccgt gtttagcaag ggcgaaaagt ttgcatcttg atgatttagc 1020
ttgactatgc gattgctttc ctggacccgt gcagctggat cccggtacgc gccgccacgg 1080
acgacggcgt cgtcggcgtt gggccgctgt cggaccgcgt gcacgtggtg tacagcctgt 1140
ccaaggacct gggcctcccg gggttccgcg tgggcgccat ctactcgtcc aacgccggcg 1200
tggtctccgc ggccaccaag atgtcgagct tcggcctggt gtcgtcccag acgcagcacc 1260
tcctggcgtc gctcctgggc gacagggact tcacgcggag gtacatcgcg gagaacacgc 1320
ggcggatcag ggagcggcgc gagcagctgg cggagggcct ggcggccgtg ggcatcgagt 1380
gcctggagag caacgcgggg ctcttctgct gggtcaacat gcggcgcctg atgcggagcc 1440
ggtcgttcga gggcgagatg gagctgtgga agagggtggt cttcgaggtg gggctcaaca 1500
tctccccggg ctcctcctgc cactgccggg agcccggctg gttccgcgtc tgctaaaggg 1560
cgaattccag cacactggcg gccgttacta gtggatccga gct 1603

<210> SEQ ID NO 55
<211> LENGTH: 3657
<212> TYPE: DNA
<213> ORGANISM: Artificial Sequence
<220> FEATURE:
<223> OTHER INFORMATION: Fragment of improved ACS6 inhibition plasmid comprising UBIZm promoter, UBIZm 5'UTR, UBIZm Intron 1, TR3, ADH1 intron 1, and TR4

<400> SEQUENCE: 55
gtgcagcgtg acccggtcgt gcccctctct agagataatg agcattgcat gtctaagtta 60

-continued

```
taaaaaatta ccacatattt tttttgtcac acttgtttga agtgcagttt atctatcttt    120
atacatatat ttaaacttta ctctacgaat aatataatct atagtactac aataatatca    180
gtgttttaga gaatcatata aatgaacagt tagacatggt ctaaaggaca attgagtatt    240
ttgacaacag gactctacag ttttatcttt ttagtgtgca tgtgttctcc tttttttttg    300
caaatagctt cacctatata atacttcatc cattttatta gtacatccat ttagggttta    360
gggttaatgg tttttataga ctaatttttt tagtacatct attttattct attttagcct    420
ctaaattaag aaaactaaaa ctctatttta gttttttat ttaataattt agatataaaa    480
tagaataaaa taaagtgact aaaaattaaa caaataccct ttaagaaatt aaaaaaaacta    540
aggaaacatt tttcttgttt cgagtagata atgccagcct gttaaacgcc gtcgacgagt    600
ctaacggaca ccaaccagcg aaccagcagc gtcgcgtcgg gccaagcgaa gcagacggca    660
cggcatctct gtcgctgcct ctggacccct ctcgagagtt ccgctccacc gttggacttg    720
ctccgctgtc ggcatccaga aattgcgtgg cggagcggca gacgtgagcc ggcacggcag    780
gcggcctcct cctcctctca cggcaccggc agctacgggg gattcctttc ccaccgctcc    840
ttcgctttcc cttcctcgcc cgccgtaata aatagacacc ccctccacac cctctttccc    900
caacctcgtg ttgttcggag cgcacacaca cacaaccaga tctcccccaa atccacccgt    960
cggcacctcc gcttcaaggt acgccgctcg tcctcccccc ccccctctc taccttctct   1020
agatcggcgt tccggtccat gcatggttag ggcccggtag ttctacttct gttcatgttt   1080
gtgttagatc cgtgtttgtg ttagatccgt gctgctagcg ttcgtacacg gatgcgacct   1140
gtacgtcaga cacgttctga ttgctaactt gccagtgttt ctctttgggg aatcctggga   1200
tggctctagc cgttccgcag acgggatcga tttcatgatt tttttgttt cgttgcatag   1260
ggtttggttt gccctttcc tttatttcaa tatatgccgt gcacttgttt gtcgggtcat   1320
cttttcatgc tttttttgt cttggttgtg atgatgtggt ctggttgggc ggtcgttcta   1380
gatcggagta gaattctgtt tcaaactacc tggtggattt attaattttg gatctgtatg   1440
tgtgtgccat acatattcat agttacgaat tgaagatgat ggatggaaat atcgatctag   1500
gataggtata catgttgatg cgggttttac tgatgcatat acagagatgc tttttgttcg   1560
cttggttgtg atgatgtggt gtggttgggc ggtcgttcat tcgttctaga tcggagtaga   1620
atactgtttc aaactacctg gtgtatttat taattttgga actgtatgtg tgtgtcatac   1680
atcttcatag ttacgagttt aagatggatg gaaatatcga tctaggatag gtatacatgt   1740
tgatgtgggt tttactgatg catatacatg atggcatatg cagcatctat tcatatgctc   1800
taaccttgag tacctatcta ttataataaa caagtatgtt ttataattat tttgatcttg   1860
atatacttgg atgatggcat atgcagcagc tatatgtgga ttttttagc cctgccttca   1920
tacgctattt atttgcttgg tactgtttct tttgtcgatg ctcaccctgt tgtttggtgt   1980
tacttctgca ggtcgacttt aacttagcct aggatccact agtaacggcc gccagtgtgc   2040
tggaattcgc cctttagcag acgcggaacc agccgggctc ccggcagtgg caggaggagc   2100
ccggggagat gttgagcccc acctcgaaga ccaccctctt ccacagctcc atctcgccct   2160
cgaacgaccg gctccgcatc aggcgccgca tgttgaccca gcagaagagc cccgcgttgc   2220
tctccaggca ctcgatgccc acggccgcca ggccctccgc cagctgctcg cgccgctccc   2280
tgatccgccg cgtgttctcc gcgatgtacc tccgcgtgaa gtccctgtcg cccaggagcg   2340
acgccaggag gtgctgcgtc tgggacgaca ccaggccgaa gctcgacatc ttggtggccg   2400
cggagaccac gccggcgttg gacgagtaga tggcgcccac gcggaacccc gggaggccca   2460
```

ggtccttgga caggctgtac accacgtgca cgcggtccga cagcggccca acgccgacga 2520
cgccgtcgtc cgtggcggcg cgcgcggcca ccacctgcag tcgacgtgca aaggtccgcc 2580
ttgtttctcc tctgtctctt gatctgacta atcttggttt atgattcgtt gagtaatttt 2640
ggggaaagct tcgtccacag ttttttttcg atgaacagtg ccgcagtggc gctgatcttg 2700
tatgctatcc tgcaatcgtg gtgaacttat ttcttttata tcctttactc ccatgaaaag 2760
gctagtaatc tttctcgatg taacatcgtc cagcactgct attaccgtgt ggtccatccg 2820
acagtctggc tgaacacatc atacgatcta tggagcaaaa atctatcttc cctgttcttt 2880
aatgaaggac gtcattttca ttagtatgat ctaggaatgt tgcaacttgc aaggaggcgt 2940
ttctttcttt gaatttaact aactcgttga gtggccctgt ttctcggacg taaggccttt 3000
gctgctccac acatgtccat tcgaatttta ccgtgtttag caagggcgaa aagtttgcat 3060
cttgatgatt tagcttgact atgcgattgc tttcctggac ccgtgcagct ggatcccggt 3120
acgcgccgcc acggacgacg gcgtcgtcgg cgttgggccg ctgtcggacc gcgtgcacgt 3180
ggtgtacagc ctgtccaagg acctgggcct cccggggttc cgcgtgggcg ccatctactc 3240
gtccaacgcc ggcgtggtct ccgcggccac caagatgtcg agcttcggcc tggtgtcgtc 3300
ccagacgcag cacctcctgg cgtcgctcct gggcgacagg gacttcacgc ggaggtacat 3360
cgcggagaac acgcggcgga tcagggagcg gcgcgagcag ctggcggagg gcctggcggc 3420
cgtgggcatc gagtgcctgg agagcaacgc ggggctcttc tgctgggtca acatgcggcg 3480
cctgatgcgg agccggtcgt tcgagggcga gatggagctg tggaagaggg tggtcttcga 3540
ggtggggctc aacatctccc cgggctcctc ctgccactgc cgggagcccg gctggttccg 3600
cgtctgctaa agggcgaatt ccagcacact ggcggccgtt actagtggat ccgagct 3657

<210> SEQ ID NO 56
<211> LENGTH: 6772
<212> TYPE: DNA
<213> ORGANISM: Artificial Sequence
<220> FEATURE:
<223> OTHER INFORMATION: Fragment of improved ACS6 inhibition plasmid

<400> SEQUENCE: 56
gtgcagcgtg acccggtcgt gcccctctct agagataatg agcattgcat gtctaagtta 60
taaaaaatta ccacatattt tttttgtcac acttgtttga agtgcagttt atctatcttt 120
atacatatat ttaaacttta ctctacgaat aatataatct atagtactac aataatatca 180
gtgttttaga gaatcatata aatgaacagt tagacatggt ctaaaggaca attgagtatt 240
ttgacaacag gactctacag ttttatcttt ttagtgtgca tgtgttctcc tttttttttg 300
caaatagctt cacctatata atacttcatc cattttatta gtacatccat ttagggttta 360
gggttaatgg tttttataga ctaatttttt tagtacatct attttattct attttagcct 420
ctaaattaag aaaactaaaa ctctatttta gttttttttat ttaataattt agatataaaa 480
tagaataaaa taaagtgact aaaaattaaa caaataccct ttaagaaatt aaaaaaaacta 540 aggaaacatt tttcttgttt cgagtagata atgccagcct gttaaacgcc gtcgacgagt 600
ctaacggaca ccaaccagcg aaccagcagc gtcgcgtcgg gccaagcgaa gcagacggca 660
cggcatctct gtcgctgcct ctggacccct ctcgagagtt ccgctccacc gttggacttg 720
ctccgctgtc ggcatccaga aattgcgtgg cggagcggca gacgtgagcc ggcacggcag 780
gcggcctcct cctcctctca cggcaccggc agctacgggg gattcctttc ccaccgctcc 840

-continued

```
ttcgctttcc cttcctcgcc cgccgtaata aatagacacc ccctccacac cctctttccc    900
caacctcgtg ttgttcggag cgcacacaca cacaaccaga tctcccccaa atccacccgt    960
cggcacctcc gcttcaaggt acgccgctcg tcctcccccc ccccccctctc taccttctct   1020
agatcggcgt tccggtccat gcatggttag ggcccggtag ttctacttct gttcatgttt   1080
gtgttagatc cgtgtttgtg ttagatccgt gctgctagcg ttcgtacacg gatgcgacct   1140
gtacgtcaga cacgttctga ttgctaactt gccagtgttt ctctttgggg aatcctggga   1200
tggctctagc cgttccgcag acgggatcga tttcatgatt ttttttgttt cgttgcatag   1260
ggtttggttt gcccttttcc tttatttcaa tatatgccgt gcacttgttt gtcgggtcat   1320
cttttcatgc ttttttttgt cttggttgtg atgatgtggt ctggttgggc ggtcgttcta   1380
gatcggagta gaattctgtt tcaaactacc tggtggattt attaattttg gatctgtatg   1440
tgtgtgccat acatattcat agttacgaat tgaagatgat ggatggaaat atcgatctag   1500
gataggtata catgttgatg cgggttttac tgatgcatat acagagatgc tttttgttcg   1560
cttggttgtg atgatgtggt gtggttgggc ggtcgttcat tcgttctaga tcggagtaga   1620
atactgtttc aaactacctg gtgtatttat taattttgga actgtatgtg tgtgtcatac   1680
atcttcatag ttacgagttt aagatggatg gaaatatcga tctaggatag gtatacatgt   1740
tgatgtgggt tttactgatg catatacatg atggcatatg cagcatctat tcatatgctc   1800
taaccttgag tacctatcta ttataataaa caagtatgtt ttataattat tttgatcttg   1860
atatacttgg atgatggcat atgcagcagc tatatgtgga tttttttagc cctgccttca   1920
tacgctattt atttgcttgg tactgtttct tttgtcgatg ctcaccctgt tgtttggtgt   1980
tacttctgca ggtcgacttt aacttagcct aggatccact agtaacggcc gccagtgtgc   2040
tggaattcgc cctttagcag acgcggaacc agccgggctc ccggcagtgg caggaggagc   2100
ccggggagat gttgagcccc acctcgaaga ccaccctctt ccacagctcc atctcgccct   2160
cgaacgaccg gctccgcatc aggcgccgca tgttgaccca gcagaagagc cccgcgttgc   2220
tctccaggca ctcgatgccc acggccgcca ggccctccgc cagctgctcg cgccgctccc   2280
tgatccgccg cgtgttctcc gcgatgtacc tccgcgtgaa gtccctgtcg cccaggagcg   2340
acgccaggag gtgctgcgtc tgggacgaca ccaggccgaa gctcgacatc ttggtggccg   2400
cggagaccac gccggcgttg gacgagtaga tggcgcccac gcggaacccc gggaggccca   2460
ggtccttgga caggctgtac accacgtgca cgcggtccga cagcggccca acgccgacga   2520
cgccgtcgtc cgtggcggcg cgcgcggcca ccacctgcag tcgacgtgca aaggtccgcc   2580
ttgtttctcc tctgtctctt gatctgacta atcttggttt atgattcgtt gagtaatttt   2640
ggggaaagct tcgtccacag tttttttttcg atgaacagtg ccgcagtggc gctgatcttg   2700
tatgctatcc tgcaatcgtg gtgaacttat ttcttttata tcctttactc ccatgaaaag   2760
gctagtaatc tttctcgatg taacatcgtc cagcactgct attaccgtgt ggtccatccg   2820
acagtctggc tgaacacatc atacgatcta tggagcaaaa atctatcttc cctgttcttt   2880
aatgaaggac gtcattttca ttagtatgat ctaggaatgt tgcaacttgc aaggaggcgt   2940
ttctttcttt gaatttaact aactcgttga gtggccctgt ttctcggacg taaggccttt   3000
gctgctccac acatgtccat tcgaatttta ccgtgtttag caagggcgaa aagtttgcat   3060
cttgatgatt tagcttgact atgcgattgc tttcctggac ccgtgcagct ggatcccggt   3120
acgcgccgcc acggacgacg gcgtcgtcgg cgttgggccg ctgtcggacc gcgtgcacgt   3180
ggtgtacagc ctgtccaagg acctgggcct cccggggttc cgcgtgggcg ccatctactc   3240
```

-continued gtccaacgcc ggcgtggtct ccgcggccac caagatgtcg agcttcggcc tggtgtcgtc 3300
ccagacgcag cacctcctgg cgtcgctcct gggcgacagg gacttcacgc ggaggtacat 3360
cgcggagaac acgcggcgga tcagggagcg gcgcgagcag ctggcggagg gcctggcggc 3420
cgtgggcatc gagtgcctgg agagcaacgc ggggctcttc tgctgggtca acatgcggcg 3480
cctgatgcgg agccggtcgt tcgagggcga gatggagctg tggaagaggg tggtcttcga 3540
ggtggggctc aacatctccc cgggctcctc ctgccactgc cgggagcccg gctggttccg 3600
cgtctgctaa agggcgaatt ccagcacact ggcggccgtt actagtggat ccgagctcga 3660
attccggtcc gggtcacccg gtccgggcct agaaggccga tctcccgggc acccagcttt 3720
cttgtacaaa gtggtgatat cggaccgatt aaactttaat tcggtccgat gcatgtatac 3780
gaagttccta ttccgaagtt cctattctac atagagtata ggaacttcac ctggtggcgc 3840
cgctagtgga tcccccgggc tgcagtgcag cgtgacccgg tcgtgcccct ctctagagat 3900
aatgagcatt gcatgtctaa gttataaaaa attaccacat atttttttg tcacacttgt 3960 ttgaagtgca gtttatctat ctttatacat atatttaaac tttactctac gaataatata 4020
atctatagta ctacaataat atcagtgttt tagagaatca tataaatgaa cagttagaca 4080
tggtctaaag gacaattgag tattttgaca acaggactct acagttttat ctttttagtg 4140
tgcatgtgtt ctcctttttt tttgcaaata gcttcaccta tataatactt catccatttt 4200
attagtacat ccatttaggg tttagggtta atggttttta tagactaatt tttttagtac 4260
atctatttta ttctatttta gcctctaaat taagaaaact aaaactctat tttagttttt 4320
ttatttaata atttagatat aaaatagaat aaaataaagt gactaaaaat taaacaaata 4380
ccctttaaga aattaaaaaa actaaggaaa catttttctt gtttcgagta gataatgcca 4440
gcctgttaaa cgccgtcgac gagtctaacg gacaccaacc agcgaaccag cagcgtcgcg 4500
tcgggccaag cgaagcagac ggcacggcat ctctgtcgct gcctctggac ccctctcgag 4560
agttccgctc caccgttgga cttgctccgc tgtcggcatc cagaaattgc gtggcggagc 4620
ggcagacgtg agccggcacg gcaggcggcc tcctcctcct ctcacggcac cggcagctac 4680
gggggattcc tttcccaccg ctccttcgct ttcccttcct cgcccgccgt aataaataga 4740
caccccctcc acaccctctt tccccaacct cgtgttgttc ggagcgcaca cacacacaac 4800
cagatctccc ccaaatccac ccgtcggcac ctccgcttca aggtacgccg ctcgtcctcc 4860
cccccccccc tctctacctt ctctagatcg gcgttccggt ccatgcatgg ttagggcccg 4920
gtagttctac ttctgttcat gtttgtgtta gatccgtgtt tgtgttagat ccgtgctgct 4980
agcgttcgta cacggatgcg acctgtacgt cagacacgtt ctgattgcta acttgccagt 5040
gtttctcttt ggggaatcct gggatggctc tagccgttcc gcagacggga tcgatttcat 5100
gatttttttt gtttcgttgc atagggtttg gtttgccctt ttcctttatt tcaatatatg 5160
ccgtgcactt gtttgtcggg tcatcttttc atgctttttt ttgtcttggt tgtgatgatg 5220
tggtctggtt gggcggtcgt tctagatcgg agtagaattc tgtttcaaac tacctggtgg 5280
atttattaat tttggatctg tatgtgtgtg ccatacatat tcatagttac gaattgaaga 5340
tgatggatgg aaatatcgat ctaggatagg tatacatgtt gatgcgggtt ttactgatgc 5400
atatacagag atgctttttg ttcgcttggt tgtgatgatg tggtgtggtt gggcggtcgt 5460
tcattcgttc tagatcggag tagaatactg tttcaaacta cctggtgtat ttattaattt 5520
tggaactgta tgtgtgtgtc atacatcttc atagttacga gtttaagatg gatggaaata 5580
tcgatctagg ataggtatac atgttgatgt gggttttact gatgcatata catgatggca 5640
tatgcagcat ctattcatat gctctaacct tgagtaccta tctattataa taaacaagta 5700
tgttttataa ttattttgat cttgatatac ttggatgatg gcatatgcag cagctatatg 5760
tggatttttt tagccctgcc ttcatacgct atttatttgc ttggtactgt ttcttttgtc 5820
gatgctcacc ctgttgtttg gtgttacttc tgcaggtcga ctttaactta gcctaggatc 5880
cacacgacac catgtccccc gagcgccgcc ccgtcgagat ccgcccggcc accgccgccg 5940
acatggccgc cgtgtgcgac atcgtgaacc actacatcga gacctccacc gtgaacttcc 6000
gcaccgagcc gcagaccccg caggagtgga tcgacgacct ggagcgcctc caggaccgct 6060
acccgtggct cgtggccgag gtggagggcg tggtggccgg catcgcctac gccggcccgt 6120
ggaaggcccg caacgcctac gactggaccg tggagtccac cgtgtacgtg tcccaccgcc 6180
accagcgcct cggcctcggc tccaccctct acacccacct cctcaagagc atggaggccc 6240
agggcttcaa gtccgtggtg gccgtgatcg gcctcccgaa cgacccgtcc gtgcgcctcc 6300
acgaggccct cggctacacc gcccgcggca ccctccgcgc cgccggctac aagcacggcg 6360
gctggcacga cgtcggcttc tggcagcgcg acttcgagct gccggccccg ccgcgcccgg 6420
tgcgcccggt gacgcagatc tgagtcgaaa cctagacttg tccatcttct ggattggcca 6480
acttaattaa tgtatgaaat aaaaggatgc acacatagtg acatgctaat cactataatg 6540
tgggcatcaa agttgtgtgt tatgtgtaat tactagttat ctgaataaaa gagaaagaga 6600
tcatccatat ttcttatcct aaatgaatgt cacgtgtctt tataattctt tgatgaacca 6660
gatgcatttc attaaccaaa tccatataca tataaatatt aatcatatat aattaatatc 6720
aattgggtta gcaaaacaaa tctagtctag gtgtgttttg cgaattgcgg cc 6772

<210> SEQ ID NO 57
<211> LENGTH: 8350
<212> TYPE: DNA
<213> ORGANISM: Artificial Sequence
<220> FEATURE:
<223> OTHER INFORMATION: Improved ACS6 inhibition expression cassette

<400> SEQUENCE: 57
gtttacccgc caatatatcc tgtcaaacac tgatagttta aactgaaggc gggaaacgac 60
aatctgatca tgagcggaga attaagggag tcacgttatg acccccgccg atgacgcggg 120
acaagccgtt ttacgtttgg aactgacaga accgcaacgt tgaaggagcc actcagcaag 180
ctggtacgat tgtaatacga ctcactatag ggcgaattga gcgctgttta aacgctcttc 240
aactggaaga gcggttacta ccggctggat ggcggggcct tgatcgtgca ccgccggcgt 300
ccggataagt gactagggtc acgtgaccct agtcacttat cgagctagtt accctatgag 360
gtgacatgaa gcgctcacgg ttactatgac ggttagcttc acgactgttg gtggcagtag 420
cgtacgactt agctatagtt ccggtagatc tgaagttcct attccgaagt tcctattctt 480
caaaaggtat aggaacttcc tcgaattgtt gtggtggggt atagaggttt gatataggtg 540
gaactgctgt agagcgtgga gatatagggg gaaagagaac gctgatgtga caagtgagtg 600
agatataggg ggagaaattt agggggaacg ccgaacacag tctaaagaag cttgggaccc 660
aaagcactct gttcgggggt tttttttttt gtctttcaac tttttgctgt aatgttattc 720
aaaataagaa aagcacttgg catggctaag aaatagagtt caacaactga acagtacagt 780
gtattatcaa tggcataaaa aacaaccctt acagcattgc cgtattttat tgatcaaaca 840
ttcaactcaa cactgacgag tggtcttcca ccgatcaacg gactaatgct gctttgtcag 900

```
atcaccggtt aagtgactag ggtcacgtga ccctagtcac ttaggttacc agagctggtc    960
acctttgtcc accaagatgg aactgcggcc gctcattaat taagtcaggc gcgcctctag   1020
ttgaagacac gttcatgtct tcatcgtaag aagacactca gtagtcttcg gccagaatgg   1080
ccatctggat tcagcaggcc tagaaggcca tttaaatcct gaggatctgg tcttcctaag   1140
gacccgggat atcacaagtt tgtacaaaaa agcaggctcc ggccagagtt acccggaccg   1200
aagcttgcat gcctgcagtg cagcgtgacc cggtcgtgcc cctctctaga gataatgagc   1260
attgcatgtc taagttataa aaaattacca catatttttt ttgtcacact tgtttgaagt   1320
gcagtttatc tatctttata catatattta aactttactc tacgaataat ataatctata   1380
gtactacaat aatatcagtg ttttagagaa tcatataaat gaacagttag acatggtcta   1440
aaggacaatt gagtattttg acaacaggac tctacagttt tatcttttta gtgtgcatgt   1500
gttctccttt ttttttgcaa atagcttcac ctatataata cttcatccat tttattagta   1560
catccattta gggtttaggg ttaatggttt ttatagacta atttttttag tacatctatt   1620
ttattctatt ttagcctcta aattaagaaa actaaaactc tattttagtt tttttattta   1680
ataatttaga tataaaatag aataaaataa agtgactaaa aattaaacaa ataccettta   1740
agaaattaaa aaaactaagg aaacattttt cttgtttcga gtagataatg ccagcctgtt   1800
aaacgccgtc gacgagtcta acggacacca accagcgaac cagcagcgtc gcgtcgggcc   1860
aagcgaagca gacggcacgg catctctgtc gctgcctctg gacccctctc gagagttccg   1920
ctccaccgtt ggacttgctc cgctgtcggc atccagaaat tgcgtggcgg agcggcagac   1980
gtgagccggc acggcaggcg gcctcctcct cctctcacgg caccggcagc tacgggggat   2040
tcctttccca ccgctccttc gctttccctt cctcgcccgc cgtaataaat agacaccccc   2100
tccacaccct ctttccccaa cctcgtgttg ttcggagcgc acacacacac aaccagatct   2160
cccccaaatc cacccgtcgg cacctccgct tcaaggtacg ccgctcgtcc tccccccccc   2220
ccctctctac cttctctaga tcggcgttcc ggtccatgca tggttagggc ccggtagttc   2280
tacttctgtt catgtttgtg ttagatccgt gtttgtgtta gatccgtgct gctagcgttc   2340
gtacacggat gcgacctgta cgtcagacac gttctgattg ctaacttgcc agtgtttctc   2400
tttggggaat cctgggatgg ctctagccgt tccgcagacg ggatcgattt catgattttt   2460
tttgtttcgt tgcatagggt ttggtttgcc cttttccttt atttcaatat atgccgtgca   2520
cttgtttgtc gggtcatctt ttcatgcttt tttttgtctt ggttgtgatg atgtggtctg   2580
gttgggcggt cgttctagat cggagtagaa ttctgtttca aactacctgg tggatttatt   2640
aattttggat ctgtatgtgt gtgccataca tattcatagt tacgaattga agatgatgga   2700
tggaaatatc gatctaggat aggtatacat gttgatgcgg gttttactga tgcatataca   2760
gagatgcttt ttgttcgctt ggttgtgatg atgtggtgtg gttgggcggt cgttcattcg   2820
ttctagatcg gagtagaata ctgtttcaaa ctacctggtg tatttattaa ttttggaact   2880
gtatgtgtgt gtcatacatc ttcatagtta cgagtttaag atggatggaa atatcgatct   2940
aggataggta tacatgttga tgtgggtttt actgatgcat atacatgatg gcatatgcag   3000
catctattca tatgctctaa ccttgagtac ctatctatta taataaacaa gtatgtttta   3060
taattatttt gatcttgata tacttggatg atggcatatg cagcagctat atgtggattt   3120
ttttagccct gccttcatac gctatttatt tgcttggtac tgtttctttt gtcgatgctc   3180
accctgttgt ttggtgttac ttctgcaggt cgactttaac ttagcctagg atccactagt   3240
```

```
aacggccgcc agtgtgctgg aattcgccct ttagcagacg cggaaccagc cgggctcccg   3300
gcagtggcag gaggagcccg gggagatgtt gagccccacc tcgaagacca ccctcttcca   3360
cagctccatc tcgccctcga acgaccggct ccgcatcagg cgccgcatgt tgacccagca   3420
gaagagcccc gcgttgctct ccaggcactc gatgcccacg gccgccaggc cctccgccag   3480
ctgctcgcgc cgctccctga tccgccgcgt gttctccgcg atgtacctcc gcgtgaagtc   3540
cctgtcgccc aggagcgacg ccaggaggtg ctgcgtctgg gacgacacca ggccgaagct   3600
cgacatcttg gtggccgcgg agaccacgcc ggcgttggac gagtagatgg cgcccacgcg   3660
gaaccccggg aggcccaggt ccttggacag gctgtacacc acgtgcacgc ggtccgacag   3720
cggcccaacg ccgacgacgc cgtcgtccgt ggcggcgcgc gcggccacca cctgcagtcg   3780
acgtgcaaag gtccgccttg tttctcctct gtctcttgat ctgactaatc ttggtttatg   3840
attcgttgag taattttggg gaaagcttcg tccacagttt tttttcgatg aacagtgccg   3900
cagtggcgct gatcttgtat gctatcctgc aatcgtggtg aacttatttc ttttatatcc   3960
tttactccca tgaaaaggct agtaatcttt ctcgatgtaa catcgtccag cactgctatt   4020
accgtgtggt ccatccgaca gtctggctga acacatcata cgatctatgg agcaaaaatc   4080
tatcttccct gttctttaat gaaggacgtc attttcatta gtatgatcta ggaatgttgc   4140
aacttgcaag gaggcgtttc tttctttgaa tttaactaac tcgttgagtg gccctgtttc   4200
tcggacgtaa ggcctttgct gctccacaca tgtccattcg aattttaccg tgtttagcaa   4260
gggcgaaaag tttgcatctt gatgatttag cttgactatg cgattgcttt cctggacccg   4320
tgcagctgga tcccggtacg cgccgccacg gacgacggcg tcgtcggcgt tgggccgctg   4380
tcggaccgcg tgcacgtggt gtacagcctg tccaaggacc tgggcctccc ggggttccgc   4440
gtgggcgcca tctactcgtc caacgccggc gtggtctccg cggccaccaa gatgtcgagc   4500
ttcggcctgg tgtcgtccca gacgcagcac ctcctggcgt cgctcctggg cgacagggac   4560
ttcacgcgga ggtacatcgc ggagaacacg cggcggatca gggagcggcg cgagcagctg   4620
gcggagggcc tggcggccgt gggcatcgag tgcctggaga gcaacgcggg gctcttctgc   4680
tgggtcaaca tgcggcgcct gatgcggagc cggtcgttcg agggcgagat ggagctgtgg   4740
aagagggtgg tcttcgaggt ggggctcaac atctccccgg gctcctcctg ccactgccgg   4800
gagcccggct ggttccgcgt ctgctaaagg gcgaattcca gcacactggc ggccgttact   4860
agtggatccg agctcgaatt ccggtccggg tcacccggtc cgggcctaga aggccgatct   4920
cccgggcacc cagctttctt gtacaaagtg gtgatatcgg accgattaaa ctttaattcg   4980
gtccgatgca tgtatacgaa gttcctattc cgaagttcct attctacata gagtatagga   5040
acttcacctg gtggcgccgc tagtggatcc cccgggctgc agtgcagcgt gacccggtcg   5100
tgcccctctc tagagataat gagcattgca tgtctaagtt ataaaaaatt accacatatt   5160
ttttttgtca cacttgtttg aagtgcagtt tatctatctt tatacatata tttaaacttt   5220
actctacgaa taatataatc tatagtacta caataatatc agtgttttag agaatcatat   5280
aaatgaacag ttagacatgg tctaaaggac aattgagtat tttgacaaca ggactctaca   5340
gttttatctt tttagtgtgc atgtgttctc cttttttttt gcaaatagct tcacctatat   5400
aatacttcat ccattttatt agtacatcca tttagggttt agggttaatg gtttttatag   5460
actaattttt ttagtacatc tattttattc tattttagcc tctaaattaa gaaaactaaa   5520
actctatttt agttttttta tttaataatt tagatataaa atagaataaa ataaagtgac   5580
taaaaattaa acaaataccc tttaagaaat taaaaaaact aaggaaacat ttttcttgtt   5640
```

-continued

```
tcgagtagat aatgccagcc tgttaaacgc cgtcgacgag tctaacggac accaaccagc   5700
gaaccagcag cgtcgcgtcg ggccaagcga agcagacggc acggcatctc tgtcgctgcc   5760
tctggacccc tctcgagagt tccgctccac cgttggactt gctccgctgt cggcatccag   5820
aaattgcgtg gcggagcggc agacgtgagc cggcacggca ggcggcctcc tcctcctctc   5880
acggcaccgg cagctacggg ggattccttt cccaccgctc cttcgctttc ccttcctcgc   5940
ccgccgtaat aaatagacac cccctccaca ccctctttcc ccaacctcgt gttgttcgga   6000
gcgcacacac acacaaccag atctccccca aatccacccg tcggcacctc cgcttcaagg   6060
tacgccgctc gtcctccccc ccccccctct ctaccttctc tagatcggcg ttccggtcca   6120
tgcatggtta gggcccggta gttctacttc tgttcatgtt tgtgttagat ccgtgtttgt   6180
gttagatccg tgctgctagc gttcgtacac ggatgcgacc tgtacgtcag acacgttctg   6240
attgctaact tgccagtgtt tctctttggg gaatcctggg atggctctag ccgttccgca   6300
gacgggatcg atttcatgat ttttttttgtt tcgttgcata gggtttggtt tgccctttc   6360
ctttatttca atatatgccg tgcacttgtt tgtcgggtca tcttttcatg cttttttttg   6420
tcttggttgt gatgatgtgg tctggttggg cggtcgttct agatcggagt agaattctgt   6480
ttcaaactac ctggtggatt tattaatttt ggatctgtat gtgtgtgcca tacatattca   6540
tagttacgaa ttgaagatga tggatggaaa tatcgatcta ggataggtat acatgttgat   6600
gcgggtttta ctgatgcata tacagagatg ctttttgttc gcttggttgt gatgatgtgg   6660
tgtggttggg cggtcgttca ttcgttctag atcggagtag aatactgttt caaactacct   6720
ggtgtattta ttaattttgg aactgtatgt gtgtgtcata catcttcata gttacgagtt   6780
taagatggat ggaaatatcg atctaggata ggtatacatg ttgatgtggg ttttactgat   6840
gcatatacat gatggcatat gcagcatcta ttcatatgct ctaaccttga gtacctatct   6900
attataataa acaagtatgt tttataatta ttttgatctt gatatacttg gatgatggca   6960
tatgcagcag ctatatgtgg attttttttag ccctgccttc atacgctatt tatttgcttg   7020
gtactgtttc ttttgtcgat gctcaccctg ttgtttggtg ttacttctgc aggtcgactt   7080
taacttagcc taggatccac acgacaccat gtcccccgag cgccgccccg tcgagatccg   7140
cccggccacc gccgccgaca tggccgccgt gtgcgacatc gtgaaccact acatcgagac   7200
ctccaccgtg aacttccgca ccgagccgca gaccccgcag gagtggatcg acgacctgga   7260
gcgcctccag gaccgctacc cgtggctcgt ggccgaggtg gagggcgtgg tggccggcat   7320
cgcctacgcc ggcccgtgga aggcccgcaa cgcctacgac tggaccgtgg agtccaccgt   7380
gtacgtgtcc caccgccacc agcgcctcgg cctcggctcc accctctaca cccacctcct   7440
caagagcatg gaggcccagg gcttcaagtc cgtggtggcc gtgatcggcc tcccgaacga   7500
cccgtccgtg cgcctccacg aggccctcgg ctacaccgcc cgcggcaccc tccgcgccgc   7560
cggctacaag cacggcggct ggcacgacgt cggcttctgg cagcgcgact tcgagctgcc   7620
ggccccgccg cgcccggtgc gcccggtgac gcagatctga gtcgaaacct agacttgtcc   7680
atcttctgga ttggccaact taattaatgt atgaaataaa aggatgcaca catagtgaca   7740
tgctaatcac tataatgtgg gcatcaaagt tgtgtgttat gtgtaattac tagttatctg   7800
aataaaagag aaagagatca tccatatttc ttatcctaaa tgaatgtcac gtgtctttat   7860
aattctttga tgaaccagat gcatttcatt aaccaaatcc atatacatat aaatattaat   7920
catatataat taatatcaat tgggttagca aaacaaatct agtctaggtg tgttttgcga   7980
```

-continued

| | |
|---|---|
| attgcggccg ctctagcgta tacgaagttc ctattccgaa gttcctattc tctagaaagt | 8040 |
| ataggaactt ctgattccga tgacttcgta ggttcctagc tcaagccgct cgtgtccaag | 8100 |
| cgtcacttac gattagctaa tgattacggc atctaggacc gactagtaag tgactagggt | 8160 |
| cacgtgaccc tagtcactta tacgtagaat taattcattc cgattaatcg tggcctcttg | 8220 |
| ctcttcagga tgaagagcta tgtttaaacg tgcaagcgct actagacaat tcagtacatt | 8280 |
| aaaaacgtcc gcaatgtgtt attaagttgt ctaagcgtca atttgtttac accacaatat | 8340 |
| atcctgccac | 8350 |